US011807669B2

(12) United States Patent
Møller et al.

(10) Patent No.: US 11,807,669 B2
(45) Date of Patent: Nov. 7, 2023

(54) **PROTEINS AND NUCLEIC ACIDS USEFUL IN VACCINES TARGETING *STAPHYLOCOCCUS AUREUS***

(71) Applicant: Evaxion Biotech ApS, København K (DK)

(72) Inventors: Niels Iversen Møller, København K (DK); Andreas Holm Mattsson, København K (DK)

(73) Assignee: Evaxion Biotech A/S, Hørsholm (DK)

( * ) Notice: Subject to any disclaimer, the term of this patent is extended or adjusted under 35 U.S.C. 154(b) by 156 days.

(21) Appl. No.: 16/600,031

(22) Filed: Oct. 11, 2019

(65) Prior Publication Data

US 2020/0031878 A1 Jan. 30, 2020

Related U.S. Application Data

(62) Division of application No. 15/101,791, filed as application No. PCT/EP2014/076398 on Dec. 3, 2014, now abandoned.

(30) Foreign Application Priority Data

Dec. 3, 2013 (EP) .................................... 13195472

(51) Int. Cl.
| | |
|---|---|
| C07K 14/31 | (2006.01) |
| A61K 39/085 | (2006.01) |
| C07K 16/12 | (2006.01) |
| C12Q 1/689 | (2018.01) |
| G01N 33/569 | (2006.01) |
| A61K 39/00 | (2006.01) |

(52) U.S. Cl.
CPC ............ *C07K 14/31* (2013.01); *A61K 39/085* (2013.01); *C07K 16/1271* (2013.01); *C12Q 1/689* (2013.01); *G01N 33/56938* (2013.01); *A61K 2039/55505* (2013.01); *G01N 2333/31* (2013.01); *G01N 2500/04* (2013.01)

(58) Field of Classification Search
CPC .. C07K 14/31; C07K 16/1271; A61K 39/085; A61K 2039/55505; C12Q 1/689; G01N 33/56938; G01N 2333/31; G01N 2500/04
See application file for complete search history.

(56) References Cited

U.S. PATENT DOCUMENTS

| | | |
|---|---|---|
| 4,683,202 A | 7/1987 | Mullis |
| 4,684,611 A | 8/1987 | Schilperoort et al. |
| 4,897,236 A | 1/1990 | Rabiger et al. |
| 4,952,500 A | 8/1990 | Finnerty et al. |
| 5,302,523 A | 4/1994 | Coffee et al. |
| 5,322,783 A | 6/1994 | Tomes et al. |
| 5,384,253 A | 1/1995 | Krzyzek et al. |
| 5,464,765 A | 11/1995 | Coffee et al. |
| 5,538,877 A | 7/1996 | Lundquist et al. |
| 5,538,880 A | 7/1996 | Lundquist et al. |
| 5,550,318 A | 8/1996 | Adams et al. |
| 5,563,055 A | 10/1996 | Townsend et al. |
| 5,580,859 A | 12/1996 | Felgner et al. |
| 5,589,466 A | 12/1996 | Felgner et al. |
| 5,591,616 A | 1/1997 | Hiei et al. |
| 5,610,042 A | 3/1997 | Chang et al. |
| 5,656,610 A | 8/1997 | Shuler et al. |
| 5,702,932 A | 12/1997 | Hoy et al. |
| 5,736,524 A | 4/1998 | Content et al. |
| 5,780,448 A | 7/1998 | Davis |
| 5,789,215 A | 8/1998 | Berns et al. |
| 5,843,650 A | 12/1998 | Segev |
| 5,846,709 A | 12/1998 | Segev |
| 5,846,783 A | 12/1998 | Wu et al. |
| 5,849,497 A | 12/1998 | Steinman |
| 5,849,546 A | 12/1998 | Sousa et al. |
| 5,849,547 A | 12/1998 | Cleuziat et al. |
| 5,858,652 A | 1/1999 | Laffler et al. |
| 5,866,366 A | 2/1999 | Kallender |
| 5,871,986 A | 2/1999 | Boyce |
| 5,916,776 A | 6/1999 | Kumar |
| 5,922,574 A | 7/1999 | Minter |
| 5,925,565 A | 7/1999 | Berlioz et al. |
| 5,928,905 A | 7/1999 | Stemmer et al. |
| 5,928,906 A | 7/1999 | Koster et al. |
| 5,932,451 A | 8/1999 | Wang et al. |
| 5,935,819 A | 8/1999 | Eichner et al. |
| 5,935,825 A | 8/1999 | Nishimura et al. |
| 5,939,291 A | 8/1999 | Loewy et al. |
| 5,942,391 A | 8/1999 | Zhang et al. |
| 5,945,100 A | 8/1999 | Fick |
| 5,981,274 A | 11/1999 | Tyrrell et al. |
| 5,994,624 A | 11/1999 | Trolinder et al. |
| 2012/0093850 A1 | 4/2012 | Bagnoli et al. |
| 2012/0282247 A1 | 11/2012 | Schneewind et al. |

FOREIGN PATENT DOCUMENTS

| | | | |
|---|---|---|---|
| GB | 2202328 | 9/1988 | |
| WO | WO8909284 | 10/1989 | |
| WO | WO9014837 | 12/1990 | |
| WO | WO9409699 | 5/1994 | |
| WO | WO9506128 | 3/1995 | |
| WO | WO-02059148 A2 * | 8/2002 | ............. A61P 43/00 |
| WO | WO02094868 | 11/2002 | |
| WO | WO2009134339 | 11/2009 | |
| WO | WO2010062814 | 6/2010 | |
| WO | WO2012136653 | 10/2012 | |

OTHER PUBLICATIONS

Greenspan et al, (Nature Biotechnology 17:936-937, 1999).*
Harlow et al (Antibodies a Laboratory Manual, Cold Spring Harbor Laboratory Press Inc., 1988).*
Colman et al. (Research in Immunology 145: 33-36, 1994).*
Houghten et al. (New Approaches to Immunization, Vaccines 86, Cold Spring Harbor Laboratory).*
Feldgarden, M. et al, "The genome sequence of *Staphylococcus aureus* strain 0160", XP002736400, (Apr. 3, 2013).

(Continued)

*Primary Examiner* — Robert A Zeman
(74) *Attorney, Agent, or Firm* — McHale & Slavin, P.A.

(57) ABSTRACT

The present invention relates to proteins and nucleic acids derived from *Staphylococcus aureus* as well as therapeutic and diagnostic uses of the proteins and nucleic acids.

17 Claims, 4 Drawing Sheets

Figure 1:
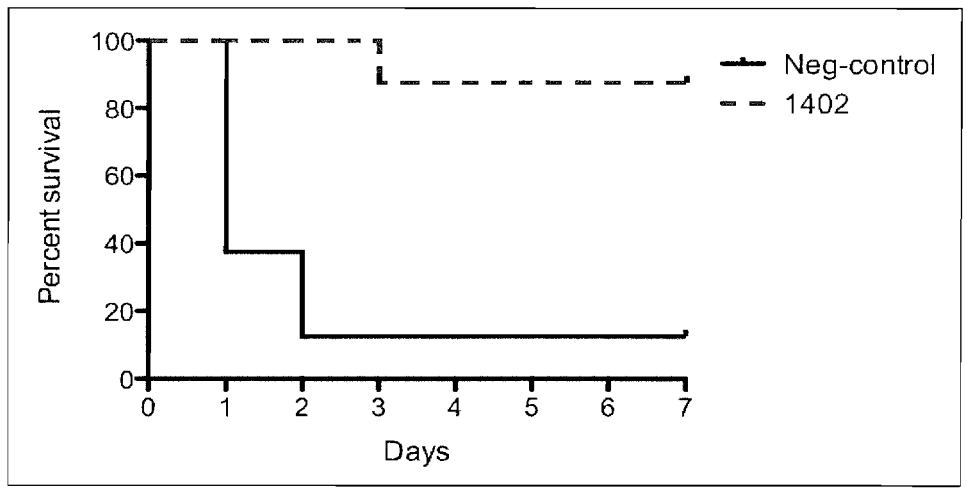

Specification includes a Sequence Listing.

(56) References Cited

OTHER PUBLICATIONS

Feldgarden, M. et al, "The genome sequence of *Staphylococcus aureus* strain M1015", XP002736401, (Apr. 3, 2013).

Feldgarden, M. et al, "The genome sequence of *Staphylococcus aureus* strain M809", XP002738862, (Jul. 13, 2010).

Perez, A. et al, "Mapping protective regions on a three-dimensional model of the Moraxella catarrhalis vaccine antigen oligopeptide permease A", American Society for Microbiology, vol. 86(3), pp. 1-14, Internet article: http://iai.asm.org, (Mar. 2018).

R. Ellis, "New technologies for making vaccines", Editors Stanley Plotkin and Edward Mortimer, W.B. Saunders Company, Philadelphia, pp. 568-575, (1988).

Skolnick, J. et al, "From genes to protein structure and function: novel applications of computational approaches in the genomic era", Tibtech, V. 18, pp. 34-39, (Jan. 2000).

Boslego, J. et al, "Gonorrhea Vaccines", Vaccines and Immunology, Editor Stanley Cryz, Pergamon Press, New York, pp. 569-575, DOI: 10.1016/0163-4453(93)97512-V, Ch. 17, (1991).

Chatterjee, V. et al, "Negative regulation of the thyroid-stimulating hormone alpha gene by thyroid hormone: Receptor interaction adjacent to the TATA box", Proc. Natl. Acad Sci., USA, vol. 86, pp. 9114-9118, (Dec. 1989).

Pyclik, M. et al, "Epitope mapping of *Streptococcus agalactiae* elongation factor Tu protein recognized by human sera", Frontiers in Microbiology, vol. 9(125), pp. 1-9, (Feb. 2018).

Petersen, B. et al, "NetTurnP-neural network prediction of beta-turns by use of evolutionary information and predicted protein sequence features", PLoS ONE, vol. 5(11), pp. 1-9, (Nov. 2010).

Larsen, J. et al, "Improved method for predicting linear b-cell epitopes", Immunome Research, vol. 2(2), DOI: https://doi.org/10.1186/1745-7580-2-2, (Apr. 2006).

Petersen, B. et al, "A genetic method for assignment of reliability scores applies to solvent accessibility predictions", BMC Structural Biology, vol. 9(51), pp. 1-10, DOI: 10 1186/1472-6807-9-51, (Jul. 2009).

Kohler, G. et al, "Continuous cultures of fused cells secreting antibody of predefined specificity", Nature, vol. 256, pp. 495-496, Aug. 1975).

Robinson, H. et al, "DNA vaccines", Seminars in Immunology, vol. 9(5), pp. 271-283, (Oct. 1997) Abstract.

Ott, G. et al, "MF59 Design and evaluation of a safe and potent adjuvant for human vaccines", Plenum Press, New York, Chapter 10, pp. 277-293, (1995).

\* cited by examiner

Protein: SAR1402 (1-327aa)
P-value (Log-rank)(Mantel-Cox): 0.001
Test group (alive mice/total mice): 7/8
Control group (alive mice/total mice): 1/8

Protein: SAR2496 (20-515aa)
P-value (Log-rank)(Mantel-Cox): 0.005
Test group (alive mice/total mice): 6/8
Control group (alive mice/total mice): 1/8

Protein: SAR2723 (28-619aa)
P-value (Log-rank)(Mantel-Cox): 0.0145
Test group (alive mice/total mice): 4/8
Control group (alive mice/total mice): 1/8

Protein: SAR2753 (36-681aa)
P-value (Log-rank)(Mantel-Cox): 0.0032
Test group (alive mice/total mice): 4/8
Control group (alive mice/total mice): 1/8

Protein: SAR2753 (36-476aa)
P-value (Log-rank)(Mantel-Cox): 0.0053
Test group (alive mice/total mice): 15/20
Control group (alive mice/total mice): 6/20

Protein: USA300HOU_2637-28-439 (SAR2716 homolog, id=93%, coverage=100%)
P-value (Log-rank)(Mantel-Cox): 0.0063
Test group (alive mice/total mice): 15/20
Control group (alive mice/total mice): 6/20

Protein: SAR1795 (25-564aa)
P-value (Log-rank)(Mantel-Cox): 0.0049
Test group (alive mice/total mice): 15/19
Control group (alive mice/total mice): 6/20

PROTEINS AND NUCLEIC ACIDS USEFUL IN VACCINES TARGETING *STAPHYLOCOCCUS AUREUS*

CROSS REFERENCE TO RELATED APPLICATIONS

In accordance with 37 C.F.R. 1.76, a claim of priority is included in an Application Data Sheet filed concurrently herewith. Accordingly, the present invention claims priority as a divisional of U.S. patent application Ser. No. 15/101,791, entitled "PROTEINS AND NUCLEIC ACIDS USEFUL IN VACCINES TARGETING *STAPHYLOCOCCUS AUREUS*", filed Jun. 3, 2016, which is a § 371 national stage entry of International Application No. PCT/EP2014/076398, entitled "PROTEINS AND NUCLEIC ACIDS USEFUL IN VACCINES TARGETING *STAPHYLOCOCCUS AUREUS*", filed Dec. 3, 2014, which claims the benefit of the priority of European Patent Application No. 13195472.9, entitled "PROTEINS AND NUCLEIC ACIDS USEFUL IN VACCINES TARGETING *STAPHYLOCOCCUS AUREUS*", filed Dec. 12, 2013, the entire contents of each are incorporated herein by reference.

FIELD OF THE INVENTION

The present invention relates to the field of antimicrobial prophylaxis and therapy. In particular the present invention relates to novel proteins and polynucleotides derived from *Staphylococcus aureus*. The invention further relates to vectors comprising the polynucleotides, transformed host organisms expressing the polynucleotides, antibodies (mono- or polyclonal) specific for the polypeptides as well as diagnostic, prophylactic and therapeutic uses and methods. Finally, also methods of preparation are part of the invention.

BACKGROUND OF THE INVENTION

Bacterial infections are in most instances successfully treated by administration of antibiotics to patients in need thereof. However, due to careless or thoughtless use of powerful antibiotics, many pathological germs become resistant against antibiotics over time. One threatening example is *Staphyloccocus aureus*. In particular in hospitals this bacterium is of relevance. So-called Methicillin Resistant *S. Aureus* (MRSA) strains jeopardize patient's survival in hospitals, in particular after surgery.

Vaccination is considered to be a very effective method of preventing infectious diseases in human and veterinary health care. Vaccination is the administration of immungenically effective amounts of antigenic material (the vaccine) to produce immunity to a disease/disease-causing pathogenic agent. Vaccines have contributed to the eradication of smallpox, the near eradication of polio, and the control of a variety of diseases, including rubella, measles, mumps, chickenpox, typhoid fever.

Before "the genomic era", vaccines were based on killed or live attenuated, microorganisms, or parts purified from them. Subunit vaccines are considered as a modern upgrade of these types of vaccine, as the subunit vaccines contain one or more protective antigens, which are more or less the weak spot of the pathogen. Hence, in order to develop subunit vaccines, it is critical to identify the proteins, which are important for inducing protection and to eliminate others.

An antigen is said to be protective if it is able to induce protection from subsequent challenge by a disease-causing infectious agent in an appropriate animal model following immunization.

The empirical approach to subunit vaccine development, which includes several steps, begins with pathogen cultivation, followed by purification into components, and then testing of antigens for protection. Apart from being time and labor consuming, this approach has several limitations that can lead to failure. It is not possible to develop vaccines using this approach for microorganisms, which cannot easily be cultured and only allows for the identification of the antigens, which can be obtained in sufficient quantities. The empirical approach has a tendency to focus on the most abundant proteins, which in some cases are not immunoprotective. In other cases, the antigen expressed during in vivo infection is not expressed during in vitro cultivation. Furthermore, antigen discovery by use of the empirical approach demands an extreme amount of proteins in order to discover the protective antigens, which are like finding needles in the haystack. This renders it a very expensive approach, and it limits the vaccine development around diseases, which is caused by pathogens with a large genome or disease areas, which perform badly in a cost-effective perspective.

OBJECT OF THE INVENTION

It is an object of embodiments of the invention to provide *S. aureus* derived antigenic polypeptides that may serve as constituents in vaccines against *S. aureus* infections and in diagnosis of *S. aureus* infections. It is also an object to provide nucleic acids, vectors, transformed cells, vaccine compositions, and other useful means for molecular cloning as well as for therapy and diagnosis with relevance for *S. aureus*.

SUMMARY OF THE INVENTION

It has been found by the present inventor(s) that *S. aureus*, in particular drug resistant *S. aureus*, expresses a number of hitherto unknown putatively surface exposed proteins which are candidates as vaccine targets as well as candidates as immunizing agents for preparation of antibodies that target *S. aureus*.

So, in a first aspect the present invention relates to a polypeptide comprising
  a) an amino acid sequence selected from the group consisting of any one of SEQ ID NOs: 1-16 and 49, or
  b) an amino acid sequence consisting of at least or exactly or at most 5 contiguous amino acid residues from any one of SEQ ID NOs: 1-16 and 49, or
  c) an amino acid sequence having a sequence identity of at least 60% with the amino acid sequence of a),
  d) an amino acid sequence having a sequence identity of at least 60% with the amino acid sequence of b), or
  e) an assembly of amino acids derived from any one of SEQ ID NOs: 1-16 and 49, which has essentially the same 3D conformation as in the protein from which said assembly is derived so as to constitute a B-cell epitope, said polypeptide being antigenic in a mammal.

In another aspect, the invention relates to an isolated nucleic acid fragment, which comprises
  i) a nucleotide sequence encoding a polypeptide of the invention, or
  ii) a nucleotide sequence consisting of any one of SEQ ID NOs: 17-48, 50, and 51.

iii) a nucleotide sequence consisting of at least or exactly or at most 10 consecutive nucleotides in any one of SEQ ID NOs: 17-48, 50, and 51,
iv) a nucleotide sequence having a sequence identity of at least 60% with the nucleotide sequence in i) or ii),
v) a nucleotide sequence having a sequence identity of at least 60% with the nucleotide sequence in iii),
vi) a nucleotide sequence complementary to the nucleotide sequence in i)-v), or vii) a nucleotide sequence which hybridizes under stringent conditions with the nucleotide sequence in i)-vi).

In a third aspect, the invention relates to a vector comprising the nucleic acid of the invention, such as a cloning vector or an expression vector.

In fourth aspect, the invention relates to a cell which is transformed so as to carry the vector of the invention.

In a fifth aspect, the invention relates to a pharmaceutical composition comprising a polypeptide of the invention, a nucleic acid fragment of the invention, a vector of the invention, or a transformed cell of the invention, and a pharmaceutically acceptable carrier, vehicle or diluent.

In a sixth aspect, the invention relates to a method for inducing immunity in an animal by administering at least once an immunogenically effective amount of a polypeptide of the invention, a nucleic acid fragment of the invention, a vector of the invention, a transformed cell of the invention, or a pharmaceutical composition of the fifth aspect of the invention so as to induce adaptive immunity against $S.$ $aureus$ in the animal.

In a seventh and eighth aspect, the invention relates to 1) a polyclonal antibody in which the antibodies specifically bind to at least one polypeptide of the invention, and which is essentially free from antibodies binding specifically to other $S.$ $aureus$ polypeptides, and to 2) an isolated monoclonal antibody or antibody analogue which binds specifically to a polypeptide of the invention. In a related ninth aspect, the invention relates to a pharmaceutical composition comprising such a polyclonal or monoclonal antibody and a pharmaceutically acceptable carrier, vehicle or diluent.

In a $10^{th}$ aspect, the invention relates to a method for prophylaxis, treatment or amelioration of infection with $S.$ $aureus$, comprising administering a therapeutically effective amount of an antibody of the $7^{th}$ or $8^{th}$ aspect of the invention or a pharmaceutical composition of the eighth aspect to an individual in need thereof.

In an $11^{th}$ aspect, the invention relates to a method for determining, quantitatively or qualitatively, the presence of $S.$ $aureus$, in particular the presence of multi-resistant $S.$ $aureus$, in a sample, the method comprising contacting the sample with an antibody of aspects 8 or 9 of the invention and detecting the presence of antibody bound to material in the sample.

In an $12^{th}$ aspect of the invention is provided a method for determining, quantitatively or qualitatively, the presence of antibodies specific for $S.$ $aureus$, in particular the presence of antibodies specific for multi-resistant $S.$ $aureus$, in a sample, the method comprising contacting the sample with a polypeptide of the invention and detecting the presence of antibody that specifically bind said polypeptide.

In a $13^{th}$ aspect, the invention relates to a method for determining, quantitatively or qualitatively, the presence of a nucleic acid characteristic of $S.$ $aureus$, in particular the presence of a nucleic acid characteristic of multi-resistant $S.$ $aureus$, in a sample, the method comprising contacting the sample with a nucleic acid fragment of the invention and detecting the presence of nucleic acid in the sample that hybridizes to said nucleic acid fragment.

In a $14^{th}$ aspect, the invention relates to a method for the preparation of the polypeptide of the invention, comprising culturing a transformed cell of the present invention, which is capable of expressing the nucleic acid of the invention, under conditions that facilitate that the transformed cell expresses the nucleic acid fragment of the invention, which encodes a polypeptide of the invention, and subsequently recovering said polypeptide, or preparing said polypeptide by means of solid or liquid phase peptide synthesis.

In a $15^{th}$ aspect, the invention relates to a method for determining whether a substance, such as an antibody, is potentially useful for treating infection with $S.$ $aureus$, the method comprising contacting the polypeptide of the invention with the substance and subsequently establishing whether the substance has at least one of the following characteristics:
1) the ability to bind specifically to said polypeptide,
2) the ability to competed with said polypeptide for specific binding to a ligand/receptor, and
3) the ability to specifically inactivate said polypeptide.

Finally, in a $16^{th}$ aspect, the invention relates to a method for determining whether a substance, such as a nucleic acid, is potentially useful for treating infection with $S.$ $aureus$, the method comprising contacting the substance with the nucleic acid fragment of claim of the invention and subsequently establishing whether the substance has either the ability to
1) bind specifically to the nucleic acid fragment, or
2) bind specifically to a nucleic acid that hybridizes specifically with the nucleic acid fragment.

LEGENDS TO THE FIGURES

FIG. 1: Survival plots for mice vaccinated with a polypeptide of the invention and a negative control, respectively. Solid line: negative control. Interrupted line: polypeptide of the invention.

Figure 2:
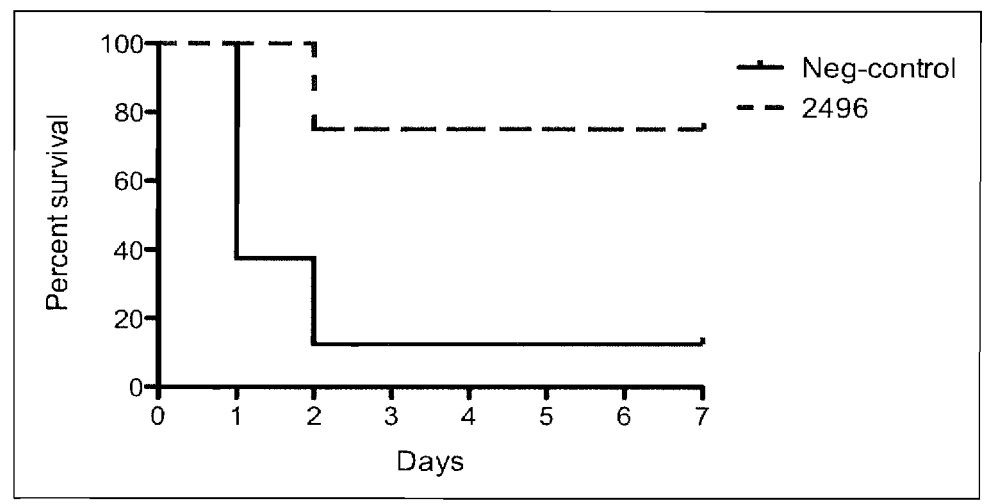

FIG. 2: Survival plots for mice vaccinated with a polypeptide of the invention and a negative control, respectively. Solid line: negative control. Interrupted line: polypeptide of the invention.

Figure 3:
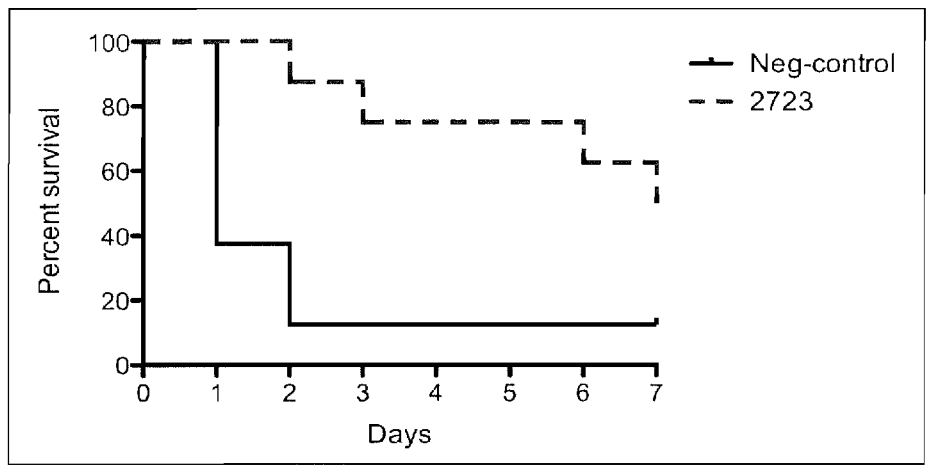

FIG. 3: Survival plots for mice vaccinated with a polypeptide of the invention and a negative control, respectively. Solid line: negative control. Interrupted line: polypeptide of the invention.

Figure 4:
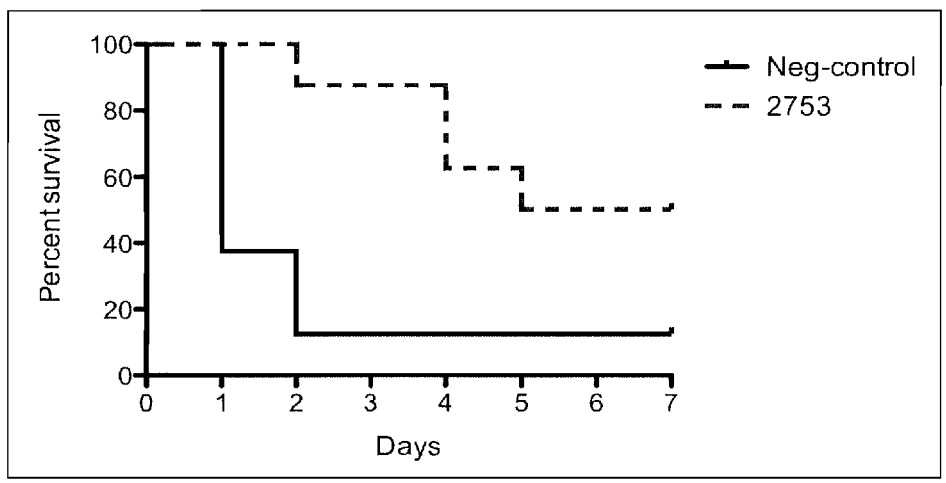

FIG. 4: Survival plots for mice vaccinated with a polypeptide of the invention and a negative control, respectively. Solid line: negative control. Interrupted line: polypeptide of the invention.

Figure 5:
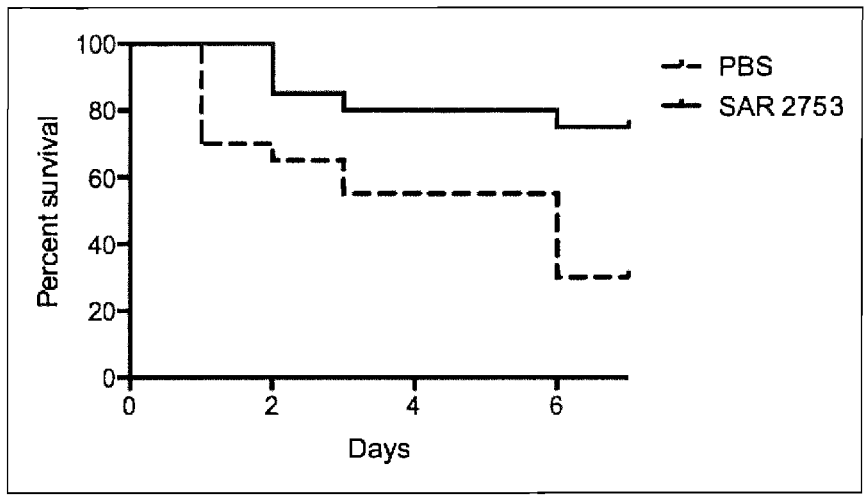

FIG. 5: Survival plots for mice vaccinated with a polypeptide of the invention and a negative control, respectively. Interrupted line: negative control. Solid line: polypeptide of the invention.

Figure 6:
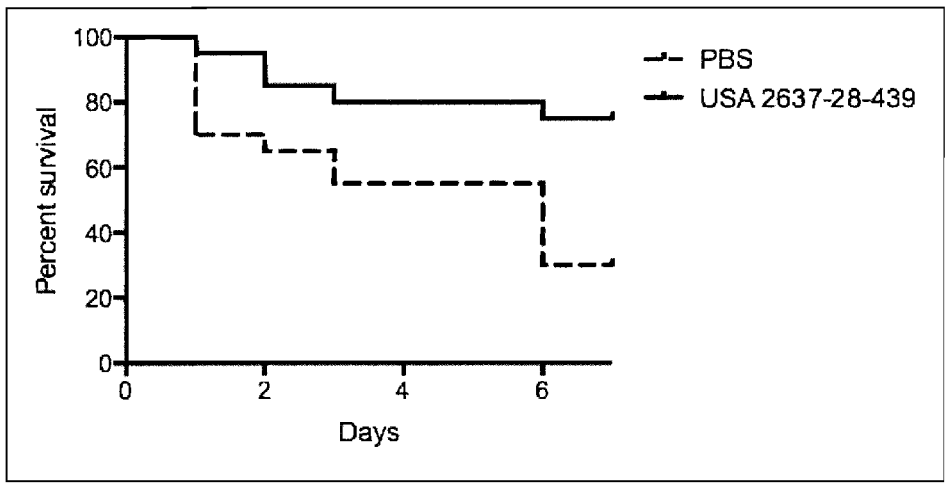

FIG. 6: Survival plots for mice vaccinated with a polypeptide of the invention and a negative control, respectively. Interrupted line: negative control. Solid line: polypeptide of the invention.

Figure 7:
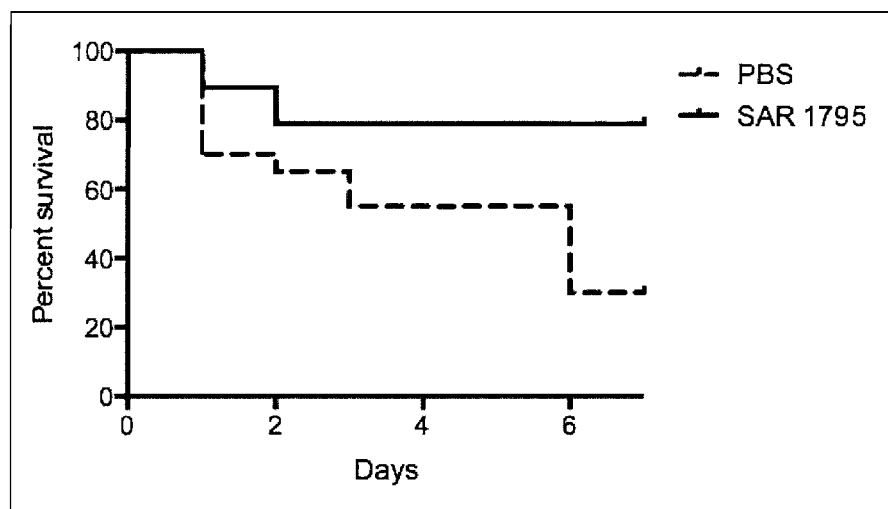

FIG. 7: Survival plots for mice vaccinated with a polypeptide of the invention and a negative control, respectively. Interrupted line: negative control. Solid line: polypeptide of the invention.

DETAILED DISCLOSURE OF THE INVENTION

Definitions

The term "polypeptide" is in the present context intended to mean both short peptides of from 2 to 10 amino acid residues, oligopeptides of from 11 to 100 amino acid residues, and polypeptides of more than 100 amino acid residues. Further-more, the term is also intended to include proteins, i.e. functional biomolecules comprising at least one polypeptide; when comprising at least two polypeptides, these may form complexes, be covalently linked, or may be non-covalently linked. The polypeptide (s) in a protein can be glycosylated and/or lipidated and/or comprise prosthetic groups.

The term "subsequence" means any consecutive stretch of at least 3 amino acids or, when relevant, of at least 3 nucleotides, derived directly from a naturally occurring amino acid sequence or nucleic acid sequence, respectively.

The term "amino acid sequence" s the order in which amino acid residues, connected by peptide bonds, lie in the chain in peptides and proteins.

The term "adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

"Sequence identity" is in the context of the present invention determined by comparing 2 optimally aligned sequences of equal length (e.g. DNA, RNA or amino acid) according to the following formula: $(N_{ref}-N_{dif}) \cdot 100/N_{ref}$, wherein $N_{ref}$ is the number of residues in one of the 2 sequences and $N_{dif}$ is the number of residues which are non-identical in the two sequences when they are aligned over their entire lengths and in the same direction. So, two sequences 5'-ATTCGGAACC-3' and 5'-ATACGGGACC-3' will provide the sequence identity 80% ($N_{ref}=10$ and $N_{dif}=2$).

An "assembly of amino acids" means two or more amino acids bound together by physical or chemical means.

The "3D conformation" is the 3 dimensional structure of a biomolecule such as a protein. In monomeric polypeptides/proteins, the 3D conformation is also termed "the tertiary structure" and denotes the relative locations in 3 dimensional space of the amino acid residues forming the polypeptide.

"An immunogenic carrier" is a molecule or moiety to which an immunogen or a hapten can be coupled in order to enhance or enable the elicitation of an immune response against the immunogen/hapten. Immunogenic carriers are in classical cases relatively large molecules (such as tetanus toxoid, KLH, diphtheria toxoid etc.) which can be fused or conjugated to an immunogen/hapten, which is not sufficiently immunogenic in its own right—typically, the immunogenic carrier is capable of eliciting a strong T-helper lymphocyte response against the combined substance constituted by the immunogen and the immunogenic carrier, and this in turn provides for improved responses against the immungon by B-lymphocytes and cytotoxic lymphocytes. More recently, the large carrier molecules have to a certain extent been substituted by so-called promiscuous T-helper epitopes, i.e. shorter peptides that are recognized by a large fraction of HLA haplotypes in a population, and which elicit T-helper lymphocyte responses.

A "T-helper lymphocyte response" is an immune response elicited on the basis of a peptide, which is able to bind to an MHC class II molecule (e.g. an HLA class II molecule) in an antigen-presenting cell and which stimulates T-helper lymphocytes in an animal species as a consequence of T-cell receptor recognition of the complex between the peptide and the MHC Class II molecule prese.

An "immunogen" is a substance of matter which is capable of inducing an adaptive immune response in a host, whose immune system is confronted with the immunogen. As such, immunogens are a subset of the larger genus "antigens", which are substances that can be recognized specifically by the immune system (e.g. when bound by antibodies or, alternatively, when fragments of the are antigens bound to MHC molecules are being recognized by T-cell receptors) but which are not necessarily capable of inducing immunity—an antigen is, however, always capable of eliciting immunity, meaning that a host that has an established memory immunity against the antigen will mount a specific immune response against the antigen.

A "hapten" is a small molecule, which can neither induce or elicit an immune response, but if conjugated to an immunogenic carrier, antibodies or TCRs that recognize the hapten can be induced upon confrontation of the immune system with the hapten carrier conjugate.

An "adaptive immune response" is an immune response in response to confrontation with an antigen or immunogen, where the immune response is specific for antigenc determinants of the antigen/immunogen—examples of adaptive immune responses are induction of antigen specific antibody production or antigen specific induction/activation of T helper lymphocytes or cytotoxic lymphocytes.

A "protective, adaptive immune response" is an antigen-specific immune response induced in a subject as a reaction to immunization (artificial or natural) with an antigen, where the immune response is capable of protecting the subject against subsequent challenges with the antigen or a pathology-related agent that includes the antigen. Typically, prophylactic vaccination aims at establishing a protective adaptive immune response against one or several pathogens.

"Stimulation of the immune system" means that a substance or composition of matter exhibits a general, non-specific immunostimulatory effect. A number of adjuvants and putative adjuvants (such as certain cytokines) share the ability to stimulate the immune system. The result of using an immunostimulating agent is an increased "alertness" of the immune system meaning that simultaneous or subsequent immunization with an immunogen induces a significantly more effective immune response compared to isolated use of the immunogen.

Hybridization under "stringent conditions" is herein defined as hybridization performed under conditions by which a probe will hybridize to its target sequence, to a detectably greater degree than to other sequences. Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Specificity is typically the function of post-hybridization washes, the critical factors being the ionic strength and temperature of the final wash solution. Generally, stringent wash temperature conditions are selected to be about 5° C. to about 2° C. lower than the melting point (Tm) for the specific sequence at a defined ionic strength and pH. The melting point, or denaturation, of DNA occurs over a narrow temperature range and represents the disruption of the double helix into its complementary single strands. The process is described by the temperature of the midpoint of transition, Tm, which is also called the melting temperature. Formulas are available in the art for the determination of melting temperatures.

The term "animal" is in the present context in general intended to denote an animal species (preferably mammalian), such as Homo sapiens, Canis domesticus, etc. and not just one single animal. However, the term also denotes a population of such an animal species, since it is important that the individuals immunized according to the method of the invention substantially all will mount an immune response against the immunogen of the present invention.

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanized antibodies, altered antibodies, univalent antibodies, Fab proteins, and single domain antibodies.

"Specific binding" denotes binding between two substances which goes beyond binding of either substance to randomly chosen substances and also goes beyond simple association between substances that tend to aggregate because they share the same overall hydrophobicity or hydrophilicity. As such, specific binding usually involves a combination of electrostatic and other interactions between two conformationally complementary areas on the two substances, meaning that the substances can "recognize" each other in a complex mixture.

The term "vector" is used to refer to a carrier nucleic acid molecule into which a heterologous nucleic acid sequence can be inserted for introduction into a cell where it can be replicated and expressed. The term further denotes certain biological vehicles useful for the same purpose, e.g. viral vectors and phage—both these infectious agents are capable of introducing a heterelogous nucleic acid sequence.

The term "expression vector" refers to a vector containing a nucleic acid sequence coding for at least part of a gene product capable of being transcribed. In some cases, when the transcription product is an mRNA molecule, this is in trun translated into a protein, polypeptide, or peptide.

SPECIFIC EMBODIMENTS OF THE INVENTION

The Polypeptides of the Invention

In some embodiments the at least 5 contiguous amino acids referred to in option b) in the definition of the first aspect of the invention constitute at least or exactly or at most 6 contiguous amino acid residues, such as at least or exactly or at most 7, at least or exactly or at most 8, at least or exactly or at most 9, at least or exactly or at most 10, at least or exactly or at most 11, at least or exactly or at most 12, at least or exactly or at most 13, at least or exactly or at most 14, at least or exactly or at most 15, at least or exactly or at most 16, at least or exactly or at most 17, at least or exactly or at most 18, at least or exactly or at most 19, at least or exactly or at most 20, at least or exactly or at most 21, at least or exactly or at most 22, at least or exactly or at most 23, at least or exactly or at most 24, at least or exactly or at most 25, at least or exactly or at most 26, at least or exactly or at most 27 at least or exactly or at most 28, at least or exactly or at most 29, at least or exactly or at most 30, at least or exactly or at most 31, at least or exactly or at most 32, at least or exactly or at most 33, at least or exactly or at most 34, at least or exactly or at most 35, at least or exactly or at most 36, at least or exactly or at most 37, at least or exactly or at most 38, at least or exactly or at most 39, at least or exactly or at most 40, at least or exactly or at most 41, at least or exactly or at most 42, at least or exactly or at most 43, at least or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52, at least or exactly or at most 53, at least or exactly or at most 54, at least or exactly or at most 55, at least or exactly or at most 56, at least or exactly or at most 57, at least or exactly or at most 58, at least or exactly or at most 59, at least or exactly or at most 60, at least or exactly or at most 61, at least or exactly or at most 62, at least or exactly or at most 63, at least or exactly or at most 64, at least or exactly or at most 65, at least or exactly or at most 66, at least or exactly or at most 67, at least or exactly or at most 68, at least or exactly or at most 69, at least or exactly or at most 70, at least or exactly or at most 71, at least or exactly or at most 72, at least or exactly or at most 73, at least or exactly or at most 74, at least or exactly or at most 75, at least or exactly or at most 76, at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, at least or exactly or at most 134, at least or exactly or at most 135, at least or exactly or at most 136, at least or exactly or at most 137, at least or exactly or at most 138, and at least or exactly or at most 139 contiguous amino acid residues.

The number of contiguous amino acids can be higher, for all of SEQ ID NOs. 2-16 and 49. Another way to phrase this is that for each of SEQ NOs: 1-16 and 49, the number of the contiguous amino acid residues is at least or exactly or at most N-n, where N is the length of the sequence ID in question and n is any integer between N-5 and 0; that is, the at least 5 contiguous amino acids can be at least any number between 5 and the length of the reference sequence minus one, in increments of one. Consequently:

Insofar as embodiment b relates to SEQ ID NO: 2-16 and 49, the at least 5 contiguous amino acids referred to in option b) in the definition of the first aspect of the invention will preferably consititute at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, at least or exactly or at most 149, at least or exactly or at most 150, at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 161, at least or exactly or at most 162, at least or exactly or at most 163, at least or exactly or at most 164, at least or exactly or at most 165, at least or exactly or at most 166, at least or exactly or at most 167, at least or exactly or at most 168, at least or exactly or at most 169, at least or exactly or at most 170, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, or at least or exactly or at most 192 contiguous amino acid residues.

Insofar as embodiment b relates to SEQ ID NO: 3-16 and 49, the at least 5 contiguous amino acids referred to in option b) in the definition of the first aspect of the invention will preferably consititute at least or exactly or at most 193, at least or exactly or at most 194, at least or exactly or at most 195, at least or exactly or at most 196, at least or exactly or at most 197, at least or exactly or at most 198, at least or exactly or at most 199, at least or exactly or at most 200, at least or exactly or at most 201, at least or exactly or at most 202, at least or exactly or at most 203, at least or exactly or at most 204, at least or exactly or at most 205, at least or exactly or at most 206, at least or exactly or at most 207, or at least or exactly or at most 208 contiguous amino acid residues.

Insofar as embodiment b relates to SEQ NO: 4-16 and 49, the at least 5 contiguous amino acids referred to in option b) in the definition of the first aspect of the invention will preferably consititute at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least or exactly or at most 222, at least or exactly or at most 223, at least or exactly or at most 224, at least or exactly or at most 225, at least or exactly or at most 226, at least or exactly or at most 227, at least or exactly or at most 228, at least or exactly or at most 229, at least or exactly or at most 230, at least or exactly or at most 231, at least or exactly or at most 232, at least or exactly or at most 233, at least or exactly or at most 234, at least or exactly or at most 235, at least or exactly or at most 236, at least or exactly or at most 237, at least or exactly or at most 238, at least or exactly or at most 239, at least or exactly or at most 240, or at least or exactly or at most 241 contiguous amino acid residues.

Insofar as embodiment b relates to SEQ ID NO: 5-16 and 49, the at least 5 contiguous amino acids referred to in option b) in the definition of the first aspect of the invention will preferably consititute at least or exactly or at most 242, at least or exactly or at most 243, at least or exactly or at most 244, at least or exactly or at most 245, at least or exactly or at most 246, at least or exactly or at most 247, at least or exactly or at most 248, at least or exactly or at most 249, at least or exactly or at most 250, at least or exactly or at most 251, at least or exactly or at most 252, at least or exactly or at most 253, at least or exactly or at most 254, at least or exactly or at most 255, at least or exactly or at most 256, at least or exactly or at most 257, at least or exactly or at most 258, at least or exactly or at most 259, at least or exactly or at most 260, at least or exactly or at most 261, at least or exactly or at most 262, at least or exactly or at most 263, at least or exactly or at most 264, at least or exactly or at most 265, at least or exactly or at most 266, at least or exactly or at most 267, at least or exactly or at most 268, at least or exactly or at most 269, at least or exactly or at most 270, at least or exactly or at most 271, at least or exactly or at most 272, at least or exactly or at most 273, at least or exactly or at most 274, at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, at least or exactly or at most 285, at least or exactly or at most 286, at least or exactly or at most 287, at least or exactly or at most 288, at least or exactly or at most 289, at least or exactly or at most 290, at least or exactly or at most 291, at least or exactly or at most 292, at least or exactly or at most 293, at least or exactly or at most 294, at least or exactly or at most 295, at least or exactly or at most 296, at least or exactly or at most 297, at least or exactly or at most 298, at least or exactly or at most 299, at least or exactly or at most 300, at least or exactly or at most 301, at least or exactly or at most 302, at least or exactly or at most 303, at least or exactly or at most 304, at least or exactly or at most 305, at least or exactly or at most 306, at least or exactly or at most 307, at least or exactly or at most 308, at least or exactly or at most 309, at least or exactly or at most 310, at least or exactly or at most 311, at least or exactly or at most 312, at least or exactly or at most 313, at least or exactly or at most 314, at least or exactly or at most 315, at least or exactly or at most 316, at least or exactly or at most 317, at least or exactly or at most 318, at least or exactly or at most 319, at least or exactly or at most 320, at least or exactly or at most 321, at least or exactly or at most 322, at least or exactly or at most 323, at least or exactly or at most 324, at least or exactly or at most 325, or at least or exactly or at most 326 contiguous amino acid residues.

Insofar as embodiment b relates to SEQ ID NO: 6-16 and 49, the at least 5 contiguous amino acids referred to in option b) in the definition of the first aspect of the invention will preferably consititute at least or exactly or at most 327, at least or exactly or at most 328, at least or exactly or at most 329, at least or exactly or at most 330, at least or exactly or at most 331, at least or exactly or at most 332, at least or exactly or at most 333, at least or exactly or at most 334, at least or exactly or at most 335, at least or exactly or at most 336, at least or exactly or at most 337, at least or exactly or at most 338, at least or exactly or at most 339, at least or exactly or at most 340, at least or exactly or at most 341, at least or exactly or at most 342, at least or exactly or at most 343, at least or exactly or at most 344, at least or exactly or at most 345, at least or exactly or at most 346, at least or exactly or at most 347, at least or exactly or at most 348, at least or exactly or at most 349, at least or exactly or at most 350, at least or exactly or at most 351, at least or exactly or at most 352, at least or exactly or at most 353, at least or exactly or at most 354, at least or exactly or at most 355, or at least or exactly or at most 356 contiguous amino acid residues.

Insofar as embodiment b relates to SEQ ID NO: 7-16 and 49, the at least 5 contiguous amino acids referred to in option b) in the definition of the first aspect of the invention will preferably consititute at least or exactly or at most 357, at least or exactly or at most 358, at least or exactly or at most 359, at least or exactly or at most 360, at least or exactly or at most 361, at least or exactly or at most 362, at least or exactly or at most 363, at least or exactly or at most 364, at least or exactly or at most 365, at least or exactly or at most 366, at least or exactly or at most 367, at least or exactly or at most 368, at least or exactly or at most 369, at least or exactly or at most 370, at least or exactly or at most 371, at least or exactly or at most 372, at least or exactly or at most 373, at least or exactly or at most 374, at least or exactly or at most 375, at least or exactly or at most 376, at least or exactly or at most 377, at least or exactly or at most 378, at least or exactly or at most 379, at least or exactly or at most 380, at least or exactly or at most 381, at least or exactly or at most 382, at least or exactly or at most 383, at least or exactly or at most 384, at least or exactly or at most 385, at least or exactly or at most 386, at least or exactly or at most 387, at least or exactly or at most 388, at least or exactly or at most 389, at least or exactly or at most 390, at least or exactly or at most 391, at least or exactly or at most 392, at least or exactly or at most 393, at least or exactly or at most 394, at least or exactly or at most 395, at least or exactly or at most 396, at least or exactly or at most 397, or at least or exactly or at most 398 contiguous amino acid residues.

Insofar as embodiment b relates to SEQ ID NO: 8-18 and 49, the at least 5 contiguous amino acids referred to in option b) in the definition of the first aspect of the invention will preferably consititute at least or exactly or at most 399, at least or exactly or at most 400, at least or exactly or at most 401, at least or exactly or at most 402, at least or exactly or at most 403, at least or exactly or at most 404, at least or exactly or at most 405, at least or exactly or at most 406, or at least or exactly or at most 407 contiguous amino acid residues.

Insofar as embodiment b relates to SEQ ID NO: 8-18, the at least 5 contiguous amino acids referred to in option b) in the definition of the first aspect of the invention will preferably consititute at least or exactly or at most 408, at least or exactly or at most 409, at least or exactly or at most 410, at least or exactly or at most 411, at least or exactly or at most 412, at least or exactly or at most 413, at least or exactly or at most 414, at least or exactly or at most 415, at least or exactly or at most 416, at least or exactly or at most 417, at least or exactly or at most 418, at least or exactly or at most 419, at least or exactly or at most 420, at least or exactly or at most 421, at least or exactly or at most 422, at least or exactly or at most 423, at least or exactly or at most 424, at least or exactly or at most 425, at least or exactly or at most 426, at least or exactly or at most 427, at least or exactly or at most 428, at least or exactly or at most 429, at least or exactly or at most 430, at least or exactly or at most 431, at least or exactly or at most 432, at least or exactly or at most 433, at least or exactly or at most 434, at least or exactly or at most 435, at least or exactly or at most 436, at least or exactly or at most 437, at least or exactly or at most 438, at least or exactly or at most 439, at least or exactly or at most 440, at least or exactly or at most 441, at least or exactly or at most 442, at least or exactly or at most 443, at least or exactly or at most 444, at least or exactly or at most 445, at least or exactly or at most 446, at least or exactly or at most 447, at least or exactly or at most 448, at least or exactly or at most 449, at least or exactly or at most 450, at least or exactly or at most 451, at least or exactly or at most 452, at least or exactly or at most 453, at least or exactly or at most 454, at least or exactly or at most 455, at least or exactly or at most 456, at least or exactly or at most 457, at least or exactly or at most 458, at least or exactly or at most 459, at least or exactly or at most 460, at least or exactly or at most 461, at least or exactly or at most 462, at least or exactly or at most 463, at least or exactly or at most 464, at least or exactly or at most 465, at least or exactly or at most 466, at least or exactly or at most 467, at least or exactly or at most 468, at least or exactly or at most 469, at least or exactly or at most 470, at least or exactly or at most 471, at least or exactly or at most 472, at least or exactly or at most 473, at least or exactly or at most 474, at least or exactly or at most 475, at least or exactly or at most 476, at least or exactly or at most 477, at least or exactly or at most 478, at least or exactly or at most 479, at least or exactly or at most 480, at least or exactly or at most 481, at least or exactly or at most 482, at least or exactly or at most 483, at least or exactly or at most 484, at least or exactly or at most 485, at least or exactly or at most 486, at least or exactly or at most 487, at least or exactly or at most 488, at least or exactly or at most 489, at least or exactly or at most 490, at least or exactly or at most 491, at least or exactly or at most 492, at least or exactly or at most 493, or at least or exactly or at most 494 contiguous amino acid residues.

Insofar as embodiment b relates to SEQ ID NO: 9-18, the at least 5 contiguous amino acids referred to in option b) in the definition of the first aspect of the invention will preferably consititute at least or exactly or at most 495, at least or exactly or at most 496, at least or exactly or at most 497, at least or exactly or at most 498, at least or exactly or at most 499, at least or exactly or at most 500, at least or exactly or at most 501, at least or exactly or at most 502, at least or exactly or at most 503, at least or exactly or at most 504, at least or exactly or at most 505, at least or exactly or at most 506 contiguous amino acid residues.

Insofar as embodiment b relates to SEQ ID NO: 10-18, the at least 5 contiguous amino acids referred to in option b) in the definition of the first aspect of the invention will preferably consititute at least or exactly or at most 507 contiguous amino acid residues or at least or exactly or at most 508 contiguous amino acid residues.

Insofar as embodiment b relates to SEQ ID NO: 11-18, the at least 5 contiguous amino acids referred to in option b) in the definition of the first aspect of the invention will preferably consititute at least or exactly or at most 509, at least or exactly or at most 510, at least or exactly or at most 511, at least or exactly or at most 512, at least or exactly or at most 513, or at least or exactly or at most 514 contiguous amino acid residues.

Insofar as embodiment b relates to SEQ ID NO: 12-18, the at least 5 contiguous amino acids referred to in option b) in the definition of the first aspect of the invention will preferably consititute at least or exactly or at most 515, at least or exactly or at most 516, at least or exactly or at most 517, at least or exactly or at most 518, at least or exactly or at most 519, at least or exactly or at most 520, at least or exactly or at most 521, at least or exactly or at most 522, at least or exactly or at most 523, at least or exactly or at most 524, at least or exactly or at most 525, at least or exactly or at most 526, at least or exactly or at most 527, at least or exactly or at most 528, at least or exactly or at most 529, at least or exactly or at most 530, at least or exactly or at most 531, at least or exactly or at most 532, at least or exactly or at most 533, at least or exactly or at most 534, at least or exactly or at most 535, at least or exactly or at most 536, at least or exactly or at most 537, at least or exactly or at most 538, at least or exactly or at most 539, at least or exactly or at most 540, at least or exactly or at most 541, at least or exactly or at most 542, at least or exactly or at most 543, at least or exactly or at most 544, at least or exactly or at most 545, at least or exactly or at most 546, at least or exactly or at most 547, at least or exactly or at most 548, at least or exactly or at most 549, at least or exactly or at most 550, at least or exactly or at most 551, at least or exactly or at most 552, at least or exactly or at most 553, at least or exactly or at most 554, at least or exactly or at most 555, at least or exactly or at most 556, at least or exactly or at most 557, at least or exactly or at most 558, at least or exactly or at most 559, at least or exactly or at most 560, at least or exactly or at most 561, at least or exactly or at most 562, or at least or exactly or at most 563 contiguous amino acid residues.

Insofar as embodiment b relates to SEQ ID NO: 13-18, the at least 5 contiguous amino acids referred to in option b) in the definition of the first aspect of the invention will preferably consititute at least or exactly or at most 564, at least or exactly or at most 565, at least or exactly or at most 566, at least or exactly or at most 567, at least or exactly or at most 568, at least or exactly or at most 569, at least or exactly or at most 570, at least or exactly or at most 571, at least or exactly or at most 572, at least or exactly or at most 573, at least or exactly or at most 574, at least or exactly or at most 575, at least or exactly or at most 576, at least or exactly or at most 577, at least or exactly or at most 578, at least or exactly or at most 579, at least or exactly or at most 580, at least or exactly or at most 581, at least or exactly or at most 582, at least or exactly or at most 583, at least or exactly or at most 584, at least or exactly or at most 585, at least or exactly or at most 586, at least or exactly or at most 587, at least or exactly or at most 588, at least or exactly or at most 589, at least or exactly or at most 590, at least or exactly or at most 591, at least or exactly or at most 592, at least or exactly or at most 593, at least or exactly or at most 594, at least or exactly or at most 595, at least or exactly or at most 596, at least or exactly or at most 597, at least or exactly or at most 598, at least or exactly or at most 599, at least or exactly or at most 600, at least or exactly or at most 601, at least or exactly or at most 602, at least or exactly or at most 603, at least or exactly or at most 604, at least or exactly or at most 605, at least or exactly or at most 606, at least or exactly or at most 607, at least or exactly or at most 608, at least or exactly or at most 609, at least or exactly or at most 610, at least or exactly or at most 611, at least or exactly or at most 612, at least or exactly or at most 613, at least or exactly or at most 614, at least or exactly or at most 615, at least or exactly or at most 616, at least or exactly or at most 617, or at least or exactly or at most 618 contiguous amino acid residues.

Insofar as embodiment b relates to SEQ ID NO: 14-18, the at least 5 contiguous amino acids referred to in option b) in the definition of the first aspect of the invention will preferably consititute at least or exactly or at most 619, at least or exactly or at most 620, at least or exactly or at most 621, at least or exactly or at most 622, at least or exactly or at most 623, at least or exactly or at most 624, at least or exactly or at most 625, at least or exactly or at most 626, at least or exactly or at most 627, at least or exactly or at most 628, at least or exactly or at most 629, at least or exactly or at most 630, at least or exactly or at most 631, at least or exactly or at most 632, at least or exactly or at most 633, at least or exactly or at most 634, at least or exactly or at most 635, at least or exactly or at most 636, at least or exactly or at most 637, at least or exactly or at most 638, at least or exactly or at most 639, at least or exactly or at most 640, at least or exactly or at most 641, at least or exactly or at most 642, at least or exactly or at most 643, at least or exactly or at most 644, at least or exactly or at most 645, at least or exactly or at most 646, at least or exactly or at most 647, at least or exactly or at most 648, at least or exactly or at most 649, at least or exactly or at most 650, at least or exactly or at most 651, at least or exactly or at most 652, at least or exactly or at most 653, at least or exactly or at most 654, at least or exactly or at most 655, at least or exactly or at most 656, at least or exactly or at most 657, at least or exactly or at most 658, at least or exactly or at most 659, at least or exactly or at most 660, at least or exactly or at most 661, at least or exactly or at most 662, at least or exactly or at most 663, at least or exactly or at most 664, at least or exactly or at most 665, at least or exactly or at most 666, at least or exactly or at most 667, at least or exactly or at most 668, at least or exactly or at most 669, at least or exactly or at most 670, at least or exactly or at most 671, at least or exactly or at most 672, at least or exactly or at most 673, at least or exactly or at most 674, at least or exactly or at most 675, at least or exactly or at most 676, at least or exactly or at most 677, at least or exactly or at most 678, at least or exactly or at most 679, or at least or exactly or at most 680 contiguous amino acid residues.

Insofar as embodiment b relates to SEQ ID NO: 15-18, the at least 5 contiguous amino acids referred to in option b) in the definition of the first aspect of the invention will preferably consititute at least or exactly or at most 681, at least or exactly or at most 682, at least or exactly or at most 683, at least or exactly or at most 684, at least or exactly or at most 685, at least or exactly or at most 686, at least or exactly or at most 687, at least or exactly or at most 688, at least or exactly or at most 689, at least or exactly or at most 690, at least or exactly or at most 691, at least or exactly or at most 692, at least or exactly or at most 693, at least or exactly or at most 694, at least or exactly or at most 695, at least or exactly or at most 696, at least or exactly or at most 697, at least or exactly or at most 698, at least or exactly or at most 699, at least or exactly or at most 700, at least or exactly or at most 701, at least or exactly or at most 702, at least or exactly or at most 703, at least or exactly or at most 704, at least or exactly or at most 705, at least or exactly or at most 706, at least or exactly or at most 707, at least or exactly or at most 708, at least or exactly or at most 709, at least or exactly or at most 710, at least or exactly or at most 711, at least or exactly or at most 712, at least or exactly or at most 713, at least or exactly or at most 714, at least or exactly or at most 715, at least or exactly or at most 716, at least or exactly or at most 717, at least or exactly or at most 718, at least or exactly or at most 719, at least or exactly or at most 720, at least or exactly or at most 721, at least or exactly or at most 722, at least or exactly or at most 723, at least or exactly or at most 724, at least or exactly or at most 725, at least or exactly or at most 726, at least or exactly or at most 727, at least or exactly or at most 728, at least or exactly or at most 729, at least or exactly or at most 730, at least or exactly or at most 731, at least or exactly or at most 732, at least or exactly or at most 733, at least or exactly or at most 734, at least or exactly or at most 735, at least or exactly or at most 736, at least or exactly or at most 737, at least or exactly or at most 738, at least or exactly or at most 739, at least or exactly or at most 740, at least or exactly or at most 741, at least or exactly or at most 742, at least or exactly or at most 743, at least or exactly or at most 744, at least or exactly or at most 745, at least or exactly or at most 746, at least or exactly or at most 747, at least or exactly or at most 748, at least or exactly or at most 749, at least or exactly or at most 750, at least or exactly or at most 751, at least or exactly or at most 752, at least or exactly or at most 753, at least or exactly or at most 754, at least or exactly or at most 755, at least or exactly or at most 756, at least or exactly or at most 757, at least or exactly or at most 758, at least or exactly or at most 759, at least or exactly or at most 760, at least or exactly or at most 761, at least or exactly or at most 762, at least or exactly or at most 763, at least or exactly or at most 764, at least or exactly or at most 765, at least or exactly or at most 766, at least or exactly or at most 767, at least or exactly or at most 768, at least or exactly or at most 769, at least or exactly or at most 770, at least or exactly or at most 771, at least or exactly or at most 772, at least or exactly or at most 773, at least or exactly or at most 774, at least or exactly or at most 775, at least or exactly or at most 776, at least or exactly or at most 777, at least or exactly or at most 778, at least or exactly or at most 779, at least or exactly or at most 780, at least or exactly or at most 781, at least or exactly or at most 782, at least or exactly or at most 783, at least or exactly or at most 784, at least or exactly or at most 785, at least or exactly or at most 786, at least or exactly or at most 787, at least or exactly or at most 788, at least or exactly or at most 789, at least or exactly or at most 790, at least or exactly or at most 791, at least or exactly or at most 792, at least or exactly or at most 793, at least or exactly or at most 794, at least or exactly or at most 795, at least or exactly or at most 796, at least or exactly or at most 797, at least or exactly or at most 798, at least or exactly or at most 799, at least or exactly or at most 800, at least or exactly or at most 801, at least or exactly or at most 802, at least or exactly or at most 803, at least or exactly or at most 804, or at least or exactly or at most 805 contiguous amino acid residues.

Insofar as embodiment b relates to SEQ ID NO: 16, the at least 5 contiguous amino acids referred to in option b) in the definition of the first aspect of the invention will preferably consititute at least or exactly or at most 806 contiguous amino acid residues or at least or exactly or at most 807 contiguous amino acid residues.

In some embodiments, the polypeptide of the invention also has a sequence identity with the amino acid sequence of a) defined above of at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%. Similarly, the polypeptide of the invention in some embodiments also has a sequence identity with the amino acid sequence of b) defined above of at least 60%, such as at least 65%, at least 70%, at least 75%, at least 80%, at least 85%, at least 90%, at least 91%, at least 92%, at least 93%, at least 94%, at least 95%, at least 96%, at least 97%, at least 98%, and at least 99%.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 42, 43, 44, 45, 46, 47, 48, 49, 50, 51, 52, 53, 54, 55, 56, 57, 58, 59, 60, 61, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 110, 111, 112, 113, 114, 115, 116, 117, 118, 119, 120, 121, 122, 123, 124, 125, 126, 127, 128, 129, 130, 131, 132, 133, 134, 135, 136 in any one of SEQ ID NOs: 1-16, if the length of the at least or exactly or at most 5 amino acid residues so permit—if the length of the at least or exactly or at most 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 137, 138, 139, 140, 141, 142, 143, 144, 145, 146, 147, 148, 149, 150, 151, 152, 153, 154, 155, 156, 157, 158, 159, 160, 171, 172, 173, 174, 175, 176, 177, 178, 179, 180, 181, 182, 183, 184, 185, 186, 187, 188 and 189 in any on of SEQ ID NOs: 2-16, if the length of the at least or exactly or at most 5 amino acid residues so permit—if the length of the at least or exactly or at most 5 amino acids is higher than 5, the N-terminal First residue will not be higher numbered than N-L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 190, 191, 192, 193, 194, 195, 196, 197, 198, 199, 200, 201, 202, 203, 204 and 205 in any one of SEQ ID NOs: 3-16, if the length of the at least or exactly or at most 5 amino acid residues so permit—if the length of the at least or exactly or at most 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 and 238 in any one of SEQ ID NOs: 4-16, if the length of the at least or exactly or at most 5 amino acid residues so permit—if the length of the at least or exactly or at most 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 239, 240, 241, 242, 243, 244, 245, 246, 247, 248, 249, 250, 251, 252, 253, 254, 255, 256, 257, 258, 259, 260, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 310, 311, 312, 313, 314, 315, 316, 317, 318, 319, 320, 321, 322 and 323 in any one of SEQ ID NOs: 5-16, if the length of the at least or exactly or at most 5 amino acid residues so permit—if the length of the at least or exactly or at most 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 324, 325, 326, 327, 328, 329, 330, 331, 332, 333, 334, 335, 336, 337, 338, 339, 340, 341, 342, 343, 344, 345, 346, 347, 348, 349, 350, 351, 352 and 353 in any one of SEQ ID NOs: 6-16, if the length of the at least or exactly or at most 5 amino acid residues so permit—if the length of the at least or exactly or at most 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394 and 395 in any one of SEQ ID NOs: 7-16, if the length of the at least or exactly or at most 5 amino acid residues so permit—if the length of the at least or exactly or at most 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490 and 491 in any one of SEQ ID NOs: 8-16, if the length of the at least or exactly or at most 5 amino acid residues so permit—if the length of the at least or exactly or at most 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 492, 493, 494, 495, 496, 497, 498, 499, 500, 501, 502 and 503 in any one of SEQ ID NOs: 9-16, if the length of the at least or exactly or at most 5 amino acid residues so permit—if the length of the at least or exactly or at most 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 504 and 505 in any one of SEQ ID NOs: 10-16, if the length of the at least or exactly or at most 5 amino acid residues so permit—if the length of the at least or exactly or at most 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 506, 507, 508, 509, 510 and 511 in any one of SEQ ID NOs: 11-16, if the length of the at least or exactly or at most 5 amino acid residues so permit—if the length of the at least or exactly or at most 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560 and 561 in any one of SEQ ID NOs: 12-16, if the length of the at least or exactly or at most 5 amino acid residues so permit—if the length of the at least or exactly or at most 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614 and 615 in any one of SEQ ID NOs: 13-16, if the length of the at least or exactly or at most 5 amino acid residues so permit—if the length of the at least or exactly or at most 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676 and 677 in SEQ ID NOs: 14-16, if the length of the at least or exactly or at most 5 amino acid residues so permit—if the length of the at least or exactly or at most 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801 and 802 in SEQ ID NOs: 15-16, if the length of the at least or exactly or at most 5 amino acid residues so permit—if the length of the at least or exactly or at most 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 803 and 804 in SEQ ID NO: 16, if the length of the at least or exactly or at most 5 amino acid residues so permit—if the length of the at least or exactly or at most 5 amino acids is higher than 5, the N-terminal first residue will not be higher numbered than N-L+1, where N is the number of amino acid residues of the reference sequence and L is the number of amino acids defined for option b.

The polypeptide of the invention is in certain embodiments also fused or conjugated to an immunogenic carrier molecule; or, phrased otherwise, the polypeptide of the invention also includes such an immunogenic carrier molecule in addition to the material derived from SEQ ID NOs. 1-16. The immunogenic carrier molecule is a typically polypeptide that induces T-helper lymphocyte responses in a majority of humans, such as immunogenic carrier proteins selected from the group consisting of keyhole limpet hemocyanino or a fragment thereof, tetanus toxoid or a fragment thereof, dipththeria toxoid or a fragment thereof. Other suitable carrier molecules are discussed infra. One further fusion partner, which is preferably incorporated is a "His tag", i.e. a stretch of amino acids, which is rich or only consists of histidinyl residues so as to facilitate protein purification.

In preferred embodiments, the polypeptide of the invention detailed above is capable of inducing an adaptive immune response against the polypeptide in a mammal, in particular in a human being. Preferably, the adaptive immune response is a protective adaptive immune response against infection with *S. aureus*, in particular multi-resistant *S. aureus*. The polypeptide may in these cases induce a humeral and/or a cellular immune response.

A particularly preferred polypeptide of the invention is derived from SEQ ID NO: 13 and is otherwise as defined above.

Epitopes

SEQ ID NOs: 1-16 include antigenic determinants (epitopes) that are as such recognized by antibodies and/or when bound to MHC molecules by T-cell receptors. For the purposes of the present invention, B-cell epitopes (i.e. antibody binding epitopes) are of particular relevance.

It is relatively uncomplicated to identify linear B-cell epitopes—one very simple approach entails that antibodies raised agains *S. aureus* or *S. aureus* derived proteins disclosed herein are tested for binding to overlapping oligomeric peptides derived from any one of SEQ ID NO: 1-16. Thereby, the regions of the *S. aureus* polypeptide which are responsible for or contribute to binding to the antibodies can be identified.

Alternatively, or additionally, one can produce mutated versions of the polypeptides of the invention, e.g. version where each single non-alanine residue in SEQ ID NOs.: 1-16 are point mutated to alanine—this method also assists in identifying complex assembled B-cell epitopes; this is the case when binding of the same antibody is modified by exchanging amino acids in different areas of the full-length polypeptide.

Also, in silico methods for B-cell epitope prediction can be employed: useful state-of-the-art systems for β-turn prediction is provided in Petersen B et al. (November 2010), Plos One 5(11): e15079; prediction of linear B-cell epitopes, cf: Larsen J E P et al. (April 2006), Immunome Research, 2:2; prediction of solvent exposed amino acids: Petersen B et al (July 2009), BMC Structural Biology, 9:51.

The Nucleic Acid Fragments of the Invention

The nucleic acid fragment of the invention referred to above is preferably is a DNA fragment (such as SEQ ID NOs: 17-32 and 50) or an RNA fragment (such as SEQ ID NOs 33-48 and 51).

The nucleic acid fragment of the invention typically consists of at least or exactly or at most 11, such as at least or exactly or at most 12, at least or exactly or at most 13, at least or exactly or at most 14, at least or exactly or at most 15, at least or exactly or at most 16, at least or exactly or at most 17 at least or exactly or at most 18, at least or exactly or at most 19, at least or exactly or at most 20, at least or exactly or at most 21, at least or exactly or at most 22, at least or exactly or at most 23, at least or exactly or at most 24, at least or exactly or at most 25, at least or exactly or at most 26, at least or exactly or at most 27, at least or exactly or at most 28, at least or exactly or at most 29, at least or exactly or at most 30, at least or exactly or at most 31, at least or exactly or at most 32, at least or exactly or at most 33, at least or exactly or at most 34, at least or exactly or at most 35, at least or exactly or at most 36, at least or exactly or at most 37, at least or exactly or at most 38, at least or exactly or at most 39, at least or exactly or at most 40, at least or exactly or at most 41, at least or exactly or at most 42, at least or exactly or at most 43, at least or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52, at least or exactly or at most 53, at least or exactly or at most 54, at least or exactly or at most 55, at least or exactly or at most 56, at least or exactly or at most 57, at least or exactly or at most 58, at least or exactly or at most 59, at least or exactly or at most 60, at least or exactly or at most 61, at least or exactly or at most 62, at least or exactly or at most 63, at least or exactly or at most 64, at least or exactly or at most 65, at least or exactly or at most 66, at least or exactly or at most 67, at least or exactly or at most 68, at least or exactly or at most 69, at least or exactly or at most 70, at least or exactly or at most 71, at least or exactly or at most 72, at least or exactly or at most 73, at least or exactly or at most 74, at least or exactly or at most 75, at least or exactly or at most 76, at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, at least or exactly or at most 134, at least or exactly or at most 135, at least or exactly or at most 136, at least or exactly or at most 137, at least or exactly or at most 138, at least or exactly or at most 139, at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, at least or exactly or at most 149, at least or exactly or at most 150, at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, at least or exactly or at most 198, at least or exactly or at most 199, at least or exactly or at most 200, at least or exactly or at most 201, at least or exactly or at most 202, at least or exactly or at most 203, at least or exactly or at most 204, at least or exactly or at most 205, at least or exactly or at most 206, at least or exactly or at most 207, at least or exactly or at most 208, at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least or exactly or at most 222, at least or exactly or at most 223, at least or exactly or at most 224, at least or exactly or at most 225, at least or exactly or at most 226, at least or exactly or at most 227, at least or exactly or at most 228, at least or exactly or at most 229, at least or exactly or at most 230, at least or exactly or at most 231, at least or exactly or at most 232, at least or exactly or at most 233, at least or exactly or at most 234, at least or exactly or at most 235, at least or exactly or at most 236, at least or exactly or at most 237, at least or exactly or at most 238, at least or exactly or at most 239, at least or exactly or at most 240, at least or exactly or at most 241, at least or exactly or at most 242, at least or exactly or at most 243, at least or exactly or at most 244, at least or exactly or at most 245, at least or exactly or at most 246, at least or exactly or at most 247, at least or exactly or at most 248, at least or exactly or at most 249, at least or exactly or at most 250, at least or exactly or at most 251, at least or exactly or at most 252, at least or exactly or at most 253, at least or exactly or at most 254, at least or exactly or at most 255, at least or exactly or at most 256, at least or exactly or at most 257, at least or exactly or at most 258, at least or exactly or at most 259, at least or exactly or at most 260, at least or exactly or at most 271, at least or exactly or at most 272, at least or exactly or at most 273, at least or exactly or at most 274, at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, at least or exactly or at most 285, at least or exactly or at most 286, at least or exactly or at most 287, at least or exactly or at most 288, at least or exactly or at most 289, at least or exactly or at most 290, at least or exactly or at most 291, at least or exactly or at most 292, at least or exactly or at most 293, at least or exactly or at most 294, at least or exactly or at most 295, at least or exactly or at most 296, at least or exactly or at most 297, at least or exactly or at most 298, at least or exactly or at most 299, at least or exactly or at most 300, at least or exactly or at most 301, at least or exactly or at most 302, at least or exactly or at most 303, at least or exactly or at most 304, at least or exactly or at most 305, at least or exactly or at most 306, at least or exactly or at most 307, at least or exactly or at most 308, at least or exactly or at most 309, at least or exactly or at most 310, at least or exactly or at most 311, at least or exactly or at most 312, at least or exactly or at most 313, at least or exactly or at most 314, at least or exactly or at most 315, at least or exactly or at most 316, at least or exactly or at most 317, at least or exactly or at most 318, at least or exactly or at most 319, at least or exactly or at most 320, at least or exactly or at most 321, at least or exactly or at most 322, at least or exactly or at most 323, at least or exactly or at most 324, at least or exactly or at most 325, at least or exactly or at most 326, at least or exactly or at most 327, at least or exactly or at most 328, at least or exactly or at most 329, at least or exactly or at most 330, at least or exactly or at most 331, at least or exactly or at most 332, at least or exactly or at most 333, at least or exactly or at most 334, at least or exactly or at most 335, at least or exactly or at most 336, at least or exactly or at most 337, at least or exactly or at most 338, at least or exactly or at most 339, at least or exactly or at most 340, at least or exactly or at most 341, at least or exactly or at most 342, at least or exactly or at most 343, at least or exactly or at most 344, at least or exactly or at most 345, at least or exactly or at most 346, at least or exactly or at most 347, at least or exactly or at most 348, at least or exactly or at most 349, at least or exactly or at most 350, at least or exactly or at most 351, at least or exactly or at most 352, at least or exactly or at most 353, at least or exactly or at most 354, at least or exactly or at most 355, at least or exactly or at most 356, at least or exactly or at most 357, at least or exactly or at most 358, at least or exactly or at most 359, at least or exactly or at most 360, at least or exactly or at most 361, at least or exactly or at most 362, at least or exactly or at most 363, at least or exactly or at most 364, at least or exactly or at most 365, at least or exactly or at most 366, at least or exactly or at most 367, at least or exactly or at most 368; at least or exactly or at most 369, at least or exactly or at most 370, at least or exactly or at most 371, at least or exactly or at most 372, at least or exactly or at most 373, at least or exactly or at most 374, at least or exactly or at most 375, at least or exactly or at most 376, at least or exactly or at most 377, at least or exactly or at most 378, at least or exactly or at most 379, at least or exactly or at most 380, at least or exactly or at most 381, at least or exactly or at most 382, at least or exactly or at most 383, at least or exactly or at most 384, at least or exactly or at most 385, at least or exactly or at most 386, at least or exactly or at most 387, at least or exactly or at most 388, at least or exactly or at most 389, at least or exactly or at most 390, at least or exactly or at most 391, at least or exactly or at most 392, at least or exactly or at most 393, at least or exactly or at most 394, at least or exactly or at most 395, at least or exactly or at most 396, at least or exactly or at most 397, at least or exactly or at most 398, at least or exactly or at most 399, at least or exactly or at most 400, at least or exactly or at most 401, at least or exactly or at most 402, at least or exactly or at most 403, at least or exactly or at most 404, at least or exactly or at most 405, at least or exactly or at most 406, at least or exactly or at most 407, at least or exactly or at most 408, at least or exactly or at most 409, at least or exactly or at most 410, at least or exactly or at most 411, at least or exactly or at most 412, at least or exactly or at most 413, at least or exactly or at most 414, at least or exactly or at most 415, at least or exactly or at most 416, at least or exactly or at most 417, at least or exactly or at most 418, at least or exactly or at most 419, at least or exactly or at most 420, at least or exactly or at most 421, at least or exactly or at most 422, and at least or exactly or at most 423 consecutive nucleotides in any one of SEQ ID NOs: 17-48, 50, and 51. Longer fragments are contemplated, i.e. fragments having at least or exactly or at most 200, at least or exactly or at most 300 at least or exactly or at most 400, at least or exactly or at most 500, at least or exactly or at most 600, at least or exactly or at most 700, at least or exactly or at most 800, at least or exactly or at most 900, at least or exactly or at most 1000, at least or exactly or at most 1500, at least or exactly or at most 2000, at least or exactly or at most 2500, at least or exactly or at most 3000, at least or exactly or at most 3500, or at least or exactly or at most 4000 nucleotides from those of SEQ ID NOs: 17-48, 50, and 51 that encompass fragments of such lengths.

The nucleic acid fragment of the invention discussed above typically has a sequence identity with the nucleotide sequence defined for i) or ii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The nucleic acid fragment of the invention discussed above may also have a sequence identity with the nucleotide sequence defined for iii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The nucleic acid fragment of the invention described above comprises in certain embodiments at least or exactly or at most X distinct nucleic acid sequences each encoding a polypeptide of the invention, where each of said X distinct nucleic acid sequences encodes at least or exactly or at most one immunogenic amino acid sequence present in or derived from any one of SEQ ID NOs: 1-16 and wherein said X distinct nucleic acid sequences together encode immunogenic amino acid sequences present in or derived from at least or exactly or at most X of SEQ ID NOs. 1-16, wherein X is an integer selected from 2, 3, 4, 5, 6, 7, 8, 9, 10, 11, 12, 13, 14, 15, and 16. In other words, such a nucleic acid fragment encodes several polypeptides of the invention. In some embodiments, the X nucleic acid sequences are expressed as separate encoded proteins and in other embodiments as "pearls on a string", i.e. fused proteins. In some embodiments, immunogenic amino acid sequences from any one of SEQ ID NO: 16 are only present in one of said X nucleic acid sequences.

It will be understood that the nucleic acid fragments of the invention may be used for both production, carrier and vaccine purposes—the latter will require that the sequences are included in expression vectors that may lead to production of immunogenic proteins in the host animal receiving the vector.

The Vectors of the Invention

Vectors of the invention fall into several categories discussed infra. One preferred vector of the invention comprises in operable linkage and in the 5'-3' direction, an expression control region comprising an enhancer/promoter for driving expression of the nucleic acid fragment defined for option i) above, optionally a signal peptide coding sequence, a nucleotide sequence defined for option i), and optionally a terminator. Hence, such a vector constitutes an expression vector useful for effecting production in cells of the polypeptide of the invention. Since the polypeptides of the invention are bacterial of origin, recombinant production is conveniently effected in bacterial host cells, so here it is preferred that the expression control region drives expression in prokaryotic cell such as a bacterium, e.g. in $E\ coli$. However, if the vector is to drive expression in mammalian cell (as would be the case for a DNA vaccine vector), the expression control region should be adapted to this particular use.

At any rate, certain vectors of the invention are capable of autonomous replication.

Also, the vector of the invention may be one that is capable of being integrated into the genome of a host cell—this is particularly useful if the vector is use in the production of stably transformed cells, where the progeny will also include the genetic information introduced via the vector. Alternatively, vectors incapable of being integrated into the genome of a mammalian host cell are useful in e.g. DNA vaccination.

Typically, the vector of the invention is selected from the group consisting of a virus, such as a attenuated virus (which may in itself be useful as a vaccine agent), a bacteriophage, a plasmid, a minichromosome, and a cosmid.

Particularly interesting vectors are viral vectors (in particular those useful as vaccine agents). These may be selected from the group consisting of a retrovirus vector, such as a lentivirus vector, an adenovirus vector, an adeno-associated virus vector, and a pox virus vector. Certain pox virus vectors are preferred, in particular vaccinia virus vectors. A particularly preferred vaccinia virus vector is a modified vaccinia Ankara (MVA) vector.

A more detailed discussion of vectors of the invention is provided in the following:

Polypeptides of the invention may be encoded by a nucleic acid molecule comprised in a vector. A nucleic acid sequence can be "heterologous," which means that it is in a context foreign to the cell in which the vector is being introduced, which includes a sequence homologous to a sequence in the cell but in a position within the host cell where it is ordinarily not found. Vectors include naked DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al, 2001; Ausubel et al, 1996, both incorporated herein by reference). In addition to encoding the polypeptides of this invention, a vector of the present invention may encode polypeptide sequences such as a tag or immunogenicity enhancing peptide (e.g. an immunogenic carrier or a fusion partner that stimulates the immune system, such as a cytokine or active fragment thereof). Useful vectors encoding such fusion proteins include pIN vectors (Inouye et al, 1985), vectors encoding a stretch of histidines, and pGEX vectors, for use in generating glutathione S-transferase (GST) soluble fusion proteins for later purification and separation or cleavage.

Vectors of the invention may be used in a host cell to produce a polypeptide of the invention that may subsequently be purified for administration to a subject or the vector may be purified for direct administration to a subject for expression of the protein in the subject (as is the case when administering a nucleic acid vaccine).

Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural state. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference).

Naturally, it may be important to employ a promoter and/or enhancer that effectively direct(s) the expression of the DNA segment in the cell type or organism chosen for expression. Those of skill in the art of molecular biology generally know the use of promoters, enhancers, and cell type combinations for protein expression (see Sambrook et al, 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Examples of inducible elements, which are regions of a nucleic acid sequence that can be activated in response to a specific stimulus, include but are not limited to Immunoglobulin Heavy Chain (Banerji et al, 1983; Gilles et al, 1983; Grosschedl et al, 1985; Atchinson et al, 1986, 1987; toiler et al, 1987; Weinberger et al, 1984; Kiledjian et al, 1988; Porton et al; 1990), Immunoglobulin Light Chain (Queen et al, 1983; Picard et al, 1984), T Cell Receptor (Luria et al, 1987; Winoto et al, 1989; Redondo et al; 1990), HLA DQα and/or DQβ (Sullivan et al, 1987), β-Interferon (Goodbourn et al, 1986; Fujita et al, 1987; Goodbourn et al, 1988), Interleukin-2 (Greene et al, 1989), Interleukin-2 Receptor (Greene et al, 1989; Lin et al, 1990), MHC Class II 5 (Koch et al, 1989), MHC Class II HLA-DRα (Sherman et al, 1989), β-Actin (Kawamoto et al, 1988; Ng et al; 1989), Muscle Creatine Kinase (MCK) (Jaynes et al, 1988; Horlick et al, 1989; Johnson et al, 1989), Prealbumin (Transthyretin) (Costa et al, 1988), Elastase I (Omitz et al, 1987), Metallothionein (MTII) (Karin et al, 1987; Culotta et al, 1989), Collagenase (Pinkert et al, 1987; Angel et al, 1987), Albumin (Pinkert et al, 1987; Tranche et al, 1989, 1990), α-Fetoprotein (Godbout et al, 1988; Campere et al, 1989), γ-Globin (Bodine et al, 1987; Perez-Stable et al, 1990), β-Globin (Trudel et al, 1987), c-fos (Cohen et al, 1987), c-HA-ras (Triesman, 1986; Deschamps et al, 1985), Insulin (Edlund et al, 1985), Neural Cell Adhesion Molecule (NCAM) (Hirsh et al, 1990), αl-Antitrypain (Larimer et al, 1990), H2B (TH2B) Histone (Hwang et al, 1990), Mouse and/or Type I Collagen (Ripe et al, 1989), Glucose-Regulated Proteins (GRP94 and GRP78) (Chang et al, 1989), Rat Growth Hormone (Larsen et al, 1986), Human Serum Amyloid A (SAA) (Edbrooke et al, 1989), Troponin I (TN I) (Yutzey et al, 1989), Platelet-Derived Growth Factor (PDGF) (Pech et al, 1989), Duchenne Muscular Dystrophy (Klamut et al, 1990), SV40 (Banerji et al, 1981; Moreau et al, 1981; Sleigh et al, 1985; Firak et al, 1986; Herr et al, 1986; Imbra et al, 1986; Kadesch et al 1986; Wang et al, 1986; Ondek et al, 1987; Kuhl et al, 1987; Schaffner et al, 1988), Polyoma (Swartzendruber et al, 1975; Vasseur et al, 1980; Katinka et al, 1980, 1981; Tyndell et al, 1981; Dandolo et al, 1983; de Villiers et al, 1984; Hen et al, 1986; Satake et al, 1988; Campbell et al, 1988), Retroviruses (Kriegler et al, 1982, 1983; Levinson et al, 1982; Kriegler et al, 1983, 1984a, b, 1988; Bosze et al, 1986; Miksicek et al, 1986; Celander et al, 1987; Thiesen et al, 1988; Celander et al, 1988; Choi et al, 1988; Reisman et al, 1989), Papilloma Virus (Campo et al, 1983; Lusky et al, 1983; Spandidos and Wilkie, 1983; Spalholz et al, 1985; Lusky et al, 1986; Cripe et al, 1987; Gloss et al, 1987; Hirochika et al, 1987; Stephens et al, 1987), Hepatitis B Virus (Bulla et al, 1986; Jameel et al, 1986; Shaul et al, 1987; Spandau et al, 1988; Vannice et al, 1988), Human Immunodeficiency Virus (Muesing et al, 1987; Hauber et al, 1988; Jakobovits et al, 1988; Feng et al, 1988; Takebe et al, 1988; Rosen et al, 1988; Berkhout et al, 1989; Laspia et al, 1989; Sharp et al, 1989; Braddock et al, 1989), Cytomegalovirus (CMV) IE (Weber et al, 1984; Boshart et al, 1985; Foecking et al, 1986), Gibbon Ape Leukemia Virus (Holbrook et al, 1987; Quinn et al, 1989).

Inducible Elements include, but are not limited to MT II—Phorbol Ester (TFA)/Heavy metals (Palmiter et al, 1982; Haslinger et al, 1985; Searle et al, 1985; Stuart et al, 1985; Imagawa et al, 1987, Karin et al, 1987; Angel et al, 1987b; McNeall et al, 1989); MMTV (mouse mammary tumor virus)—Glucocorticoids (Huang et al, 1981; Lee et al, 1981; Majors et al, 1983; Chandler et al, 1983; Lee et al, 1984; Ponta et al, 1985; Sakai et al, 1988); β-Interferon—poly (rl)x/poly(rc) (Tavernier et al, 1983); Adenovirus 5 E2—EIA (Imperiale et al, 1984); Collagenase—Phorbol Ester (TPA) (Angel et al, 1987a); Stromelysin—Phorbol Ester (TPA) (Angel et al, 1987b); SV40—Phorbol Ester (TPA) (Angel et al, 1987b); Murine MX Gene—Interferon, Newcastle Disease Virus (Hug et al, 1988); GRP78 Gene—A23187 (Resendez et al, 1988); α-2-Macroglobulin—IL-6 (Kunz et al, 1989); Vimentin—Serum (Rittling et al, 1989); MHC Class I Gene H-2Kb—Interferon (Blanar et al, 1989); HSP70-E1A/SV40 Large T Antigen (Taylor et al, 1989, 1990a, 1990b); Proliferin—Phorbol Ester/TPA (Mordacq et al, 1989); Tumor Necrosis Factor—PMA (Hensel et al, 1989); and Thyroid Stimulating Hormonea Gene—Thyroid Hormone (Chatterjee et al, 1989).

Also contemplated as useful in the present invention are the dectin-1 and dectin-2 promoters. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

In various embodiments, the human cytomegalovirus (CMV) immediate early gene promoter, the SV40 early promoter, and the Rous sarcoma virus long terminal repeat can be used to obtain high level expression of a related polynucleotide to this invention. The use of other viral or mammalian cellular or bacterial phage promoters, which are well known in the art, to achieve expression of polynucleotides is contemplated as well.

In embodiments in which a vector is administered to a subject for expression of the protein, it is contemplated that a desirable promoter for use with the vector is one that is not down-regulated by cytokines or one that is strong enough that even if down-regulated, it produces an effective amount of the protein/polypeptide of the current invention in a subject to elicit an immune response. Non-limiting examples of these are CMV IE and RSV LTR. In other embodiments, a promoter that is up-regulated in the presence of cytokines is employed. The MHC I promoter increases expression in the presence of IFN-γ.

Tissue specific promoters can be used, particularly if expression is in cells in which expression of an antigen is desirable, such as dendritic cells or macrophages. The mammalian MHC I and MHC II promoters are examples of such tissue-specific promoters. 2. Initiation Signals and Internal Ribosome Binding Sites (IRES).

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic and may be operable in bacteria or mammalian cells. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the. ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

2. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al, 1999, Levenson et al, 1998, and Cocea, 1997, incorporated herein by reference.) Frequently, a vector is linearized or fragmented using a restriction enzyme that cuts within the MCS to enable exogenous sequences to be ligated to the vector. Techniques involving restriction enzymes and ligation reactions are well known to those of skill in the art of recombinant technology.

3. Splicing Sites

Most transcribed eukaryotic RNA molecules will undergo RNA splicing to remove introns from the primary transcripts. If relevant in the context of vectors of the present invention, vectors containing genomic eukaryotic sequences may require donor and/or acceptor splicing sites to ensure proper processing of the transcript for protein expression. (See Chandler et al, 1997, incorporated herein by reference.)

4. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (poly A) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

Terminators contemplated for use in the invention include any known terminator of transcription described herein or known to one of ordinary skill in the art, including but not limited to, for example, the bovine growth hormone terminator or viral termination sequences, such as the SV40 terminator. In certain embodiments, the termination signal may be a lack of transcribable or translatable sequence, such as due to a sequence truncation.

5. Polyadenylation Signals

In expression, particularly eukaryotic expression (as is relevant in nucleic acid vaccination), one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

6. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

7. Selectable and Screenable Markers

In certain embodiments of the invention, cells containing a nucleic acid construct of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, markers that confer resistance to neomycin, puromycin, hygromycin, DHFR, GPT, zeocin or histidinol are useful selectable markers. In addition to markers conferring a phenotype that allows for the discrimination of transformants based on the implementation of conditions, other types of markers including screenable markers such as GFP for colorimetric analysis. Alternatively, screenable enzymes such as herpes simplex virus thymidine kinase (tk) or chloramphenicol acetyltransferase (CAT) may be utilized. One of skill in the art would also know how to employ immunologic markers that can be used in conjunction with FACS analysis. The marker used is not believed to be important, so long as it is capable of being expressed simultaneously with the nucleic acid encoding a protein of the invention. Further examples of selectable and screenable markers are well known to one of skill in the art.

The Transformed Cells of the Invention

Transformed cells of the invention are useful as organisms for producing the polypeptide of the invention, but also as simple "containers" of nucleic acids and vectors of the invention.

Certain transformed cells of the invention are capable of replicating the nucleic acid fragment defined for option i) of the second aspect of the invention. Preferred transformed cells of the invention are capable of expressing the nucleic acid fragment defined for option i).

For recombinant production it is convenient, but not a prerequisite that the transformed cell according is prokaryotic, such as a bacterium, but generally both prokaryotic cells and eukaryotic cells may be used.

Suitable prokaryotic cells are bacterial cells selected from the group consisting of *Escherichia* (such as *E. coli.*), *Bacillus* [e.g. *Bacillus subtilis*], *Salmonella*, and *Mycobacterium* [preferably non-pathogenic, e.g. *M. bovis* BCG].

Eukaryotic cells can be in the form of yeasts (such as *Saccharomyces cerevisiae*) and protozoans. Alternatively, the transformed eukaryotic cells are derived from a multicellular organism such as a fungus, an insect cell, a plant cell, or a mammalian cell.

For production purposes, it is advantageous that the transformed cell of the invention is is stably transformed by having the nucleic acid defined above for option i) stably integrated into its genome, and in certain embodiments it is also preferred that the transformed cell secretes or carries on its surface the polypeptide of the invention, since this facilitates recovery of the polypeptides produced. A particular version of this embodiment is one where the transformed cell is a bacterium and secretion of the polypeptide of the invention is into the periplasmic space.

As noted above, stably transformed cells are preferred—these i.a. allows that cell lines comprised of transformed cells as defined herein may be established—such cell lines are particularly preferred aspects of the invention.

Further details on cells and cell lines are presented in the following:

Suitable cells for recombinant nucleic acid expression of the nucleic acid fragments of the present invention are prokaryotes and eukaryotes. Examples of prokaryotic cells include *E. coli*; members of the *Staphylococcus* genus, such as *S. epidermidis*; members of the *Lactobacillus* genus, such as *L. plantarum*; members of the *Lactococcus* genus, such as *L. lactis*; members of the *Bacillus* genus, such as *B. subtilis*; members of the *Corynebacterium* genus such as *C. glutamicum*; and members of the *Pseudomonas* genus such as *Ps. fluorescens*. Examples of eukaryotic cells include mammalian cells; insect cells; yeast cells such as members of the *Saccharomyces* genus (e.g. *S. cerevisiae*), members of the *Pichia* genus (e.g. *P. pastoris*), members of the *Hansenula* genus (e.g. *H. polymorpha*), members of the *Kluyveromyces* genus (e.g. *K. lactis* or *K. fragilis*) and members of the *Schizosaccharomyces* genus (e.g. *S. pombe*).

Techniques for recombinant gene production, introduction into a cell, and recombinant gene expression are well known in the art. Examples of such techniques are provided in references such as Ausubel, Current Protocols in Molecular Biology, John Wiley, 1987-2002, and Sambrook et al., Molecular Cloning, A Laboratory Manual, 2nd Edition, Cold Spring Harbor Laboratory Press, 1989.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org) or from other depository institutions such as Deutsche Sammlung vor Micrroorganismen and Zellkulturen (DSM). An appropriate host can be determined by one of skill in the art based on the vector backbone and the desired result. A plasmid or cosmid, for example, can be introduced into a prokaryote host cell for replication of many vectors or expression of encoded proteins. Bacterial cells used as host cells for vector replication and/or expression include *Staphylococcus* strains, DH5α, JMI 09, and KC8, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe*, and *Pichia pastoris*.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote—and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ Baculovirus expression system from CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Amplification of Nucleic Acids

Nucleic acids used as a template for amplification may be isolated from cells, tissues or other samples according to standard methodologies (Sambrook et al, 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to sequences of genes identified herein are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Methods of Gene Transfer

Suitable methods for nucleic acid delivery to effect expression of compositions of the present invention are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al, 1987); by liposome mediated transfection (Nicolau and Sene, 1982; Fraley et al, 1979; Nicolau et al, 1987; Wong et al, 1980; Kaneda et al, 1989; Kato et al, 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated, herein by reference); by agitation with silicon carbide fibers (Kaeppler et al, 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); or by PEG mediated transformation of protoplasts (Omirulleh et al, 1993; U.S. Pat. Nos. 4,684,611 and 4,952,500, each incorporated herein by reference); by desiccation/inhibition mediated DNA uptake (Potrykus et al, 1985). Through the application of techniques such as these, organelle(s), cell(s), tissue(s) or organism(s) may be stably or transiently transformed.

The Antibodies of the Invention—and Their Production/Isolation

Antibodies directed against the proteins of the invention are useful for affinity chromatography, immunoassays, and for distinguishing/identifying *staphylococcus* proteins as well as for passive immunization and therapy.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 µg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antiserum is obtained by bleeding the immunized animal into a glass or plastic container, incubating the blood at 25 C for one hour, followed by incubating at 4 C for 2-18 hours. The serum is recovered by centrifugation (eg. 1,000 g for 10 minutes). About 20-50 ml per bleed may be obtained from rabbits.

Monoclonal antibodies are prepared using the standard method of Kohler & Milstein [Nature (1975) 256: 495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective I aedium (elg. hypexanthine, aminopterin, thymidine medium, "HAT"). The resulting hybridomas are plated by limiting dilution, and are assayed for production of antibodies, which bind specifically to the immunizing antigen (and which do not bind to unrelated antigens). The selected MAb-secreting hybridomas are then cultured either in vitro (eg. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly 32p and 125I), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, 1151 may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with, 125I, or with an anti-biotin MAb labeled with HRP. Other permutations and possibilities will be readily apparent to those of ordinary skill in the art, and are considered as equivalents within the scope of the instant invention.

According to the invention, the isolated monoclonal antibody or antibody analogue is preferably a monoclonal antibody selected from a multi-domain antibody such as a murine antibody, a chimeric antibody such as a humanized antibody, a fully human antibody, and single-domain antibody of a llama or a camel, or which is an antibody analogue selected from a fragment of an antibody such as an Fab or an $F(ab')_2$, an scFV; cf. also the definition of the term "antibody" presented above.

Compositions of the Invention; Vaccine

Pharmaceutical compositions, in particular vaccines, according to the invention may either be prophylactic (ie. to prevent infection) or therapeutic (ie, to treat disease after infection).

Such vaccines comprise immunizing antigen(s), immunogen(s), polypeptide(s), protein(s) or nucleic acid(s), usually in combination with "pharmaceutically acceptable carriers", which include any carrier that does not itself induce the production of antibodies harmful to the individual receiving the composition.

In some embodiments of the invention, the pharmaceutical compositions such as vaccines include merely one single antigen, immunogen, polypeptide, protein, nucleic acid or vector of the invention, but in other embodiments, the pharmaceutical compositions comprise "cocktails" of the antigens or of the immunogens or of the polypeptides or of the protein or of the nucleic acids or of the vectors of the invention.

In particularly interesting embodiments, the pharmaceutical composition is an MVA vector mentioned herein, which encodes and can effect expression of at least 2 nucleic acid fragments of the invention.

Another interesting embodiment of a pharmaceutical composition comprises RNA as the active principle, i.e. at least one mRNA encoding a polypeptide of the invention.

An embodiment of a pharmaceutical composition of the invention comprises Y or at least Y or at most Y distinct polypeptides of the invention described above, where each of said Y or at least Y or at most Y distinct polypeptides comprises an immunogenic amino acid sequence present in or derived from any one of SEQ ID NOs: 1-16 and wherein said Y or at least Y or at most Y distinct polypeptides together comprise immunogenic amino acid sequences present in or derived from Y or at least Y or at most Y of SEQ ID NOs. 1-16, wherein Y is an integer selected from 2, 3, 4, 5, 6, 7, 8, 9, 10, 11, 12, 13, 14, 15, and 16.

Another embodiment of the pharmaceutical composition of the invention comprises Z or at least Z or at most Z distinct nucleic acid molecules (such as DNA and RNA) each encoding a polypeptide of the invention, where each of said Z or at least Z or at most Z distinct nucleic acid molecules encodes an immunogenic amino acid sequence present in or derived from any one of SEQ ID NOs: 1-16 and wherein said at Z or least Z distinct nucleic acid molecules together encode immunogenic amino acid sequences present in or derived from Z or at least Z or at most Z of SEQ ID NOs. 1-16, wherein Z is an integer selected from 2, 3, 4, 5, 6, 7, 8, 9, 10, 11, 12, 13, 14, 15, and 16.

Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles.

Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogen, cf. the description of immunogenic carriers supra.

The pharmaceutical compositions of the invention thus typically contain an immunological adjuvant, which is commonly an aluminum based adjuvant or one of the other adjuvants described in the following:

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (WO 90/14837; Chapter 10 in Vaccine design: the subunit and adjuvant approach, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi adjuvant system (RAS), (Ribi Immunochem, Hamilton, Mont.) containing 2% Squalene, 0.2% Tween 80, and one or more bacterial cell wall components from the group consisting of monophosphoryl lipid A (MPL), trehalose dimycolate (TDM), and cell wall skeleton (CWS), preferably MPL+CWS (Detox™); (3) saponin adjuvants such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12, etc.), interferons (eg. gamma interferon), macrophage colony stimulating factor (M-CSF), tumor necrosis factor (TNF), etc.; and (6) other substances that act as immunostimulating agents to enhance the effectiveness of the composition. Alum and MF59™ adjuvants are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2"-2'-dipalmitoyl-sn-glycero-3-hydroxyphosphoryloxy)-ethylamine (MTP-PE), etc.

The immunogenic compositions (eg. the immunizing antigen or immunogen or polypeptide or protein or nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunollogically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. nonhuma primate, primate, etc.), the capacity of the individual's immune system to synthesize antibodies or generally mount an immune response, the degree of protection desired, the formulation of the vaccine, the treating doctor's assessment of the medical situation, and other relevant factors. It is expected that the amount will fall in a relatively broad range that can be determined through routine trials. However, for the purposes of protein vaccination, the amount administered per immunization is typically in the range between 0.5 μg and 500 mg (however, often not higher than 5,000 μg), and very often in the range between 10 and 200 μg.

The immunogenic compositions are conventionally administered parenterally, eg, by injection, either subcutaneously, intramuscularly, or transdermally/transcutaneously (eg. WO98/20734). Additional formulations suitable for other modes of administration include oral and pulmonary formulations, suppositories, and transdermal applications. In the case of nucleic acid vaccination, also the intravenous or intraarterial routes may be applicable.

Dosage treatment may be a single dose schedule or a multiple dose schedule. The vaccine may be administered in conjunction with other immunoregulatory agents.

As an alternative to protein-based vaccines, DNA vaccination (also termed nucleic acid vaccination or gene vaccination) may be used [eg. Robinson & Torres (1997) Seminars in Immunol 9: 271-283; Donnelly et al. (1997) Annu Rev Immunol 15: 617-648; later herein].

A further aspect of the invention is as mentioned above the recognition that combination vaccines can be provided, wherein 2 or more antigens disclosed herein are combined to enhance the immune response by the vaccinated animal, including to optimize initial immune response and duration of immunity. For the purposes of this aspect of the invention, multiple antigenic fragments derived from the same, longer protein can also be used, such as the use of a combination of different lengths of polypeptide sequence fragments from one protein.

Thus, embodiments of the invention relate to a composition (or the use as a vaccine thereof) comprising 2 distinct (i.e. non-identical) proteinaceaous immunogens disclosed herein wherein the first of said immunogens is SEQ ID NO: 1 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, and 16 or in combination with a variant or fragment disclosed herein of any one of SEQ ID NOs: 1, 2, 3, 4, 5, 6, 7, 8, 9, 10, 11, 12, 13, 14, 15, and 16.

Also, embodiments of the invention relate to a composition (or the use as a vaccine thereof) comprising 2 distinct (i.e. non-identical) proteinaceaous immunogens disclosed herein wherein the first of said immunogens is SEQ ID NO: 2 or a variant or fragment thereof disclosed herein in combination with a proteinaceous immunogen selected from any one of SEQ ID NOs: 1, 3, 3, 4, 5, 6, 7, 8, 9, 10, 11, 12, 13, 14, 15, and 16 or in combination with a variant or fragment disclosed herein of any one of SEQ ID NOs: 1, 2, 3, 4, 5, 6, 7, 8, 9, 10, 11, 12, 13, 14, 15, and 16.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 3 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, and 16 or in combination with a variant or fragment disclosed herein of any one of SEQ ID NOs: 1, 2, 3, 4, 5, 6, 7, 8, 9, 10, 11, 12, 13, 14, 15, and 16.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 4 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, and 16 or in combination with a variant or fragment disclosed herein of any one of SEQ NOs: 1, 2, 3, 4, 5, 6, 7, 8, 9, 10, 11, 12, 13, 14, 15, and 16.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 5 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, and 16 or in combination with a variant or fragment disclosed herein of any one of SEQ ID NOs: 1, 2, 3, 4, 5, 6, 7, 8, 9, 10, 11, 12, 13, 14, 15, and 16.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 6 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, and 16 or in combination with a variant or fragment disclosed herein of any one of SEQ ID NOs: 1, 2, 3, 4, 5, 6, 7, 8, 9, 10, 11, 12, 13, 14, 15, and 16.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 7 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, and 16 or in combination with a variant or fragment disclosed herein of any one of SEQ ID NOs: 1, 2, 3, 4, 5, 6, 7, 8, 9, 10, 11, 12, 13, 14, 15, and 16.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 8 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, and 16 or in combination with a variant or fragment disclosed herein of any one of SEQ ID NOs: 1, 2, 3, 4, 5, 6, 7, 8, 9, 10, 11, 12, 13, 14, 15, and 16.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 9 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, and 16 or in combination with a variant or fragment disclosed herein of any one of SEQ ID NOs: 1, 2, 3, 4, 5, 6, 7, 8, 9, 10, 11, 12, 13, 14, 15, and 16.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 10 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, and 16 or in combination with a variant or fragment disclosed herein of any one of SEQ ID NOs: 1, 2, 3, 4, 5, 6, 7, 8, 9, 10, 11, 12, 13, 14, 15, and 16.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 11 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, and 16 or in combination with a variant or fragment disclosed herein of any one of SEQ ID NOs: 1, 2, 3, 4, 5, 6, 7, 8, 9, 10, 11, 12, 13, 14, 15, and 16.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 12 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, and 16 or in combination with a variant or fragment disclosed herein of any one of SEQ ID NOs: 1, 2, 3, 4, 5, 6, 7, 8, 9, 10, 11, 12, 13, 14, 15, and 16.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 13 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, and 16 or in combination with a variant or fragment disclosed herein of any one of SEQ ID NOs: 1, 2, 3, 4, 5, 6, 7, 8, 9, 10, 11, 12, 13, 14, 15, and 16.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 14 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, and 16 or in combination with a variant or fragment disclosed herein of any one of SEQ ID NOs: 1, 2, 3, 4, 5, 6, 7, 8, 9, 10, 11, 12, 13, 14, 15, and 16.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 15 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, and 16 or in combination with a variant or fragment disclosed herein of any one of SEQ ID NOs: 1, 2, 3, 4, 5, 6, 7, 8, 9, 10, 11, 12, 13, 14, 15, and 16.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 16 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, and 16 or in combination with a variant or fragment disclosed herein of any one of SEQ ID NOs: 1, 2, 3, 4, 5, 6, 7, 8, 9, 10, 11, 12, 13, 14, 15, and 16.

Treatment Methods of the Invention

The method of the sixth aspect of the invention generally relates to induction of immunity and as such also entails method that relate to treatment, prophylaxis and amelioration of disease.

When immunization methods entail that a polypeptide of the invention or a composition comprising such a polypeptide is administered the animal (e.g. the human) typically receives between 0.5 and 5,000 μg of the polypeptide of the invention per administration.

In preferred embodiments of the sixth aspect, the immunization scheme includes that the animal (e.g. the human) receives a priming administration and one or more booster administrations.

Preferred embodiments of the 6$^{th}$ aspect of the invention comprise that the administration is for the purpose of inducing protective immunity against *S. aureus*. In this embodiment it is particularly preferred that the protective immunity is effective in reducing the risk of attracting infection with *S. aureus* or is effective in treating or ameliorating infection with *S. aureus*.

As mentioned herein, the preferred vaccines of the invention induce humoral immunity, so it is preferred that the administration is for the purpose of inducing antibodies specific for *S. aureus* and wherein said antibodies or B-lymphocytes producing said antibodies are subsequently recovered from the animal.

But, as also mentioned the method of the 6$^{th}$ aspect may also be useful in antibody production, so in other embodiments the administration is for the purpose of inducing antibodies specific for *S. aureus* and wherein B-lymphocytes producing said antibodies are subsequently recovered from the animal and used for preparation of monoclonal antibodies.

Pharmaceutical compositions can as mentioned above comprise polypeptides, antibodies, or nucleic acids of the invention. The pharmaceutical compositions will comprise a therapeutically effective amount thereof.

The term "therapeutically effective amount" or "prophylactically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. Reference is however made to the ranges for dosages of immunologically effective amounts of polypeptides, cf. above.

However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N. J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

As is apparent from the claims, the invention also relates to related embodiments to the treatment and prophylaxis disclosed herein: the invention also includes embodiments where the polypeptide of the invention is for use as a pharmaceutical, in particular for use as a pharmaceutical in the treatment, prophylaxis or amelioration of infection with *S. aureus;* the nucleic acid fragment of the invention or the vector of the invention is for use as a pharmaceutical, in particular for use as a pharmaceutical in the treatment, prophylaxis or amelioration of infection with *S. aureus;* the transformed cell of the invention is for use as a pharmaceutical, in particular for use as a pharmaceutical in the treatment, prophylaxis or amelioration of infection with *S. aureus.* the antibody, antibody fragment or antibody analogue of the invention is for use as a pharmaceutical, in particular for use as a pharmaceutical in the treatment, prophylaxis or amelioration of infection with *S. aureus.*

EXAMPLE

Testing *S. Aureus* Derived Vaccines in Mice Challenged with MRSA

Expression and Purification of *S. Aureus* Genes

1. Gene fragments that encode the selected *S. aureus* polypeptides of the invention are prepared synthetically and are introduced into the pQE-1 vector (Qiagen) from Genscript. The fragments are inserted by blunt ended ligation into the the PVU II site in the 5'-end, immediately following the vector's coding region for the 6 histidinyl residues. In the 3'-end, all inserted gene fragments include a stop codon.

2. The vectors from 1 are transfected into the *E. Coli* M15[pREP4] strain, which contains an expression as well as a repressor plasmid facilitating proper expression.

3. The vectors from 1 are further inserted into the *E. coli* XL1 Blue for long-time storage.

4. The transfected and selected clones are tested for expression in small scale whereby optimum conditions for expression in terms of the amount of IPTG, the density of cells and the time of expression induction are determined.

5. From the information obtained in 4, large scale cultures are established; subsequently the expression products are harvested and purified on a Ni-NTA column.

6. Purity and yield of the large-scale expression is investigated by means of SDS-PAGE and spectrophotometry, where after the proteins are aliquoted for use in immunization experiments and other experiments.

Immunization and *S. Aureus* Challenge Infection in Mice 1. 2 months old NMRI mice were used.
2. Groups of at least 8 mice were used for immunization. The mice were immunized 3 times (at day 0, 14, and 28) prior to challenge infection. A control group was treated according to an identical protocol with the exception that an irrelevant protein antigen or phosphate buffered saline was used for immunization.

1st immunization:
25 µg protein (per mice) was mixed with 100 µl aluminum hydroxide (Alhydrogel 2.0%, Brenntag) per 125 ug protein and incubated with end-over-end rotation for 15 min. Freund's incomplete adjuvant (sigma) was added in the volume 1:1 and the mixture was vortexed thoroughly for 1 hour. This mixture was injected subcutaneously.

2nd and 3rd immunization:
The mice were booster injected intraperitoneally with 2 weeks interval, using the same amount of protein mixed with aluminum hydroxide and physiological saline solution.

3. 14 days after the last immunization, a number of bacteria ($2 \times 10^9$ cells) corresponding to a predetermined $LD_{90}$ in the control group of mice was administered intraperitoneally to all mice.

The cells were handled cold and kept on ice until use. The stock solution of MRSA cells were thawed on ice and then the appropriate amount of cells was diluted in sterile physiological saline (total volume per mouse 500 µl).

The survival was surveilled twice daily in the first 48 hours after challenge and once daily in the subsequent 7 days. The mice were sacrificed if they showed signs of suffering. The mice were monitored with respect to loss of weight and body temperature using an implanted chip. The organs of the mice were used for determination of CFU counts for for SAR1402 (SEQ ID NO: 5), SAR 2723 (SEQ ID NO: 13) and SAR2753 (SEQ ID NO: 14).

The results from 7 polypeptide vaccinations are presented in the Figures.

FIG. 1 shows the survival curves for 8 mice immunized with full-length SAR1402 (SEQ ID NO: 5) and 8 mice immunized with negative control. Survival in the vaccinated group at day 7 was 7/8 mice, whereas only 1/8 mice in the control group survived. The increased survival in the vaccinated group is statistically highly significant (P=0.001 according to a Log-rank Mantel-Cox test).

FIG. 2 shows the survival curves for 8 mice immunized with amino acids 20-515 of SAR2496 (SEQ ID NO: 11) and 8 mice immunized with negative control. Survival in the vaccinated group at day 7 was 6/8 mice, whereas only 1/8 mice in the control group survived. The increased survival in the vaccinated group is statistically highly significant (P=0.005 according to a Log-rank Mantel-Cox test).

FIG. 3 shows the survival curves for 8 mice immunized with amino acids 28-619 of SAR2723 (SEQ ID NO: 13) and 8 mice immunized with negative control. Survival in the vaccinated group at day 7 was 4/8 mice, whereas only 1/8 mice in the control group survived. The increased survival in the vaccinated group is statistically highly significant (P=0.0145 according to a Log-rank Mantel-Cox test).

FIG. 4 shows the survival curves for 8 mice immunized with amino acids 36-681 of SAR2753 (SEQ ID NO: 14) and 8 mice immunized with negative control. Survival in the vaccinated group at day 7 was 4/8 mice, whereas only 1/8 mice in the control group survived. The increased survival in the vaccinated group is statistically highly significant (P=0.0032 according to a Log-rank Mantel-Cox test).

FIG. 5 shows the survival curves for 20 mice immunized with amino acids 28-619 of SAR2723 (SEQ ID NO: 13) and 20 mice immunized with negative control (phosphate buffered saline, PBS). Survival in the vaccinated group at day 7 was 15/20 mice, whereas only 6/20 mice in the control group survived. The increased survival in the vaccinated group is statistically highly significant (P=0.0053 according to a Log-rank Mantel-Cox test).

FIG. 6 shows the survival curves for 20 mice immunized with a homologue of SAR2716 (USA300HOU_2637_28_439 shown in SEQ ID NO: 49) and 20 mice immunized with negative control (PBS). Survival in the vaccinated group at day 7 was 15/20 mice, whereas only 6/20 mice in the control group survived. The increased survival in the vaccinated group is statistically highly significant (P=0.0063 according to a Log-rank Mantel-Cox test). USA300HOU_2637_28_439 has a sequence identity with SEQ ID NO: 10, residues 28-439, of 93%.

FIG. 7 shows the survival curves for 19 mice immunized with amino acids 25-564 of SAR1795 (SEQ ID NO: 12) and 20 mice immunized with negative control (PBS). Survival in the vaccinated group at day 7 was 15/19 mice, whereas only 6/20 mice in the control group survived. The increased survival in the vaccinated group is statistically highly significant (P=0.0049 according to a Log-rank Mantel-Cox test).

SEQUENCE INFORMATION

The sequence listing included sets forth the sequences of polypeptides and nucleic acids of the present invention. For easy reference, the sequences are presented in the following:

The polypeptides of the present invention have the following amino acid sequences:

```
SEQ IN NO: 1
MAKGNLFKAILGIGGAVAAVLVTRKDSRDKLKAEYNKYKQDPQSYKDNAKDKATQLGTIANIETIKEVK

TNPKEYANRLKNNPKAFFEEEKSKFTEYDNKTDESIEKGKFDDEGGAAPNNNLRIVTEEDLKKNKNALS

DKE
```

SEQ IN NO: 2
MKKLVSIVGATLLLAGCGSQNLAPLEEKTTDLREDNHQLKLDIQELNQQISDSKSKIKGLEKDKENSKK

TASNNTKIKLMNVTSTYYDKVAKALKSYNDIEKDVSKIVKGDKNVQSKLNQISNDIQSAHTSYKDAIDG

LSLSDDDKKTSKNIDKLNSDLNHAFDDIKNGYQNKDKKQLTKGQQALSKLNLNAKS

SEQ IN NO: 3
MKKLVTGLLALSLFLAACGQDSDQQKDSNKEKDDKAKTEQQDKKTNDSSKDKKDNKDDSKDVNKDNKDN

SANDNQQQSNSNATNNDQNQTNNNQSNSGQTTNNQKSSYVAPYYGQNAAPVARQIYPFNGNKSQALQQL

PNFQTALNAANNEANKFGNGHKVYNIDYSIEEHNGNYKYVFSFKDPNVNGKYSIVTVDYTGQAMVTDPN

YQQ

SEQ IN NO: 4
MKKVMGILLASTLILGACGHHQDSAKKESTSHKKKENIDNEELNEELKEFKSKKNMDIKIKGDTIVSDK

FEAKIKEPFIINEKDEKKKYIAFKMEITAKKDDKDLNPSSISHDYINITQDDKNTVNKLRDGYLLSDKN

YKDWTEHNQDQIKKGKTAQAMFIYELRGDGNINLNVHKYSEDKTVDSKSFKFSKLKTEDFSHRAETREE

VEKKEKEFEEEYKKEQEREKEKEKQKDDDHSGLDEV

SEQ IN NO: 5
MKKWQFVGTTALGATLLLGACGGGNGGSGNSDLKGEAKGDGSSTVAPIVEKLNEKWAQDHSDAKISAGQ

AGTGAGFQKFIAGDIDFADASRPIKDEEKQKLQDKNIKYKEFKIAQDGVTVAVNKENDFVDELDKQQLK

AIYSGKAKTWKDVNSKWPDKKINAVSPNSSHGTYDFFENEVMNKEDIKAEKNADTNAIVSSVTKNKEGI

GYFGYNFYVQNKDKLKEVKIKDENGKATEPTKKTIQDNSYALSRPLFIYVNEKALKDNKVMSEFIKFVL

EDKGKAAEEGGYVAAPEKTYKSQLDDLKAFIDKNQKSDDKKSDDKKSEDKK

SEQ IN NO: 6
MKGKFLKVSSLFVATLTTATLVSSPAANALSSKAMDNHPQQTQTDKQQTPKIQKGGNLKPLEQRERANV

ILPNNDRHQITDTTNGHYAPVTYIQVEAPTGTFIASGVVVGKDTLLTNKHIVDATHGDPHALKAFASAI

NQDNYPNGGFTAEQITKYSGEGDLAIVKFSPNEQNKHIGEVVKPATMSNNAETQVNQNITVTGYPGDKP

VATMWESKGKITYLKGEAMQYDLSTTGGNSGSPVFNEKNEVIGIHWGGVPNQFNGAVFINENVRNFLKQ

NIEDINFANDDHPNNPDNPDNPNNPDNPNNPDNPNNPDNPDNPNNPDNPNNPDNIPNNPDQPNINPNIN

PDNGDNNNSDNPDAA

SEQ IN NO: 7
MKRTLVLLITAIFILAACGNHKDDQAGKDNQKHNNSSNQVKEIATDKNVQGDNYRTLLPFKESQARGLL

QDNMANSYNGGDFEDGLLNLSKEVFPTDKYLYQDGQFLDKKTINAYLNLKYTKREIDKMSEKDKKDKKA

NENLGLNPSHEGETDPEKIAEKSPAYLSNILEQDFYGGGDTKGKNIKGMTIGLAMNSVYYYKKEKDGPT

FSKKLDDSEVKKQGKQMASEILSRLRENDDLKDIPIHFAIYKQSSEDSITPGEFITQATAEKSQTKLNE

WHNINEKSALLPSSTAADYDENLNNNFKQFNDNLQSYFSNIFTQAVGKVKFVDKKPQRLVVDLPIDYYG

QAETIGITQYVTEQANKYFDKIDNYEIRIKDGNQPRALISKTKDDKEPQVHIYSN

SEQ IN NO: 8
MRENFKLRKMKVGLVSVAITMLYIMTNGQAEASEANEKPSTNQESKVVSQTEQNSKETKTVESNKNFVK

LDTIKPGAQKITGTTLPNHYVLLTVDGKSADSVENGGLGFVEANDKGEFEYPLNNRKIVHNQEIEVSSS

SPDLGEDEEDEEVEEASTDKAGVEEESTEAKVTYTTPRYEKAYEIPKEQLKEKDGHHQVFIEPITEGSG

IIKGHTSVKGKVALSINNKENFEESVKGGVSKEDTKASSDGIWMPIDDKGYFNFDFKTKRFDNLELKEG

NDISLTFAPDDEEDALKPLIFKTKVTSLEDIDKAETKYDHTKLNKVKVLDNVKEDLHVDEIYGSLYHTD

KGKGILDKEGTKVIKGKTKFANAVVKVDSELGEAQLFPDLQVNEKGEFSFDSHGAGFRLQNGEKLNFTV

VDPITGDLLSNEFVSKEIDIEETPEQKADREFDEKLENTPAYYKLYGDKIVGFDTNDFPITWFYPLGEK

KVERTTPKLEK

SEQ IN NO: 9
MSKKLKIIIPIIIVLLLIGGIAWGVYAFFANTPKNTYLKSEQQTAKMYKDYFNDRFENEVKFQEKMKDN

SFLSSLELSADASDEIVKGLGIPKSVVNASKIKMSYGHDPKKEKSMINLEPTIADSALGKFQLAADKDK

HYFESPLFKGKYSVNNSDLLSTYSKLTGEDEETAKENGITNQQLNLNTLFSNAQAQQSDYSKIAEKYSE

LIVDKLDDDNFDKGKKEEIKVNGEKYKVRPVTLTLSRADTKKITLAVLEEAKKDKDLKKLMEEQGTTKD

FEKDIKKAIDDVKETKKDEFAKIQSKIYTEKHTIVKREITITDKENNKTKIKGTNTLEDDKLKLDYALD

FDQDKYTYAEAKYTIKGVSSKEKDNKYSDKYEFGKKTEYDESKIKLDNQEKVDGTKRQDKGKITVALDK

YSDENEFTFENNIDSDVKNNTQKSTLNIGIKYAEEPINFILKSSTKLKADIDFDDSGAKDFNSLSSKDR

EKLEKEIEKNGGKMFESILKKASK

SEQ IN NO: 10
MRKFSRYAFTSMATVTLLSSLTPAALASDTNHKPATSDINFEITQKSDAVKALKELPKSENVKNHYQDY

SVTDVKTDKKGFTHYTLQPSVDGVHAPDKEVKVHADKSGKVVLINGDTDAKKVKPTNKVTLSKDEAADK

AFNAVKIDKNKAKNLQDDVIKENKVEIDGDSNKYIYNIELITVTPEISHWKVKIDADTGAVVEKTNLVK

EAAATGTGKGVLGDTKDININSIDGGFSLEDLTHQGKLSAYNFNDQTGQATLITNEDENFVKDDQRAGV

DANYYAKQTYDYYKNTFGRESYDNHGSPIVSLTHVNHYGGQDNRNNAAWIGDKMIYGDGDGRTFTNLSG

ANDVVAHELTHGVTQETANLEYKDQSGALNESFSDVFGYFVDDEDFLMGEDVYTPGKEGDALRSMSNPE

QFGQPSHMKDYVYTEKDNGGVHTNSGIPNKAAYNVIQAIGKSKSEQIYYRALTEYLTSNSNFKDCKDAL

YQAAKDLYDEQTAEQVYEAWNEVGVE

SEQ IN NO: 11
MKKKLGMLLLVPAVTLSLAACGNDDGKDKDGKVTIKTTVYPLQSFAEQIGGKHVKVSSIYPAGTDLHSY

EPTQKDILSASKSDLFMYTGDNLDPVAKKVASTIKDKDKKLSLEDKLDKAKLLTDQHEHGEEHEHEGHD

HGKEEHHHHGGYDPHVWLDPKINQTFAKEIKDELVKKDPKHKDDYEKNYKKLNDDLKKIDNDMKQVTKD

KQGNAVFISHESIGYLADRYGFVQKGIQNMNAEDPSQKELTKIVKEIRDSNAKYILYEDNVANKVTETI

RKETDAKPLKFYNMESLNKEQQKKDNITYQSLMKSNIENIGKALDSGVKVKDDKAESKHDKAISDGYFK

DEQVKDRELSDYAGEWQSVYPYLKDGILDEVMEHKAENDPKKSAKDLKAYYDKGYKTDITNIDIKGNEI

TFTKDGTKHTGKYEYNGKKTLKYPKGNRGVRFMFKLVDGNDKDLPKFIQFSDHNIAPKKAEHFHIFMGN

DNDALLKEMDNWPTYYPSKLNKDQIKEEMLAH

SEQ IN NO: 12
MVLYIILAIIVIILIAVGVLFYLRSNKRQIIEKAIERKNEIETLPFDQNLAQLSKLNLKGETKTKYDAM

KKDNVESINKYLAPVEEKIHNAEALLDKFSFNASQCEIDDANELMDSYEQSYQQQLEDVNEIIALYKDN

DELYDKCKVDYREMKRDVLANRHQFGEAASLLETEIEKFEPRLEQYEVLKADGNYVQAHNHIAALNEQM

KQLRSYMEEIPELIRETQKELPGQFQDLKYGCRDLKVEGYDLDHVKVDSTLQSLKTELSFVEPLISRLE

LEEANDKLANINDKLDDMYDLIEHEVKAKNDVEETKDIITDNLFKAKDMNYTLQTEIEYVRENYYINES

DAQSVRQFENEIQSLISVYDDILKEMSKSAVRYSEVQDNLQYLEDHVTVINDKQEKLQNHLIQLREDEA

EAEDNILLRVQSKKEEVYRRLLASNLTSVPERFIIMKNEIDHEVRDVNEQFSERPIHVKQLKDKVSKIV

IQMNTFEDEANDVLVNAVYAEKLIQYGNRYRKDYSNVDKSLNEAERLFKNINRYKRAIEIAEQALESVE

PGVTKHIEEEVIKQ

SEQ IN NO: 13
MPKNKILIYLLSTTLVLPTLVSPTAYADTPQKDTTAKTTSHDSKKSTDDETSKDTTSKDIDKADNNNTS

NQDNNDKKVKTIDDSTSDSNNIIDFIYKNLPQTNINQLLTKNKYDDNYSLTTLIQNLFNLNSDISDYEQ

PRNGEKSTNDSNKNSDNSIKNDTDTQSSKQDKADNQKAPKSNNTKPSTSNKQPNSPKPTQPNQSNSQPA

SDDKVNQKSSSKDNQSMSDSALDSILDQYSEDAKKTQKDYASQSKKDKNEKSNTKNPQLPTQDELKHKS

KPAQSFNNDVNQKDIRATSLFETDPSISNNDDSGQFNVVDSKDTRQFVKSIAKDAHRIGQDNDIYASVM

-continued

IAQAILESDSGRSALAKSPNHNLFGIKGAFEGNSVPFNTLEADGNQLYSINAGFRKYPSTKESLKDYSD
LIKNGIDGNRTIYKPTWKSEADSYKDATSHLSKTYATDPNYAKKLNSIIKHYQLTQFDDERMPDLDKYE
RSIKDYDDSSDEFKPFREVSDNMPYPHGQCTWYVYNRMKQFGTSISGDLGDAHNWNNRAQYRDYQVSHT
PKRHAAVVFEAGQFGADQHYGHVAFVEKVNSDGSIVISESNVKGLGIISHRTINAAAAEELSYITGK

SEQ IN NO: 14
MMKSQNKYSIRKFSVGASSILIATLLFLSGGQAQAAEKQVNMGNSQEDTVTAQSIGDQQTRENANYQRE
NGVDEQQHTENLTKNLHNDKTISEENHRKTDDLNKDQLKDDKKSSLNNKNIQRDTTKNNNANPRDVNQG
LEQAINDGKQSKVASQQQSKEADNSQDLNANNNLPSQSRTKVSPSLNKSDQTSQREIVNETEIEKVQPQ
QKNQANDKITDHNFNNEQEVKPQKDEKTLSVSDLKNNQKSPVEPTKDNDKKNGLNLLKSSAVATLPNKG
TKELTAKAKGDQTNKVAKQGQYKNQDPIVLVHGFNGFTDDINPSVLAHYWGGNKMNIRQDLEENGYKAY
EASISAFGSNYDRAVELYYYIKGGRVDYGAAHAAKYGHERYGKTYEGIYKDWKPGQKVHLVGHSMGGQT
IRQLEELLRNGSREEIEYQKKHSGEISPLFKGNNDNMISSITTLGTPHNGTHASDLAGNEALVRQIVFD
IGKMFGNKNSRVDFGLAQWGLKQKPNESYIDYVKRVKQSNLWKSKDNGFYDLTREGATDLNRKTSLNPN
IVYKTYTGEATHKALNSDRQKADLNMFFPFVITGNLIGKATEKEWRENDGLVSVISSQHPFNQAYTNAT
DKIQKGIWQVTPTKHDWDHVDFVGQDSSDTVRTREELQDFWHHLADDLVKTEKVTDTKQA

SEQ IN NO: 15
MTNKMKKWQKLSTITLLMTGVIALNNGEFRNVDKHQIAVADTNVQTPDYEKLKKTWLDVNYGYDQYDEN
NQDMKKKFDAKEKEAKKLLDDMKTDTNRTYLWSGAENLETNSSHMTKTYRNIEKIAESMQHKNTVLKTV
ENKLKIKEALDWMNKNVYGKNPSQKVEDLTKNRKGQTTPKNNSLNWWDYEIGTPRALTNTLLLMDDMLT
KDEMKNYSKPISTYAPSSDKILSSVGESEDAKGGNLVDISKVKLLESVIEEDVDNILKKSIDSFNKVFT
YVQDSATGKGRNGFYKDGSYIDHQDVPYTGAYGVVLLEGISQMMPMIKESPFKTTQDNATLSNWIDEGF
MPLIYKGEMMDLSRGRAISRENETSHTASATVMKSLLRLNDTMDDSTKTRYKQIVKTSVNSDSSYNQNN
YLNSYSDIAKMKKLMNDSTISKNDLTQQLKIYNDMDRVTYHNKDLDFAFGLSMTSKNIARYENINGENL
KGWHTGAGMSYLYNSDVKHYRDNFWATADMTCLPGTTTLNDMPSTNTKNDKSFVGGTKLNNKYASIGMD
FENQDKTLTAKKSYFILNIDKIVFLGTGIKSTDSSKNPVTSVENRKANGYKLFKDDIEITTSDVNAQET
HSVFLESNIDTKKNIGYHFLDKPKITVKKESHTGKWSEINKSQKKDDKKDEYYEVTQTHNTSDSKYAYV
LYPGLSKSDFKSKNNNVSIVKQDEDFHVIKDNDGVFAGVNYSDNTKSFDINGITVELKEKGMFVIKKKD
DKAYKCSFYNPETTNTASNIESKIFIKGYTITNKSVINSNDAGVNFELTK

SEQ IN NO: 16
MTYRMKKWQKLSTITLLMAGVITLNGGEFRSIDKHQIAVADTNVQTTDYEKLRNIWLDVNYGYDKYDEN
NPDMKKKFEATENEAEKLLKEMKTESDRKYLWESSKDLDTKSADMTRTYRNIEKISEAMKHKNTKLKTD
ENKTKVKDALEWLHKNAYGKEPDKKVADLTSNFKNKTSRNTNLNWWDYEIGTPRALTNTLILLQEDFTD
EEKKKYTAPIKTFAPDSDKILSSVGKSEPAKGGNLVDISKVKLLESIIEEDKDMMKKSIDSFNITVFTY
AQNSATGKERNGFYKDGSYIDHQDVPYTGAYGVVLLEGISQMMPMIKETPFNDSNQNDTTLKSWIDDGF
MPLIYKGEMMDLSRGRAISRENETSHSASATVMKSLLRLSDTMDKSTKAKYKKIVKTSVESDSSYKQTD
YLSSYSDISKMKSLMEDSTISTNGLTQQLKIYNDMDRVTYHNKGLDFAFGLSMTSKNVARYESINGENL
KGWHTGAGMSYLYNSDVKHYRDNFWATADMKRLAGTTTLDNEEPKSTDVKKSSKTFVGGTKFDDQHASI
GMDFENQDKTLTAKKSYFILNDKIVFLGTGIKSTDSSKNPVTTIENRKANDYKLYKDDTQTTNSDNQET
NSLFLESTNSTQNNIGYHFLNESKITVKKESHTGKWSDINKSQKDIQKTDEYYEVTQKHSNTDSKYAYV
LYPGLSKDVFKSKASKVTVVKQEDDFHVVKDNESVWAGINYSDSAKTFEINNTKVEVKAKGMFILTKKD
DNTYECSFYNPESTNSVSDIESKISMTGYSIINKNTSTSNESGVRFELTK

-continued

SEQ ID NO: 49:
IDSKNKPANSDIKFEVTQKSDAVKALKELPKSENVKNIYQDYAVTDVKTDKKGFTHYTLQPSVDGVHAP

DKEVKVHADKSGKVVLINGDTDAKKVKPTNKVTLSKDDAADKAFKAVKIDKIVKAKNLKDKVIKENKVE

IDGDSNKYVYNVELITVTPEISHWKVKIDAQTGEILEKMNLVKEAAETGKGKGVLGDTKDININSIDGG

FSLEDLTHQGKLSAFSFNDQTGQATLITNEDENFVKDEQRAGVDANYYAKQTYDYYKDTFGRESYDNQG

SPIVSLTHVNNYGGQDNIRNNAAWIGDKMIYGDGDGRTFTSLSGANDVVAHELTHGVTQETANLEYKDQ

SGALNESFSDVFGYFVDDEDFLMGEDVYTPGKEGDALRSMSNPEQFGQPAHNIKDYVFTEKDNGGVHTN

S

The nucleic acid fragments of the present invention have the following sequences:

SEQ IN NO: 17
ATGGCAAAAGGTAATTTATTTAAAGCGATTTTAGGTATAGGTGGCGCTGTAGCAGCTGTACTTGTTACACG

TAAAGATAGTCGTGACAAGCTGAAAGCAGAATATAATAAATACAAACAAGATCCTCAAAGCTATAAGATA

ATGCTAAGGATAAAGCGACGCAATTAGGAACAATTGCAAATGAAACAATTAAAGAAGTAAAAACAAATCCG

AAAGAATATGCTAATAGATTAAAAAATAATCCAAAAGCATTTTTCGAAGAAGAAAAATCAAAATTTACCGA

ATATGACAATAAGACTGACGAAAGTATTGAAAAAGGTAAATTTGATGATGAAGGTGGCGCAGCACCAAATA

ATAATTTACGTATCGTCACTGAAGAAGATTTAAAAAAGAATAAAAATGCATTGTCTGATAAAGAATAA

SEQ IN NO: 18
ATGAAAAAATTGGTTTCAATTGTTGGCGCAACATTATTGTTAGCTGGATGTGGATCACAAAATTTAGCACC

ATTAGAAGAAAAAACAACAGATTTAAGAGAAGATAATCATCAACTCAAACTAGATATTCAAGAACTTAATC

AACAAATTAGTGATTCTAAATCTAAAATTAAAGGGCTTGAAAAGGATAAAGAAAATAGTAAAAAAACTGCA

TCTAATAATACGAAAATTAAATTGATGAATGTTACATCAACATACTACGACAAAGTTGCTAAAGCTTTGAA

ATCCTATAACGATATTGAAAAGGATGTAAGTAAAAACAAAGGCGATAAGAATGTTCAATCGAAATTAAATC

AAATTTCTAATGATATTCAAAGTGCTCACACTTCATACAAAGATGCTATCGATGGTTTATCACTTAGTGAT

GATGATAAAAAAACGTCTAAAAATATCGATAAATTAAACTCTGATTTGAATCATGCATTTGATGATATTAA

AAATGGCTATCAAAATAAAGATAAAAAACAACTTACAAAAGGACAACAAGCGTTGTCAAAATTAAACTTAA

ATGCAAAATCATGA

SEQ IN NO: 19
ATGAAAAAATTAGTTACAGGGTTATTAGCATTATCATTATTTTTAGCTGCATGTGGTCAAGATAGTGACCA

ACAAAAAGACAGTAATAAAGAAAAAGATGATAAAGCGAAAACTGAACAACAAGATAAAAAAACAAATGATT

CATCTAAAGATAAGAAAGACAATAAAGATGATAGTAAAGACGTAAACAAAGATAATAAAGATAATAGTGCA

AACGATAACCAGCAACAATCTAATTCAAATGCAACAAACAATGACCAAAATCAAACGAATAATAACCAGTC

AAACAGTGGACAAACGACTAACAATCAAAAATCAAGTTACGTTGCACCATATTATGGACAAAACGCAGCGC

CAGTGGCTCGTCAAATTTATCCATTTAATGGTAATAAATCACAAGCATTACAACAATTGCCTAATTTCCAA

ACAGCTTTAAATGCAGCTAACAACGAAGCAAATAAATTTGGTAATGGTCATAAAGTTTATAATGATTATTC

AATTGAAGAACATAATGGTAACTATAAGTATGTTTTTAGTTTTAAAGACCCAAACGTAAATGGAAAATATT

CAATTGTAACGGTTGATTATACTGGACAAGCAATGGTTACTGATCCAAACTACCAACAATAA

SEQ IN NO: 20
ATGAAAAAAGTAATGGGGATATTATTAGCAAGTACACTTATCTTAGGTGCTTGTGGACATCATCAAGATAG

TGCAAAAAAAGAGAGCACTAGTCACAAAAAGAAAGAAAATGACAATGAAGAATTAAATGAAGAACTTAAAG

AATTTAAAGCAAAAAAAATATGGATATAAAAATTAAAGGCGATACTATTGTTAGTGACAAATTTGAAGCT

AAAATAAAAGAACCGTTTATCATCAATGAAAAAGATGAGAAAAAGAAATATATCGCTTTTAAAATGGAAAT

TACTGCTAAAAAAGACGATAAAGATTTAAATCCATCTTCTATTTCTCATGACTATATTAATATCACTCAAG

```
ATGATAAAAATACAGTAAATAAATTAAGAGATGGTTATCTTTTAAGTGATAAAAATTATAAAGATTGGACA

GAACATAACCAAGATCAAATTAAAAAAGGCAAAACTGCACAAGCCATGTTTATCTATGAGTTAAGAGGTGA

TGGAAACATTAATTTAAATGTCCATAAATACTCAGAAGATAAAACAGTTGATTCTAAATCATTCAAATTTA

GTAAACTTAAAACCGAAGATTTTTCTCATAGAGCGGAAACAAGGGAAGAAGTAGAAAAGAAAGAAAAAGAA

TTTGAAGAAGAGTACAAAAAAGAACAAGAACGAGAGAAAGAAAAAGAAAAGCAAAAGATGACGACCACAG

TGGTTTAGATGAAGTATAA
                                                 SEQ IN NO: 21
ATGAAAAAATGGCAATTTGTTGGTACTACAGCTTTAGGTGCAACACTATTATTAGGTGCTTGTGGTGGCGG

TAATGGTGGCAGTGGTAATAGTGATTTAAAAGGGGAAGCTAAAGGGGATGGCTCATCAACAGTAGCACCAA

TTGTGGAGAAATTAAATGAAAAATGGGCTCAAGATCACTCGGATGCTAAAATCTCAGCAGGACAAGCTGGT

ACAGGTGCTGGTTTCCAAAAATTCATTGCAGGAGATATCGACTTCGCTGATGCTTCTAGACCAATTAAAGA

TGAAGAGAAGCAAAAATTACAAGATAAGAATATCAAATACAAAGAATTCAAAATTGCGCAAGATGGTGTAA

CGGTTGCTGTAAATAAAGAAAATGATTTTGTAGATGAATTAGACAAACAGCAATTAAAAGCAATTTATTCT

GGAAAAGCTAAAACATGGAAAGATGTTAATAGTAAATGGCCAGATAAAAAAATAAATGCTGTATCACCAAA

CTCAAGTCATGGTACTTATGACTTCTTTGAAAATGAAGTAATGAATAAAGAAGATATTAAAGCAGAAAAAA

ATGCTGATACAAATGCTATCGTTTCTTCTGTAACGAAAAACAAAGAGGGAATCGGATACTTTGGATATAAC

TTCTACGTACAAAATAAAGATAAATTAAAAGAAGTTAAAATCAAAGATGAAAATGGTAAAGCAACAGAGCC

TACGAAAAAACAATTCAAGATAACTCTTATGCATTAAGTAGACCATTATTCATTTATGTAAATGAAAAAG

CATTGAAAGATAATAAAGTAATGTCAGAATTTATCAAATTCGTCTTAGAAGATAAAGGTAAAGCAGCTGAA

GAAGGTGGATATGTAGCAGCACCAGAGAAAACATACAAATCACAATTAGATGATTTAAAAGCATTTATTGA

TAAAAATCAAAAATCAGACGACAAGAAATCTGATGATAAAAAGTCTGAAGACAAGAAATAA
                                                 SEQ IN NO: 22
ATGAAAGGTAAATTTTTAAAAGTTAGTTCTTTATTCGTTGCAACTTTGACAACAGCGACACTTGTGAGTTC

TCCAGCAGCAAATGCGTTATCTTCAAAAGCTATGGACAATCATCCAACAAACGCAGACAGACAAACAGC

AAACACCTAAGATTCAAAAAGGCGGTAACCTTAAACCATTAGAACAACGTGAACGCGCTAATGTTATATTA

CCAAATAACGATCGTCACCAAATCACAGATACAACGAATGGTCATTATGCACCTGTTACTTATATTCAAGT

TGAAGCACCTACTGGTACATTTATTGCTTCTGGTGTAGTTGTAGGTAAAGATACACTTTTAACAAATAAAC

ACATCGTAGATGCTACGCACGGTGATCCTCATGCTTTAAAAGCATTCGCTTCTGCAATTAACCAAGACAAT

TATCCTAATGGTGGTTTCACTGCTGAACAAATCACTAAATATTCAGGCGAAGGTGATTTAGCAATCGTTAA

ATTCTCCCCTAATGAGCAAAACAAACATATTGGCGAAGTAGTTAAACCAGCAACAATGAGTAATAATGCTG

AAACACAAGTTAACCAAATATTACTGTAACAGGATATCCTGGTGATAAACCTGTCGCAACAATGTGGGAA

AGTAAAGGAAAAATAACGTACTTAAAAGGTGAAGCAATGCAATATGATTTAAGTACAACTGGTGGTAACTC

AGGTTCACCTGTATTTAATGAAAAAAATGAAGTCATTGGCATTCATTGGGGTGGCGTTCCAAATCAATTTA

ACGGTGCAGTATTTATTAATGAAAATGTACGCAACTTCTTAAAACAAAATATTGAAGATATCAATTTCGCA

AATGATGACCACCCTAACAACCCTGATAATCCAGACAATCCAAATAATCCGGACAATCCTAACAACCCTGA

TAACCCTAACAACCCTGATAATCCAGACAATCCTAATAATCCTGATAACCCTAACAACCCGGACAATCCAA

ATAACCCTGACCAACCTAACAACCCAAATAACCCGGACAATGGCGATAACAATAATTCAGACAACCCTGAC

GCTGCATAA
                                                 SEQ IN NO: 23
ATGAAGCGTACATTAGTATTATTGATTACAGCTATCTTTATACTCGCTGCTTGTGGTAACCATAAGGATGA

CCAGGCTGGAAAAGATAATCAAAAACATAACAATAGTTCAAATCAAGTAAAAGAAATTGCTACGGATAAAA

ATGTACAAGGTGATAACTATCGTACATTGTTACCATTTAAAGAAAGCCAGGCAAGAGGACTTTTACAAGAT

AACATGGCAAATAGTTATAATGGCGGCGACTTTGAAGATGGTTTATTGAACTTAAGTAAAGAAGTGTTTCC
```

```
                                                                -continued
AACAGACAAATATTTGTATCAAGATGGTCAATTTTTGGACAAGAAAACAATTAATGCCTATTTAAATCTTA

AGTATACAAAACGTGAAATCGATAAAATGTCTGAAAAAGATAAAAAAGACAAGAAAGCGAATGAAAATTTA

GGACTTAATCCATCACACGAAGGTGAAACAGATCCTGAAAAGATTGCAGAAAATCACCAGCCTATTTATC

TAACATTTTAGAGCAAGATTTTTATGGTGGTGGAGATACAAAAGGTAAGAATATTAAAGGTATGACGATTG

GTTTAGCTATGAATAGTGTTTATTACTATAAAAAAGAAAAAGATGGACCGACTTTTAGTAAAAAACTAGAT

GATAGCGAAGTTAAAAAGCAAGGTAAACAAATGGCTAGTGAGATATTATCAAGGTTACGTGAAATGATGA

TTTAAAAGATATACCAATTCATTTTGCAATTTATAAGCAATCAAGTGAAGATTCAATCACACCAGGTGAAT

TTATCACTCAAGCGACTGCAGAAAAGAGTCAAACAAAGCTTAATGAATGGCATAATATCAATGAAAAATCA

GCTTTATTACCTTCTTCAACAGCAGCAGATTATGATGAAAATTTAAATAATAATTTCAAGCAATTTAATGA

TAATTTGCAATCATATTTTTCTAATTTCACACAAGCAGTAGGAAAAGTTAAATTTGTTGATAAAAAGCCAC

AACGATTAGTAGTAGATTTACCAATCGATTACTATGGACAAGCTGAAACAATTGGTATTACACAGTACGTT

ACTGAACAAGCGAATAAATATTTCGATAAAATCGATAACTATGAAATTCGGATTAAAGATGGTAACCAACC

ACGTGCTTTAATTAGTAAGACAAAAGATGACAAAGAACCGCAAGTTCATATTTACAGTAATTAA

SEQ IN NO: 24
ATGAGGGAAAATTTTAAGTTACGTAAAATGAAAGTCGGGTTAGTATCTGTTGCAATTACAATGTTATATAT

CATGACAAACGGACAAGCAGAAGCATCAGAGGCTAATGAGAAGCCAAGTACAAATCAAGAATCAAAAGTTG

TTTCACAGACTGAACAAAATTCAAAAGAAACAAAAACAGTAGAATCTAATAAGAACTTTGTTAAATTAGAT

ACTATTAAACCTGGAGCTCAAAAGATAACGGGAACTACTTTACCAAATCACTATGTTTTATTAACAGTTGA

TGGGAAAAGTGCGGATTCAGTAGAAAATGGCGGTTTGGGTTTTGTTGAAGCAAATGACAAAGGAGAATTTG

AGTACCCTTTAAATAATCGTAAAATTGTTCATAATCAAGAAATTGAGGTTTCGTCGTCAAGCCCTGATTTA

GGTGAAGATGAAGAAGATGAAGAGGTGGAAGAAGCTTCAACTGATAAAGCTGGCGTTGAGGAAGAAAGTAC

AGAAGCTAAAGTTACTTACACAACACCGCGATATGAAAAAGCGTATGAAATACCGAAAGAACAACTAAAAG

AAAAAGATGGACATCACCAAGTTTTTATCGAACCTATTACTGAAGGATCAGGTATTATTAAAGGGCATACG

TCTGTAAAAGGTAAAGTTGCTTTATCTATTAATAATAAATTTATTAATTTTGAAGAGAGCGTTAAGGGCGG

AGTTAGTAAAGAAGACACTAAAGCTAGTTCAGATGGTATCTGGATGCCTATTGATGACAAAGGATACTTTA

ACTTTGACTTCAAAACGAAACGTTTCGATAATTTAGAGTTAAAAGAAGGTAATGACATTTCACTAACATTT

GCACCTGATGATGAAGAAGATGCATTAAAACCTTTAATTTTCAAAACTAAAGTAACGAGCTTAGAAGATAT

CGATAAAGCAGAAACTAAATATGACCATACTAAACTCAACAAAGTGAAAGTTTTAGATAATGTTAAAGAAG

ATTTACATGTTGATGAAATATATGGAAGCTTATATCATACAGACAAAGGTAAAGGTATTCTTGATAAAGAA

GGTACTAAAGTAATTAAAGGAAAGACTAAATTCGCGAATGCAGTAGTGAAGGTAGACTCTGAACTAGGTGA

AGCACAATTATTCCCTGATTTACAAGTAAATGAAAAAGGTGAATTTAGCTTTGACTCACATGGTGCTGGTT

TTAGATTACAAAATGGAGAAAAATTAAACTTCACAGTGGTTGATCCTATTACAGGTGACTTGTTAAGTAAT

GAGTTTGTTTCTAAAGAGATTGATATTGAAGAAACACCTGAACAAAAAGCGGATCGTGAGTTTGACGAAAA

ACTTGAAAATACGCCTGCTTACTACAAGTTATACGGCGATAAAATAGTTGGATTCGATACTAACGATTTCC

CGATTACTTGGTTCTATCCATTGGGTGAAAAGAAAGTTGAACGTACAACACCTAAATTAGAAAAATAA

SEQ IN NO: 25
ATGTCTAAAAAGTTAAAAATTATAATTCCTATTATTATTGTCTTATTATTAATAGGTGGAATCGCATGGGG

AGTTTATGCATTTTTTGCAAACACACCGAAAAATACATACTTAAAAAGTGAACAACAAACTGCAAAAATGT

ATAAAGATTATTTTAATGACCGTTTTGAAAACGAAGTGAAGTTCCAAGAAAAGATGAAAGATAATTCATTT

TTATCTTCATTAGAATTAAGCGCAGATGCATCTGATGAAATTGTTAAAGGGCTTGGTATTCCTAAATCTGT

TGTTAATGCTTCGAAAATTAAAATGTCATATGGACATGATCCTAAAAAAGAGAAATCAATGATTAATCTTG

AACCAACAATAGCAGACTCTGCATTAGGGAAATTCCAGTTAGCTGCAGATAAAGATAAGCATTATTTCGAA
```

-continued

TCACCATTATTTAAAGGGAAATATAGTGTTAATAATTCTGATTTATTATCAACTTATTCAAAACTTACAGG

TGAAGATGAAGAAACAGCAAAAGAAAATGGTATTACAAACCAACAACTAAATTTAAATACTCTTTTCAGTA

ATGCTCAAGCACAACAAAGTGACTACAGCAAAATTGCCGAAAAATATTCCGAACTTATTGTCGACAAATTA

GATGACGATAATTTTGATAAAGGTAAAAAAGAAGAAATTAAGGTTAATGGTGAAAAGTACAAAGTTAGACC

TGTCACGTTAACACTTAGCAGAGCTGACACTAAAAAAATTACATTAGCTGTATTAGAAGAAGCTAAAAAGG

ATAAAGACCTTAAAAAATTAATGGAAGAACAAGGTACTACAAAAGACTTTGAAAAAGACATTAAAAAAGCA

ATTGACGATGTCAAAGAAACTAAAAAGGATGAATTTGCTAAAATTCAATCTAAAATTTATACCGAAAAACA

TACGATTGTAAAACGAGAAATTACTATTACGACAAAGAAAATAATAAAACTAAAATCAAAGGTACTAATA

CTTTAGAAGACGATAAGTTAAAACTAGATTACGCACTTGATTTCGATCAAGATAAATACACGTATGCTGAA

GCGAAATATACAATTAAAGGCGTATCTTCTAAGGAAAAAGACAATAAATACAGTGATAAATACGAATTTGG

TAAAAAGACAGAATATGATGAATCAAAAATCAAATTAGATAACCAAGAAAAAGTAGATGGCACAAAACGTC

AAGATAAAGGTAAAATCACTGTCGCGTTAGATAAATATAGCGACGAAAATGAATTCACTTTTGAAAATAAT

ATAGATTCTGACGTAAAAAATAACACTCAGAAATCTACGTTAAATATCGGCATCAAATATGCTGAAGAACC

AATTAATTTCATTTTAAAATCTAGCACAAAATTGAAAGCAGATATTGATTTTGATGATAGTGGTGCGAAAG

ATTTCAATAGTCTATCTTCAAAAGACCGTGAAAAACTTGAAAAAGAAATCGAAAAAAATGGCGGCAAAATG

TTTGAATCAATTTTAAAAAAGGCATCTAAATAA

SEQ IN NO: 26
GTGAGGAAATTTTCAAGATATGCATTTACAAGTATGGCAACAGTAACGTTGCTGAGCTCTTTGACACCTGC

AGCACTAGCGAGTGATACGAATCACAAACCAGCAACTTCAGATATTAATTTTGAAATCACGCAAAAGAGTG

ATGCAGTTAAAGCATTAAAAGAGTTACCTAAATCTGAAAATGTGAAAAATCATTATCAAGATTACTCTGTT

ACAGATGTAAAAACAGATAAGAAAGGATTCACGCATTACACGTTACAACCGAGTGTGGATGGTGTGCATGC

GCCTGACAAAGAAGTGAAAGTGCATGCGGACAAATCGGGTAAAGTCGTTTTAATCAACGGTGATACTGATG

CGAAGAAAGTAAAGCCGACAAATAAAGTGACATTAAGCAAGGATGAAGCGGCTGACAAAGCATTTAACGCA

GTTAAGATTGATAAAAATAAAGCTAAAAACCTCCAAGATGACGTTATCAAAGAAAATAAAGTCGAAATCGA

TGGTGACAGTAATAAATACATTTACAATATTGAATTAATTACAGTAACACCAGAAATTTCACATTGGAAAG

TTAAAATTGATGCAGACACAGGAGCAGTTGTTGAAAAAACGAACTTAGTTAAAGAAGCAGCAGCAACTGGC

ACAGGTAAAGGTGTGCTTGGAGATACAAAAGATATCAATATCAATAGTATTGATGGTGGATTTAGTTTAGA

GGATTTGACGCATCAAGGTAAATTATCAGCATACAATTTTAACGATCAAACAGGTCAAGCGACATTAATTA

CTAATGAAGATGAAAACTTCGTCAAAGATGATCAACGTGCTGGTGTAGATGCGAATTATTATGCTAAACAA

ACATATGATTACTACAAAAATACATTTGGTCGTGAGTCTTACGATAACCATGGTAGTCCAATAGTCTCATT

AACACATGTAAATCATTATGGTGGACAAGATAACAGAAATAACGCTGCATGGATTGGAGACAAAATGATTT

ATGGTGATGGCGATGGCCGCACGTTTACAAATTTATCAGGTGCAAATGACGTAGTAGCACATGAGTTAACA

CATGGCGTGACACAAGAAACGGCGAATTTAGAGTATAAAGATCAATCTGGTGCGTTAAATGAAAGCTTTTC

AGATGTTTTGGATACTTTGTAGATGATGAGGATTTCTTGATGGGTGAAGATGTTTACACACCAGGAAAAG

AGGGAGATGCTTTACGAAGCATGTCAAACCCAGAACAATTTGGTCAACCATCTCATATGAAAGACTATGTA

TACACTGAAAAAGATAACGGTGGTGTGCATACGAATTCTGGCATTCCAAATAAAGCAGCTTATAACGTAAT

TCAAGCAATAGGGAAATCTAAATCAGAACAAATTTACTACCGAGCATTAACGGAATACTTAACAAGTAATT

CAAACTTCAAAGATTGTAAAGATGCATTATACCAAGCGGCTAAAGATTTATATGACGAGCAAACAGCTGAA

CAAGTATATGAAGCATGGAACGAAGTTGGCGTCGAGTAA

SEQ IN NO: 27
ATGAAAAAGAAATTAGGTATGTTACTTCTTGTACCAGCCGTAACTTTATCATTAGCCGCATGTGGGAATGA

TGATGGAAAAGATAAAGATGGCAAGGTAACAATTAAAACGACAGTTTATCCATTGCAATCATTTGCAGAGC

-continued

```
AAATTGGTGGAAAACACGTGAAGGTATCATCAATCTATCCAGCAGGGACAGATTTACATAGCTATGAACCA

ACACAAAAGATATATTAAGTGCAAGCAAGTCAGACTTGTTTATGTATACAGGGGATAATTTAGATCCGGT

TGCTAAGAAAGTTGCATCTACTATTAAAGATAAAGATAAAAAACTGTCTTTAGAAGATAAATTAGATAAAG

CAAAGCTTTTAACTGATCAACACGAACATGGTGAAGAGCATGAACATGAGGGACATGATCATGGGAAAGAA

GAACATCATCATCATGGCGGATATGATCCACACGTATGGTTAGATCCTAAAATTAACCAAACTTTCGCTAA

AGAAATTAAAGATGAATTAGTGAAGAAAGATCCAAAACATAAAGATGACTATGAGAAAAACTACAAAAAAT

TAAACGACGATCTTAAGAAAATTGATAACGATATGAAGCAAGTTACTAAAGATAAGCAAGGTAATGCAGTA

TTCATTTCACATGAATCAATTGGATACTTAGCTGATCGTTATGGTTTTGTTCAAAAAGGTATTCAAAACAT

GAATGCTGAAGATCCATCACAAAAAGAATTGACTAAAATTGTTAAAGAAATTAGAGATAGCAATGCTAAAT

ATATTCTTTACGAAGATAATGTTGCGAATAAAGTGACTGAAACAATTCGTAAAGAAACAGATGCGAAGCCT

TTAAAATTCTACAACATGGAGTCTTTAAATAAAGAACAACAGAAAAAAGATAATATTACCTATCAATCATT

AATGAAATCGAATATTGAAAATATCGGTAAAGCTTTAGCAGTGGTGTTAAAGTGAAAGACGACAAAGCTG

AAAGTAAACACGACAAAGCAATTTCTGATGGGTATTTTAAAGATGAGCAAGTTAAAGACCGTGAATTAAGC

GATTATGCTGGTGAATGGCAATCTGTTTACCCTTACTTAAAAGACGGTACGCTTGATGAAGTGATGGAACA

TAAAGCTGAAAATGATCCGAAGAAATCTGCTAAAGATTTAAAAGCTTATTATGACAAAGGATATAAAACTG

ATATTACTAACATTGATATAAAAGGAAATGAAATTACATTTACTAAAGATGGTACGAAACACACTGGTAAA

TATGAATACAATGGTAAGAAAACATTGAAATATCCTAAAGGTAACCGTGGCGTGAGATTTATGTTTAAATT

GGTCGATGGTAATGATAAAGACTTACCGAAATTCATCCAATTTAGCGATCACAACATTGCACCTAAAAAGG

CAGAACACTTCCATATCTTTATGGGTAATGATAATGACGCGTTATTAAAAGAAATGGATAACTGGCCAACA

TATTATCCTTCAAAATTAAATAAAGACCAAATCAAAGAAGAAATGTTAGCGCATTAA

SEQ IN NO: 28
ATGGTGTTATATATCATTTTGGCAATAATTGTGATTATATTGATTGCTGTAGGTGTATTATTCTATTTACG

TTCAAATAAAAGACAAATAATAGAAAAAGCAATCGAACGTAAAAATGAAATTGAAACGTTACCTTTTGATC

AAAACCTTGCACAATTATCTAAGTTGAATTTAAAAGGTGAAACAAAAACGAAATACGATGCAATGAAAAAG

GACAACGTAGAAAGTACAAATAAGTATCTAGCTCCTGTGGAAGAAAAAATCCATAATGCTGAGGCTTTATT

AGATAAATTTAGTTTCAACGCATCTCAATGTGAAATTGATGATGCAAATGAGTTGATGGATAGTTACGAAC

AAAGCTATCAGCAACAATTAGAAGATGTAAATGAAATTATTGCGTTATACAAAGATAATGATGAATTATAT

GACAAATGTAAGGTTGATTATCGTGAAATGAAACGTGATGTGTTTAGCAAATCGTCATCAATTTGGTGAGGC

AGCAAGTCTTCTTGAAACTGAAATTGAAAATTCGAGCCAAGGTTAGAGCAATATGAAGTACTAAAAGCTG

ATGGTAATTATGTACAAGCGCACAACCATATAGCTGCCTTGAATGAACAAATGAAACAGCTAAGATCTTAT

ATGGAAGAAATACCAGAATTAATTAGAGAAACTCAAAAAGAATTACCTGGTCAATTCCAAGATTTAAAATA

TGGTTGCCGTGATCTTAAAGTTGAAGGGTATGATCTGGATCACGTAAAAGTAGACAGTACATTACAAAGCT

TAAAAACAGAGCTTAGTTTCGTTGAACCATTAATTAGTCGCTTAGAATTAGAAGAAGCTAATGATAAACTA

GCTAATATCAATGATAAGTTAGATGACATGTATGATTTAATTGAACATGAAGTTAAAGCTAAAAATGATGT

CGAAGAAACAAAAGATATCATTACGGATAACTTATTCAAAGCAAAAGACATGAATTATACATTGCAAACAG

AAATTGAATATGTACGTGAAAACTACTATATAAATGAATCTGATGCTCAGAGTGTTCGTCAATTTGAAAAT

GAAATTCAAAGTTTAATTTCTGTATATGATGATATTTTAAAAGAAATGTCTAAATCTGCTGTACGATATAG

CGAGGTTCAGGATAATTTACAATATTTAGAAGATCATGTCACAGTTATTAATGACAAACAAGAAAAGCTAC

AAAATCATCTGATTCAATTGCGTGAAGATGAAGCAGAAGCAGAAGACAATCTGTTACGAGTACAATCGAAG

AAAGAAGAAGTGTATCGTCGATTACTTGCTTCTAACTTAACAAGCGTTCCTGAAAGGTTTATCATCATGAA

AAATGAAATTGATCATGAAGTTCGTGATGTTAACGAACAATTTAGTGAACGTCCAATACACGTTAAACAGT
```

```
TAAAAGATAAAGTGTCTAAAATTGTGATTCAAATGAATACATTTGAAGATGAAGCAAATGATGTTCTTGTT

AATGCTGTTTATGCAGAGAAATTAATTCAATATGGAAATAGATATCGTAAGGACTATAGCAATGTTGATAA

GAGCTTAAATGAAGCTGAACGATTATTTAAAAATAATCGCTATAAGCGTGCGATTGAAATTGCAGAGCAAG

CTCTTGAAAGTGTTGAGCCAGGTGTCACTAAACATATTGAAGAAGAAGTTATTAAGCAATAG
```

SEQ IN NO: 29
```
ATGCCTAAAAATAAAATTTTAATTTATTTGCTATCAACTACGCTCGTATTACCTACTTTAGTTTCACCTAC

CGCTTATGCTGACACACCTCAAAAAGATACTACAGCTAAGACAACATCTCATGATTCCAAAAAATCTACTG

ATGATGAAACTTCTAAGGATACTACAAGTAAAGATATTGATAAAGCAGACAACAATAATACTAGTAACCAA

GACAATAACGACAAAAAAGTTAAAACTATAGACGACAGCACTTCAGACTCTAACAATATCATTGATTTTAT

TTATAAGAATTTACCACAAACCAATATAAACCAATTGCTAACCAAAAATAAATACGATGATAATTACTCAT

TAACAACTTTAATCCAAAACTTATTCAATTTAAATTCGGATATTTCTGATTACGAACAACCTCGTAATGGT

GAAAAGTCAACAAATGATTCGAATAAAAACAGTGATAATAGCATCAAAAATGATACGGATACGCAATCATC

TAAACAAGATAAAGCAGACAATCAAAAAGCACCTAAATCAAACAATACAAAACCAAGTACATCTAATAAGC

AACCAAATTCGCCAAAGCCAACACAACCAAATCAATCAAATAGTCAACCAGCAAGTGACGATAAAGTAAAT

CAAAAATCTTCATCGAAAGATAATCAATCAATGTCAGATTCGGCTTTAGATTCTATTTTGGATCAATACAG

TGAAGATGCAAAGAAAACACAAAAAGATTACGCATCTCAATCTAAAAAAGACAAAAATGAAAAATCTAATA

CAAAGAATCCACAGTTACCAACACAAGATGAATTGAAACATAAATCTAAACCTGCTCAATCATTCAATAAC

GATGTTAATCAAAGGATACACGTGCAACATCACTATTCGAAACAGATCCTAGTATATCTAACAATGATGA

TAGTGGACAATTTAACGTTGTTGACTCAAAAGATACACGTCAATTTGTCAAATCAATTGCTAAAGATGCAC

ACCGCATTGGTCAAGATAACGATATTTATGCGTCTGTCATGATTGCCCAAGCAATCTTAGAATCTGACTCA

GGTCGTAGTGCTTTAGCTAAGTCACCAAACCATAATTTATTCGGTATCAAAGGTGCTTTTGAAGGGAATTC

TGTTCCTTTTAACACATTAGAAGCTGATGGTAATCAATTGTATAGTATTAATGCTGGATTCCGAAAATATC

CAAGCACGAAAGAATCACTAAAAGATTACTCTGACCTTATTAAAAATGGTATTGATGGCAATCGAACAATT

TATAAACCAACATGGAAATCGGAAGCCGATTCTTATAAAGATGCAACATCACACTTATCTAAAACATATGC

TACAGATCCAAACTATGCTAAGAAATTAAACAGTATTATTAAACACTATCAATTAACTCAGTTTGACGATG

AACGTATGCCAGATTTAGATAAATATGAACGTTCTATCAAGGATTATGATGATTCATCAGATGAATTCAAA

CCTTTCCGCGAGGTATCTGATAATATGCCATATCCACATGGCCAATGTACTTGGTACGTATATAACCGTAT

GAAACAATTTGGTACATCTATCTCAGGTGATTTAGGTGATGCACATAATTGGAATAATCGAGCTCAATACC

GTGATTATCAAGTAAGTCATACACCAAAACGTCATGCTGCTGTTGTATTTGAGGCTGGACAATTTGGTGCA

GATCAACATTACGGTCATGTAGCATTTGTTGAAAAAGTTAACAGTGATGGTTCTATCGTTATTTCAGAATC

CAATGTTAAAGGATTAGGTATCATTTCTCATAGAACTATCAATGCAGCTGCCGCTGAAGAATTATCATATA

TTACAGGTAAATAA
```

SEQ IN NO: 30
```
ATGATGAAAAGTCAAAATAAGTATAGTATTCGTAAATTTAGTGTAGGTGCATCTTCCATTTTAATAGCTAC

ATTACTATTTTAAGTGGTGGACAAGCACAAGCAGCTGAGAAGCAAGTGAATATGGGAAATTCACAGGAGG

ATACAGTTACAGCACAATCTATTGGGGATCAACAAACTAGGGAAAATGCTAATTATCAACGTGAAAACGGT

GTTGACGAACAGCAACATACTGAAAATTTAACTAAGAACTTGCATAATGATAAAACAATATCAGAAGAAAA

TCATCGTAAAACAGATGATTTGAATAAAGATCAACTAAAGGATGATAAAAAATCATCGCTTAATAATAAAA

ATATTCAACGTGATACAACAAAAAATAACAATGCTAATCCTAGGGATGTAAATCAAGGGTTAGAACAGGCT

ATTAATGATGGCAAACAAGTAAAGTGGCGTCACAGCAACAGTCAAAAGAGGCAGATAATAGTCAAGACTT

AAACGCTAATAACAATCTACCTTCACAAAGTCGAACAAAGGTATCACCATCATTAAATAAGTCAGATCAAA

CAAGTCAACGAGAAATTGTTAATGAGACAGAAATAGAGAAAGTACAACCGCAACAAAAGAATCAAGCGAAT
```

-continued

GATAAAATTACTGACCACAATTTTAACAATGAACAAGAAGTGAAACCTCAAAAAGACGAAAAAACACTATC
AGTTTCAGATTTAAAAAACAATCAAAAATCACCAGTTGAACCAACAAAGGACAATGACAAGAAAAATGGAT
TAAATTTATTAAAAAGTAGTGCAGTAGCAACGTTACCAAACAAAGGGACAAAGGAACTTACTGCAAAAGCG
AAAGGTGATCAAACGAATAAAGTTGCCAAACAAGGGCAGTATAAAAATCAAGATCCTATAGTTTTAGTGCA
TGGTTTCAATGGGTTTACAGATGATATTAATCCTTCAGTGTTAGCTCATTATTGGGCGGTAATAAAATGA
ACATTCGCCAAGATTTAGAAGAAAATGGTTACAAAGCTTATGAAGCAAGTATAAGTGCTTTTGGAAGTAAC
TATGACCGCGCAGTTGAACTTTATTATTATATCAAAGGCGGTCGTGTAGATTATGGTGCAGCACATGCAGC
AAAATATGGACATGAACGTTATGGAAAAACATACGAAGGAATTTACAAAGACTGGAAACCAGGACAGAAGG
TACACCTTGTTGGACATAGTATGGGTGGTCAAACGATACGTCAACTAGAAGAATTACTGCGTAATGGTAGT
CGTGAAGAAATAGAGTATCAAAAGAAACATAGTGGCGAAATTTCTCCACTATTCAAAGGTAATAATGACAA
TATGATTTCATCAATTACTACTTTAGGAACGCCACATAATGGAACGCATGCTTCAGATTTAGCTGGTAATG
AAGCTTTAGTGAGACAAATTGTATTTGATATCGGTAAAATGTTTGGTAATAAAAATTCAAGAGTAGACTTC
GGGTTGGCTCAATGGGGTCTAAAACAGAAGCCAAATGAATCATATATTGATTATGTCAAACGCGTTAAACA
ATCTAATTTATGGAAATCAAAAGATAATGGATTTTACGATCTGACGCGTGAGGGTGCAACAGATTTAAATC
GTAAAACGTCGTTGAACCCTAACATTGTGTATAAAACATACACTGGTGAAGCAACGCACAAAGCATTAAAT
AGCGATAGACAAAAAGCAGACTTAAATATGTTTTTCCCATTTGTGATTACTGGTAACTTAATCGGTAAAGC
TACTGAAAAGAATGGCGAGAAAACGATGGTTTAGTATCCGTTATTCTTCTCAACATCCATTTAATCAAG
CTTATACAAATGCGACGGATAAAATTCAAAAAGGCATTTGGCAAGTAACGCCTACAAAACATGATTGGGAT
CATGTTGATTTTGTCGGACAAGATAGTTCTGATACAGTGCGCACAAGAGAAGAATTACAAGATTTTTGGCA
TCATTTAGCAGACGATTTAGTGAAAACTGAAAAGGTGACTGATACTAAGCAAGCATAA

SEQ IN NO: 31
ATGACAAATAAAATGAAGAAATGGCAAAAATTATCCACCATTACGTTATTAATGACCGGAGTGATTGCTTT
AAATAATGGTGAATTTAGAAATGTTGATAAACATCAAATCGCTGTGGCTGATACGAATGTTCAAACGCCAG
ATTATGAAAAATTGAAGAAGACGTGGCTCGACGTTAACTACGGTTATGATCAGTATGATGAGAATAATCAA
GATATGAAGAAGAAGTTTGATGCTAAAGAAAAAGAAGCCAAGAAGTTACTTGATGACATGAAAACTGATAC
GAATAGAACATATTTGTGGTCAGGAGCTGAAAACCTTGAAACTAATTCTTCTCACATGACAAAAACCTATC
GTAATATCGAGAAAATCGCAGAATCAATGCAACATAAGAATACGGTATTAAAAACAGTTGAAAACAAGTTG
AAAATAAAAGAAGCCCTAGATTGGATGCACAAAAATGTTTATGGCAAGAATCCTTCTCAAAAAGTCGAGGA
TTTAACTAAAAATCGTAAGGGGCAAACTACACCCAAGAATAACTCATTGAATTGGTGGGATTATGAAATTG
GTACGCCAAGAGCATTAACAAATACACTACTTCTAATGGATGATATGCTCACTAAAGATGAAATGAAAAAT
TATTCAAAACCTATTAGTACATATGCACCATCCAGTGACAAAATTTTATCTTCTGTTGGTGAATCAGAAGA
TGCTAAAGGTGGAAATTTAGTGGACATTTCTAAAGTAAAACTTTTAGAAAGTGTTATTGAAGAAGATGTAG
ATATGTTGAAAAAGTCTATAGATTCTTTTAATAAAGTGTTCACTTATGTTCAAGATTCTGCCACTGGTAAA
GGTCGCAATGGATTCTATAAAGATGGCTCTTACATTGATCATCAAGATGTCCCTTACACTGGTGCTTATGG
TGTTGTACTATTAGAGGGTATTTCTCAAATGATGCCGATGATAAAAGAATCTCCTTTTAAAACTACACAAG
ATAATGCTACATTAAGCAATTGGATTGACGAAGGGTTTATGCCATTAATCTATAAAGGTGAAATGATGGAT
TTATCACGAGGTAGAGCTATCAGTCGTGAAATGAAACGAGTCATACAGCGTCAGCGACTGTAATGAAATC
ATTGTTGAGATTGAATGATACCATGGATGATTCAACAAAAACTAGATATAAGCAAATCGTTAAAACTTCTG
TTAATTCTGATTCAAGTTACAACCAAAATAATTATTTAAATTCATATTCAGACATAGCTAAAATGAAAAAG
TTAATGAATGATAGTACTATTTCTAAAAACGATTTAACACAGCAACTTAAAATATATAATGACATGGATCG
TGTCACCTATCACAATAAAGACCTGGACTTTGCATTTGGTTTAAGTATGACATCGAAAAACATCGCACGAT

-continued

ACGAAAATATCAACGGAGAGAACTTAAAAGGTTGGCACACCGGTGCAGGCATGTCTTATTTATATAACAGC
GATGTCAAACACTATCGCGATAACTTCTGGGCAACAGCCGATATGACTTGTCTTCCAGGCACTACTACTTT
AAATGATATGCCATCTACTAATACTAAGAATGATAAATCTTTTGTTGGCGGGACAAAATTAAATAATAAAT
ACGCAAGCATCGGTATGGATTTTGAAAATCAGGACAAAACTTTAACTGCCAAAAAATCATATTTCATATTA
AACGATAAAATTGTCTTCTTAGGAACTGGCATTAAAAGTACTGATTCATCAAAGAATCCAGTTACAAGTGT
TGAAAATCGCAAAGCAAATGGGTATAAATTATTTAAAGATGATATTGAAATTACCACTTCAGATGTTAATG
CTCAGGAAACCCATTCAGTCTTTTTAGAGTCCAACGATACTAAAAAGAACATTGGTTATCATTTCTTAGAC
AAGCCAAAAATAACTGTAAAAAAAGAAAGTCATACTGGTAAGTGGAGTGAAATTAATAAAAGTCAAAAAA
AGATGACAAAAAGATGAGTATTATGAAGTAACTCAAACACATAATACATCTGACAGTAAATATGCATATG
TTTTGTATCCTGGTTTATCAAAAAGTGATTTTAAATCGAAGAATAATAATGTAAGTATTGTTAAACAAGAT
GAAGATTTTCATGTGATAAAAGATAATGATGGCGTATTTGCTGGGGTTAATTATAGTGATAATACTAAATC
TTTTGATATAAACGGAATTACTGTTGAATTAAAAGAAAAAGGCATGTTTGTAATTAAAAAGAAAGATGATA
AAGCATATAAATGTAGCTTCTATAATCCTGAAACTACAAATACCGCTTCAAATATAGAATCAAAAATTTTT
ATTAAAGGTTACACCATAACTAATAAAAGTGTCATAAACTCTAATGATGCTGGTGTAAACTTTGAATTAAC
TAAATAA

SEQ IN NO: 32

ATGACATATAGAATGAAGAAATGGCAAAAATTGTCCACCATTACGTTATTAATGGCTGGTGTGATTACTTT
GAATGGTGGTGAATTCAGAAGTATTGATAAACATCAAATCGCTGTGGCTGATACGAATGTTCAAACGACAG
ATTATGAAAAGTTGAGGAACATATGGCTGGACGTTAACTATGGTTATGATAAGTATGATGAGAATAATCCA
GATATGAAGAAGAAGTTTGAGGCTACGGAGAATGAGGCAGAGAAATTACTCAAGGAAATGAAAACTGAAAG
TGATAGGAAATACTTGTGGGAAAGCTCAAAAGATTTAGATACGAAGTCTGCGGATATGACTCGTACCTATC
GTAATATTGAGAAAATCTCAGAAGCGATGAAACATAAAAATACTAAATTAAAAACAGATGAAAACAAGACA
AAAGTAAAAGATGCACTTGAGTGGCTGCATAAAAATGCATATGGAAAAGAACCAGATAAAAAAGTTGCTGA
TTTGACCTCAAACTTTAAAAATAAAACTTCTAGAAATACCAACTTAAATTGGTGGGATTATGAAATTGGAA
CACCTAGAGCATTAACAAATACGCTTATACTCTTACAAGAAGATTTCACTGATGAAGAAAGAAAAAATAT
ACAGCTCCTATTAAAACTTTCGCCCCAGATAGTGACAAAATATTATCTTCTGTAGGAAAATCTGAACCTGC
TAAAGGCGGAAATTTAGTAGACATTTCTAAAGTAAAACTTTTAGAAAGTATTATCGAAGAAGACAAAGATA
TGATGAAAAAGTCTATAGATTCATTTAATACAGTCTTCACTTACGCGCAAAATTCTGCCACTGGAAAAGAA
CGTAATGGATTCTATAAAGATGGCTCTTACATTGATCATCAAGACGTCCCATACACTGGTGCTTATGGCGT
TGTACTATTAGAGGGTATTTCTCAAATGATGCCGATGATAAAAGAAACACCTTTTAATGATAGTAACCAAA
ATGATACAACCTTAAAATCATGGATTGACGACGGATTTATGCCACTCATTTATAAAGGTGAAATGATGGAT
TTATCAAGAGGTAGAGCTATCAGTCGTGAAATGAAACGAGTCACTCAGCATCTGCAACAGTAATGAAATC
ATTGTTGAGATTGAGTGATACCATGGATAAGTCTACAAAAGCTAAATATAAAAGATTGTCAAGACTTCAG
TAGAGTCAGATTCAAGTTATAAACAAACCGATTATTTAAGCTCTTATTCGGATATAAGCAAATGAAGTCT
TTAATGGAAGACAGCACTATTTCTACTAACGGTTTAACACAACAACTTAAAATATATAATGACATGGATCG
TGTCACCTATCACAATAAAGGCTTAGACTTTGCATTTGGTTTAAGTATGACGTCGAAAAACGTCGCACGTT
ACGAAAGTATCAACGGAGAGAACTTAAAAGGTTGGCACACTGGTGCTGGAATGTCTTATTTATACAATAGC
GATGTGAAACACTACCGTGATAACTTCTGGGCGACAGCTGATATGAAACGTTTAGCAGGTACTACAACTTT
AGATAATGAAGAACCTAAAGTACGGATGTTAAAAGTCTAGTAAAACTTTTGTAGGAGGAACAAAATTCG
ATGACCAACATGCTAGTATCGGAATGGATTTTGAAAATCAGGACAAAACTTTAACTGCCAAAAAATCATAT
TTCATATTAAACGATAAAATTGTCTTCTTAGGAACTGGCATTAAAAGTACTGATTCATCAAAGAATCCAGT

-continued

TACAACGATTGAAAATCGCAAAGCGAATGATTATAAATTATATAAAGATGATACGCAAACAACCAATTCCG

ATAATCAGGAAACCAATTCCCTCTTTTTAGAGTCAACGAATAGCACTCAAAACAATATAGGTTATCATTTT

TTAAACGAATCGAAAATAACTGTAAAAAAAGAAAGTCATACTGGTAAGTGGAGTGATATAAATAAAAGCCA

AAAGGATATACAAAAAACTGATGAGTATTATGAAGTAACTCAAAAGCATTCTAATACAGATAGTAAATATG

CATATGTGTTGTATCCAGGCTTATCTAAAGATGTCTTTAAATCCAAAGCAAGCAAAGTAACTGTCGTTAAG

CAAGAAGATGACTTCCACGTTGTGAAAGATAATGAATCGGTTTGGGCTGGTATCAATTATAGTGATAGCGC

TAAAACTTTTGAAATTAATAACACTAAAGTCGAAGTTAAAGCCAAAGGAATGTTTATTCTTACAAAGAAAG

ATGATAACACTTATGAATGTAGCTTCTATAATCCCGAATCTACAAATTCCGTTTCAGATATTGAATCTAAA

ATTTCAATGACTGGATACTCTATTATAAACAAAAATACGTCGACTTCTAATGAATCCGGCGTACGCTTTGA

ATTAACTAAATAA

SEQ IN NO: 33

AUGGCAAAGGUAAUUUAUUUAAAGCGAUUUUAGGUAUAGGUGGCGCUGUAGCAGCUGUACUUGUUACACG

UAAAGAUAGUCGUGACAAGCUGAAAGCAGAAUAUAAUAAAUACAAACAAGAUCCUCAAAGCUAUAAAGAUA

AUGCUAAGGAUAAAGCGACGCAAUUAGGAACAAUUGCAAAUGAAACAAUUAAAGAAGUAAAAACAAAUCCG

AAAGAAUAUGCUAAUAGAUUAAAAAAUAAUCCAAAAGCAUUUUUCGAAGAAGAAAAAUCAAAAUUUACCGA

AUAUGACAAUAAGACUGACGAAAGUAUUGAAAAAGGUAAAUUUGAUGAUGAAGGUGGCGCAGCACCAAAUA

AUAAUUUACGUAUCGUCACUGAAGAAGAUUUAAAAAAGAAUAAAAAUGCAUUGUCUGAUAAAGAAUAA

SEQ IN NO: 34

AUGAAAAAAUUGGUUUCAAUUGUUGGCGCAACAUUAUUGUUAGCUGGAUGUGGAUCACAAAAAUUUAGCACC

AUUAGAAGAAAAAACAACAGAUUUAAGAGAAGAUAAUCAUCAACUCAAACUAGAUAUUCAAGAACUUAAUC

AACAAAUUAGUGAUUCUAAAUCUAAAAUUAAAGGGCUUGAAAAGGAUAAAGAAAAUAGUAAAAAAACUGCA

UCUAAUAAUACGAAAAUUAAAUUGAUGAAUGUUACAUCAACAUACUACGACAAAGUUGCUAAAGCUUUGAA

AUCCUAUAACGAUAUUGAAAAGGAUGUAAGUAAAAACAAAGGCGAUAAGAAUGUUCAAUCGAAAUUAAAUC

AAAUUUCUAAUGAUAUUCAAAGUGCUCACACUUCAUACAAAGAUGCUAUCGAUGGUUUAUCACUUAGUGAU

GAUGAUAAAAAAACGUCUAAAAAUAUCGAUAAAUUAAACUCUGAUUUGAAUCAUGCAUUUGAUGAUAUUAA

AAAUGGCUAUCAAAAUAAAGAUAAAAAACAACUUACAAAAGGACAACAAGCGUUGUCAAAAUUAAACUUAA

AUGCAAAAUCAUGA

SEQ IN NO: 35

AUGAAAAAAUUAGUUACAGGGUUAUUAGCAUUAUCAUUAUUUUUAGCUGCAUGUGGUCAAGAUAGUGACCA

ACAAAAAGACAGUAAUAAAGAAAAAGAUGAUAAAGCGAAAACUGAACAACAAGAUAAAAAAACAAAUGAUU

CAUCUAAAGAUAAGAAAGACAAUAAAGAUGAUAGUAAAGACGUAAACAAAGAUAAUAAAGAUAAUAGUGCA

AACGAUAACCAGCAACAAUCUAAUUCAAAUGCAACAAACAAUGACCAAAAUCAAACGAAUAAUAACCAGUC

AAACAGUGGACAAACGACUAACAAUCAAAAAUCAAGUUACGUUGCACCAUAUUAUGGACAAAACGCAGCGC

CAGUGGCUCGUCAAAUUUAUCCAUUUAAUGGUAAUAAAUCACAAGCAUUACAACAAUUGCCUAAUUUCCAA

ACAGCUUUAAAUGCAGCUAACAACGAAGCAAAUAAAUUUGGUAAUGGUCAUAAAGUUUAUAAUGAUUAUUC

AAUUGAAGAACAUAAUGGUAACUAUAAGUAUGUUUUUAGUUUUAAAGACCCAAACGUAAAUGGAAAAUAUU

CAAUUGUAACGGUUGAUUAUACUGGACAAGCAAUGGUUACUGAUCCAAACUACCAACAAUAA

SEQ IN NO: 36

AUGAAAAAGUAAUGGGGAUAUUAUUAGCAAGUACACUUAUCUUAGGUGCUUGUGGACAUCAUCAAGAUAG

UGCAAAAAAGAGAGCACUAGUCACAAAAAGAAAGAAAAAUGACAAUGAAGAAUUAAAUGAAGAACUUAAAG

AAUUUAAAGCAAAAAAAUAUGGAUAUAAAAAUUAAAGGCGAUACUAUUGUUAGUGACAAAUUUGAAGCU

AAAAUAAAAGAACCGUUUAUCAUCAAUGAAAAAGAUGAGAAAAAGAAAUAUCGCUUUUAAAAUGGAAAU

UACUGCUAAAAAAGACGAUAAAGAUUUAAAUCCAUCUUCUAUUUCUCAUGACUAUAUUAAUAUCACUCAAG

-continued

AUGAUAAAAAUACAGUAAAUAAAUUAAGAGAUGGUUAUCUUUUAAGUGAUAAAAAUUAUAAAGAUUGGACA

GAACAUAACCAAGAUCAAAUUAAAAAAGGCAAAACUGCACAAGCCAUGUUUAUCUAUGAGUUAAGAGGUGA

UGGAAACAUUAAUUUAAAUGUCCAUAAAUACUCAGAAGAUAAAACAGUUGAUUCUAAAUCAUUCAAAUUUA

GUAAACUUAAAACCGAAGAUUUUUCUCAUAGAGCGGAAACAAGGGAAGAAGUAGAAAAGAAAGAAAAAGAA

UUUGAAGAAGAGUACAAAAAAGAACAAGAACGAGAGAAAGAAAAAGAAAAGCAAAAGAUGACGACCACAG

UGGUUUAGAUGAAGUAUAA

SEQ IN NO: 37

AUGAAAAAAUGGCAAUUUGUUGGUACUACAGCUUUAGGUGCAACACUAUUAUUAGGUGCUUGUGGUGGCGG

UAAUGGUGGCAGUGGUAAUAGUGAUUUAAAAGGGGAAGCUAAAGGGGAUGGCUCAUCAACAGUAGCACCAA

UUGUGGAGAAAUUAAAUGAAAAAUGGGCUCAAGAUCACUCGGAUGCUAAAAUCUCAGCAGGACAAGCUGGU

ACAGGUGCUGGUUUCCAAAAAUUCAUUGCAGGAGAUAUCGACUUCGCUGAUGCUUCUAGACCAAUUAAAGA

UGAAGAGAAGCAAAAAUUACAAGAUAAGAAUAUCAAAUACAAAGAAUUCAAAAUUGCGCAAGAUGGUGUAA

CGGUUGCUGUAAAUAAAGAAAAUGAUUUUGUAGAUGAAUUAGACAAACAGCAAUUAAAAGCAAUUUAUUCU

GGAAAAGCUAAAACAUGGAAAGAUGUUAAUAGUAAAUGGCCAGAUAAAAAAAUAAAUGCUGUAUCACCAAA

CUCAAGUCAUGGUACUUAUGACUUCUUUGAAAAUGAAGUAAUGAAUAAAGAAGAUAUUAAAGCAGAAAAAA

AUGCUGAUACAAAUGCUAUCGUUUCUUCUGUAACGAAAAACAAAGAGGGAAUCGGAUACUUUGGAUAUAAC

UUCUACGUACAAAAUAAAGAUAAAUUAAAAGAAGUUAAAAUCAAAGAUGAAAAUGGUAAAGCAACAGAGCC

UACGAAAAAAACAAUUCAAGAUAACUCUUAUGCAUUAAGUAGACCAUUAUUCAUUUAUGUAAAUGAAAAAG

CAUUGAAAGAUAAUAAAGUAAUGUCAGAAUUUAUCAAAUUCGUCUUAGAAGAUAAAGGUAAAGCAGCUGAA

GAAGGUGGAUAUGUAGCAGCACCAGAGAAAACAUACAAAUCACAAUUAGAUGAUUUAAAAGCAUUUAUUGA

UAAAAAUCAAAAAUCAGACGACAAGAAAUCUGAUGAUAAAAAGUCUGAAGACAAGAAAUAA

SEQ IN NO: 38

AUGAAAGGUAAAUUUUUAAAAGUUAGUUCUUUAUUCGUUGCAACUUUGACAACAGCGACACUUGUGAGUUC

UCCAGCAGCAAAUGCGUUAUCUUCAAAAGCUAUGGACAAUCAUCCACAACAAACGCAGACAGACAAACAGC

AAACACCUAAGAUUCAAAAAGGCGGUAACCUUAAACCAUUAGAACAACGUGAACGCGCUAAUGUUAUAUUA

CCAAAUAACGAUCGUCACCAAAUCACAGAUACAACGAAUGGUCAUUAUGCACCUGUUACUUAUAUUCAAGU

UGAAGCACCUACUGGUACAUUUAUUGCUUCUGGUGUAGUUGUAGGUAAAGAUACACUUUUAACAAAUAAAC

ACAUCGUAGAUGCUACGCACGGUGAUCCUCAUGCUUUAAAAGCAUUCGCUUCUGCAAUUAACCAAGACAAU

UAUCCUAAUGGUGGUUUCACUGCUGAACAAAUCACUAAAUAUUCAGGCGAAGGUGAUUUAGCAAUCGUUAA

AUUCUCCCCUAAUGAGCAAAACAAACAUAUUGGCGAAGUAGUUAAACCAGCAACAAUGAGUAAUAAUGCUG

AAACACAAGUUAACCAAAAUAUUACUGUAACAGGAUAUCCUGGUGAUAAACCUGUCGCAACAAUGUGGGAA

AGUAAAGGAAAAAUAACGUACUUAAAAGGUGAAGCAAUGCAAUAUGAUUUAAGUACAACUGGUGGUAACUC

AGGUUCACCUGUAUUUAAUGAAAAAAAUGAAGUCAUUGGCAUUCAUUGGGGUGGCGUUCCAAAUCAAUUUA

ACGGUGCAGUAUUUAUUAAUGAAAAUGUACGCAACUUCUUAAAACAAAAUAUUGAAGAUAUCAAUUUCGCA

AAUGAUGACCACCCUAACAACCCUGAUAAUCCAGACAAUCCAAAUAAUCCGGACAAUCCUAACAACCCUGA

UAACCCUAACAACCCUGAUAAUCCAGACAAUCCUAAUAAUCCUGAUAACCCUAACAACCCGGACAAUCCAA

AUAACCCUGACCAACCUAACAACCCAAAUAACCCGGACAAUGGCGAUAACAAUAAUUCAGACAACCCUGAC

GCUGCAUAA

SEQ IN NO: 39

AUGAAGCGUACAUUAGUAUUAAUUGAUUACAGCUAUCUUUAUACUCGCUGCUUGUGGUAACCAUAAGGAUGA

CCAGGCUGGAAAAGAUAAUCAAAAACAUAACAAUAGUUCAAAUCAAGUAAAAGAAAUUGCUACGGAUAAAA

AUGUACAAGGUGAUAACUAUCGUACAUUGUUACCAUUUAAAGAAAGCCAGGCAAGAGGACUUUUACAAGAU

```
AACAUGGCAAAUAGUUAUAAUGGCGGCGACUUUGAAGAUGGUUUAUUGAACUUAAGUAAAGAAGUGUUUCC

AACAGACAAAUAUUUGUAUCAAGAUGGUCAAUUUUUGGACAAGAAAACAAUUAAUGCCUAUUUAAAUCUUA

AGUAUACAAAACGUGAAAUCGAUAAAAUGUCUGAAAAAGAUAAAAAAGACAAGAAAGCGAAUGAAAAUUUA

GGACUUAAUCCAUCACACGAAGGUGAAACAGAUCCUGAAAAGAUUGCAGAAAAAUCACCAGCCUAUUUAUC

UAACAUUUUAGAGCAAGAUUUUUAUGGUGGUGGAGAUACAAAAGGUAAGAAUAUUAAAGGUAUGACGAUUG

GUUUAGCUAUGAAUAGUGUUUAUUACUAUAAAAAAGAAAAAGAUGGACCGACUUUUAGUAAAAAACUAGAU

GAUAGCGAAGUUAAAAAGCAAGGUAAACAAAUGGCUAGUGAGAUAUUAUCAAGGUUACGUGAAAAUGAUGA

UUUAAAAGAUAUACCAAUUCAUUUUGCAAUUUAUAAGCAAUCAAGUGAAGAUUCAAUCACACCAGGUGAAU

UUAUCACUCAAGCGACUGCAGAAAAGAGUCAAACAAAGCUUAAUGAAUGGCAUAAUAUCAAUGAAAAAUCA

GCUUUAUUACCUUCUUCAACAGCAGCAGAUUAUGAUGAAAAUUUAAAAUAAUAAUUUCAAGCAAUUUAAUGA

UAAUUUGCAAUCAUAUUUUUCUAAUUUCACACAAGCAGUAGGAAAAGUUAAAUUUGUUGAUAAAAAGCCAC

AACGAUUAGUAGUAGAUUUACCAAUCGAUUACUAUGGACAAGCUGAAACAAUUGGUAUUACACAGUACGUU

ACUGAACAAGCGAAUAAAUAUUUCGAUAAAAUCGAUAACUAUGAAAUUCGGAUUAAAGAUGGUAACCAACC

ACGUGCUUUAAUUAGUAAGACAAAAGAUGACAAAGAACCGCAAGUUCAUAUUUACAGUAAUUAA

SEQ IN NO: 40
AUGAGGGAAAAUUUUAAGUUACGUAAAAUGAAAGUCGGGUUAGUAUCUGUUGCAAUUACAAUGUUAUAUAU

CAUGACAAACGGACAAGCAGAAGCAUCAGAGGCUAAUGAGAAGCCAAGUACAAAUCAAGAAUCAAAAGUUG

UUUCACAGACUGAACAAAAUUCAAAAGAAACAAAAACAGUAGAAUCUAAUAAGAACUUUGUUAAAUUAGAU

ACUAUUAAACCUGGAGCUCAAAAGAUAACGGGAACUACUUUACCAAAUCACUAUGUUUUAUUAACAGUUGA

UGGGAAAAGUGCGGAUUCAGUAGAAAAUGGCGGUUUGGGUUUUGUUGAAGCAAAUGACAAAGGAGAAUUUG

AGUACCCUUUAAAUAAUCGUAAAAUUGUUCAUAAUCAAGAAAUUGAGGUUUCGUCGUCAAGCCCUGAUUUA

GGUGAAGAUGAAGAAGAUGAAGAGGUGGAAGAAGCUUCAACUGAUAAAGCUGGCGUUGAGGAAGAAAGUAC

AGAAGCUAAAGUUACUUACACAACACCGCGAUAUGAAAAAGCGUAUGAAAUACCGAAAGAACAACUAAAAG

AAAAAGAUGGACAUCACCAAGUUUUUAUCGAACCUAUUACUGAAGGAUCAGGUAUUAUUAAAGGGCAUACG

UCUGUAAAGGUAAAGUUGCUUUAUCUAUUAAUAAUAAAUUUAUUAAUUUUGAAGAGAGCGUUAAGGGCGG

AGUUAGUAAAGAAGACACUAAAGCUAGUUCAGAUGGUAUCUGGAUGCCUAUUGAUGACAAAGGAUACUUUA

ACUUUGACUUCAAAACGAAACGUUUCGAUAAUUUAGAGUUAAAAGAAGGUAAUGACAUUUCACUAACAUUU

GCACCUGAUGAUGAAGAAGAUGCAUUAAAACCUUUAAUUUUCAAAACUAAAGUAACGAGCUUAGAAGAUAU

CGAUAAAGCAGAAACUAAAUAUGACCAUACUAAACUCAACAAAGUGAAAGUUUUAGAUAAUGUUAAAGAAG

AUUUACAUGUUGAUGAAAUAUAUGGAAGCUUUAUCAUACAGACAAAGGUAAAGGUAUUCUUGAUAAAGAA

GGUACUAAAGUAAUUAAAGGAAAGACUAAAUUCGCGAAUGCAGUAGUGAAGGUAGACUCUGAACUAGGUGA

AGCACAAUUAUUCCCUGAUUUACAAGUAAAUGAAAAGGUGAAUUUAGCUUUGACUCACAUGGUGCUGGUU

UUAGAUUACAAAAUGGAGAAAAAUUAAACUUCACAGUGGUUGAUCCUAUUACAGGUGACUUGUUAAGUAAU

GAGUUUGUUUCUAAAGAGAUUGAUAUUGAAGAAACACCUGAACAAAAAGCGGAUCGUGAGUUUGACGAAAA

ACUUGAAAAUACGCCUGCUUACUACAAGUUAUACGGCGAUAAAAUAGUUGGAUUCGAUACUAACGAUUUCC

CGAUUACUUGGUUCUAUCCAUGGGUGAAAAGAAAGUUGAACGUACAACACCUAAAUUAGAAAAAUAA

SEQ IN NO: 41
AUGUCUAAAAGUUAAAAUUAUAAUUCCUAUUAUUAUUGUCUUAUUAUUAAUAGGUGGAAUCGCAUGGGG

AGUUUAUGCAUUUUUUGCAAACACACCGAAAAAUACAUACUUAAAAAGUGAACAACAAACUGCAAAAAUGU

AUAAAGAUUAUUUUAAUGACCGUUUUGAAAACGAAGUGAAGUUCCAAGAAAAGAUGAAAGAUAAUUCAUUU

UUAUCUUCAUUAGAAUUAAGCGCAGAUGCAUCUGAUGAAAUUGUUAAAGGGCUUGGUAUUCCUAAAUCUGU

UGUUAAUGCUUCGAAAAUUAAAAUGUCAUAUGGACAUGAUCCUAAAAAAGAGAAAUCAAUGAUUAAUCUUG
```

-continued

AACCAACAAUAGCAGACUCUGCAUUAGGGAAAUUCCAGUUAGCUGCAGAUAAAGAUAAGCAUUAUUUCGAA

UCACCAUUAUUUAAAGGGAAAUAUAGUGUUAAUAAUUCUGAUUUAUUAUCAACUUAUUCAAAACUUACAGG

UGAAGAUGAAGAAACAGCAAAAGAAAAUGGUAUUACAAACCAACAACUAAAUUUAAAUACUCUUUUCAGUA

AUGCUCAAGCACAACAAAGUGACUACAGCAAAAUUGCCGAAAAAUAUUCCGAACUUAUUGUCGACAAAUUA

GAUGACGAUAAUUUUGAUAAAGGUAAAAAAGAAGAAAUUAAGGUUAAUGGUGAAAAGUACAAAGUUAGACC

UGUCACGUUAACACUUAGCAGAGCUGACACUAAAAAAAAUUACAUUAGCUGUAUUAGAAGAAGCUAAAAAGG

AUAAAGACCUUAAAAAAUUAAUGGAAGAACAAGGUACUACAAAAGACUUUGAAAAAGACAUUAAAAAAGCA

AUUGACGAUGUCAAAGAAACUAAAAAGGAUGAAUUUGCUAAAAUUCAAUCUAAAAUUUAUACCGAAAAACA

UACGAUUGUAAAACGAGAAAUUACUAUUACAGACAAAGAAAAUAAUAAAACUAAAAUCAAAGGUACUAAUA

CUUUAGAAGACGAUAAGUUAAAACUAGAUUACGCACUUGAUUUCGAUCAAGAUAAAUACACGUAUGCUGAA

GCGAAAUAUACAAUUAAAGGCGUAUCUUCUAAGGAAAAAGACAAUAAAUACAGUGAUAAAUACGAAUUUGG

UAAAAAGACAGAAUAUGAUGAAUCAAAAAUCAAAUUAGAUAACCAAGAAAAAGUAGAUGGCACAAAACGUC

AAGAUAAAGGUAAAAUCACUGUCGCGUUAGAUAAAUAUAGCGACGAAAAUGAAUUCACUUUUGAAAAUAAU

AUAGAUUCUGACGUAAAAAAUAACACUCAGAAAUCUACGUUAAAUAUCGGCAUCAAAUAUGCUGAAGAACC

AAUUAAUUUCAUUUUAAAAUCUAGCACAAAAUUGAAAGCAGAUAUUGAUUUUGAUGAUAGUGGUGCGAAAG

AUUUCAAUAGUCUAUCUUCAAAAGACCGUGAAAAACUUGAAAAAGAAAUCGAAAAAAAUGGCGGCAAAAUG

UUUGAAUCAAUUUUAAAAAAGGCAUCUAAAUAA

SEQ IN NO: 42

GUGAGGAAAUUUUCAAGAUAUGCAUUUACAAGUAUGGCAACAGUAACGUUGCUGAGCUCUUUGACACCUGC

AGCACUAGCGAGUGAUACGAAUCACAAACCAGCAACUUCAGAUAUUAAUUUUGAAAUCACGCAAAAGAGUG

AUGCAGUUAAAGCAUUAAAAGAGUUACCUAAAUCUGAAAAUGUGAAAAAUCAUUAUCAAGAUUACUCUGUU

ACAGAUGUAAAAACAGAUAAGAAAGGAUUCACGCAUUACACGUUACAACCGAGUGUGGAUGGUGUGCAUGC

GCCUGACAAAGAAGUGAAAGUGCAUGCGGACAAAUCGGGUAAAGUCGUUUUAAUCAACGGUGAUACUGAUG

CGAAGAAAGUAAAGCCGACAAAUAAAGUGACAUUAAGCAAGGAUGAAGCGGCUGACAAAGCAUUUAACGCA

GUUAAGAUUGAUAAAAAUAAAGCUAAAAACCUCCAAGAUGACGUUAUCAAAGAAAAUAAAGUCGAAAUCGA

UGGUGACAGUAAUAAAUACAUUUACAAUAUUGAAUUAAUUACAGUAACACCAGAAAUUUCACAUUGGAAAG

UUAAAAUUGAUGCAGACACAGGAGCAGUUGUUGAAAAAACGAACUUAGUUAAAGAAGCAGCAGCAACUGGC

ACAGGUAAAGGUGUGCUUGGAGAUACAAAAGAUAUCAAUAUCAAUAGUAUUGAUGGUGGAUUUAGUUUAGA

GGAUUUGACGCAUCAAGGUAAAUUAUCAGCAUACAAUUUUAACGAUCAAACAGGUCAAGCGACAUUAAUUA

CUAAUGAAGAUGAAAACUUCGUCAAAGAUGAUCAACGUGCUGGUGUAGAUGCGAAUUAUUAUGCUAAACAA

ACAUAUGAUUACUACAAAAAUACAUUUGGUCGUGAGUCUUACGAUAACCAUGGUAGUCCAAUAGUCUCAUU

AACACAUGUAAAUCAUUAUGGUGGACAAGAUAACAGAAAUAACGCUGCAUGGAUUGGAGACAAAAUGAUUU

AUGGUGAUGGCGAUGGCCGCACGUUUACAAAUUUAUCAGGUGCAAAUGACGUAGUAGCACAUGAGUUAACA

CAUGGCGUGACACAAGAAACGGCGAAUUUAGAGUAUAAAGAUCAAUCUGGUGCGUUAAAUGAAAGCUUUUC

AGAUGUUUUUGGAUACUUUGUAGAUGAUGAGGAUUUCUUGAUGGGUGAAGAUGUUUACACACCAGGAAAAG

AGGGAGAUGCUUUACGAAGCAUGUCAAACCCAGAACAAUUUGGUCAACCAUCUCAUAUGAAAGACUAUGUA

UACACUGAAAAGAUAACGGUGGUGUGCAUACGAAUUCUGGCAUUCCAAAUAAAGCAGCUUUAUAACGUAAU

UCAAGCAAUAGGGAAAUCUAAAUCAGAACAAAUUUACUACCGAGCAUUAACGGAAUACUUAACAAGUAAUU

CAAACUUCAAAGAUUGUAAAGAUGCAUUAUACCAAGCGGCUAAAGAUUUAUAUGACGAGCAAACAGCUGAA

CAAGUAUAUGAAGCAUGGAACGAAGUUGGCGUCGAGUAA

-continued

SEQ IN NO: 43
AUGAAAAAGAAAUUAGGUAUGUUACUUCUUGUACCAGCCGUAACUUUAUCAUUAGCCGCAUGUGGGAAUGA
UGAUGGAAAAGAUAAAGAUGGCAAGGUAACAAUUAAAACGACAGUUUAUCCAUUGCAAUCAUUUGCAGAGC
AAAUUGGUGGAAAACACGUGAAGGUAUCAUCAAUCUAUCCAGCAGGGACAGAUUUACAUAGCUAUGAACCA
ACACAAAAAGAUAUAUUAAGUGCAAGCAAGUCAGACUUGUUUAUGUAUACAGGGGAUAAUUUAGAUCCGGU
UGCUAAGAAAGUUGCAUCUACUAUUAAAGAUAAAGAUAAAAAACUGUCUUUAGAAGAUAAAUUAGAUAAAG
CAAAGCUUUUAACUGAUCAACACGAACAUGGUGAAGAGCAUGAACAUGAGGGACAUGAUCAUGGGAAAGAA
GAACAUCAUCAUCAUGGCGGAUAUGAUCCACACGUAUGGUUAGAUCCUAAAAUUAACCAAACUUUCGCUAA
AGAAAUUAAAGAUGAAUUAGUGAAGAAAGAUCCAAAACAUAAAGAUGACUAUGAGAAAAACUACAAAAAAU
UAAACGACGAUCUUAAGAAAAUUGAUAACGAUAUGAAGCAAGUUACUAAAGAUAAGCAAGGUAAUGCAGUA
UUCAUUUCACAUGAAUCAAUUGGAUACUUAGCUGAUCGUUAUGGUUUUGUUCAAAAAGGUAUUCAAAACAU
GAAUGCUGAAGAUCCAUCACAAAAAGAAUUGACUAAAAUUGUUAAAGAAAUUAGAGAUAGCAAUGCUAAAU
AUAUUCUUUACGAAGAUAAUGUUGCGAAUAAAGUGACUGAAACAAUUCGUAAAGAAACAGAUGCGAAGCCU
UUAAAAUUCUACAACAUGGAGUCUUUAAAUAAAGAACAACAGAAAAAAGAUAAUAUUACCUAUCAAUCAUU
AAUGAAAUCGAAUAUUGAAAAUAUCGGUAAAGCUUUAGACAGUGGUGUUAAAGUGAAAGACGACAAAGCUG
AAAGUAAACACGACAAAGCAAUUUCUGAUGGGUAUUUUAAAGAUGAGCAAGUUAAAGACCGUGAAUUAAGC
GAUUAUGCUGGUGAAUGGCAAUCUGUUUACCCUUACUUAAAAGACGGUACGCUUGAUGAAGUGAUGGAACA
UAAAGCUGAAAAUGAUCCGAAAAAUCUGCUAAAGAUUUAAAAGCUUAUUAUGACAAAGGAUAUAAAACUGA
UAUUACUAACAUUGAUAUAAAAGGAAAUGAAAUUACAUUUACUAAAGAUGGUACGAAACACACUGGUAAAU
AUGAAUACAAUGGUAAGAAAACAUUGAAAUAUCCUAAAGGUAACCGUGGCGUGAGAUUUAUGUUUAAAUUG
GUCGAUGGUAAUGAUAAAGACUUACCGAAAUUCAUCCAAUUUAGCGAUCACAACAUUGCACCUAAAAAGGC
AGAACACUUCCAUAUCUUUAUGGGUAAUGAUAAUGACGCGUUAUUAAAAGAAAUGGAUAACUGGCCAACAU
AUUAUCCUUCAAAAUUAAAUAAAGACCAAAUCAAAGAAGAAAUGUUAGCGCAUUAA

SEQ IN NO: 44
AUGGUGUUAUAUAUCAUUUUGGCAAUAAUUGUGAUUAUAUUGAUUGCUGUAGGUGUAUUAUUCUAUUUACG
UUCAAAUAAAAGACAAAUAAUAGAAAAAGCAAUCGAACGUAAAAAUGAAAUUGAAACGUUACCUUUUGAUC
AAAACCUUGCACAAUUAUCUAAGUUGAAUUUAAAAGGUGAAACAAAAACGAAAUACGAUGCAAUGAAAAAG
GACAACGUAGAAAGUACAAAUAAGUAUCUAGCUCCUGUGGAAGAAAAAAUCCAUAAUGCUGAGGCUUUAUU
AGAUAAAUUUAGUUUCAACGCAUCUCAAUGUGAAAUUGAUGAUGCAAAUGAGUUGAUGGAUAGUUACGAAC
AAAGCUAUCAGCAACAAUUAGAAGAUGUAAAUGAAAUUAUUGCGUUAUACAAAGAUAAUGAUGAAUUAUAU
GACAAAUGUAAGGUUGAUUAUCGUGAAAUGAAACGUGAUGUUUUAGCAAAUCGUCAUCAAUUUGGUGAGGC
AGCAAGUCUUCUUGAAACUGAAAUUGAAAAAUUCGAGCCAAGGUUAGAGCAAUAUGAAGUACUAAAAGCUG
AUGGUAAUUAUGUACAAGCGCACAACCAUAUAGCUGCCUUGAAUGAACAAAUGAAACAGCUAAGAUCUUAU
AUGGAAGAAAUACCAGAAUUAAUUAGAGAAACUCAAAAAGAAUUACCUGGUCAAUUCCAAGAUUUAAAAUA
UGGUUGCCGUGAUCUUAAAGUUGAAGGGUAUGAUCUGGAUCACGUAAAAGUAGACAGUACAUUACAAAGCU
UAAAAACAGAGCUUAGUUUCGUUGAACCAUUAAUUAGUCGCUUAGAAUUAGAAGAAGCUAAUGAUAAACUA
GCUAAUAUCAAUGAUAAGUUAGAUGACAUGUAUGAUUUAAUUGAACAUGAAGUUAAAGCUAAAAAUGAUGU
CGAAGAAACAAAAGAUAUCAUUACGGAUAACUUAUUCAAAGCAAAAGACAUGAAUUAUACAUUGCAAACAG
AAAUUGAAUAUGUACGUGAAAACUACUAUAUAAAUGAAUCUGAUGCUCAGAGUGUUCGUCAAUUUGAAAAU
GAAAUUCAAAGUUUAAUUUCUGUAUAUGAUGAUAUUUAAAAGAAAUGUCUAAAUCUGCUGUACGAUAUAG
CGAGGUUCAGGAUAAUUUACAAUAUUUUAGAAGAUCAUGUCACAGUUAUUAAUGACAAACAAGAAAAGCUAC
AAAAUCAUCUGAUUCAAUUGCGUGAAGAUGAAGCAGAAGCAGAAGACAAUCUGUUACGAGUACAAUCGAAG

```
AAAGAAGAAGUGUAUCGUCGAUUACUUGCUUCUAACUUAACAAGCGUUCCUGAAAGGUUUAUCAUCAUGAA

AAAUGAAAUUGAUCAUGAAGUUCGUGAUGUUAACGAACAAUUUAGUGAACGUCCAAUACACGUUAAACAGU

UAAAAGAUAAAGUGUCUAAAAUUGUGAUUCAAAUGAAUACAUUUGAAGAUGAAGCAAAUGAUGUUCUUGUU

AAUGCUGUUUAUGCAGAGAAAUUAAUUCAAUAUGGAAAUAGAUAUCGUAAGGACUAUAGCAAUGUUGAUAA

GAGCUUAAAUGAAGCUGAACGAUUAUUUAAAAAUAAUCGCUAUAAGCGUGCGAUUGAAAUUGCAGAGCAAG

CUCUUGAAAGUGUUGAGCCAGGUGUCACUAAACAUAUUGAAGAAGAAGUUAUUAAGCAAUAG
```

SEQ IN NO: 45
```
AUGCCUAAAAAUAAAAUUUUAAUUUAUUGCUAUCAACUACGCUCGUAUUACCUACUUUAGUUUCACCUAC

CGCUUAUGCUGACACACCUCAAAAAGAUACUACAGCUAAGACAACAUCUCAUGAUUCCAAAAAAUCUACUG

AUGAUGAAACUUCUAAGGAUACUACAAGUAAAGAUAUUGAUAAAGCAGACAACAAUAAUACUAGUAACCAA

GACAAUAACGACAAAAAGUUAAAACUAUAGACGACAGCACUUCAGACUCUAACAAUAUCAUUGAUUUUAU

UUAUAAGAAUUUACCACAAACCAAUAUAAACCAAUUGCUAACCAAAAAUAAAUACGAUGAUAAUUACUCAU

UAACAACUUUAAUCCAAAACUUAUUCAAUUUAAAUUCGGAUAUUUCUGAUUACGAACAACCUCGUAAUGGU

GAAAAGUCAACAAAUGAUUCGAAUAAAAACAGUGAUAAUAGCAUCAAAAAUGAUACGGAUACGCAAUCAUC

UAAACAAGAUAAAGCAGACAAUCAAAAAGCACCUAAAUCAAACAAUACAAAACCAAGUACAUCUAAUAAGC

AACCAAAUUCGCCAAAGCCAACACAACCAAAUCAAUCAAAUAGUCAACCAGCAAGUGACGAUAAAGUAAAU

CAAAAAUCUUCAUCGAAAGAUAAUCAAUCAAUGUCAGAUUCGGCUUUAGAUUCUAUUUUGGAUCAAUACAG

UGAAGAUGCAAAGAAAACACAAAAAGAUUACGCAUCUCAAUCUAAAAAAGACAAAAAUGAAAAAUCUAAUA

CAAAGAAUCCACAGUUACCAACACAAGAUGAAUUGAAACAUAAAUCUAAACCUGCUCAAUCAUUCAAUAAC

GAUGUUAAUCAAAGGAUACACGUGCAACAUCACUAUUCGAAACAGAUCCUAGUAUAUCUAACAAUGAUGA

UAGUGGACAAUUUAACGUUGUUGACUCAAAAGAUACACGUCAAUUUGUCAAAUCAAUUGCUAAAGAUGCAC

ACCGCAUUGGUCAAGAUAACGAUAUUUAUGCGUCUGUCAUGAUUGCCCAAGCAAUCUUAGAAUCUGACUCA

GGUCGUAGUGCUUUAGCUAAGUCACCAAACCAUAAUUUAUUCGGUAUCAAAGGUGCUUUUGAAGGGAAUUC

UGUUCCUUUUAACACAUUAGAAGCUGAUGGUAAUCAAUUGUAUAGUAUUAAUGCUGGAUUCCGAAAAUAUC

CAAGCACGAAAGAAUCACUAAAAGAUUACUCUGACCUUAUUAAAAAUGGUAUUGAUGGCAAUCGAACAAUU

UAUAAACCAACAUGGAAAUCGGAAGCCGAUUCUUAUAAAGAUGCAACAUCACACUUAUCUAAAACAUAUGC

UACAGAUCCAAACUAUGCUAAGAAAUUAAACAGUAUUAUUAAACACUAUCAAUUAACUCAGUUUGACGAUG

AACGUAUGCCAGAUUUAGAUAAAUAUGAACGUUCUAUCAAGGAUUAUGAUGAUUCAUCAGAUGAAUUCAAA

CCUUUCCGCGAGGUAUCUGAUAAUAUGCCAUAUCCACAUGGCCAAUGUACUUGGUACGUAUAUAACCGUAU

GAAACAAUUUGGUACAUCUAUCUCAGGUGAUUUAGGUGAUGCACAUAAUUGGAAUAAUCGAGCUCAAUACC

GUGAUUAUCAAGUAAGUCAUACACCAAAACGUCAUGCUGCUGUUGUAUUUGAGGCUGGACAAUUUGGUGCA

GAUCAACAUUACGGUCAUGUAGCAUUUGUUGAAAAAGUUAACAGUGAUGGUUCUAUCGUUAUUUCAGAAUC

CAAUGUUAAAGGAUUAGGUAUCAUUUCUCAUAGAACUAUCAAUGCAGCUGCCGCUGAAGAAUUAUCAUAUA

UUACAGGUAAAUAA
```

SEQ IN NO: 46
```
AUGAUGAAAGUCAAAUAAGUAUAGUAUUCGUAAAUUUAGUGUAGGUGCAUCUUCCAUUUUAAUAGCUAC

AUUACUAUUUUUAAGUGGUGGACAAGCACAAGCAGCUGAGAAGCAAGUGAAUAUGGGAAAUUCACAGGAGG

AUACAGUUACAGCACAAUCUAUUGGGAUCAACAAACUAGGGAAAAUGCUAAUUAUCAACGUGAAAACGGU

GUUGACGAACAGCAACAUACUGAAAAUUUAACUAAGAACUUGCAUAAUGAUAAAACAAUAUCAGAAGAAAA

UCAUCGUAAACAGAUGAUUUGAAUAAAGAUCAACUAAAGGAUGAUAAAAAAAUCAUCGCUUAAUAAUAAAA

AUAUUCAACGUGAUACAACAAAAAAUAACAAUGCUAAUCCUAGGGAUGUAAAUCAAGGGUUAGAACAGGCU

AUUAAUGAUGGCAAACAAAGUAAAGUGGCGUCACAGCAACAGUCAAAAGAGGCAGAUAAUAGUCAAGACUU
```

-continued

AAACGCUAAUAACAAUCUACCUUCACAAAGUCGAACAAAGGUAUCACCAUCAUUAAAUAAGUCAGAUCAAA

CAAGUCAACGAGAAAUUGUUAAUGAGACAGAAAUAGAGAAAGUACAACCGCAACAAAAGAAUCAAGCGAAU

GAUAAAAUUACUGACCACAAUUUUAACAAUGAACAAGAAGUGAAACCUCAAAAGACGAAAAAACACUAUC

AGUUUCAGAUUUAAAAAACAAUCAAAAAUCACCAGUUGAACCAACAAAGGACAAUGACAAGAAAAAUGGAU

UAAAUUUAUUAAAAAGUAGUGCAGUAGCAACGUUACCAAACAAAGGGACAAAGGAACUUACUGCAAAAGCG

AAAGGUGAUCAAACGAAUAAAGUUGCCAAACAAGGGCAGUAUAAAAAUCAAGAUCCUAUAGUUUUAGUGCA

UGGUUUCAAUGGGUUUACAGAUGAUAUUAAUCCUUCAGUGUUAGCUCAUUAUUGGGGCGGUAAUAAAAUGA

ACAUUCGCCAAGAUUUAGAAGAAAAUGGUUACAAAGCUUAUGAAGCAAGUAUAAGUGCUUUUGGAAGUAAC

UAUGACCGCGCAGUUGAACUUUAUUAUUAUAUCAAAGGCGGUCGUGUAGAUUAUGGUGCAGCACAUGCAGC

AAAAUAUGGACAUGAACGUUAUGGAAAAACAUACGAAGGAAUUUACAAAGACUGGAAACCAGGACAGAAGG

UACACCUUGUUGGACAUAGUAUGGGUGGUCAAACGAUACGUCAACUAGAAGAAUUACUGCGUAAUGGUAGU

CGUGAAGAAAUAGAGUAUCAAAAGAAACAUAGUGGCGAAAUUUCUCCACUAUUCAAAGGUAAUAAUGACAA

UAUGAUUUCAUCAAUUACUACUUUAGGAACGCCACAUAAUGGAACGCAUGCUUCAGAUUUAGCUGGUAAUG

AAGCUUUAGUGAGACAAAUUGUAUUUGAUAUCGGUAAAAUGUUUGGUAAUAAAAAUUCAAGAGUAGACUUC

GGGUUGGCUCAAUGGGGUCUAAAACAGAAGCCAAAUGAAUCAUAUAUUGAUUAUGUCAAACGCGUUAAACA

AUCUAAUUUAUGGAAAUCAAAAGAUAAUGGAUUUUACGAUCUGACGCGUGAGGGUGCAACAGAUUUAAAUC

GUAAAACGUCGUUGAACCCUAACAUUGUGUAUAAAACAUACACUGGUGAAGCAACGCACAAAGCAUUAAAU

AGCGAUAGACAAAAAGCAGACUUAAAUAUGUUUUUCCCAUUUGUGAUUACUGGUAACUUAAUCGGUAAAGC

UACUGAAAAGAAUGGCGAGAAAACGAUGGUUUAGUAUCCGUUAUUUCUUCAACAUCCAUUUAAUCAAG

CUUAUACAAAUGCGACGGAUAAAAUUCAAAAAGGCAUUUGGCAAGUAACGCCUACAAAACAUGAUUGGGAU

CAUGUUGAUUUUGUCGGACAAGAUAGUUCUGAUACAGUGCGCACAAGAGAAGAAUUACAAGAUUUUUGGCA

UCAUUUAGCAGACGAUUUAGUGAAACUGAAAAGGUGACUGAUACUAAGCAAGCAUAA

SEQ IN NO: 47

AUGACAAAUAAAAUGAAGAAAUGGCAAAAAUUAUCCACCAUUACGUUAUUAAUGACCGGAGUGAUUGCUUU

AAAUAAUGGUGAAUUUAGAAAUGUUGAUAAAACAUCAAAUCGCUGUGGCUGAUACGAAUGUUCAAACGCCAG

AUUAUGAAAAAUUGAAGAAGACGUGGCUCGACGUUAACUACGGUUAUGAUCAGUAUGAUGAGAAUAAUCAA

GAUAUGAAGAAGAAGUUUGAUGCUAAAGAAAAAGAAGCCAAGAAGUUACUUGAUGACAUGAAAACUGAUAC

GAAUAGAACAUAUUUGUGGUCAGGAGCUGAAAACCUUGAAACUAAUUCUUCUCACAUGACAAAAACCUAUC

GUAAUAUCGAGAAAAUCGCAGAAUCAAUGCAACAUAAGAAUACGGUAUUAAAAACAGUUGAAAACAAGUUG

AAAAUAAAAGAAGCCCUAGAUUGGAUGCACAAAAAUGUUUAUGGCAAGAAUCCUUCUCAAAAAGUCGAGGA

UUUAACUAAAAAUCGUAAGGGGCAAACUACACCCAAGAAUAACUCAUUGAAUUGGUGGGAUUAUGAAAUUG

GUACGCCAAGAGCAUUAACAAAUACACUACUUCUAAUGGAUGAUAUGCUCACUAAAGAUGAAAUGAAAAAU

UAUUCAAAACCUAUUAGUACAUAUGCACCAUCCAGUGACAAAAUUUUAUCUUCUGUUGGUGAAUCAGAAGA

UGCUAAAGGUGGAAAUUUAGUGGACAUUUCUAAAGUAAAACUUUUAGAAAGUGUUAUUGAAGAAGAUGUAG

AUAUGUUGAAAAGUCUAUAGAUUCUUUUAAUAAAGUGUUCACUUAUGUUCAAGAUUCUGCCACUGGUAAA

GGUCGCAAUGGAUUCUAUAAAGAUGGCUCUUACAUUGAUCAUCAAGAUGUCCCUUACACUGGUGCUUAUGG

UGUUGUACUAUUAGAGGGUAUUUCUCAAAUGAUGCCGAUGAUAAAAGAAUCUCCUUUUAAAACUACACAAG

AUAAUGCUACAUUAAGCAAUUGGAUUGACGAAGGGUUUAUGCCAUUAAUCUAUAAAGGUGAAAUGAUGGAU

UUAUCACGAGGUAGAGCUAUCAGUCGUGAAAAUGAAACGAGUCAUACAGCGUCAGCGACUGUAAUGAAAUC

AUUGUUGAGAUUGAAUGAUACCAUGGAUGAUUCAACAAAAACUAGAUAUAAGCAAAUCGUUAAAACUUCUG

UUAAUUCUGAUUCAAGUUACAACCAAAAUAAUUAUUUAAAUUCAUAUUCAGACAUAGCUAAAAUGAAAAAG

-continued

UUAAUGAAUGAUAGUACUAUUUCUAAAAACGAUUUAACACAGCAACUUAAAAUAUAUAAUGACAUGGAUCG

UGUCACCUAUCACAAUAAAGACCUGGACUUUGCAUUUGGUUUAAGUAUGACAUCGAAAAACAUCGCACGAU

ACGAAAAUAUCAACGGAGAGAACUUAAAAGGUUGGCACACCGGUGCAGGCAUGUCUUAUUUAUAUAACAGC

GAUGUCAAACACUAUCGCGAUAACUUCUGGGCAACAGCCGAUAUGACUUGUCUUCCAGGCACUACUACUUU

AAAUGAUAUGCCAUCUACUAAUACUAAGAAUGAUAAAUCUUUUGUUGGCGGGACAAAAUUAAAUAAUAAAU

ACGCAAGCAUCGGUAUGGAUUUUGAAAAUCAGGACAAAACUUUAACUGCCAAAAAAUCAUAUUUCAUAUUA

AACGAUAAAAUUGUCUUCUUAGGAACUGGCAUUAAAAGUACUGAUUCAUCAAAGAAUCCAGUUACAAGUGU

UGAAAAUCGCAAAGCAAAUGGGUAUAAAUUAUUUAAAGAUGAUAUUGAAAUUACCACUUCAGAUGUUAAUG

CUCAGGAAACCCAUUCAGUCUUUUUAGAGUCCAACGAUACUAAAAAGAACAUUGGUUAUCAUUUCUUAGAC

AAGCCAAAAAUAACUGUAAAAAAGAAAGUCAUACUGGUAAGUGGAGUGAAAUUAAUAAAAGUCAAAAAAA

AGAUGACAAAAAAGAUGAGUAUUAUGAAGUAACUCAAACACAUAAUACAUCUGACAGUAAAUAUGCAUAUG

UUUUGUAUCCUGGUUUAUCAAAAAGUGAUUUUAAAUCGAAGAAUAAUAAUGUAAGUAUUGUUAAACAAGAU

GAAGAUUUUCAUGUGAUAAAAGAUAAUGAUGGCGUAUUUGCUGGGGUUAAUUAUAGUGAUAAUACUAAAUC

UUUUGAUAUAAACGGAAUUACUGUUGAAUUAAAAGAAAAAGGCAUGUUUGUAAUUAAAAAGAAAGAUGAUA

AAGCAUAUAAAUGUAGCUUCUAUAAUCCUGAAACUACAAAUACCGCUUCAAAUAUAGAAUCAAAAAUUUUU

AUUAAAGGUUACACCAUAACUAAUAAAAGUGUCAUAAACUCUAAUGAUGCUGGUGUAAACUUUGAAUUAAC

UAAAUAA

SEQ IN NO: 48
AUGACAUAUAGAAUGAAGAAAUGGCAAAAAUUGUCCACCAUUACGUUAUUAAUGGCUGGUGUGAUUACUUU

GAAUGGUGGUGAAUUCAGAAGUAUUGAUAAACAUCAAAUCGCUGUGGCUGAUACGAAUGUUCAAACGACAG

AUUAUGAAAAGUUGAGGAACAUAUGGCUGGACGUUAACUAUGGUUAUGAUAAGUAUGAUGAGAAUAAUCCA

GAUAUGAAGAAGAAGUUUGAGGCUACGGAGAAUGAGGCAGAGAAAUUACUCAAGGAAAUGAAAACUGAAAG

UGAUAGGAAAUACUUGUGGGAAAGCUCAAAAGAUUUAGAUACGAAGUCUGCGGAUAUGACUCGUACCUAUC

GUAAUAUUGAGAAAAUCUCAGAAGCGAUGAAACAUAAAAAAUACUAAAUUAAAAACAGAUGAAAACAAGACA

AAAGUAAAAGAUGCACUUGAGUGGCUGCAUAAAAAUGCAUAUGGAAAAGAACCAGAUAAAAAAGUUGCUGA

UUUGACCUCAAACUUUAAAAAUAAAACUUCUAGAAAUACCAACUUAAAUUGGUGGGAUUAUGAAAUUGGAA

CACCUAGAGCAUUAACAAAUACGCUUUAUACUCUUACAAGAAGAUUUCACUGAUGAAGAAAAGAAAAAUAU

ACAGCUCCUAUUAAAACUUUCGCCCCAGAUAGUGACAAAAUAUUAUCUUCUGUAGGAAAAUCUGAACCUGC

UAAAGGCGGAAAUUUAGUAGACAUUUCUAAAGUAAAACUUUUAGAAAGUAUUAUCGAAGAAGACAAAGAUA

UGAUGAAAAGUCUAUAGAUUCAUUUAAUACAGUCUUCACUUACGCGCAAAAUUCUGCCACUGGAAAAGAA

CGUAAUGGAUUCUAUAAAGAUGGCUCUUACAUUGAUCAUCAAGACGUCCCAUACACUGGUGCUUAUGGCGU

UGUACUAUUAGAGGGUAUUUCUCAAAUGAUGCCGAUGAUAAAAGAAACACCUUUUAAUGAUAGUAACCAAA

AUGAUACAACCUUAAAAUCAUGGAUUGACGACGGAUUUAUGCCACUCAUUUAUAAAGGUGAAAUGAUGGAU

UUAUCAAGAGGUAGAGCUAUCAGUCGUGAAAAUGAAACGAGUCACUCAGCAUCUGCAACAGUAAUGAAAUC

AUUGUUGAGAUUGAGUGAUACCAUGGAUAAGUCUACAAAAGCUAAAUAUAAAAGAUUGUCAAGACUUCAG

UAGAGUCAGAUUCAAGUUAUAAACAAACCGAUUAUUUAAGCUCUUAUUCGGAUAUAAGCAAAUGAAGUCU

UUAAUGGAAGACAGCACUAUUUCUACUAACGGUUUAACACAACAACUUAAAAAUAUAUAAUGACAUGGAUCG

UGUCACCUAUCACAAUAAAGGCUUAGACUUUGCAUUUGGUUUAAGUAUGACGUCGAAAAACGUCGCACGUU

ACGAAAGUAUCAACGGAGAGAACUUAAAAGGUUGGCACACUGGUGCUGGAAUGUCUUAUUUAUACAAUAGC

GAUGUGAAACACUACCGUGAUAACUUCUGGGCGACAGCUGAUAUGAAACGUUUAGCAGGUACUACAACUUU

AGAUAAUGAAGAACCUAAAAGUACGGAUGUUAAAAGUCUAGUAAAACUUUUGUAGGAGGAACAAAAUUCG

AUGACCAACAUGCUAGUAUCGGAAUGGAUUUUGAAAAUCAGGACAAAACUUUAACUGCCAAAAAAUCAUAU

-continued

UUCAUAUUAAACGAUAAAAUUGUCUUCUUAGGAACUGGCAUUAAAAGUACUGAUUCAUCAAAGAAUCCAGU

UACAACGAUUGAAAAUCGCAAAGCGAAUGAUUAUAAAUUAUAUAAAGAUGAUACGCAAACAACCAAUUCCG

AUAAUCAGGAAACCAAUUCCCUCUUUUUAGAGUCAACGAAUAGCACUCAAAACAAUAUAGGUUAUCAUUUU

UUAAACGAAUCGAAAAUAACUGUAAAAAAAGAAAGUCAUACUGGUAAGUGGAGUGAUAUAAAUAAAAGCCA

AAAGGAUAUACAAAAAACUGAUGAGUAUUAUGAAGUAACUCAAAAGCAUUCUAAUACAGAUAGUAAAUAUG

CAUAUGUGUUGUAUCCAGGCUUAUCUAAAGAUGUCUUUAAAUCCAAAGCAAGCAAAGUAACUGUCGUUAAG

CAAGAAGAUGACUUCCACGUUGUGAAAGAUAAUGAAUCGGUUUGGGCUGGUAUCAAUUAUAGUGAUAGCGC

UAAAACUUUUGAAAUUAAUAACACUAAAGUCGAAGUUAAAGCCAAAGGAAUGUUUAUUCUUACAAAGAAAG

AUGAUAACACUUAUGAAUGUAGCUUCUAUAAUCCCGAAUCUACAAAUUCCGUUUCAGAUAUUGAAUCUAAA

AUUUCAAUGACUGGAUACUCUAUUAUAAACAAAAAUACGUCGACUUCUAAUGAAUCCGGCUACGCUUUGA

AUUAACUAAAUAA

SEQ ID NO: 50
ATTGATTCAAAAAATAAACCAGCTAATTCTGATATTAAATTTGAGGTGACTCAAAAGAGTGATGCGGTCAA

AGCATTAAAAGAATTGCCTAAATCCGAAAATGTAAAAAATATTTATCAAGATTACGCTGTTACTGATGTAA

AAACTGATAAAAAAGGATTTACGCATTATACATTGCAACCGAGTGTTGATGGTGTTCATGCACCTGACAAA

GAAGTGAAAGTACACGCAGACAAATCAGGAAAAGTCGTTTTAATCAATGGGGATACTGATGCGAAGAAAGT

AAAGCCAACGAATAAAGTGACATTAAGTAAAGATGACGCAGCCGACAAAGCATTTAAAGCAGTTAAGATTG

ATAAGAATAAAGCGAAAAATCTTAAAGATAAAGTCATTAAAGAAAACAAAGTTGAAATCGATGGTGACAGT

AATAAATACGTTTATAATGTTGAGTTAATTACAGTGACACCAGAAATTTCACATTGGAAAGTTAAAATTGA

TGCTCAAACTGGCGAAATTTTAGAAAAAATGAACTTAGTTAAAGAAGCTGCAGAAACTGGTAAAGGAAAAG

GTGTACTTGGCGATACAAAAGATATCAATATCAATAGTATTGACGGTGGATTTAGCCTAGAAGATTTAACG

CATCAAGGTAAATTATCAGCATTTAGCTTTAATGATCAAACAGGTCAAGCAACATTGATTACTAATGAAGA

TGAAAACTTCGTAAAAGATGAGCAACGTGCTGGCGTAGATGCAAATTATTACGCTAAACAAACATATGATT

ATTACAAAGACACATTTGGTCGTGAATCATATGACAACCAAGGTAGTCCAATTGTTTCATTAACGCATGTT

AATAACTACGGTGGTCAAGATAACAGAAATAATGCCGCATGGATCGGTGACAAAATGATCTATGGTGATGG

TGATGGTCGCACATTCACAAGTTTATCGGGTGCAAATGACGTAGTAGCACACGAATTAACACACGGTGTGA

CACAAGAGACAGCGAACTTAGAATATAAGGACCAGTCAGGCGCTCTAAATGAAAGCTTTTCAGATGTTTTT

GGATACTTTGTAGATGACGAGGATTTCTTAATGGGTGAAGATGTCTACACACCTGGAAAAGAGGGAGACGC

TTTACGCAGCATGTCAAACCCAGAACAATTTGGTCAACCAGCTCATATGAAAGACTATGTATTCACTGAAA

AAGATAATGGTGGCGTACATACGAATTCTTAA

SEQ ID NO: 51
AUUGAUUCAAAAAAUAAACCAGCUAAUUCUGAUAUUAAAUUUGAGGUGACUCAAAAGAGUGAUGCGGUCAA

AGCAUUAAAAGAAUUGCCUAAAUCCGAAAAUGUAAAAAAUAUUUAUCAAGAUUACGCUGUUACUGAUGUAA

AAACUGAUAAAAAAGGAUUUACGCAUUAUACAUUGCAACCGAGUGUUGAUGGUGUUCAUGCACCUGACAAA

GAAGUGAAAGUACACGCAGACAAAUCAGGAAAAGUCGUUUUAAUCAAUGGGGAUACUGAUGCGAAGAAAGU

AAAGCCAACGAAUAAAGUGACAUUAAGUAAAGAUGACGCAGCCGACAAAGCAUUUAAAGCAGUUAAGAUUG

AUAAGAAUAAAGCGAAAAAUCUUAAAGAUAAAGUCAUUAAAGAAAACAAAGUUGAAAUCGAUGGUGACAGU

AAUAAAUACGUUUAUAAUGUUGAGUUAAUUACAGUGACACCAGAAAUUUCACAUUGGAAAGUUAAAAUUGA

UGCUCAAACUGGCGAAAUUUUAGAAAAAAUGAACUUAGUUAAAGAAGCUGCAGAAACUGGUAAAGGAAAAG

GUGUACUUGGCGAUACAAAAGAUAUCAAUAUCAAUAGUAUUGACGGUGGAUUUAGCCUAGAAGAUUUAACG

CAUCAAGGUAAAUUAUCAGCAUUUAGCUUUAAUGAUCAAACAGGUCAAGCAACAUUGAUUACUAAUGAAGA

UGAAAACUUCGUAAAAGAUGAGCAACGUGCUGGCGUAGAUGCAAAUUAUUACGCUAAACAAACAUAUGAUU

-continued

```
AUUACAAAGACACAUUUGGUCGUGAAUCAUAUGACAACCAAGGUAGUCCAAUUGUUUCAUUAACGCAUGUU

AAUAACUACGGUGGUCAAGAUAACAGAAAUAAUGCCGCAUGGAUCGGUGACAAAAUGAUCUAUGGUGAUGG

UGAUGGUCGCACAUUCACAAGUUUAUCGGGUGCAAAUGACGUAGUAGCACACGAAUUAACACACGGUGUGA

CACAAGAGACAGCGAACUUAGAAUAUAAGGACCAGUCAGGCGCUCUAAAUGAAAGCUUUUCAGAUGUUUUU

GGAUACUUUGUAGAUGACGAGGAUUUCUUAAUGGGUGAAGAUGUCUACACACCUGGAAAAGAGGGAGACGC

UUUACGCAGCAUGUCAAACCCAGAACAAUUUGGUCAACCAGCUCAUAUGAAAGACUAUGUAUUCACUGAAA

AAGAUAAUGGUGGCGUACAUACGAAUUCUUAA
```

The polypeptides of the present invention are also designated as follows herein:

| SEQ ID NO: 1: | SAR1837 |
|---|---|
| SEQ ID NO: 2: | SAR1608 |
| SEQ ID NO: 3: | SAR2457 |
| SEQ ID NO: 4: | SAR0839 |
| SEQ ID NO: 5: | SAR1402 |
| SEQ ID NO: 6: | SAR1022 |
| SEQ ID NO: 7: | SAR1995 |
| SEQ ID NO: 8: | SAR0436 |
| SEQ ID NO: 49: | USA300HOU_2637_28_439 |
| SEQ ID NO: 9: | SAR0277 |
| SEQ ID NO: 10: | SAR2716 |
| SEQ ID NO: 11: | SAR2496 |
| SEQ ID NO: 12: | SAR1795 |
| SEQ ID NO: 13: | SAR2723 |
| SEQ ID NO: 14: | SAR2753 |
| SEQ ID NO: 15: | SAR1892 |
| SEQ ID NO: 16: | SAR2292 |

The invention claimed is:

1. A pharmaceutical composition comprising a polypeptide and a pharmaceutically acceptable carrier, vehicle or diluent, and which further comprises an immunological adjuvant, wherein the polypeptide comprises:
   a) an amino acid sequence consisting of SEQ ID NO: 10, or
   b) an amino acid sequence consisting of at least or exactly 90 contiguous amino acid residues from SEQ ID NO: 10, or
   c) an amino acid sequence having a sequence identity of at least 95% with the amino acid sequence of a).

2. The pharmaceutical composition according to claim 1, wherein the adjuvant is an aluminum based adjuvant.

3. The composition according to claim 1, wherein the at least or exactly 90 contiguous amino acid residues are at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly Or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, at least or exactly or at most 134, at least or exactly or at most 135, at least or exactly or at most 136, at least or exactly or at most 137, at least or exactly or at most 138, at least or exactly or at most 139, at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, at least or exactly or at most 149, at least or exactly or at most 150, at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 161, at least or exactly or at most 162, at least or exactly or at most 163, at least or exactly or at most 164, at least or exactly or at most 165, at least or exactly or at most 166, at least or exactly or at most 167, at least or exactly or at most 168, at least or exactly or at most 169, at least or exactly or at most 170, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, at least or exactly or at most 198, at least or exactly or at most 199, at least or exactly or at most 200, at least or exactly or at most 201, at least or exactly or at most 202, at least or exactly or at most 203, at least or exactly or at most 204, at least or exactly or at most 205, at least or exactly or at most 206, at least or exactly or at most 207, at least or exactly or at most 208, at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least or exactly or at most 222, at least or exactly or at most 223, at least or exactly or at most 224, at least or exactly or at most 225, at least or exactly or at most 226, at least or exactly or at most 227, at least or exactly or at most 228, at least or exactly or at most 229, at least or exactly or at most 230, at least or exactly or at most 231, at least or exactly or at most 232, at least or exactly or at most 233, at least or exactly or at most 234, at least or exactly or at most 235, at least or exactly or at most 236, at least or exactly or at most 237, at least or exactly or at most 238, at least or exactly or at most 239, at least or exactly or at most 240, at least or exactly or at most 241, at least or exactly or at most 242, at least or exactly or at most 243, at least or exactly or at most 244, at least or exactly or at most 245, at least or exactly or at most 246, at least or exactly or at most 247, at least or exactly or at most 248, at least or exactly or at most 249, at least or exactly or at most 250, at least or exactly or at most 251, at least or exactly or at most 252, at least or exactly or at most 253, at least or exactly or at most 254, at least or exactly or at most 255, at least or exactly or at most 256, at least or exactly or at most 257, at least or exactly or at most 258, at least or exactly or at most 259, at least or exactly or at most 260, at least or exactly or at most 261, at least or exactly or at most 262, at least or exactly or at most 263, at least or exactly or at most 264, at least or exactly or at most 265, at least or exactly or at most 266, at least or exactly or at most 267, at least or exactly or at most 268, at least or exactly or at most 269, at least or exactly or at most 270, at least or exactly or at most 271, at least or exactly or at most 272, at least or exactly or at most 273, at least or exactly or at most 274, at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, at least or exactly or at most 285, at least or exactly or at most 286, at least or exactly or at most 287, at least or exactly or at most 288, at least or exactly or at most 289, at least or exactly or at most 290, at least or exactly or at most 291, at least or exactly or at most 292, at least or exactly or at most 293, at least or exactly or at most 294, at least or exactly or at most 295, at least or exactly or at most 296, at least or exactly or at most 297, at least or exactly or at most 298, at least or exactly or at most 299, at least or exactly or at most 300, at least or exactly or at most 301, at least or exactly or at most 302, at least or exactly or at most 303, at least or exactly or at most 304, at least or exactly or at most 305, at least or exactly or at most 306, at least or exactly or at most 307, at least or exactly or at most 308, at least or exactly or at most 309, at least or exactly or at most 310, at least or exactly or at most 311, at least or exactly or at most 312, at least or exactly or at most 313, at least or exactly or at most 314, at least or exactly or at most 315, at least or exactly or at most 316, at least or exactly or at most 317, at least or exactly or at most 318, at least or exactly or at most 319, at least or exactly or at most 320, at least or exactly or at most 321, at least or exactly or at most 322, at least or exactly or at most 323, at least or exactly or at most 324, at least or exactly or at most 325, at least or exactly or at most 326, at least or exactly or at most 327, at least or exactly or at most 328, at least or exactly or at most 329, at least or exactly or at most 330, at least or exactly or at most 331, at least or exactly or at most 332, at least or exactly or at most 333, at least or exactly or at most 334, at least or exactly or at most 335, at least or exactly or at most 336, at least or exactly or at most 337, at least or exactly or at most 338, at least or exactly or at most 339, at least or exactly or at most 340, at least or exactly or at most 341, at least or exactly or at most 342, at least or exactly or at most 343, at least or exactly or at most 344, at least or exactly or at most 345, at least or exactly or at most 346, at least or exactly or at most 347, at least or exactly or at most 348, at least or exactly or at most 349, at least or exactly or at most 350, at least or exactly or at most 351, at least or exactly or at most 352, at least or exactly or at most 353, at least or exactly or at most 354, at least or exactly or at most 355, at least or exactly or at most 356, at least or exactly or at most 357, at least or exactly or at most 358, at least or exactly or at most 359, at least or exactly or at most 360, at least or exactly or at most 361, at least or exactly or at most 362, at least or exactly or at most 363, at least or exactly or at most 364, at least or exactly or at most 365, at least or exactly or at most 366, at least or exactly or at most 367, at least or exactly or at most 368, at least or exactly or at most 369, at least or exactly or at most 370, at least or exactly or at most 371, at least or exactly or at most 372, at least or exactly or at most 373, at least or exactly or at most 374, at least or exactly or at most 375, at least or exactly or at most 376, at least or exactly or at most 377, at least or exactly or at most 378, at least or exactly or at most 379, at least or exactly or at most 380, at least or exactly or at most 381, at least or exactly or at most 382, at least or exactly or at most 383, at least or exactly or at most 384, at least or exactly or at most 385, at least or exactly or at most 386, at least or exactly or at most 387, at least or exactly or at most 388, at least or exactly or at most 389, at least or exactly or at most 390, at least or exactly or at most 391, at least or exactly or at most 392, at least or exactly or at most 393, at least or exactly or at most 394, at least or exactly or at most 395, at least or exactly or at most 396, at least or exactly or at most exactly or at most 397, at least or exactly or at most 398, at least or exactly or at most 399, at least or exactly or at most 400, at least or exactly or at most 401, at least or exactly or at most 402, at least or exactly or at most 403, at least or exactly or at most 404, at least or exactly or at most 405, at least or exactly or at most 406, at least or exactly or at most 407, at least or exactly or at most 408, at least or exactly or at most 409, at least or exactly or at most 410, at least or exactly or at most 411, at least or exactly or at most 412, at least or exactly or at most 413, at least or exactly or at most 414, at least or exactly or at most 415, at least or exactly or at most 416, at least or exactly or at most 417, at least or exactly or at most 418, at least or exactly or at most 419, at least or exactly or at most 420, at least or exactly or at most 421, at least or exactly or at most 422, at least or exactly or at most 423, at least or exactly or at most 424, at least or exactly or at most 425, at least or exactly or at most 426, at least or exactly or at most 427, at least or exactly or at most 428, at least or exactly or at most 429, at least or exactly or at most 430, at least or exactly or at most 431, at least or exactly or at most 432, at least or exactly or at most 433, at least or exactly or at most 434, at least or exactly or at most 435, at least or exactly or at most 436, at least or exactly or at most 437, at least or exactly or at most 438, at least or exactly or at most 439, at least or exactly or at most 440, at least or exactly or at most 441, at least or exactly or at most 442, at least or exactly or at most 443, at least or exactly or at most 444, at least or exactly or at most 445, at least or exactly or at most 446, at least or exactly or at most 447, at least or exactly or at most 448, at least or exactly or at most 449, at least or exactly or at most 450, at least or exactly or at most 451, at least or exactly or at most 452, at least or exactly or at most 453, at least or exactly or at most 454, at least or exactly or at most 455, at least or exactly or at most 456, at least or exactly or at most 457, at least or exactly or at most 458, at least or exactly or at most 459, at least or exactly or at most 460, at least or exactly or at most 461, at least or exactly or at most 462, at least or exactly or at most 463, at least or exactly or at most 464, at least or exactly or at most 465, at least or exactly or at most 466, at least or exactly or at most 467, at least or exactly or at most 468, at least or exactly or at most 469, at least or exactly or at most 470, at least or exactly or at most 471, at least or exactly or at most 472, at least or exactly or at most 473, at least or exactly or at most 474, at least or exactly or at most 475, at least or exactly or at most 476, at least or exactly or at most 477, at least or exactly or at most 478, at least or exactly or at most 479, at least or exactly or at most 480, at least or exactly or at most 481, at least or exactly or at most 482, at least or exactly or at most 483, at least or exactly or at most 484, at least or exactly or at most 485, at least or exactly or at most 486, at least or exactly or at most 487, at least or exactly or at most 488, at least or exactly or at most 489, at least or exactly or at most 490, at least or exactly or at most 491, at least or exactly or at most 492, at least or exactly or at most 493, at least or exactly or at most 494, at least or exactly or at most 495, at least or exactly or at most 496, at least or exactly or at most 497, at least or exactly or at most 498, at least or exactly or at most 499, at least or exactly or at most 500, at least or exactly or at most 501, at least or exactly or at most 502, at least or exactly or at most 503, at least or exactly or at most 504, at least or exactly or at most 505, at least or exactly or at most 506, at least or exactly or at most 507 contiguous amino acid residues, or at least or exactly or at most 508 contiguous amino acid residues.

4. The composition according to claim 1, wherein the sequence identity in option c) is selected from at least 96%, at least 97%, at least 98%, and at least 99%.

5. The composition according to claim 1, wherein the at least or exactly 90 contiguous amino acid residues in option b have an N-terminal amino acid residue corresponding to any one of amino acid residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 42, 43, 44, 45, 46, 47, 48, 49, 50, 51, 52, 53, 54, 55, 56, 57, 58, 59, 60, 61, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, and 410 in SEQ ID NO: 10, wherein the N-terminal first residue will not be higher numbered than 510-L, where L is the number of amino acids defined for option b.

6. The composition according to claim 1, wherein the polypeptide is fused or conjugated to an immunogenic carrier molecule.

7. The composition according to claim 6, wherein the immunogenic carrier molecule is a polypeptide that induces T-helper lymphocyte responses in a majority of humans.

8. The composition according to claim 7, wherein the immunogenic carrier molecule is selected from the group consisting of keyhole limpet hemocyanin or a fragment thereof, tetanus toxoid or a fragment thereof, and diphtheria toxoid or a fragment thereof.

9. The composition according to claim 1, wherein the polypeptide is capable of inducing an adaptive immune response against the polypeptide in a human being.

10. A pharmaceutical composition comprising a polypeptide and a pharmaceutically acceptable vehicle or diluent, and which further comprises an immunological adjuvant, wherein the polypeptide has at least 90% sequence identity with at least 90 consecutive amino acid residues of SEQ ID NO: 10 and which further comprises:
  i) residues 154-176 of SEQ ID NO: 10 or a sequence having at least 85$ identity therewith, or
  ii) residues 195-214 of SEQ ID NO: 10 or a sequence having at least 70% sequence identity therewith, or
  iii) residues 248-271 of SEQ ID NO: 10 or a sequence having at least 90% sequence identity therewith, or
  iv) residues 291-313 of SEQ ID NO: 10 or a sequence having at least 90% sequence identity therewith, or
  v) residues 1-153 of SEQ ID NO: 10 or a sequence having at least 91% sequence identity therewith, or
  vi) residues 341-427 of SEQ ID NO: 10 or a sequence having at least 97% sequence identity therewith.

11. The pharmaceutical composition according to claim 10, wherein the adjuvant is an aluminum based adjuvant.

12. The composition according to claim 10, wherein the at least or exactly 90 contiguous amino acid residues are at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, at least or exactly or at most 134, at least or exactly or at most 135, at least or exactly or at most 136, at least or exactly or at most 137, at least or exactly or at most 138, at least or exactly or at most 139, at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, at least or exactly or at most 149, at least or exactly or at most 150, at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 161, at least or exactly or at most 162, at least or exactly or at most 163, at least or exactly or at most 164, at least or exactly or at most 165, at least or exactly or at most 166, at least or exactly or at most 167, at least or exactly or at most 168, at least or exactly or at most 169, at least or exactly or at most 170, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, at least or exactly or at most 198, at least or exactly or at most 199, at least or exactly or at most 200, at least or exactly or at most 201, at least or exactly or at most 202, at least or exactly or at most 203, at least or exactly or at most 204, at least or exactly or at most 205, at least or exactly or at most 206, at least or exactly or at most 207, at least or exactly or at most 208, at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least or exactly or at most 222, at least or exactly or at most 223, at least or exactly or at most 224, at least or exactly or at most 225, at least or exactly or at most 226, at least or exactly or at most 227, at least or exactly or at most 228, at least or exactly or at most 229, at least or exactly or at most 230, at least or exactly or at most 231, at least or exactly or at most 232, at least or exactly or at most 233, at least or exactly or at most 234, at least or exactly or at most 235, at least or exactly or at most 236, at least or exactly or at most 237, at least or exactly or at most 238, at least or exactly or at most 239, at least or exactly or at most 240, at least or exactly or at most 241, at least or exactly or at most 242, at least or exactly or at most 243, at least or exactly or at most 244, at least or exactly or at most 245, at least or exactly or at most 246, at least or exactly or at most 247, at least or exactly or at most 248, at least or exactly or at most 249, at least or exactly or at most 250, at least or exactly or at most 251, at least or exactly or at most 252, at least or exactly or at most 253, at least or exactly or at most 254, at least or exactly or at most 255, at least or exactly or at most 256, at least or exactly or at most 257, at least or exactly or at most 258, at least or exactly or at most 259, at least or exactly or at most 260, at least or exactly or at most 261, at least or exactly or at most 262, at least or exactly or at most 263, at least or exactly or at most 264, at least or exactly or at most 265, at least or exactly or at most 266, at least or exactly or at most 267, at least or exactly or at most 268, at least or exactly or at most 269, at least or exactly or at most 270, at least or exactly or at most 271, at least or exactly or at most 272, at least or exactly or at most 273, at least or exactly or at most 274, at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, at least or exactly or at most 285, at least or exactly or at most 286, at least or exactly or at most 287, at least or exactly or at most 288, at least or exactly or at most 289, at least or exactly or at most 290, at least or exactly or at most 291, at least or exactly or at most 292, at least or exactly or at most 293, at least or exactly or at most 294, at least or exactly or at most 295, at least or exactly or at most 296, at least or exactly or at most 297, at least or exactly or at most 298, at least or exactly or at most 299, at least or exactly or at most 300, at least or exactly or at most 301, at least or exactly or at most 302, at least or exactly or at most 303, at least or exactly or at most 304, at least or exactly or at most 305, at least or exactly or at most 306, at least or exactly or at most 307, at least or exactly or at most 308, at least or exactly or at most 309, at least or exactly or at most 310, at least or exactly or at most 311, at least or exactly or at most 312, at least or exactly or at most 313, at least or exactly or at most 314, at least or exactly or at most 315, at least or exactly or at most 316, at least or exactly or at most 317, at least or exactly or at most 318, at least or exactly or at most 319, at least or exactly or at most 320, at least or exactly or at most 321, at least or exactly or at most 322, at least or exactly or at most 323, at least or exactly or at most 324, at least or exactly or at most 325, at least or exactly or at most 326, at least or exactly or at most 327, at least or exactly or at most 328, at least or exactly or at most 329, at least or exactly or at most 330, at least or exactly or at most 331, at least or exactly or at most 332, at least or exactly or at most 333, at least or exactly or at most 334, at least or exactly or at most 335, at least or exactly or at most 336, at least or exactly or at most 337, at least or exactly or at most 338, at least or exactly or at most 339, at least or exactly or at most 340, at least or exactly or at most 341, at least or exactly or at most 342, at least or exactly or at most 343, at least or exactly or at most 344, at least or exactly or at most 345, at least or exactly or at most 346, at least or exactly or at most 347, at least or exactly or at most 348, at least or exactly or at most 349, at least or exactly or at most 350, at least or exactly or at most 351, at least or exactly or at most 352, at least or exactly or at most 353, at least or exactly or at most 354, at least or exactly or at most 355, at least or exactly or at most 356, at least or exactly or at most 357, at least or exactly or at most 358, at least or exactly or at most 359, at least or exactly or at most 360, at least or exactly or at most 361, at least or exactly or at most 362, at least or exactly or at most 363, at least or exactly or at most 364, at least or exactly or at most 365, at least or exactly or at most 366, at least or exactly or at most 367, at least or exactly or at most 368, at least or exactly or at most 369, at least or exactly or at most 370, at least or exactly or at most 371, at least or exactly or at most 372, at least or exactly or at most 373, at least or exactly or at most 374, at least or exactly or at most 375, at least or exactly or at most 376, at least or exactly or at most 377, at least or exactly or at most 378, at least or exactly or at most 379, at least or exactly or at most 380, at least or exactly or at most 381, at least or exactly or at most 382, at least or exactly or at most 383, at least or exactly or at most 384, at least or exactly or at most 385, at least or exactly or at most 386, at least or exactly or at most 387, at least or exactly or at most 388, at least or exactly or at most 389, at least or exactly or at most 390, at least or exactly or at most 391, at least or exactly or at most 392, at least or exactly or at most 393, at least or exactly or at most 394, at least or exactly or at most 395, at least or exactly or at most 396, at least or exactly or at most 397, at least or exactly or at most 398, at least or exactly or at most 399, at least or exactly or at most 400, at least or exactly or at most 401, at least or exactly or at most 402, at least or exactly or at most 403, at least or exactly or at most 404, at least or exactly or at most 405, at least or exactly or at most 406, at least or exactly or at most 407, at least or exactly or at most 408, at least or exactly or at most 409, at least or exactly or at most 410, at least or exactly or at most 411, at least or exactly or at most 412, at least or exactly or at most 413, at least or exactly or at most 414, at least or exactly or at most 415, at least or exactly or at most 416, at least or exactly or at most 417, at least or exactly or at most 418, at least or exactly or at most 419, at least or exactly or at most 420, at least or exactly or at most 421, at least or exactly or at most 422, at least or exactly or at most 423, at least or exactly or at most 424, at least or exactly or at most 425, at least or exactly or at most 426, at least or exactly or at most 427, at least or exactly or at most 428, at least or exactly or at most 429, at least or exactly or at most 430, at least or exactly or at most 431, at least or exactly or at most 432, at least or exactly or at most 433, at least or exactly or at most 434, at least or exactly or at most 435, at least or exactly or at most 436, at least or exactly or at most 437, at least or exactly or at most 438, at least or exactly or at most 439, at least or exactly or at most 440, at least or exactly or at most 441, at least or exactly exactly or at most 442, at least or exactly or at most 443, at least or exactly or at most 444, at least or exactly or at most 445, at least or exactly or at most 446, at least or exactly or at most 447, at least or exactly or at most 448, at least or exactly or at most 449, at least or exactly or at most 450, at least or exactly or at most 451, at least or exactly or at most 452, at least or exactly or at most 453, at least or exactly or at most 454, at least or exactly or at most 455, at least or exactly or at most 456, at least or exactly or at most 457, at least or exactly or at most 458, at least or exactly or at most 459, at least or exactly or at most 460, at least or exactly or at most 461, at least or exactly or at most 462, at least or exactly or at most 463, at least or exactly or at most 464, at least or exactly or at most 465, at least or exactly or at most 466, at least or exactly or at most 467, at least or exactly or at most 468, at least or exactly or at most 469, at least or exactly or at most 470, at least or exactly or at most 471, at least or exactly or at most 472, at least or exactly or at most 473, at least or exactly or at most 474, at least or exactly or at most 475, at least or exactly or at most 476, at least or exactly or at most 477, at least or exactly or at most 478, at least or exactly or at most 479, at least or exactly or at most 480, at least or exactly or at most 481, at least or exactly or at most 482, at least or exactly or at most 483, at least or exactly or at most 484, at least or exactly or at most 485, at least or exactly or at most 486, at least or exactly or at most 487, at least or exactly or at most 488, at least or exactly or at most 489, at least or exactly or at most least or exactly or at most 490, at least or exactly or at most 491, at least or exactly or at most 492, at least or exactly or at most 493, at least or exactly or at most 494, at least or exactly or at most 495, at least or exactly or at most 496, at least or exactly or at most 497, at least or exactly or at most 498, at least or exactly or at most 499, at least or exactly or at most 500, at least or exactly or at most 501, at least or exactly or at most 502, at least or exactly or at most 503, at least or exactly or at most 504, at least or exactly or at most 505, at least or exactly or at most 506, at least or exactly or at most 507 contiguous amino acid residues, or at least or exactly or at most 508 contiguous amino acid residues.

13. The composition according to claim 10, wherein the at least or exactly or at most 90 contiguous amino acid residues have an N-terminal amino acid residue corresponding to any one of amino acid residues any one of amino acid residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 42, 43, 44, 45, 46, 47, 48, 49, 50, 51, 52, 53, 54, 55, 56, 57, 58, 59, 60, 61, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, and 410 in SEQ ID NO: 10, wherein the N-terminal first residue will not be higher numbered than 510-L, where L is the number of amino acids defined for option b.

14. The composition according to claim 10, wherein the polypeptide is fused or conjugated to an immunogenic carrier molecule.

15. The composition according to claim 14, wherein the immunogenic carrier molecule is a polypeptide that induces T-helper lymphocyte responses in a majority of humans.

16. The composition according to claim 15, wherein the immunogenic carrier molecule is selected from the group consisting of keyhole limpet hemocyanin or a fragment thereof, tetanus toxoid or a fragment thereof, and diphtheria toxoid or a fragment thereof.

17. The composition according to claim 10, wherein the polypeptide is capable of inducing an adaptive immune response against the polypeptide in a human being.

* * * * *

SEQUENCE LISTING

```
<160> NUMBER OF SEQ ID NOS: 51

<210> SEQ ID NO 1
<211> LENGTH: 140
<212> TYPE: PRT
<213> ORGANISM: Staphylococcus aureus

<400> SEQUENCE: 1

Met Ala Lys Gly Asn Leu Phe Lys Ala Ile Leu Gly Ile Gly Gly Ala
1               5                   10                  15

Val Ala Ala Val Leu Val Thr Arg Lys Asp Ser Arg Asp Lys Leu Lys
            20                  25                  30

Ala Glu Tyr Asn Lys Tyr Lys Gln Asp Pro Gln Ser Tyr Lys Asp Asn
        35                  40                  45

Ala Lys Asp Lys Ala Thr Gln Leu Gly Thr Ile Ala Asn Glu Thr Ile
    50                  55                  60

Lys Glu Val Lys Thr Asn Pro Lys Glu Tyr Ala Asn Arg Leu Lys Asn
65                  70                  75                  80

Asn Pro Lys Ala Phe Phe Glu Glu Lys Ser Lys Phe Thr Glu Tyr
                85                  90                  95

Asp Asn Lys Thr Asp Glu Ser Ile Glu Lys Gly Lys Phe Asp Asp Glu
            100                 105                 110

Gly Gly Ala Ala Pro Asn Asn Asn Leu Arg Ile Val Thr Glu Glu Asp
        115                 120                 125

Leu Lys Lys Asn Lys Asn Ala Leu Ser Asp Lys Glu
    130                 135                 140

<210> SEQ ID NO 2
<211> LENGTH: 193
<212> TYPE: PRT
<213> ORGANISM: Staphylococcus aureus
```

<400> SEQUENCE: 2

```
Met Lys Lys Leu Val Ser Ile Val Gly Ala Thr Leu Leu Leu Ala Gly
1               5                   10                  15
Cys Gly Ser Gln Asn Leu Ala Pro Leu Glu Lys Thr Thr Asp Leu
            20                  25                  30
Arg Glu Asp Asn His Gln Leu Lys Leu Asp Ile Gln Glu Leu Asn Gln
                35                  40                  45
Gln Ile Ser Asp Ser Lys Ser Lys Ile Lys Gly Leu Glu Lys Asp Lys
        50                  55                  60
Glu Asn Ser Lys Lys Thr Ala Ser Asn Asn Thr Lys Ile Lys Leu Met
65                  70                  75                  80
Asn Val Thr Ser Thr Tyr Tyr Asp Lys Val Ala Lys Ala Leu Lys Ser
                85                  90                  95
Tyr Asn Asp Ile Glu Lys Asp Val Ser Lys Asn Lys Gly Asp Lys Asn
                100                 105                 110
Val Gln Ser Lys Leu Asn Gln Ile Ser Asn Asp Ile Gln Ser Ala His
            115                 120                 125
Thr Ser Tyr Lys Asp Ala Ile Asp Gly Leu Ser Leu Ser Asp Asp Asp
    130                 135                 140
Lys Lys Thr Ser Lys Asn Ile Asp Lys Leu Asn Ser Asp Leu Asn His
145                 150                 155                 160
Ala Phe Asp Asp Ile Lys Asn Gly Tyr Gln Asn Lys Asp Lys Lys Gln
                165                 170                 175
Leu Thr Lys Gly Gln Gln Ala Leu Ser Lys Leu Asn Leu Asn Ala Lys
            180                 185                 190
Ser
```

<210> SEQ ID NO 3
<211> LENGTH: 209
<212> TYPE: PRT
<213> ORGANISM: Staphylococcus aureus

<400> SEQUENCE: 3

```
Met Lys Lys Leu Val Thr Gly Leu Leu Ala Leu Ser Leu Phe Leu Ala
1               5                   10                  15
Ala Cys Gly Gln Asp Ser Asp Gln Gln Lys Asp Ser Asn Lys Glu Lys
            20                  25                  30
Asp Asp Lys Ala Lys Thr Glu Gln Gln Asp Lys Lys Thr Asn Asp Ser
        35                  40                  45
Ser Lys Asp Lys Lys Asp Asn Lys Asp Ser Lys Asp Val Asn Lys
    50                  55                  60
Asp Asn Lys Asp Asn Ser Ala Asn Asp Asn Gln Gln Ser Asn Ser
65                  70                  75                  80
Asn Ala Thr Asn Asn Asp Gln Asn Gln Thr Asn Asn Asn Gln Ser Asn
                85                  90                  95
Ser Gly Gln Thr Thr Asn Asn Gln Lys Ser Ser Tyr Val Ala Pro Tyr
                100                 105                 110
Tyr Gly Gln Asn Ala Ala Pro Val Ala Arg Gln Ile Tyr Pro Phe Asn
            115                 120                 125
Gly Asn Lys Ser Gln Ala Leu Gln Gln Leu Pro Asn Phe Gln Thr Ala
    130                 135                 140
Leu Asn Ala Ala Asn Asn Glu Ala Asn Lys Phe Gly Asn Gly His Lys
145                 150                 155                 160
```

```
Val Tyr Asn Asp Tyr Ser Ile Glu Glu His Asn Gly Asn Tyr Lys Tyr
                165                 170                 175

Val Phe Ser Phe Lys Asp Pro Asn Val Asn Gly Lys Tyr Ser Ile Val
            180                 185                 190

Thr Val Asp Tyr Thr Gly Gln Ala Met Val Thr Asp Pro Asn Tyr Gln
        195                 200                 205

Gln

<210> SEQ ID NO 4
<211> LENGTH: 242
<212> TYPE: PRT
<213> ORGANISM: Staphylococcus aureus

<400> SEQUENCE: 4

Met Lys Lys Val Met Gly Ile Leu Leu Ala Ser Thr Leu Ile Leu Gly
1               5                   10                  15

Ala Cys Gly His His Gln Asp Ser Ala Lys Lys Glu Ser Thr Ser His
            20                  25                  30

Lys Lys Lys Glu Asn Asp Asn Glu Glu Leu Asn Glu Glu Leu Lys Glu
        35                  40                  45

Phe Lys Ser Lys Asn Met Asp Ile Lys Ile Lys Gly Asp Thr Ile
    50                  55                  60

Val Ser Asp Lys Phe Glu Ala Lys Ile Lys Glu Pro Phe Ile Ile Asn
65                  70                  75                  80

Glu Lys Asp Glu Lys Lys Tyr Ile Ala Phe Lys Met Glu Ile Thr
                85                  90                  95

Ala Lys Lys Asp Asp Lys Asp Leu Asn Pro Ser Ser Ile Ser His Asp
            100                 105                 110

Tyr Ile Asn Ile Thr Gln Asp Asp Lys Asn Thr Val Asn Lys Leu Arg
        115                 120                 125

Asp Gly Tyr Leu Leu Ser Asp Lys Asn Tyr Lys Asp Trp Thr Glu His
130                 135                 140

Asn Gln Asp Gln Ile Lys Lys Gly Lys Thr Ala Gln Ala Met Phe Ile
145                 150                 155                 160

Tyr Glu Leu Arg Gly Asp Gly Asn Ile Asn Leu Asn Val His Lys Tyr
                165                 170                 175

Ser Glu Asp Lys Thr Val Asp Ser Lys Ser Phe Lys Phe Ser Lys Leu
            180                 185                 190

Lys Thr Glu Asp Phe Ser His Arg Ala Glu Thr Arg Glu Glu Val Glu
        195                 200                 205

Lys Lys Glu Lys Glu Phe Glu Glu Tyr Lys Lys Glu Gln Glu Arg
    210                 215                 220

Glu Lys Glu Lys Glu Lys Gln Lys Asp Asp His Ser Gly Leu Asp
225                 230                 235                 240

Glu Val

<210> SEQ ID NO 5
<211> LENGTH: 327
<212> TYPE: PRT
<213> ORGANISM: Staphylococcus aureus

<400> SEQUENCE: 5

Met Lys Lys Trp Gln Phe Val Gly Thr Thr Ala Leu Gly Ala Thr Leu
1               5                   10                  15

Leu Leu Gly Ala Cys Gly Gly Asn Gly Gly Ser Gly Asn Ser Asp
            20                  25                  30
```

```
Leu Lys Gly Glu Ala Lys Gly Asp Gly Ser Ser Thr Val Ala Pro Ile
             35                  40                  45

Val Glu Lys Leu Asn Glu Lys Trp Ala Gln Asp His Ser Asp Ala Lys
 50                  55                  60

Ile Ser Ala Gly Gln Ala Gly Thr Gly Ala Gly Phe Gln Lys Phe Ile
 65                  70                  75                  80

Ala Gly Asp Ile Asp Phe Ala Asp Ala Ser Arg Pro Ile Lys Asp Glu
                 85                  90                  95

Glu Lys Gln Lys Leu Gln Asp Lys Asn Ile Lys Tyr Lys Glu Phe Lys
            100                 105                 110

Ile Ala Gln Asp Gly Val Thr Val Ala Val Asn Lys Glu Asn Asp Phe
        115                 120                 125

Val Asp Glu Leu Asp Lys Gln Gln Leu Lys Ala Ile Tyr Ser Gly Lys
    130                 135                 140

Ala Lys Thr Trp Lys Asp Val Asn Ser Lys Trp Pro Asp Lys Lys Ile
145                 150                 155                 160

Asn Ala Val Ser Pro Asn Ser Ser His Gly Thr Tyr Asp Phe Phe Glu
                165                 170                 175

Asn Glu Val Met Asn Lys Glu Asp Ile Lys Ala Glu Lys Asn Ala Asp
            180                 185                 190

Thr Asn Ala Ile Val Ser Ser Val Thr Lys Asn Lys Glu Gly Ile Gly
        195                 200                 205

Tyr Phe Gly Tyr Asn Phe Tyr Val Gln Asn Lys Asp Lys Leu Lys Glu
    210                 215                 220

Val Lys Ile Lys Asp Glu Asn Gly Lys Ala Thr Glu Pro Thr Lys Lys
225                 230                 235                 240

Thr Ile Gln Asp Asn Ser Tyr Ala Leu Ser Arg Pro Leu Phe Ile Tyr
                245                 250                 255

Val Asn Glu Lys Ala Leu Lys Asp Asn Lys Val Met Ser Glu Phe Ile
            260                 265                 270

Lys Phe Val Leu Glu Asp Lys Gly Lys Ala Ala Glu Gly Gly Tyr
        275                 280                 285

Val Ala Ala Pro Glu Lys Thr Tyr Lys Ser Gln Leu Asp Asp Leu Lys
    290                 295                 300

Ala Phe Ile Asp Lys Asn Gln Lys Ser Asp Lys Lys Ser Asp Asp
305                 310                 315                 320

Lys Lys Ser Glu Asp Lys Lys
                325

<210> SEQ ID NO 6
<211> LENGTH: 357
<212> TYPE: PRT
<213> ORGANISM: Staphylococcus aureus

<400> SEQUENCE: 6

Met Lys Gly Lys Phe Leu Lys Val Ser Ser Leu Phe Val Ala Thr Leu
 1               5                  10                  15

Thr Thr Ala Thr Leu Val Ser Ser Pro Ala Ala Asn Ala Leu Ser Ser
             20                  25                  30

Lys Ala Met Asp Asn His Pro Gln Gln Thr Gln Thr Asp Lys Gln Gln
         35                  40                  45

Thr Pro Lys Ile Gln Lys Gly Gly Asn Leu Lys Pro Leu Glu Gln Arg
     50                  55                  60

Glu Arg Ala Asn Val Ile Leu Pro Asn Asn Asp Arg His Gln Ile Thr
 65                  70                  75                  80
```

Asp Thr Thr Asn Gly His Tyr Ala Pro Val Thr Tyr Ile Gln Val Glu
            85                  90                  95

Ala Pro Thr Gly Thr Phe Ile Ala Ser Gly Val Val Gly Lys Asp
        100                 105                 110

Thr Leu Leu Thr Asn Lys His Ile Val Asp Ala Thr His Gly Asp Pro
            115                 120                 125

His Ala Leu Lys Ala Phe Ala Ser Ala Ile Asn Gln Asp Asn Tyr Pro
130                 135                 140

Asn Gly Gly Phe Thr Ala Glu Gln Ile Thr Lys Tyr Ser Gly Glu Gly
145                 150                 155                 160

Asp Leu Ala Ile Val Lys Phe Ser Pro Asn Glu Gln Asn Lys His Ile
                165                 170                 175

Gly Glu Val Val Lys Pro Ala Thr Met Ser Asn Asn Ala Glu Thr Gln
            180                 185                 190

Val Asn Gln Asn Ile Thr Val Thr Gly Tyr Pro Gly Asp Lys Pro Val
        195                 200                 205

Ala Thr Met Trp Glu Ser Lys Gly Lys Ile Thr Tyr Leu Lys Gly Glu
    210                 215                 220

Ala Met Gln Tyr Asp Leu Ser Thr Thr Gly Gly Asn Ser Gly Ser Pro
225                 230                 235                 240

Val Phe Asn Glu Lys Asn Glu Val Ile Gly Ile His Trp Gly Gly Val
                245                 250                 255

Pro Asn Gln Phe Asn Gly Ala Val Phe Ile Asn Glu Asn Val Arg Asn
            260                 265                 270

Phe Leu Lys Gln Asn Ile Glu Asp Ile Asn Phe Ala Asn Asp His
        275                 280                 285

Pro Asn Asn Pro Asp Asn Pro Asp Asn Pro Asn Asn Pro Asp Asn Pro
290                 295                 300

Asn Asn Pro Asp Asn Pro Asn Asn Pro Asp Asn Pro Asn Asn Pro Asn
305                 310                 315                 320

Asn Pro Asp Asn Pro Asn Asn Pro Asp Asn Pro Asn Asn Pro Asp Gln
            325                 330                 335

Pro Asn Asn Pro Asn Asn Pro Asp Asn Gly Asp Asn Asn Asn Ser Asp
            340                 345                 350

Asn Pro Asp Ala Ala
        355

<210> SEQ ID NO 7
<211> LENGTH: 399
<212> TYPE: PRT
<213> ORGANISM: Staphylococcus aureus

<400> SEQUENCE: 7

Met Lys Arg Thr Leu Val Leu Leu Ile Thr Ala Ile Phe Ile Leu Ala
1               5                   10                  15

Ala Cys Gly Asn His Lys Asp Asp Gln Ala Gly Lys Asp Asn Gln Lys
            20                  25                  30

His Asn Asn Ser Ser Asn Gln Val Lys Glu Ile Ala Thr Asp Lys Asn
        35                  40                  45

Val Gln Gly Asp Asn Tyr Arg Thr Leu Leu Pro Phe Lys Glu Ser Gln
    50                  55                  60

Ala Arg Gly Leu Leu Gln Asp Asn Met Ala Asn Ser Tyr Asn Gly Gly
65                  70                  75                  80

Asp Phe Glu Asp Gly Leu Leu Asn Leu Ser Lys Glu Val Phe Pro Thr
                85                  90                  95

Asp Lys Tyr Leu Tyr Gln Asp Gly Gln Phe Leu Asp Lys Lys Thr Ile
            100                 105                 110

Asn Ala Tyr Leu Asn Leu Lys Tyr Thr Lys Arg Glu Ile Asp Lys Met
            115                 120                 125

Ser Glu Lys Asp Lys Asp Lys Lys Ala Asn Glu Asn Leu Gly Leu
    130                 135                 140

Asn Pro Ser His Glu Gly Glu Thr Asp Pro Glu Lys Ile Ala Glu Lys
145                 150                 155                 160

Ser Pro Ala Tyr Leu Ser Asn Ile Leu Glu Gln Asp Phe Tyr Gly Gly
                165                 170                 175

Gly Asp Thr Lys Gly Lys Asn Ile Lys Gly Met Thr Ile Gly Leu Ala
            180                 185                 190

Met Asn Ser Val Tyr Tyr Lys Lys Glu Lys Asp Gly Pro Thr Phe
            195                 200                 205

Ser Lys Lys Leu Asp Asp Ser Glu Val Lys Lys Gln Gly Lys Gln Met
    210                 215                 220

Ala Ser Glu Ile Leu Ser Arg Leu Arg Glu Asn Asp Asp Leu Lys Asp
225                 230                 235                 240

Ile Pro Ile His Phe Ala Ile Tyr Lys Gln Ser Ser Glu Asp Ser Ile
                245                 250                 255

Thr Pro Gly Glu Phe Ile Thr Gln Ala Thr Glu Lys Ser Gln Thr
            260                 265                 270

Lys Leu Asn Glu Trp His Asn Ile Asn Glu Lys Ser Ala Leu Leu Pro
    275                 280                 285

Ser Ser Thr Ala Ala Asp Tyr Asp Glu Asn Leu Asn Asn Phe Lys
290                 295                 300

Gln Phe Asn Asp Asn Leu Gln Ser Tyr Phe Ser Asn Phe Thr Gln Ala
305                 310                 315                 320

Val Gly Lys Val Lys Phe Val Asp Lys Pro Gln Arg Leu Val Val
                325                 330                 335

Asp Leu Pro Ile Asp Tyr Tyr Gly Gln Ala Glu Thr Ile Gly Ile Thr
            340                 345                 350

Gln Tyr Val Thr Glu Gln Ala Asn Lys Tyr Phe Asp Lys Ile Asp Asn
            355                 360                 365

Tyr Glu Ile Arg Ile Lys Asp Gly Asn Gln Pro Arg Ala Leu Ile Ser
370                 375                 380

Lys Thr Lys Asp Asp Lys Glu Pro Gln Val His Ile Tyr Ser Asn
385                 390                 395

<210> SEQ ID NO 8
<211> LENGTH: 495
<212> TYPE: PRT
<213> ORGANISM: Staphylococcus aureus

<400> SEQUENCE: 8

Met Arg Glu Asn Phe Lys Leu Arg Lys Met Lys Val Gly Leu Val Ser
1               5                   10                  15

Val Ala Ile Thr Met Leu Tyr Ile Met Thr Asn Gly Gln Ala Glu Ala
            20                  25                  30

Ser Glu Ala Asn Glu Lys Pro Ser Thr Asn Gln Glu Ser Lys Val Val
        35                  40                  45

Ser Gln Thr Glu Gln Asn Ser Lys Glu Thr Lys Thr Val Glu Ser Asn
    50                  55                  60

Lys Asn Phe Val Lys Leu Asp Thr Ile Lys Pro Gly Ala Gln Lys Ile
65                  70                  75                  80

```
Thr Gly Thr Thr Leu Pro Asn His Tyr Val Leu Leu Thr Val Asp Gly
                85                  90                  95
Lys Ser Ala Asp Ser Val Glu Asn Gly Gly Leu Gly Phe Val Glu Ala
            100                 105                 110
Asn Asp Lys Gly Glu Phe Glu Tyr Pro Leu Asn Asn Arg Lys Ile Val
        115                 120                 125
His Asn Gln Glu Ile Glu Val Ser Ser Ser Pro Asp Leu Gly Glu
    130                 135                 140
Asp Glu Glu Asp Glu Glu Val Glu Glu Ala Ser Thr Asp Lys Ala Gly
145                 150                 155                 160
Val Glu Glu Glu Ser Thr Glu Ala Lys Val Thr Tyr Thr Thr Pro Arg
                165                 170                 175
Tyr Glu Lys Ala Tyr Glu Ile Pro Lys Glu Gln Leu Lys Glu Lys Asp
            180                 185                 190
Gly His His Gln Val Phe Ile Glu Pro Ile Thr Glu Gly Ser Gly Ile
        195                 200                 205
Ile Lys Gly His Thr Ser Val Lys Gly Lys Val Ala Leu Ser Ile Asn
    210                 215                 220
Asn Lys Phe Ile Asn Phe Glu Glu Ser Val Lys Gly Val Ser Lys
225                 230                 235                 240
Glu Asp Thr Lys Ala Ser Ser Asp Gly Ile Trp Met Pro Ile Asp Asp
                245                 250                 255
Lys Gly Tyr Phe Asn Phe Asp Phe Lys Thr Lys Arg Phe Asp Asn Leu
            260                 265                 270
Glu Leu Lys Glu Gly Asn Asp Ile Ser Leu Thr Phe Ala Pro Asp Asp
        275                 280                 285
Glu Glu Asp Ala Leu Lys Pro Leu Ile Phe Lys Thr Lys Val Thr Ser
    290                 295                 300
Leu Glu Asp Ile Asp Lys Ala Glu Thr Lys Tyr Asp His Thr Lys Leu
305                 310                 315                 320
Asn Lys Val Lys Val Leu Asp Asn Val Lys Glu Asp Leu His Val Asp
                325                 330                 335
Glu Ile Tyr Gly Ser Leu Tyr His Thr Asp Lys Gly Lys Gly Ile Leu
            340                 345                 350
Asp Lys Glu Gly Thr Lys Val Ile Lys Gly Lys Thr Lys Phe Ala Asn
        355                 360                 365
Ala Val Val Lys Val Asp Ser Glu Leu Gly Glu Ala Gln Leu Phe Pro
    370                 375                 380
Asp Leu Gln Val Asn Glu Lys Gly Glu Phe Ser Phe Asp Ser His Gly
385                 390                 395                 400
Ala Gly Phe Arg Leu Gln Asn Gly Glu Lys Leu Asn Phe Thr Val Val
                405                 410                 415
Asp Pro Ile Thr Gly Asp Leu Leu Ser Asn Glu Phe Val Ser Lys Glu
            420                 425                 430
Ile Asp Ile Glu Glu Thr Pro Glu Gln Lys Ala Asp Arg Glu Phe Asp
        435                 440                 445
Glu Lys Leu Glu Asn Thr Pro Ala Tyr Tyr Lys Leu Tyr Gly Asp Lys
    450                 455                 460
Ile Val Gly Phe Asp Thr Asn Asp Phe Pro Ile Thr Trp Phe Tyr Pro
465                 470                 475                 480
Leu Gly Glu Lys Lys Val Glu Arg Thr Thr Pro Lys Leu Glu Lys
                485                 490                 495
```

```
<210> SEQ ID NO 9
<211> LENGTH: 507
<212> TYPE: PRT
<213> ORGANISM: Staphylococcus aureus

<400> SEQUENCE: 9

Met Ser Lys Lys Leu Lys Ile Ile Pro Ile Ile Val Leu Leu
 1               5                  10                  15

Leu Ile Gly Gly Ile Ala Trp Gly Val Tyr Ala Phe Ala Asn Thr
             20                  25                  30

Pro Lys Asn Thr Tyr Leu Lys Ser Glu Gln Thr Ala Lys Met Tyr
             35                  40                  45

Lys Asp Tyr Phe Asn Asp Arg Phe Glu Asn Glu Val Lys Phe Gln Glu
 50                  55                  60

Lys Met Lys Asp Asn Ser Phe Leu Ser Ser Leu Glu Leu Ser Ala Asp
 65                  70                  75                  80

Ala Ser Asp Glu Ile Val Lys Gly Leu Gly Ile Pro Lys Ser Val Val
                     85                  90                  95

Asn Ala Ser Lys Ile Lys Met Ser Tyr Gly His Asp Pro Lys Lys Glu
            100                 105                 110

Lys Ser Met Ile Asn Leu Glu Pro Thr Ile Ala Asp Ser Ala Leu Gly
            115                 120                 125

Lys Phe Gln Leu Ala Ala Asp Lys Asp Lys His Tyr Phe Glu Ser Pro
130                 135                 140

Leu Phe Lys Gly Lys Tyr Ser Val Asn Asn Ser Asp Leu Leu Ser Thr
145                 150                 155                 160

Tyr Ser Lys Leu Thr Gly Glu Asp Glu Glu Thr Ala Lys Glu Asn Gly
                165                 170                 175

Ile Thr Asn Gln Gln Leu Asn Leu Asn Thr Leu Phe Ser Asn Ala Gln
            180                 185                 190

Ala Gln Gln Ser Asp Tyr Ser Lys Ile Ala Glu Lys Tyr Ser Glu Leu
            195                 200                 205

Ile Val Asp Lys Leu Asp Asp Asn Phe Asp Lys Gly Lys Lys Glu
210                 215                 220

Glu Ile Lys Val Asn Gly Glu Lys Tyr Lys Val Arg Pro Val Thr Leu
225                 230                 235                 240

Thr Leu Ser Arg Ala Asp Thr Lys Lys Ile Thr Leu Ala Val Leu Glu
                245                 250                 255

Glu Ala Lys Lys Asp Lys Asp Leu Lys Lys Leu Met Glu Glu Gln Gly
            260                 265                 270

Thr Thr Lys Asp Phe Glu Lys Asp Ile Lys Lys Ala Ile Asp Asp Val
            275                 280                 285

Lys Glu Thr Lys Lys Asp Glu Phe Ala Lys Ile Gln Ser Lys Ile Tyr
290                 295                 300

Thr Glu Lys His Thr Ile Val Lys Arg Glu Ile Thr Ile Thr Asp Lys
305                 310                 315                 320

Glu Asn Asn Lys Thr Lys Ile Lys Gly Thr Asn Thr Leu Glu Asp Asp
                325                 330                 335

Lys Leu Lys Leu Asp Tyr Ala Leu Asp Phe Asp Gln Asp Lys Tyr Thr
            340                 345                 350

Tyr Ala Glu Ala Lys Tyr Thr Ile Lys Gly Val Ser Ser Lys Glu Lys
            355                 360                 365

Asp Asn Lys Tyr Ser Asp Lys Tyr Glu Phe Gly Lys Lys Thr Glu Tyr
370                 375                 380
```

-continued

```
Asp Glu Ser Lys Ile Lys Leu Asp Asn Gln Glu Lys Val Asp Gly Thr
385                 390                 395                 400

Lys Arg Gln Asp Lys Gly Lys Ile Thr Val Ala Leu Asp Lys Tyr Ser
            405                 410                 415

Asp Glu Asn Glu Phe Thr Phe Glu Asn Asn Ile Asp Ser Asp Val Lys
        420                 425                 430

Asn Asn Thr Gln Lys Ser Thr Leu Asn Ile Gly Ile Lys Tyr Ala Glu
    435                 440                 445

Glu Pro Ile Asn Phe Ile Leu Lys Ser Ser Thr Lys Leu Lys Ala Asp
450                 455                 460

Ile Asp Phe Asp Ser Gly Ala Lys Asp Phe Asn Ser Leu Ser Ser
465                 470                 475                 480

Lys Asp Arg Glu Lys Leu Glu Lys Glu Ile Glu Lys Asn Gly Gly Lys
            485                 490                 495

Met Phe Glu Ser Ile Leu Lys Lys Ala Ser Lys
                500                 505

<210> SEQ ID NO 10
<211> LENGTH: 509
<212> TYPE: PRT
<213> ORGANISM: Staphylococcus aureus

<400> SEQUENCE: 10

Met Arg Lys Phe Ser Arg Tyr Ala Phe Thr Ser Met Ala Thr Val Thr
1               5                   10                  15

Leu Leu Ser Ser Leu Thr Pro Ala Ala Leu Ala Ser Asp Thr Asn His
            20                  25                  30

Lys Pro Ala Thr Ser Asp Ile Asn Phe Glu Ile Thr Gln Lys Ser Asp
        35                  40                  45

Ala Val Lys Ala Leu Lys Glu Leu Pro Lys Ser Glu Asn Val Lys Asn
    50                  55                  60

His Tyr Gln Asp Tyr Ser Val Thr Asp Val Lys Thr Asp Lys Lys Gly
65                  70                  75                  80

Phe Thr His Tyr Thr Leu Gln Pro Ser Val Asp Gly Val His Ala Pro
                85                  90                  95

Asp Lys Glu Val Lys Val His Ala Asp Lys Ser Gly Lys Val Val Leu
            100                 105                 110

Ile Asn Gly Asp Thr Asp Ala Lys Lys Val Lys Pro Thr Asn Lys Val
        115                 120                 125

Thr Leu Ser Lys Asp Glu Ala Ala Asp Lys Ala Phe Asn Ala Val Lys
    130                 135                 140

Ile Asp Lys Asn Lys Ala Lys Asn Leu Gln Asp Asp Val Ile Lys Glu
145                 150                 155                 160

Asn Lys Val Glu Ile Asp Gly Asp Ser Asn Lys Tyr Ile Tyr Asn Ile
                165                 170                 175

Glu Leu Ile Thr Val Thr Pro Glu Ile Ser His Trp Lys Val Lys Ile
            180                 185                 190

Asp Ala Asp Thr Gly Ala Val Val Glu Lys Thr Asn Leu Val Lys Glu
        195                 200                 205

Ala Ala Ala Thr Gly Thr Gly Lys Gly Val Leu Gly Asp Thr Lys Asp
    210                 215                 220

Ile Asn Ile Asn Ser Ile Asp Gly Gly Phe Ser Leu Glu Asp Leu Thr
225                 230                 235                 240

His Gln Gly Lys Leu Ser Ala Tyr Asn Phe Asn Asp Gln Thr Gly Gln
                245                 250                 255
```

```
Ala Thr Leu Ile Thr Asn Glu Asp Glu Asn Phe Val Lys Asp Asp Gln
            260                 265                 270

Arg Ala Gly Val Asp Ala Asn Tyr Tyr Ala Lys Gln Thr Tyr Asp Tyr
            275                 280                 285

Tyr Lys Asn Thr Phe Gly Arg Glu Ser Tyr Asp Asn His Gly Ser Pro
            290                 295                 300

Ile Val Ser Leu Thr His Val Asn His Tyr Gly Gly Gln Asp Asn Arg
305                 310                 315                 320

Asn Asn Ala Ala Trp Ile Gly Asp Lys Met Ile Tyr Gly Asp Gly Asp
            325                 330                 335

Gly Arg Thr Phe Thr Asn Leu Ser Gly Ala Asn Asp Val Val Ala His
            340                 345                 350

Glu Leu Thr His Gly Val Thr Gln Glu Thr Ala Asn Leu Glu Tyr Lys
            355                 360                 365

Asp Gln Ser Gly Ala Leu Asn Glu Ser Phe Ser Asp Val Phe Gly Tyr
            370                 375                 380

Phe Val Asp Asp Glu Asp Phe Leu Met Gly Glu Asp Val Tyr Thr Pro
385                 390                 395                 400

Gly Lys Glu Gly Asp Ala Leu Arg Ser Met Ser Asn Pro Glu Gln Phe
            405                 410                 415

Gly Gln Pro Ser His Met Lys Asp Tyr Val Tyr Thr Glu Lys Asp Asn
            420                 425                 430

Gly Gly Val His Thr Asn Ser Gly Ile Pro Asn Lys Ala Ala Tyr Asn
            435                 440                 445

Val Ile Gln Ala Ile Gly Lys Ser Lys Ser Glu Gln Ile Tyr Tyr Arg
450                 455                 460

Ala Leu Thr Glu Tyr Leu Thr Ser Asn Ser Asn Phe Lys Asp Cys Lys
465                 470                 475                 480

Asp Ala Leu Tyr Gln Ala Ala Lys Asp Leu Tyr Asp Glu Gln Thr Ala
            485                 490                 495

Glu Gln Val Tyr Glu Ala Trp Asn Glu Val Gly Val Glu
            500                 505

<210> SEQ ID NO 11
<211> LENGTH: 515
<212> TYPE: PRT
<213> ORGANISM: Staphylococcus aureus

<400> SEQUENCE: 11

Met Lys Lys Lys Leu Gly Met Leu Leu Leu Val Pro Ala Val Thr Leu
1               5                   10                  15

Ser Leu Ala Ala Cys Gly Asn Asp Asp Gly Lys Asp Lys Asp Gly Lys
            20                  25                  30

Val Thr Ile Lys Thr Thr Val Tyr Pro Leu Gln Ser Phe Ala Glu Gln
            35                  40                  45

Ile Gly Gly Lys His Val Lys Val Ser Ser Ile Tyr Pro Ala Gly Thr
            50                  55                  60

Asp Leu His Ser Tyr Glu Pro Thr Gln Lys Asp Ile Leu Ser Ala Ser
65                  70                  75                  80

Lys Ser Asp Leu Phe Met Tyr Thr Gly Asp Asn Leu Asp Pro Val Ala
            85                  90                  95

Lys Lys Val Ala Ser Thr Ile Lys Asp Lys Lys Lys Leu Ser Leu
            100                 105                 110

Glu Asp Lys Leu Asp Lys Ala Lys Leu Leu Thr Asp Gln His Glu His
            115                 120                 125
```

```
Gly Glu Glu His Glu His Gly His Asp His Gly Lys Glu His
    130                 135                 140

His His His Gly Gly Tyr Asp Pro His Val Trp Leu Asp Pro Lys Ile
145                 150                 155                 160

Asn Gln Thr Phe Ala Lys Glu Ile Lys Asp Glu Leu Val Lys Lys Asp
                165                 170                 175

Pro Lys His Lys Asp Asp Tyr Glu Lys Asn Tyr Lys Lys Leu Asn Asp
            180                 185                 190

Asp Leu Lys Lys Ile Asp Asn Asp Met Lys Gln Val Thr Lys Asp Lys
        195                 200                 205

Gln Gly Asn Ala Val Phe Ile Ser His Glu Ser Ile Gly Tyr Leu Ala
    210                 215                 220

Asp Arg Tyr Gly Phe Val Gln Lys Gly Ile Gln Asn Met Asn Ala Glu
225                 230                 235                 240

Asp Pro Ser Gln Lys Glu Leu Thr Lys Ile Val Lys Glu Ile Arg Asp
                245                 250                 255

Ser Asn Ala Lys Tyr Ile Leu Tyr Glu Asp Asn Val Ala Asn Lys Val
            260                 265                 270

Thr Glu Thr Ile Arg Lys Glu Thr Asp Ala Lys Pro Leu Lys Phe Tyr
        275                 280                 285

Asn Met Glu Ser Leu Asn Lys Glu Gln Gln Lys Lys Asp Asn Ile Thr
    290                 295                 300

Tyr Gln Ser Leu Met Lys Ser Asn Ile Glu Asn Ile Gly Lys Ala Leu
305                 310                 315                 320

Asp Ser Gly Val Lys Val Lys Asp Asp Lys Ala Glu Ser Lys His Asp
                325                 330                 335

Lys Ala Ile Ser Asp Gly Tyr Phe Lys Asp Glu Gln Val Lys Asp Arg
            340                 345                 350

Glu Leu Ser Asp Tyr Ala Gly Glu Trp Gln Ser Val Tyr Pro Tyr Leu
        355                 360                 365

Lys Asp Gly Thr Leu Asp Glu Val Met Glu His Lys Ala Glu Asn Asp
    370                 375                 380

Pro Lys Lys Ser Ala Lys Asp Leu Lys Ala Tyr Tyr Asp Lys Gly Tyr
385                 390                 395                 400

Lys Thr Asp Ile Thr Asn Ile Asp Ile Lys Gly Asn Glu Ile Thr Phe
                405                 410                 415

Thr Lys Asp Gly Thr Lys His Thr Gly Lys Tyr Glu Tyr Asn Gly Lys
            420                 425                 430

Lys Thr Leu Lys Tyr Pro Lys Gly Asn Arg Gly Val Arg Phe Met Phe
        435                 440                 445

Lys Leu Val Asp Gly Asn Asp Lys Asp Leu Pro Lys Phe Ile Gln Phe
    450                 455                 460

Ser Asp His Asn Ile Ala Pro Lys Lys Ala Glu His Phe His Ile Phe
465                 470                 475                 480

Met Gly Asn Asp Asn Asp Ala Leu Leu Lys Glu Met Asp Asn Trp Pro
                485                 490                 495

Thr Tyr Tyr Pro Ser Lys Leu Asn Lys Asp Gln Ile Lys Glu Glu Met
            500                 505                 510

Leu Ala His
        515
```

<210> SEQ ID NO 12
<211> LENGTH: 564
<212> TYPE: PRT
<213> ORGANISM: Staphylococcus aureus

<400> SEQUENCE: 12

```
Met Val Leu Tyr Ile Ile Leu Ala Ile Ile Val Ile Ile Leu Ile Ala
1               5                   10                  15

Val Gly Val Leu Phe Tyr Leu Arg Ser Asn Lys Arg Gln Ile Ile Glu
            20                  25                  30

Lys Ala Ile Glu Arg Lys Asn Glu Ile Glu Thr Leu Pro Phe Asp Gln
        35                  40                  45

Asn Leu Ala Gln Leu Ser Lys Leu Asn Leu Lys Gly Glu Thr Lys Thr
    50                  55                  60

Lys Tyr Asp Ala Met Lys Lys Asp Asn Val Glu Ser Thr Asn Lys Tyr
65                  70                  75                  80

Leu Ala Pro Val Glu Glu Lys Ile His Asn Ala Glu Ala Leu Leu Asp
                85                  90                  95

Lys Phe Ser Phe Asn Ala Ser Gln Cys Glu Ile Asp Ala Asn Glu
            100                 105                 110

Leu Met Asp Ser Tyr Glu Gln Ser Tyr Gln Gln Leu Glu Asp Val
        115                 120                 125

Asn Glu Ile Ile Ala Leu Tyr Lys Asp Asn Asp Glu Leu Tyr Asp Lys
    130                 135                 140

Cys Lys Val Asp Tyr Arg Glu Met Lys Arg Asp Val Leu Ala Asn Arg
145                 150                 155                 160

His Gln Phe Gly Glu Ala Ala Ser Leu Leu Glu Thr Glu Ile Glu Lys
                165                 170                 175

Phe Glu Pro Arg Leu Glu Gln Tyr Glu Val Leu Lys Ala Asp Gly Asn
            180                 185                 190

Tyr Val Gln Ala His Asn His Ile Ala Ala Leu Asn Glu Gln Met Lys
        195                 200                 205

Gln Leu Arg Ser Tyr Met Glu Glu Ile Pro Glu Leu Ile Arg Glu Thr
    210                 215                 220

Gln Lys Glu Leu Pro Gly Gln Phe Gln Asp Leu Lys Tyr Gly Cys Arg
225                 230                 235                 240

Asp Leu Lys Val Glu Gly Tyr Asp Leu Asp His Val Lys Val Asp Ser
                245                 250                 255

Thr Leu Gln Ser Leu Lys Thr Glu Leu Ser Phe Val Glu Pro Leu Ile
            260                 265                 270

Ser Arg Leu Glu Leu Glu Glu Ala Asn Asp Lys Leu Ala Asn Ile Asn
        275                 280                 285

Asp Lys Leu Asp Asp Met Tyr Asp Leu Ile Glu His Glu Val Lys Ala
    290                 295                 300

Lys Asn Asp Val Glu Glu Thr Lys Asp Ile Ile Thr Asp Asn Leu Phe
305                 310                 315                 320

Lys Ala Lys Asp Met Asn Tyr Thr Leu Gln Thr Glu Ile Glu Tyr Val
                325                 330                 335

Arg Glu Asn Tyr Tyr Ile Asn Glu Ser Asp Ala Gln Ser Val Arg Gln
            340                 345                 350

Phe Glu Asn Glu Ile Gln Ser Leu Ile Ser Val Tyr Asp Asp Ile Leu
        355                 360                 365

Lys Glu Met Ser Lys Ser Ala Val Arg Tyr Ser Glu Val Gln Asp Asn
    370                 375                 380
```

```
Leu Gln Tyr Leu Glu Asp His Val Thr Val Ile Asn Asp Lys Gln Glu
385                 390                 395                 400

Lys Leu Gln Asn His Leu Ile Gln Leu Arg Glu Asp Glu Ala Glu Ala
            405                 410                 415

Glu Asp Asn Leu Leu Arg Val Gln Ser Lys Lys Glu Glu Val Tyr Arg
            420                 425                 430

Arg Leu Leu Ala Ser Asn Leu Thr Ser Val Pro Glu Arg Phe Ile Ile
            435                 440                 445

Met Lys Asn Glu Ile Asp His Glu Val Arg Asp Val Asn Glu Gln Phe
450                 455                 460

Ser Glu Arg Pro Ile His Val Lys Gln Leu Lys Asp Lys Val Ser Lys
465                 470                 475                 480

Ile Val Ile Gln Met Asn Thr Phe Glu Asp Glu Ala Asn Asp Val Leu
                485                 490                 495

Val Asn Ala Val Tyr Ala Glu Lys Leu Ile Gln Tyr Gly Asn Arg Tyr
                500                 505                 510

Arg Lys Asp Tyr Ser Asn Val Asp Lys Ser Leu Asn Glu Ala Glu Arg
            515                 520                 525

Leu Phe Lys Asn Asn Arg Tyr Lys Arg Ala Ile Glu Ile Ala Glu Gln
530                 535                 540

Ala Leu Glu Ser Val Glu Pro Gly Val Thr Lys His Ile Glu Glu Glu
545                 550                 555                 560

Val Ile Lys Gln

<210> SEQ ID NO 13
<211> LENGTH: 619
<212> TYPE: PRT
<213> ORGANISM: Staphylococcus aureus

<400> SEQUENCE: 13

Met Pro Lys Asn Lys Ile Leu Ile Tyr Leu Leu Ser Thr Thr Leu Val
1               5                   10                  15

Leu Pro Thr Leu Val Ser Pro Thr Ala Tyr Ala Asp Thr Pro Gln Lys
            20                  25                  30

Asp Thr Thr Ala Lys Thr Thr Ser His Asp Ser Lys Lys Ser Thr Asp
        35                  40                  45

Asp Glu Thr Ser Lys Asp Thr Thr Ser Lys Asp Ile Asp Lys Ala Asp
50                  55                  60

Asn Asn Asn Thr Ser Asn Gln Asp Asn Asn Asp Lys Lys Val Lys Thr
65                  70                  75                  80

Ile Asp Asp Ser Thr Ser Asp Ser Asn Asn Ile Ile Asp Phe Ile Tyr
                85                  90                  95

Lys Asn Leu Pro Gln Thr Asn Ile Asn Gln Leu Leu Thr Lys Asn Lys
            100                 105                 110

Tyr Asp Asp Asn Tyr Ser Leu Thr Thr Leu Ile Gln Asn Leu Phe Asn
        115                 120                 125

Leu Asn Ser Asp Ile Ser Asp Tyr Glu Gln Pro Arg Asn Gly Glu Lys
130                 135                 140

Ser Thr Asn Asp Ser Asn Lys Asn Ser Asp Asn Ser Ile Lys Asn Asp
145                 150                 155                 160

Thr Asp Thr Gln Ser Ser Lys Gln Asp Lys Ala Asp Asn Gln Lys Ala
                165                 170                 175

Pro Lys Ser Asn Asn Thr Lys Pro Ser Thr Ser Asn Lys Gln Pro Asn
            180                 185                 190
```

```
Ser Pro Lys Pro Thr Gln Pro Asn Gln Ser Asn Ser Gln Pro Ala Ser
            195                 200                 205

Asp Asp Lys Val Asn Gln Lys Ser Ser Ser Lys Asp Asn Gln Ser Met
    210                 215                 220

Ser Asp Ser Ala Leu Asp Ser Ile Leu Asp Gln Tyr Ser Glu Asp Ala
225                 230                 235                 240

Lys Lys Thr Gln Lys Asp Tyr Ala Ser Gln Ser Lys Lys Asp Lys Asn
                245                 250                 255

Glu Lys Ser Asn Thr Lys Asn Pro Gln Leu Pro Thr Gln Asp Glu Leu
            260                 265                 270

Lys His Lys Ser Lys Pro Ala Gln Ser Phe Asn Asn Asp Val Asn Gln
        275                 280                 285

Lys Asp Thr Arg Ala Thr Ser Leu Phe Glu Thr Asp Pro Ser Ile Ser
    290                 295                 300

Asn Asn Asp Asp Ser Gly Gln Phe Asn Val Val Asp Ser Lys Asp Thr
305                 310                 315                 320

Arg Gln Phe Val Lys Ser Ile Ala Lys Asp Ala His Arg Ile Gly Gln
                325                 330                 335

Asp Asn Asp Ile Tyr Ala Ser Val Met Ile Ala Gln Ala Ile Leu Glu
            340                 345                 350

Ser Asp Ser Gly Arg Ser Ala Leu Ala Lys Ser Pro Asn His Asn Leu
        355                 360                 365

Phe Gly Ile Lys Gly Ala Phe Glu Gly Asn Ser Val Pro Phe Asn Thr
    370                 375                 380

Leu Glu Ala Asp Gly Asn Gln Leu Tyr Ser Ile Asn Ala Gly Phe Arg
385                 390                 395                 400

Lys Tyr Pro Ser Thr Lys Glu Ser Leu Lys Asp Tyr Ser Asp Leu Ile
                405                 410                 415

Lys Asn Gly Ile Asp Gly Asn Arg Thr Ile Tyr Lys Pro Thr Trp Lys
            420                 425                 430

Ser Glu Ala Asp Ser Tyr Lys Asp Ala Thr Ser His Leu Ser Lys Thr
        435                 440                 445

Tyr Ala Thr Asp Pro Asn Tyr Ala Lys Lys Leu Asn Ser Ile Ile Lys
    450                 455                 460

His Tyr Gln Leu Thr Gln Phe Asp Asp Glu Arg Met Pro Asp Leu Asp
465                 470                 475                 480

Lys Tyr Glu Arg Ser Ile Lys Asp Tyr Asp Asp Ser Ser Asp Glu Phe
                485                 490                 495

Lys Pro Phe Arg Glu Val Ser Asp Asn Met Pro Tyr Pro His Gly Gln
            500                 505                 510

Cys Thr Trp Tyr Val Tyr Asn Arg Met Lys Gln Phe Gly Thr Ser Ile
        515                 520                 525

Ser Gly Asp Leu Gly Asp Ala His Asn Trp Asn Asn Arg Ala Gln Tyr
    530                 535                 540

Arg Asp Tyr Gln Val Ser His Thr Pro Lys Arg His Ala Ala Val Val
545                 550                 555                 560

Phe Glu Ala Gly Gln Phe Gly Ala Asp Gln His Tyr Gly His Val Ala
                565                 570                 575

Phe Val Glu Lys Val Asn Ser Asp Gly Ser Ile Val Ile Ser Glu Ser
            580                 585                 590
```

-continued

Asn Val Lys Gly Leu Gly Ile Ile Ser His Arg Thr Ile Asn Ala Ala
            595                 600                 605

Ala Ala Glu Glu Leu Ser Tyr Ile Thr Gly Lys
    610                 615

<210> SEQ ID NO 14
<211> LENGTH: 681
<212> TYPE: PRT
<213> ORGANISM: Staphylococcus aureus

<400> SEQUENCE: 14

Met Met Lys Ser Gln Asn Lys Tyr Ser Ile Arg Lys Phe Ser Val Gly
1               5                   10                  15

Ala Ser Ser Ile Leu Ile Ala Thr Leu Leu Phe Leu Ser Gly Gly Gln
                20                  25                  30

Ala Gln Ala Ala Glu Lys Gln Val Asn Met Gly Asn Ser Gln Glu Asp
            35                  40                  45

Thr Val Thr Ala Gln Ser Ile Gly Asp Gln Gln Thr Arg Glu Asn Ala
    50                  55                  60

Asn Tyr Gln Arg Glu Asn Gly Val Asp Glu Gln Gln His Thr Glu Asn
65                  70                  75                  80

Leu Thr Lys Asn Leu His Asn Asp Lys Thr Ile Ser Glu Glu Asn His
                85                  90                  95

Arg Lys Thr Asp Asp Leu Asn Lys Asp Gln Leu Lys Asp Asp Lys Lys
            100                 105                 110

Ser Ser Leu Asn Asn Lys Asn Ile Gln Arg Asp Thr Thr Lys Asn Asn
        115                 120                 125

Asn Ala Asn Pro Arg Asp Val Asn Gln Gly Leu Glu Gln Ala Ile Asn
    130                 135                 140

Asp Gly Lys Gln Ser Lys Val Ala Ser Gln Gln Ser Lys Glu Ala
145                 150                 155                 160

Asp Asn Ser Gln Asp Leu Asn Ala Asn Asn Leu Pro Ser Gln Ser
                165                 170                 175

Arg Thr Lys Val Ser Pro Ser Leu Asn Lys Ser Asp Gln Thr Ser Gln
            180                 185                 190

Arg Glu Ile Val Asn Glu Thr Glu Ile Glu Lys Val Gln Pro Gln Gln
        195                 200                 205

Lys Asn Gln Ala Asn Asp Lys Ile Thr Asp His Asn Phe Asn Asn Glu
    210                 215                 220

Gln Glu Val Lys Pro Gln Lys Asp Glu Lys Thr Leu Ser Val Ser Asp
225                 230                 235                 240

Leu Lys Asn Asn Gln Lys Ser Pro Val Glu Pro Thr Lys Asp Asn Asp
                245                 250                 255

Lys Lys Asn Gly Leu Asn Leu Leu Lys Ser Ser Ala Val Ala Thr Leu
            260                 265                 270

Pro Asn Lys Gly Thr Lys Glu Leu Thr Ala Lys Ala Lys Gly Asp Gln
        275                 280                 285

Thr Asn Lys Val Ala Lys Gln Gly Gln Tyr Lys Asn Gln Asp Pro Ile
    290                 295                 300

Val Leu Val His Gly Phe Asn Gly Phe Thr Asp Asp Ile Asn Pro Ser
305                 310                 315                 320

Val Leu Ala His Tyr Trp Gly Gly Asn Lys Met Asn Ile Arg Gln Asp
                325                 330                 335

Leu Glu Glu Asn Gly Tyr Lys Ala Tyr Glu Ala Ser Ile Ser Ala Phe
            340                 345                 350

Gly Ser Asn Tyr Asp Arg Ala Val Glu Leu Tyr Tyr Ile Lys Gly
            355                 360                 365

Gly Arg Val Asp Tyr Gly Ala Ala His Ala Ala Lys Tyr Gly His Glu
370                 375                 380

Arg Tyr Gly Lys Thr Tyr Glu Gly Ile Tyr Lys Asp Trp Lys Pro Gly
385                 390                 395                 400

Gln Lys Val His Leu Val Gly His Ser Met Gly Gly Gln Thr Ile Arg
            405                 410                 415

Gln Leu Glu Glu Leu Leu Arg Asn Gly Ser Arg Glu Gly Ile Glu Tyr
            420                 425                 430

Gln Lys Lys His Ser Gly Glu Ile Ser Pro Leu Phe Lys Gly Asn Asn
            435                 440                 445

Asp Asn Met Ile Ser Ser Ile Thr Thr Leu Gly Thr Pro His Asn Gly
            450                 455                 460

Thr His Ala Ser Asp Leu Ala Gly Asn Glu Ala Leu Val Arg Gln Ile
465                 470                 475                 480

Val Phe Asp Ile Gly Lys Met Phe Gly Asn Lys Asn Ser Arg Val Asp
                485                 490                 495

Phe Gly Leu Ala Gln Trp Gly Leu Lys Gln Lys Pro Asn Glu Ser Tyr
            500                 505                 510

Ile Asp Tyr Val Lys Arg Val Lys Gln Ser Asn Leu Trp Lys Ser Lys
            515                 520                 525

Asp Asn Gly Phe Tyr Asp Leu Thr Arg Glu Gly Ala Thr Asp Leu Asn
            530                 535                 540

Arg Lys Thr Ser Leu Asn Pro Asn Ile Val Tyr Lys Thr Tyr Thr Gly
545                 550                 555                 560

Glu Ala Thr His Lys Ala Leu Asn Ser Asp Arg Gln Lys Ala Asp Leu
                565                 570                 575

Asn Met Phe Phe Pro Phe Val Ile Thr Gly Asn Leu Ile Gly Lys Ala
            580                 585                 590

Thr Glu Lys Glu Trp Arg Glu Asn Asp Gly Leu Val Ser Val Ile Ser
            595                 600                 605

Ser Gln His Pro Phe Asn Gln Ala Tyr Thr Asn Ala Thr Asp Lys Ile
610                 615                 620

Gln Lys Gly Ile Trp Gln Val Thr Pro Thr Lys His Asp Trp Asp His
625                 630                 635                 640

Val Asp Phe Val Gly Gln Asp Ser Ser Asp Thr Val Arg Thr Arg Glu
                645                 650                 655

Glu Leu Gln Asp Phe Trp His His Leu Ala Asp Asp Leu Val Lys Thr
            660                 665                 670

Glu Lys Val Thr Asp Thr Lys Gln Ala
            675                 680

<210> SEQ ID NO 15
<211> LENGTH: 806
<212> TYPE: PRT
<213> ORGANISM: Staphylococcus aureus

<400> SEQUENCE: 15

Met Thr Asn Lys Met Lys Lys Trp Gln Lys Leu Ser Thr Ile Thr Leu
1               5                   10                  15

Leu Met Thr Gly Val Ile Ala Leu Asn Asn Gly Glu Phe Arg Asn Val
                20                  25                  30

Asp Lys His Gln Ile Ala Val Ala Asp Thr Asn Val Gln Thr Pro Asp
            35                  40                  45

-continued

Tyr Glu Lys Leu Lys Lys Thr Trp Leu Asp Val Asn Tyr Gly Tyr Asp
     50                  55                  60

Gln Tyr Asp Glu Asn Asn Gln Asp Met Lys Lys Lys Phe Asp Ala Lys
 65                  70                  75                  80

Glu Lys Glu Ala Lys Lys Leu Leu Asp Asp Met Lys Thr Asp Thr Asn
                 85                  90                  95

Arg Thr Tyr Leu Trp Ser Gly Ala Glu Asn Leu Glu Thr Asn Ser Ser
                100                 105                 110

His Met Thr Lys Thr Tyr Arg Asn Ile Glu Lys Ile Ala Glu Ser Met
            115                 120                 125

Gln His Lys Asn Thr Val Leu Lys Thr Val Glu Asn Lys Leu Lys Ile
130                 135                 140

Lys Glu Ala Leu Asp Trp Met His Lys Asn Val Tyr Gly Lys Asn Pro
145                 150                 155                 160

Ser Gln Lys Val Glu Asp Leu Thr Lys Asn Arg Lys Gly Gln Thr Thr
                165                 170                 175

Pro Lys Asn Asn Ser Leu Asn Trp Trp Asp Tyr Glu Ile Gly Thr Pro
            180                 185                 190

Arg Ala Leu Thr Asn Thr Leu Leu Met Asp Asp Met Leu Thr Lys
                195                 200                 205

Asp Glu Met Lys Asn Tyr Ser Lys Pro Ile Ser Thr Tyr Ala Pro Ser
210                 215                 220

Ser Asp Lys Ile Leu Ser Ser Val Gly Glu Ser Glu Asp Ala Lys Gly
225                 230                 235                 240

Gly Asn Leu Val Asp Ile Ser Lys Val Lys Leu Leu Glu Ser Val Ile
                245                 250                 255

Glu Glu Asp Val Asp Met Leu Lys Lys Ser Ile Asp Ser Phe Asn Lys
            260                 265                 270

Val Phe Thr Tyr Val Gln Asp Ser Ala Thr Gly Lys Gly Arg Asn Gly
            275                 280                 285

Phe Tyr Lys Asp Gly Ser Tyr Ile Asp His Gln Asp Val Pro Tyr Thr
290                 295                 300

Gly Ala Tyr Gly Val Val Leu Glu Gly Ile Ser Gln Met Met Pro
305                 310                 315                 320

Met Ile Lys Glu Ser Pro Phe Lys Thr Thr Gln Asp Asn Ala Thr Leu
                325                 330                 335

Ser Asn Trp Ile Asp Glu Gly Phe Met Pro Leu Ile Tyr Lys Gly Glu
            340                 345                 350

Met Met Asp Leu Ser Arg Gly Arg Ala Ile Ser Arg Glu Asn Glu Thr
            355                 360                 365

Ser His Thr Ala Ser Ala Thr Val Met Lys Ser Leu Leu Arg Leu Asn
            370                 375                 380

Asp Thr Met Asp Asp Ser Thr Lys Thr Arg Tyr Lys Gln Ile Val Lys
385                 390                 395                 400

Thr Ser Val Asn Ser Asp Ser Ser Tyr Asn Gln Asn Tyr Leu Asn
                405                 410                 415

Ser Tyr Ser Asp Ile Ala Lys Met Lys Lys Leu Met Asn Asp Ser Thr
            420                 425                 430

Ile Ser Lys Asn Asp Leu Thr Gln Gln Leu Lys Ile Tyr Asn Asp Met
            435                 440                 445

Asp Arg Val Thr Tyr His Asn Lys Asp Leu Asp Phe Ala Phe Gly Leu
450                 455                 460

```
Ser Met Thr Ser Lys Asn Ile Ala Arg Tyr Glu Asn Ile Asn Gly Glu
465                 470                 475                 480

Asn Leu Lys Gly Trp His Thr Gly Ala Gly Met Ser Tyr Leu Tyr Asn
                485                 490                 495

Ser Asp Val Lys His Tyr Arg Asp Asn Phe Trp Ala Thr Ala Asp Met
            500                 505                 510

Thr Cys Leu Pro Gly Thr Thr Thr Leu Asn Asp Met Pro Ser Thr Asn
            515                 520                 525

Thr Lys Asn Asp Lys Ser Phe Val Gly Thr Lys Leu Asn Asn Lys
        530                 535                 540

Tyr Ala Ser Ile Gly Met Asp Phe Glu Asn Gln Asp Lys Thr Leu Thr
545                 550                 555                 560

Ala Lys Lys Ser Tyr Phe Ile Leu Asn Asp Lys Ile Val Phe Leu Gly
                565                 570                 575

Thr Gly Ile Lys Ser Thr Asp Ser Ser Lys Asn Pro Val Thr Ser Val
            580                 585                 590

Glu Asn Arg Lys Ala Asn Gly Tyr Lys Leu Phe Lys Asp Asp Ile Glu
        595                 600                 605

Ile Thr Thr Ser Asp Val Asn Ala Gln Glu Thr His Ser Val Phe Leu
610                 615                 620

Glu Ser Asn Asp Thr Lys Lys Asn Ile Gly Tyr His Phe Leu Asp Lys
625                 630                 635                 640

Pro Lys Ile Thr Val Lys Lys Glu Ser His Thr Gly Lys Trp Ser Glu
                645                 650                 655

Ile Asn Lys Ser Gln Lys Lys Asp Asp Lys Lys Asp Glu Tyr Tyr Glu
            660                 665                 670

Val Thr Gln Thr His Asn Thr Ser Asp Ser Lys Tyr Ala Tyr Val Leu
        675                 680                 685

Tyr Pro Gly Leu Ser Lys Ser Asp Phe Lys Ser Lys Asn Asn Asn Val
690                 695                 700

Ser Ile Val Lys Gln Asp Glu Asp Phe His Val Ile Lys Asp Asn Asp
705                 710                 715                 720

Gly Val Phe Ala Gly Val Asn Tyr Ser Asp Asn Thr Lys Ser Phe Asp
                725                 730                 735

Ile Asn Gly Ile Thr Val Glu Leu Lys Glu Lys Gly Met Phe Val Ile
            740                 745                 750

Lys Lys Lys Asp Asp Lys Ala Tyr Lys Cys Ser Phe Tyr Asn Pro Glu
        755                 760                 765

Thr Thr Asn Thr Ala Ser Asn Ile Glu Ser Lys Ile Phe Ile Lys Gly
770                 775                 780

Tyr Thr Ile Thr Asn Lys Ser Val Ile Asn Ser Asn Asp Ala Gly Val
785                 790                 795                 800

Asn Phe Glu Leu Thr Lys
                805

<210> SEQ ID NO 16
<211> LENGTH: 808
<212> TYPE: PRT
<213> ORGANISM: Staphylococcus aureus

<400> SEQUENCE: 16

Met Thr Tyr Arg Met Lys Lys Trp Gln Lys Leu Ser Thr Ile Thr Leu
1               5                   10                  15

Leu Met Ala Gly Val Ile Thr Leu Asn Gly Gly Glu Phe Arg Ser Ile
                20                  25                  30
```

-continued

Asp Lys His Gln Ile Ala Val Ala Asp Thr Asn Val Gln Thr Thr Asp
            35                  40                  45

Tyr Glu Lys Leu Arg Asn Ile Trp Leu Asp Val Asn Tyr Gly Tyr Asp
 50                  55                  60

Lys Tyr Asp Glu Asn Asn Pro Asp Met Lys Lys Phe Glu Ala Thr
 65                  70                  75                  80

Glu Asn Glu Ala Glu Lys Leu Leu Lys Glu Met Lys Thr Glu Ser Asp
                    85                  90                  95

Arg Lys Tyr Leu Trp Glu Ser Ser Lys Asp Leu Asp Thr Lys Ser Ala
                100                 105                 110

Asp Met Thr Arg Thr Tyr Arg Asn Ile Glu Lys Ile Ser Glu Ala Met
            115                 120                 125

Lys His Lys Asn Thr Lys Leu Lys Thr Asp Glu Asn Lys Thr Lys Val
            130                 135                 140

Lys Asp Ala Leu Glu Trp Leu His Lys Asn Ala Tyr Gly Lys Glu Pro
145                 150                 155                 160

Asp Lys Lys Val Ala Asp Leu Thr Ser Asn Phe Lys Asn Lys Thr Ser
                165                 170                 175

Arg Asn Thr Asn Leu Asn Trp Trp Asp Tyr Glu Ile Gly Thr Pro Arg
                180                 185                 190

Ala Leu Thr Asn Thr Leu Ile Leu Gln Glu Asp Phe Thr Asp Glu
            195                 200                 205

Glu Lys Lys Lys Tyr Thr Ala Pro Ile Lys Thr Phe Ala Pro Asp Ser
210                 215                 220

Asp Lys Ile Leu Ser Ser Val Gly Lys Ser Glu Pro Ala Lys Gly Gly
225                 230                 235                 240

Asn Leu Val Asp Ile Ser Lys Val Lys Leu Leu Glu Ser Ile Ile Glu
                245                 250                 255

Glu Asp Lys Asp Met Met Lys Lys Ser Ile Asp Ser Phe Asn Thr Val
                260                 265                 270

Phe Thr Tyr Ala Gln Asn Ser Ala Thr Gly Lys Glu Arg Asn Gly Phe
            275                 280                 285

Tyr Lys Asp Gly Ser Tyr Ile Asp His Gln Asp Val Pro Tyr Thr Gly
            290                 295                 300

Ala Tyr Gly Val Val Leu Leu Glu Gly Ile Ser Gln Met Met Pro Met
305                 310                 315                 320

Ile Lys Glu Thr Pro Phe Asn Asp Ser Asn Gln Asn Asp Thr Thr Leu
                325                 330                 335

Lys Ser Trp Ile Asp Asp Gly Phe Met Pro Leu Ile Tyr Lys Gly Glu
                340                 345                 350

Met Met Asp Leu Ser Arg Gly Arg Ala Ile Ser Arg Glu Asn Glu Thr
            355                 360                 365

Ser His Ser Ala Ser Ala Thr Val Met Lys Ser Leu Leu Arg Leu Ser
            370                 375                 380

Asp Thr Met Asp Lys Ser Thr Lys Ala Lys Tyr Lys Lys Ile Val Lys
385                 390                 395                 400

Thr Ser Val Glu Ser Asp Ser Ser Tyr Lys Gln Thr Asp Tyr Leu Ser
                405                 410                 415

Ser Tyr Ser Asp Ile Ser Lys Met Lys Ser Leu Met Glu Asp Ser Thr
                420                 425                 430

Ile Ser Thr Asn Gly Leu Thr Gln Gln Leu Lys Ile Tyr Asn Asp Met
            435                 440                 445

Asp Arg Val Thr Tyr His Asn Lys Gly Leu Asp Phe Ala Phe Gly Leu
    450                 455                 460

Ser Met Thr Ser Lys Asn Val Ala Arg Tyr Glu Ser Ile Asn Gly Glu
465                 470                 475                 480

Asn Leu Lys Gly Trp His Thr Gly Ala Gly Met Ser Tyr Leu Tyr Asn
                485                 490                 495

Ser Asp Val Lys His Tyr Arg Asp Asn Phe Trp Ala Thr Ala Asp Met
            500                 505                 510

Lys Arg Leu Ala Gly Thr Thr Thr Leu Asp Asn Glu Glu Pro Lys Ser
                515                 520                 525

Thr Asp Val Lys Lys Ser Lys Thr Phe Val Gly Gly Thr Lys Phe
    530                 535                 540

Asp Asp Gln His Ala Ser Ile Gly Met Asp Phe Glu Asn Gln Asp Lys
545                 550                 555                 560

Thr Leu Thr Ala Lys Lys Ser Tyr Phe Ile Leu Asn Asp Lys Ile Val
                565                 570                 575

Phe Leu Gly Thr Gly Ile Lys Ser Thr Asp Ser Ser Lys Asn Pro Val
                580                 585                 590

Thr Thr Ile Glu Asn Arg Lys Ala Asn Asp Tyr Lys Leu Tyr Lys Asp
                595                 600                 605

Asp Thr Gln Thr Thr Asn Ser Asp Asn Gln Glu Thr Asn Ser Leu Phe
    610                 615                 620

Leu Glu Ser Thr Asn Ser Thr Gln Asn Asn Ile Gly Tyr His Phe Leu
625                 630                 635                 640

Asn Glu Ser Lys Ile Thr Val Lys Lys Glu Ser His Thr Gly Lys Trp
                645                 650                 655

Ser Asp Ile Asn Lys Ser Gln Lys Asp Ile Gln Lys Thr Asp Glu Tyr
                660                 665                 670

Tyr Glu Val Thr Gln Lys His Ser Asn Thr Asp Ser Lys Tyr Ala Tyr
    675                 680                 685

Val Leu Tyr Pro Gly Leu Ser Lys Asp Val Phe Lys Ser Lys Ala Ser
    690                 695                 700

Lys Val Thr Val Lys Gln Glu Asp Asp Phe His Val Val Lys Asp
705                 710                 715                 720

Asn Glu Ser Val Trp Ala Gly Ile Asn Tyr Ser Asp Ser Ala Lys Thr
                725                 730                 735

Phe Glu Ile Asn Asn Thr Lys Val Glu Val Lys Ala Lys Gly Met Phe
                740                 745                 750

Ile Leu Thr Lys Lys Asp Asp Asn Thr Tyr Glu Cys Ser Phe Tyr Asn
    755                 760                 765

Pro Glu Ser Thr Asn Ser Val Ser Asp Ile Glu Ser Lys Ile Ser Met
770                 775                 780

Thr Gly Tyr Ser Ile Ile Asn Lys Asn Thr Ser Thr Ser Asn Glu Ser
785                 790                 795                 800

Gly Val Arg Phe Glu Leu Thr Lys
                805

<210> SEQ ID NO 17
<211> LENGTH: 423
<212> TYPE: DNA
<213> ORGANISM: Staphylococcus aureus

<400> SEQUENCE: 17

```
atggcaaaag gtaatttatt taaagcgatt ttaggtatag gtggcgctgt agcagctgta      60
cttgttacac gtaaagatag tcgtgacaag ctgaaagcag aatataataa atacaaacaa     120
gatcctcaaa gctataaaga taatgctaag gataaagcga cgcaattagg aacaattgca     180
aatgaaacaa ttaaagaagt aaaaacaaat ccgaaagaat atgctaatag attaaaaaat     240
aatccaaaag cattttttcga agaagaaaaa tcaaaattta ccgaatatga caataagact    300
gacgaaagta ttgaaaaagg taaatttgat gatgaaggtg gcgcagcacc aaataataat    360
ttacgtatcg tcactgaaga agatttaaaa aagaataaaa atgcattgtc tgataaagaa    420
taa                                                                    423
```

<210> SEQ ID NO 18
<211> LENGTH: 582
<212> TYPE: DNA
<213> ORGANISM: Staphylococcus aureus

<400> SEQUENCE: 18

```
atgaaaaaat tggtttcaat tgttggcgca acattattgt tagctggatg tggatcacaa      60
aatttagcac cattagaaga aaaaacaaca gatttaagag aagataatca tcaactcaaa     120
ctagatattc aagaacttaa tcaacaaatt agtgattcta atctaaaat taagggctt     180
gaaaaggata agaaaatag taaaaaaact gcatctaata tacgaaaat taaattgatg     240
aatgttacat caacatacta cgacaaagtt gctaaagctt tgaaatccta taacgatatt    300
gaaaaggatg taagtaaaaa caaggcgat aagaatgttc aatcgaaatt aaatcaaatt    360
tctaatgata ttcaaagtgc tcacacttca tacaaagatg ctatcgatgg tttatcactt    420
agtgatgatg ataaaaaaac gtctaaaaat atcgataaat taaactctga tttgaatcat    480
gcatttgatg atattaaaaa tggctatcaa aataaagata aaaaacaact tacaaaagga    540
caacaagcgt tgtcaaaatt aaacttaaat gcaaaatcat ga                       582
```

<210> SEQ ID NO 19
<211> LENGTH: 630
<212> TYPE: DNA
<213> ORGANISM: Staphylococcus aureus

<400> SEQUENCE: 19

```
atgaaaaaat tagttacagg gttattagca ttatcattat ttttagctgc atgtggtcaa      60
gatagtgacc aacaaaaaga cagtaataaa gaaaaagatg ataaagcgaa aactgaacaa     120
caagataaaa aaacaaatga ttcatctaaa gataagaaag acaataaaga tgatagtaaa     180
gacgtaaaca aagataataa agataatagt gcaaacgata ccagcaaca atctaattca     240
aatgcaacaa acaatgacca aaatcaaacg aataataacc agtcaaacag tggacaaacg    300
actaacaatc aaaaatcaag ttacgttgca ccatattatg gacaaaacgc agcgccagtg    360
gctcgtcaaa tttatccatt taatggtaat aaatcacaag cattacaaca attgcctaat    420
ttccaaacag ctttaaatgc agctaacaac gaagcaaata aatttggtaa tggtcataaa    480
gtttataatg attattcaat tgaagaacat aatggtaact ataagtatgt ttttagtttt    540
aaagacccaa acgtaaatgg aaaatattca attgtaacgg ttgattatac tggacaagca    600
atggttactg atccaaacta ccaacaataa                                     630
```

```
<210> SEQ ID NO 20
<211> LENGTH: 729
<212> TYPE: DNA
<213> ORGANISM: Staphylococcus aureus

<400> SEQUENCE: 20
atgaaaaaag taatggggat attattagca agtacactta tcttaggtgc ttgtggacat      60
catcaagata gtgcaaaaaa agagagcact agtcacaaaa agaaagaaaa tgacaatgaa     120
gaattaaatg aagaacttaa agaatttaaa agcaaaaaaa atatggatat aaaaattaaa     180
ggcgatacta tgttagtga caaatttgaa gctaaaataa agaaccgtt tatcatcaat       240 gaaaaagatg agaaaaagaa atatatcgct tttaaaatgg aaattactgc taaaaaagac     300
gataaagatt taaatccatc ttctatttct catgactata ttaatatcac tcaagatgat     360
aaaaatacag taaataaatt aagagatggt tatcttttaa gtgataaaaa ttataaagat     420
tggacagaac ataaccaaga tcaaattaaa aaaggcaaaa ctgcacaagc catgtttatc     480
tatgagttaa gaggtgatgg aaacattaat ttaaatgtcc ataaatactc agaagataaa     540
acagttgatt ctaaatcatt caaatttagt aaacttaaaa ccgaagattt ttctcataga     600
gcggaaacaa gggaagaagt agaaaagaaa gaaaaagaat tgaagaaga gtacaaaaaa      660 gaacaagaac gagagaaaga aaagaaaag caaaaagatg acgaccacag tggtttagat     720
gaagtataa                                                              729

<210> SEQ ID NO 21
<211> LENGTH: 984
<212> TYPE: DNA
<213> ORGANISM: Staphylococcus aureus

<400> SEQUENCE: 21
atgaaaaaat ggcaatttgt tggtactaca gctttaggtg caacactatt attaggtgct      60
tgtggtggcg gtaatggtgg cagtggtaat agtgatttaa aggggaagc taaaggggat      120 ggctcatcaa cagtagcacc aattgtggag aaattaaatg aaaaatgggc tcaagatcac     180
tcggatgcta aaatctcagc aggacaagct ggtacaggtg ctggtttcca aaaattcatt     240
gcaggagata tcgacttcgc tgatgcttct agaccaatta agatgaaga gaagcaaaaa      300 ttacaagata agaatatcaa atacaaagaa ttcaaaattg cgcaagatgg tgtaacggtt     360
gctgtaaata agaaaatga ttttgtagat gaattagaca acagcaatt aaaagcaatt     420 tattctggaa aagctaaaac atggaaagat gttaatagta atggccaga taaaaaata      480 aatgctgtat caccaaactc aagtcatggt acttatgact tctttgaaaa tgaagtaatg     540
aataaagaag atattaaagc agaaaaaaat gctgatacaa atgctatcgt tcttctgta      600 acgaaaaaca aagagggaat cggatacttt ggatataact tctacgtaca aaataaagat     660
aaattaaaag aagttaaaat caaagatgaa atggtaaag caacagagcc tacgaaaaaa     720
acaattcaag ataactctta tgcattaagt agaccattat tcatttatgt aaatgaaaaa     780
gcattgaaag ataataaagt aatgtcagaa tttatcaaat tcgtcttaga agataaaggt     840
aaagcagctg aagaaggtgg atatgtagca gcaccagaga aaacatacaa atcacaatta     900
gatgatttaa aagcatttat tgataaaaat caaaaatcag acgacaagaa atctgatgat     960
aaaaagtctg aagacaagaa ataa                                            984
```

```
<210> SEQ ID NO 22
<211> LENGTH: 1074
<212> TYPE: DNA
<213> ORGANISM: Staphylococcus aureus

<400> SEQUENCE: 22
atgaaaggta aatttttaaa agttagttct ttattcgttg caactttgac aacagcgaca      60
cttgtgagtt ctccagcagc aaatgcgtta tcttcaaaag ctatggacaa tcatccacaa     120
caaacgcaga cagacaaaca gcaaacacct aagattcaaa aaggcggtaa ccttaaacca     180
ttagaacaac gtgaacgcgc taatgttata ttaccaaata cgatcgtca ccaaatcaca      240 gatacaacga atggtcatta tgcacctgtt acttatattc aagttgaagc acctactggt     300
acatttattg cttctggtgt agttgtaggt aaagatacac ttttaacaaa taaacacatc     360
gtagatgcta cgcacggtga tcctcatgct ttaaaagcat tcgcttctgc aattaaccaa     420
gacaattatc ctaatggtgg tttcactgct gaacaaatca ctaaatattc aggcgaaggt     480
gatttagcaa tcgttaaatt ctcccctaat gagcaaaaca acatattgg cgaagtagtt      540 aaaccagcaa caatgagtaa taatgctgaa acacaagtta accaaaatat tactgtaaca     600
ggatatcctg gtgataaacc tgtcgcaaca atgtgggaaa gtaaaggaaa ataacgtac      660 ttaaaaggtg aagcaatgca atatgattta agtacaactg gtggtaactc aggttcacct     720
gtatttaatg aaaaaaatga agtcattggc attcattggg gtggcgttcc aaatcaattt     780
aacggtgcag tatttattaa tgaaaatgta cgcaacttct taaaacaaaa tattgaagat     840
atcaatttcg caaatgatga ccaccctaac aaccctgata tccagacaa tccaaataat      900 ccggacaatc ctaacaaccc tgataaccct aacaaccctg ataatccaga caatcctaat     960
aatcctgata accctaacaa cccggacaat ccaaataacc ctgaccaacc taacaaccca    1020
aataacccgg acaatggcga taacaataat tcagacaacc ctgacgctgc ataa          1074

<210> SEQ ID NO 23
<211> LENGTH: 1200
<212> TYPE: DNA
<213> ORGANISM: Staphylococcus aureus

<400> SEQUENCE: 23
atgaagcgta cattagtatt attgattaca gctatcttta tactcgctgc ttgtggtaac      60
cataaggatg accaggctgg aaaagataat caaaaacata caatagttc aaatcaagta      120 aaagaaattg ctacggataa aaatgtacaa ggtgataact atcgtacatt gttaccattt     180
aaagaaagcc aggcaagagg acttttacaa gataacatgg caaatagtta taatggcggc     240
gactttgaag atggttttat tgaacttaagt aaagaagtgt ttccaacaga caaatatttg    300
tatcaagatg gtcaattttt ggacaagaaa acaattaatg cctatttaaa tcttaagtat     360
acaaaacgtg aaatcgataa aatgtctgaa aaagataaaa agacaagaa agcgaatgaa      420 aatttaggac ttaatccatc acacgaaggt gaaacagatc ctgaaaagat tgcagaaaaa     480
tcaccagcct atttatctaa cattttagag caagattttt atggtggtgg agatacaaaa     540
ggtaagaata ttaaaggtat gacgattggt ttagctatga atagtgttta ttactataaa     600
aaagaaaaag atggaccgac ttttagtaaa aaactagatg atagcgaagt taaaagcaa      660 ggtaaacaaa tggctagtga gatattatca aggttacgtg aaatgatga tttaaaagat     720 ataccaattc atttttgcaat ttataagcaa tcaagtgaag attcaatcac accaggtgaa    780
tttatcactc aagcgactgc agaaaagagt caaacaaagc ttaatgaatg gcataatatc    840
```

| aatgaaaaat cagctttatt accttcttca acagcagcag attatgatga aaatttaaat | 900 |
| aataatttca agcaatttaa tgataatttg caatcatatt tttctaattt cacacaagca | 960 |
| gtaggaaaag ttaaatttgt tgataaaaag ccacaacgat tagtagtaga tttaccaatc | 1020 |
| gattactatg gacaagctga aacaattggt attacacagt acgttactga acaagcgaat | 1080 |
| aaatatttcg ataaaatcga taactatgaa attcggatta aagatggtaa ccaaccacgt | 1140 |
| gctttaatta gtaagacaaa agatgacaaa gaaccgcaag ttcatatttta cagtaattaa | 1200 |

<210> SEQ ID NO 24
<211> LENGTH: 1488
<212> TYPE: DNA
<213> ORGANISM: Staphylococcus aureus

<400> SEQUENCE: 24

| atgagggaaa attttaagtt acgtaaaatg aaagtcgggt tagtatctgt tgcaattaca | 60 |
| atgttatata tcatgacaaa cggacaagca gaagcatcag aggctaatga gaagccaagt | 120 |
| acaaatcaag aatcaaaagt tgtttcacag actgaacaaa attcaaaaga aacaaaaaca | 180 |
| gtagaatcta ataagaactt tgttaaatta gatactatta aacctggagc tcaaaagata | 240 |
| acgggaacta ctttaccaaa tcactatgtt ttattaacag ttgatgggaa aagtgcggat | 300 |
| tcagtagaaa atggcggttt gggttttgtt gaagcaaatg acaaaggaga atttgagtac | 360 |
| cctttaaata atcgtaaaat tgttcataat caagaaattg aggtttcgtc gtcaagccct | 420 |
| gatttaggtg aagatgaaga agatgaagag gtggaagaag cttcaactga taaagctggc | 480 |
| gttgaggaag aaagtacaga agctaaagtt acttacacaa caccgcgata tgaaaaagcg | 540 |
| tatgaaatac cgaaagaaca actaaaagaa aaagatggac atcaccaagt ttttatcgaa | 600 |
| cctattactg aaggatcagg tattattaaa gggcatacgc tgtaaaagg taaagttgct | 660 |
| ttatctatta ataataaatt tattaatttt gaagagagcg ttaagggcgg agttagtaaa | 720 |
| gaagacacta aagctagttc agatggtatc tggatgccta ttgatgacaa aggatacttt | 780 |
| aactttgact tcaaaacgaa acgtttcgat aatttagagt taaaagaagg taatgacatt | 840 |
| tcactaacat ttgcacctga tgatgaagaa gatgcattaa aacctttaat tttcaaaact | 900 |
| aaagtaacga gcttagaaga tatcgataaa gcagaaacta aatatgacca tactaaactc | 960 |
| aacaaagtga agtttttaga taatgttaaa gaagatttac atgttgatga aatatatgga | 1020 |
| agcttatatc atacagacaa aggtaaaggt attcttgata agaaggtac taaagtaatt | 1080 |
| aaaggaaaga ctaaattcgc gaatgcagta gtgaaggtag actctgaact aggtgaagca | 1140 |
| caattattcc ctgatttaca agtaaatgaa aaaggtgaat ttagctttga ctcacatggt | 1200 |
| gctggtttta gattacaaaa tggagaaaaa ttaaacttca cagtggttga tcctattaca | 1260 |
| ggtgacttgt taagtaatga gtttgttctc aaagagattg atattgaaga acacctgaa | 1320 |
| caaaaagcgg atcgtgagtt tgacgaaaaa cttgaaaata cgcctgctta ctacaagtta | 1380 |
| tacggcgata aatagttgg attcgatact aacgatttcc cgattacttg gttctatcca | 1440 |
| ttgggtgaaa agaaagttga acgtacaaca cctaaattag aaaaataa | 1488 |

<210> SEQ ID NO 25
<211> LENGTH: 1524
<212> TYPE: DNA
<213> ORGANISM: Staphylococcus aureus

```
<400> SEQUENCE: 25
atgtctaaaa agttaaaaat tataattcct attattattg tcttattatt aataggtgga        60
atcgcatggg gagtttatgc attttttgca acacaccga aaaatacata cttaaaaagt       120
gaacaacaaa ctgcaaaaat gtataaagat tattttaatg accgttttga aaacgaagtg       180
aagttccaag aaaagatgaa agataattca tttttatctt cattagaatt aagcgcagat       240
gcatctgatg aaattgttaa agggcttggt attcctaaat ctgttgttaa tgcttcgaaa       300
attaaaatgt catatggaca tgatcctaaa aaagagaaat caatgattaa tcttgaacca       360
acaatagcag actctgcatt agggaaattc cagttagctg cagataaaga taagcattat       420
ttcgaatcac cattatttaa agggaaatat agtgttaata attctgattt attatcaact       480
tattcaaaac ttacaggtga agatgaagaa acagcaaaag aaaatggtat tacaaaccaa       540
caactaaatt taaatactct tttcagtaat gctcaagcac aacaaagtga ctacagcaaa       600
attgccgaaa atattccga acttattgtc gacaaattag atgacgataa ttttgataaa       660
ggtaaaaaag aagaaattaa ggttaatggt gaaaagtaca aagttagacc tgtcacgtta       720
acacttagca gagctgacac taaaaaaatt acattagctg tattagaaga agctaaaaag       780
gataaagacc ttaaaaaatt aatggaagaa caaggtacta caaaagactt tgaaaaagac       840
attaaaaaag caattgacga tgtcaaagaa actaaaaagg atgaatttgc taaaattcaa       900
tctaaaattt ataccgaaaa acatacgatt gtaaaacgag aaattactat tacagacaaa       960
gaaaataata aaactaaaat caaaggtact aatactttag aagacgataa gttaaaacta      1020
gattacgcac ttgatttcga tcaagataaa tacacgtatg ctgaagcgaa atatacaatt      1080
aaaggcgtat cttctaagga aaaagacaat aaatacagtg ataaatacga atttggtaaa      1140
aagacagaat atgatgaatc aaaaatcaaa ttagataacc aagaaaaagt agatggcaca      1200
aaacgtcaag ataaaggtaa aatcactgtc gcgttagata aatatagcga cgaaaatgaa      1260 ttcactttttg aaaataatat agattctgac gtaaaaaata acactcagaa atctacgtta      1320
aatatcggca tcaaatatgc tgaagaacca attaatttca ttttaaaatc tagcacaaaa      1380
ttgaaagcag atattgattt tgatgatagt ggtgcgaaag atttcaatag tctatcttca      1440
aaagaccgtg aaaaacttga aaaagaaatc gaaaaaaatg gcggcaaaat gtttgaatca      1500
attttaaaaa aggcatctaa ataa                                             1524

<210> SEQ ID NO 26
<211> LENGTH: 1530
<212> TYPE: DNA
<213> ORGANISM: Staphylococcus aureus

<400> SEQUENCE: 26
gtgaggaaat tttcaagata tgcatttaca agtatggcaa cagtaacgtt gctgagctct        60
ttgacacctg cagcactagc gagtgatacg aatcacaaac cagcaacttc agatattaat       120
tttgaaatca cgcaaaagag tgatgcagtt aaagcattaa aagagttacc taaatctgaa       180
aatgtgaaaa atcattatca agattactct gttacagatg taaaaacaga taagaaagga       240
ttcacgcatt acacgttaca accgagtgtg gatggtgtgc atgcgcctga caagaagtg        300 aaagtgcatg cggacaaatc gggtaaagtc gttttaatca acggtgatac tgatgcgaag       360
aaagtaaagc cgacaaataa agtgacatta agcaaggatg aagcggctga caaagcattt       420
aacgcagtta agattgataa aaataaagct aaaaacctcc aagatgacgt tatcaaagaa       480
aataaagtcg aaatcgatgg tgacagtaat aaaatacattt acaatattga attaattaca       540
```

```
gtaacaccag aaatttcaca ttggaaagtt aaaattgatg cagacacagg agcagttgtt    600
gaaaaaacga acttagttaa agaagcagca gcaactggca caggtaaagg tgtgcttgga    660
gatacaaaag atatcaatat caatagtatt gatggtggat ttagtttaga ggatttgacg    720
catcaaggta aattatcagc atacaatttt aacgatcaaa caggtcaagc gacattaatt    780
actaatgaag atgaaaactt cgtcaaagat gatcaacgtg ctggtgtaga tgcgaattat    840
tatgctaaac aaacatatga ttactacaaa aatacatttg gtcgtgagtc ttacgataac    900
catggtagtc caatagtctc attaacacat gtaaatcatt atggtggaca agataacaga    960
aataacgctg catggattgg agacaaaatg atttatggtg atggcgatgg ccgcacgttt   1020
acaaatttat caggtgcaaa tgacgtagta gcacatgagt aacacatgg cgtgacacaa   1080 gaaacggcga atttagagta taagatcaa tctggtgcgt aaatgaaag cttttcagat   1140 gttttggat actttgtaga tgatgaggat ttcttgatgg gtgaagatgt ttacacacca   1200 ggaaagagg gagatgcttt acgaagcatg tcaaacccag aacaatttgg tcaaccatct   1260
catatgaaag actatgtata cactgaaaaa gataacggtg gtgtgcatac gaattctggc   1320
attccaaata aagcagctta taacgtaatt caagcaatag ggaaatctaa atcagaacaa   1380
atttactacc gagcattaac ggaatactta acaagtaatt caaacttcaa agattgtaaa   1440
gatgcattat accaagcggc taaagattta tatgacgagc aaacagctga caagtatat   1500 gaagcatgga acgaagttgg cgtcgagtaa                                     1530

<210> SEQ ID NO 27
<211> LENGTH: 1548
<212> TYPE: DNA
<213> ORGANISM: Staphylococcus aureus

<400> SEQUENCE: 27
atgaaaaaga aattaggtat gttacttctt gtaccagccg taactttatc attagccgca     60
tgtgggaatg atgatggaaa agataaagat ggcaaggtaa caattaaaac gacagtttat    120
ccattgcaat catttgcaga gcaaattggt ggaaaacacg tgaaggtatc atcaatctat    180
ccagcaggga cagatttaca tagctatgaa ccaacacaaa aagatatatt aagtgcaagc    240
aagtcagact tgtttatgta tacaggggat aatttagatc cggttgctaa gaaagttgca    300
tctactatta aagataaaga taaaaaactg tcttttagaag ataaaattaga taaagcaaag    360 cttttaactg atcaacacga acatggtgaa gagcatgaac atgagggaca tgatcatggg    420
aaagaagaac atcatcatca tggcggatat gatccacacg tatggttaga tcctaaaatt    480
aaccaaactt tcgctaaaga aattaaagat gaattagtga agaaagatcc aaaacataaa    540
gatgactatg agaaaaacta caaaaaatta acgacgatc ttaagaaaat tgataacgat    600
atgaagcaag ttactaaaga taagcaaggt aatgcagtat tcatttcaca tgaatcaatt    660
ggatacttag ctgatcgtta tggttttgtt caaaaaggta ttcaaaacat gaatgctgaa    720
gatccatcac aaaaagaatt gactaaaatt gttaaagaaa ttagagatag caatgctaaa    780
tatattcttt acgaagataa tgttgcgaat aaagtgactg aaacaattcg taaagaaaca    840
gatgcgaagc ctttaaaatt ctacaacatg gagtctttaa ataagaaaca acagaaaaaa    900
gataatatta cctatcaatc attaatgaaa tcgaatattg aaaatatcgg taagctttta    960
gacagtggtg ttaaagtgaa agacgacaaa gctgaaagta acacgacaa agcaatttct   1020 gatgggtatt ttaaagatga gcaagttaaa gaccgtgaat taagcgatta tgctggtgaa   1080
tggcaatctg tttaccctta cttaaaagac ggtacgcttg atgaagtgat ggaacataaa   1140
```

| | |
|---|---|
| gctgaaaatg atccgaagaa atctgctaaa gatttaaaag cttattatga caaggatat | 1200 |
| aaaactgata ttactaacat tgatataaaa ggaaatgaaa ttacatttac taaagatggt | 1260 |
| acgaaacaca ctggtaaata tgaatacaat ggtaagaaaa cattgaaata tcctaaaggt | 1320 |
| aaccgtggcg tgagatttat gtttaaattg gtcgatggta atgataaaga cttaccgaaa | 1380 |
| ttcatccaat ttagcgatca caacattgca cctaaaaagg cagaacactt ccatatcttt | 1440 |
| atgggtaatg ataatgacgc gttattaaaa gaaatggata actggccaac atattatcct | 1500 |
| tcaaaattaa ataaagacca aatcaaagaa gaaatgttag cgcattaa | 1548 |

<210> SEQ ID NO 28
<211> LENGTH: 1695
<212> TYPE: DNA
<213> ORGANISM: Staphylococcus aureus

<400> SEQUENCE: 28

| | |
|---|---|
| atggtgttat atatcatttt ggcaataatt gtgattatat tgattgctgt aggtgtatta | 60 |
| ttctatttac gttcaaataa aagacaaata atagaaaaag caatcgaacg taaaaatgaa | 120 |
| attgaaacgt tacctttga tcaaaacctt gcacaattat ctaagttgaa tttaaaaggt | 180 |
| gaaacaaaaa cgaaatacga tgcaatgaaa aaggacaacg tagaaagtac aaataagtat | 240 |
| ctagctcctg tggaagaaaa aatccataat gctgaggctt tattagataa atttagtttc | 300 |
| aacgcatctc aatgtgaaat tgatgatgca atgagttga tggatagtta cgaacaaagc | 360 |
| tatcagcaac aattagaaga tgtaaatgaa attattgcgt tatacaaaga taatgatgaa | 420 |
| ttatatgaca aatgtaaggt tgattatcgt gaaatgaaac gtgatgtttt agcaaatcgt | 480 |
| catcaatttg gtgaggcagc aagtcttctt gaaactgaaa ttgaaaaatt cgagccaagg | 540 |
| ttagagcaat atgaagtact aaaagctgat ggtaattatg tacaagcgca caaccatata | 600 |
| gctgccttga tgaacaaat gaaacagcta agatcttata tggaagaaat accagaatta | 660 |
| attagagaaa ctcaaaaaga attacctggt caattccaag attttaaaata tggttgccgt | 720 |
| gatcttaaag ttgaagggta tgatctggat cacgtaaaag tagacagtac attacaaagc | 780 |
| ttaaaaacag agcttagttt cgttgaacca ttaattagtc gcttagaatt agaagaagct | 840 |
| aatgataaac tagctaatat caatgataag ttagatgaca tgtatgattt aattgaacat | 900 |
| gaagttaaag ctaaaaatga tgtcgaagaa acaaaagata tcattacgga taacttattc | 960 |
| aaagcaaaag acatgaatta tacattgcaa acagaaattg aatatgtacg tgaaaactac | 1020 |
| tatataaatg aatctgatgc tcagagtgtt cgtcaatttg aaaatgaaat tcaaagttta | 1080 |
| atttctgtat atgatgatat tttaaaagaa atgtctaaat ctgctgtacg atatagcgag | 1140 |
| gttcaggata atttacaata tttagaagat catgtcacag ttattaatga caaacaagaa | 1200 |
| aagctacaaa atcatctgat tcaattgcgt gaagatgaag cagaagcaga agacaatctg | 1260 |
| ttacgagtac aatcgaagaa agaagaagtg tatcgtcgat tacttgcttc taacttaaca | 1320 |
| agcgttcctg aaaggtttat catcatgaaa atgaaattg atcatgaagt tcgtgatgtt | 1380 |
| aacgaacaat ttagtgaacg tccaatacac gttaaacagt taaagataa agtgtctaaa | 1440 |
| attgtgattc aaatgaatac atttgaagat gaagcaaatg atgttcttgt taatgctgtt | 1500 |
| tatgcagaga attaattca atatggaaat agatatcgta aggactatag caatgttgat | 1560 |
| aagagcttaa atgaagctga acgattattt aaaaataatc gctataagcg tgcgattgaa | 1620 |
| attgcagagc aagctcttga aagtgttgag ccaggtgtca ctaaacatat tgaagaagaa | 1680 |
| gttattaagc aatag | 1695 |

<210> SEQ ID NO 29
<211> LENGTH: 1860
<212> TYPE: DNA
<213> ORGANISM: Staphylococcus aureus

<400> SEQUENCE: 29

```
atgcctaaaa ataaaatttt aatttatttg ctatcaacta cgctcgtatt acctacttta      60
gtttcaccta ccgcttatgc tgacacacct caaaaagata ctacagctaa gacaacatct     120
catgattcca aaaatctact gatgatgaa acttctaagg atactacaag taaagatatt      180
gataaagcag acaacaataa tactagtaac caagacaata cgacaaaaa agttaaaact      240
atagacgaca gcacttcaga ctctaacaat atcattgatt ttatttataa gaatttacca     300
caaaccaata taaccaatt gctaaccaaa aataaatacg atgataatta ctcattaaca      360
actttaatcc aaaacttatt caatttaaat tcggatattt ctgattacga acaacctcgt     420
aatggtgaaa agtcaacaaa tgattcgaat aaaaacagtg ataatagcat caaaaatgat     480
acggatacgc aatcatctaa acaagataaa gcagacaatc aaaaagcacc taatcaaac      540
aatacaaaac caagtacatc taataagcaa ccaaattcgc aaagccaac acaaccaaat      600
caatcaaata gtcaaccagc aagtgacgat aaagtaaatc aaaaatcttc atcgaaagat     660
aatcaatcaa tgtcagattc ggctttagat tctattttgg atcaatacag tgaagatgca     720
aagaaaacac aaaaagatta cgcatctcaa tctaaaaaag acaaaaatga aaaatctaat     780
acaaagaatc cacagttacc aacacaagat gaattgaaac ataaatctaa acctgctcaa     840
tcattcaata acgatgttaa tcaaaaggat acacgtgcaa catcactatt cgaaacagat     900
cctagtatat ctaacaatga tgatagtgga caatttaacg ttgttgactc aaaagataca     960
cgtcaatttg tcaaatcaat tgctaaagat gcacaccgca ttggtcaaga taacgatatt    1020
tatgcgtctg tcatgattgc ccaagcaatc ttagaatctg actcaggtcg tagtgcttta    1080
gctaagtcac aaaccataa tttattcggt atcaaaggtg cttttgaagg gaattctgtt    1140
ccttttaaca cattagaagc tgatggtaat caattgtata gtattaatgc tggattccga    1200
aaatatccaa gcacgaaaga atcactaaaa gattactctg accttattaa aaatggtatt    1260
gatggcaatc gaacaatta taaccaaca tggaaatcgg aagccgattc ttataaagat     1320
gcaacatcac acttatctaa aacatatgct acagatccaa actatgctaa gaaattaaac    1380
agtattatta aacactatca attaactcag tttgacgatg aacgtatgcc agatttagat    1440
aaatatgaac gttctatcaa ggattatgat gattcatcag atgaattcaa acctttccgc    1500
gaggtatctg ataatatgcc atatccacat ggccaatgta cttggtacgt atataaccgt    1560
atgaaacaat ttggtacatc tatctcaggt gatttaggtg atgcacataa ttggaataat    1620
cgagctcaat accgtgatta tcaagtaagt catacaccaa acgtcatgc tgctgttgta    1680
tttgaggctg acaatttgg tgcagatcaa cattacggtc atgtagcatt tgttgaaaaa    1740
gttaacagtg atggttctat cgttatttca gaatccaatg ttaaaggatt aggtatcatt    1800
tctcatagaa ctatcaatgc agctgccgct gaagaattat catatattac aggtaaataa    1860
```

<210> SEQ ID NO 30
<211> LENGTH: 2046
<212> TYPE: DNA
<213> ORGANISM: Staphylococcus aureus

<400> SEQUENCE: 30

```
atgatgaaaa gtcaaaataa gtatagtatt cgtaaattta gtgtaggtgc atcttccatt      60
ttaatagcta cattactatt tttaagtggt ggacaagcac aagcagctga aagcaagtg     120
aatatgggaa attcacagga ggatacagtt acagcacaat ctattgggga tcaacaaact    180
agggaaaatg ctaattatca acgtgaaaac ggtgttgacg aacagcaaca tactgaaaat    240
ttaactaaga acttgcataa tgataaaaca atatcagaag aaaatcatcg taaaacagat    300
gatttgaata aagatcaact aaaggatgat aaaaaatcat cgcttaataa taaaaatatt    360
caacgtgata caacaaaaaa taacaatgct aatcctaggg atgtaaatca agggttagaa    420
caggctatta atgatggcaa acaaagtaaa gtggcgtcac agcaacagtc aaaagaggca    480
gataatagtc aagacttaaa cgctaataac aatctaccct cacaaagtcg aacaaaggta    540
tcaccatcat taaataagtc agatcaaaca agtcaacgag aaattgttaa tgagacagaa    600
atagagaaag tacaaccgca acaaaagaat caagcgaatg ataaaattac tgaccacaat    660
tttaacaatg aacaagaagt gaaacctcaa aaagacgaaa aaacactatc agtttcagat    720
ttaaaaaaca atcaaaaatc accagttgaa ccaacaaagg acaatgacaa gaaaaatgga    780
ttaaatttat taaaaagtag tgcagtagca acgttaccaa acaaagggac aaaggaactt    840
actgcaaaag cgaaggtga tcaaacgaat aaagttgcca acaagggca gtataaaaat    900
caagatccta tagtttttagt gcatggtttc aatgggttta cagtgatat taatccttca    960
gtgttagctc attattgggg cggtaataaa atgaacattc gccaagattt agaagaaaat   1020
ggttacaaag cttatgaagc aagtataagt gcttttggaa gtaactatga ccgcgcagtt   1080
gaactttatt attatatcaa aggcggtcgt gtagattatg gtgcagcaca tgcagcaaaa   1140
tatggacatg aacgttatgg aaaaacatac gaaggaattt acaaagactg gaaaccagga   1200
cagaaggtac accttgttgg acatagtatg ggtggtcaaa cgatacgtca actagaagaa   1260
ttactgcgta atggtagtcg tgaagaaata gagtatcaaa agaaacatag tggcgaaatt   1320
tctccactat tcaaaggtaa taatgacaat atgatttcat caattactac tttaggaacg   1380
ccacataatg gaacgcatgc ttcagattta gctggtaatg aagctttagt gagacaaatt   1440
gtatttgata tcggtaaaat gtttggtaat aaaaaattcaa gagtagactt cgggttggct   1500
caatggggtc taaaacagaa gccaaatgaa tcatatattg attatgtcaa acgcgttaaa   1560
caatctaatt tatggaaatc aaaagataat ggattttacg atctgacgcg tgagggtgca   1620
acagatttaa atcgtaaaac gtcgttgaac cctaacattg tgtataaaac atacactggt   1680
gaagcaacgc acaaagcatt aaatagcgat agacaaaaag cagacttaaa tatgttttc    1740
ccatttgtga ttactggtaa cttaatcggt aaagctactg aaaagaatg gcgagaaaac    1800
gatggtttag tatccgttat ttcttctcaa catccattta tcaagcttta caaatgcg     1860
acggataaaa ttcaaaaagg catttggcaa gtaacgccta caaacatga ttgggatcat    1920
gttgattttg tcggacaaga tagttctgat acagtgcgca caagagaaga attacaagat   1980
ttttggcatc atttagcaga cgatttagtg aaaactgaaa aggtgactga tactaagcaa   2040
gcataa                                                              2046
```

<210> SEQ ID NO 31
<211> LENGTH: 2421
<212> TYPE: DNA
<213> ORGANISM: Staphylococcus aureus

```
<400> SEQUENCE: 31
atgacaaata aaatgaagaa atggcaaaaa ttatccacca ttacgttatt aatgaccgga      60
gtgattgctt taaataatgg tgaatttaga aatgttgata acatcaaat cgctgtggct     120 gatacgaatg ttcaaacgcc agattatgaa aaattgaaga agacgtggct cgacgttaac    180
tacggttatg atcagtatga tgagaataat caagatatga agaagaagtt tgatgctaaa    240
gaaaaagaag ccaagaagtt acttgatgac atgaaaactg atacgaatag aacatatttg    300
tggtcaggag ctgaaaacct tgaaactaat tcttctcaca tgacaaaaac ctatcgtaat    360
atcgagaaaa tcgcagaatc aatgcaacat aagaatacgg tattaaaaac agttgaaaac    420
aagttgaaaa taaagaagc cctagattgg atgcacaaaa atgtttatgg caagaatcct    480
tctcaaaaag tcgaggattt aactaaaaat cgtaaggggc aaactacacc caagaataac    540
tcattgaatt ggtgggatta tgaaattggt acgccaagag cattaacaaa tacactactt    600
ctaatggatg atatgctcac taaagatgaa atgaaaaatt attcaaaacc tattagtaca    660
tatgcaccat ccagtgacaa aattttatct tctgttggtg aatcagaaga tgctaaaggt    720
ggaaatttag tggacatttc taaagtaaaa cttttagaaa gtgttattga agaagatgta    780
gatatgttga aaaagtctat agattctttt aataaagtgt tcacttatgt tcaagattct    840
gccactggta aaggtcgcaa tggattctat aaagatggct cttacattga tcatcaagat    900
gtcccttaca ctggtgctta tggtgttgta ctattagagg gtatttctca aatgatgccg    960
atgataaaag aatctccttt taaaactaca caagataatg ctacattaag caattggatt   1020
gacgaagggt ttatgccatt aatctataaa ggtgaaatga tggatttatc acgaggtaga   1080
gctatcagtc gtgaaaatga aacgagtcat acagcgtcag cgactgtaat gaaatcattg   1140
ttgagattga atgataccat ggatgattca acaaaaacta gatataagca aatcgttaaa   1200
acttctgtta attctgattc aagttacaac caaaataatt atttaaattc atattcagac   1260
atagctaaaa tgaaaaagtt aatgaatgat agtactattt ctaaaaacga tttaacacag   1320
caacttaaaa tatataatga catggatcgt gtcacctatc acaataaaga cctggacttt   1380
gcatttggtt taagtatgac atcgaaaaac atcgcacgat acgaaaatat caacggagag   1440
aacttaaaag gttggcacac cggtgcaggc atgtcttatt tatataacag cgatgtcaaa   1500
cactatcgcg ataacttctg ggcaacagcc gatatgactt gtcttccagg cactactact   1560
ttaaatgata tgccatctac taatactaag aatgataaat cttttgttgg cgggacaaaa   1620
ttaaataata aatacgcaag catcggtatg gattttgaaa atcaggacaa aactttaact   1680
gccaaaaaat catatttcat attaaacgat aaaattgtct tcttaggaac tggcattaaa   1740
agtactgatt catcaaagaa tccagttaca agtgttgaaa atcgcaaagc aaatgggtat   1800
aaattattta agatgatat tgaaattacc acttcagatg ttaatgctca ggaaacccat   1860
tcagtctttt tagagtccaa cgatactaaa aagaacattg ttatcattt cttagacaag   1920 ccaaaaataa ctgtaaaaaa agaaagtcat actggtaagt gggagtgaaat taataaaagt   1980 caaaaaaaag atgacaaaaa agatgagtat tatgaagtaa ctcaaacaca taatacatct   2040
gacagtaaat atgcatatgt tttgtatcct ggtttatcaa aaagtgattt taaatcgaag   2100
aataataatg taagtattgt taaacaagat gaagattttc atgtgataaa agataatgat   2160
ggcgtatttg ctgggggttaa ttatagtgat aatactaaat cttttgatat aaacggaatt   2220
actgttgaat taaagaaaaa aggcatgttt gtaattaaaa agaaagatga taagcatat   2280 aaatgtagct tctataatcc tgaaactaca aataccgctt caaatataga atcaaaaatt   2340
```

```
tttattaaag gttacaccat aactaataaa agtgtcataa actctaatga tgctggtgta      2400
aactttgaat taactaaata a                                                2421

<210> SEQ ID NO 32
<211> LENGTH: 2427
<212> TYPE: DNA
<213> ORGANISM: Staphylococcus aureus

<400> SEQUENCE: 32
atgacatata gaatgaagaa atggcaaaaa ttgtccacca ttacgttatt aatggctggt        60
gtgattactt tgaatggtgg tgaattcaga agtattgata acatcaaat cgctgtggct       120 gatacgaatg ttcaaacgac agattatgaa agttgagga acatatggct ggacgttaac       180
tatggttatg ataagtatga tgagaataat ccagatatga agaagaagtt tgaggctacg       240
gagaatgagg cagagaaatt actcaaggaa atgaaaactg aaagtgatag gaaatacttg       300
tgggaaagct caaagatttt agatacgaag tctgcggata tgactcgtac ctatcgtaat       360
attgagaaaa tctcagaagc gatgaaacat aaaaatacta aattaaaaac agatgaaaac       420
aagacaaaag taaagatgc acttgagtgg ctgcataaaa atgcatatgg aaaagaacca       480
gataaaaaag ttgctgattt gacctcaaac tttaaaaata aacttctag aaataccaac       540 ttaaattggt gggattatga aattggaaca cctagagcat taacaaatac gcttatactc       600
ttacaagaag atttcactga tgaagaaaag aaaaaatata cagctcctat taaaactttc       660
gccccagata gtgacaaaat attatcttct gtaggaaaat ctgaacctgc taaaggcgga       720
aatttagtag acatttctaa agtaaaactt ttagaaagta ttatcgaaga agacaaagat       780
atgatgaaaa agtctatga ttcatttaat acagtcttca cttacgcgca aaattctgcc       840
actggaaaag aacgtaatgg attctataaa gatggctctt acattgatca tcaagacgtc       900
ccatacactg gtgcttatgg cgttgtacta ttagagggta tttctcaaat gatgccgatg       960
ataaaagaaa cacctttaa tgatagtaac caaaatgata caaccttaaa atcatggatt      1020
gacgacggat ttatgccact catttataaa ggtgaaatga tggatttatc aagaggtaga      1080
gctatcagtc gtgaaaatga aacgagtcac tcagcatctg caacagtaat gaaatcattg      1140
ttgagattga gtgataccat ggataagtct acaaaagcta atataaaaa gattgtcaag      1200 acttcagtag agtcagattc aagttataaa caaaccgatt attttaagctc ttattcggat      1260 ataagcaaaa tgaagtcttt aatggaagac agcactattt ctactaacgg tttaacacaa      1320
caacttaaaa tatataatga catggatcgt gtcacctatc acaataaagg cttagacttt      1380
gcatttggtt taagtatgac gtcgaaaaac gtcgcacgtt acgaaagtat caacggagag      1440
aacttaaaag gttggcacac tggtgctgga atgtcttatt tatacaatag cgatgtgaaa      1500
cactaccgtg ataacttctg ggcgacagct gatatgaaac gtttagcagg tactacaact      1560
ttagataatg aagaacctaa agtacggat gttaaaaagt ctagtaaaac tttttgtagga      1620 ggaacaaaat tcgatgacca acatgctagt atcggaatgg attttgaaaa tcaggacaaa      1680
actttaactg ccaaaaaatc atatttcata ttaaacgata aaattgtctt cttaggaact      1740
ggcattaaaa gtactgattc atcaaagaat ccagttacaa cgattgaaaa tcgcaaagcg      1800
aatgattata aattatataa agatgatacg caaacaacca attccgataa tcaggaaacc      1860
aattccctct ttttagagtc aacgaatagc actcaaaaca atataggtta tcattttta      1920 aacgaatcga aaataactgt aaaaaagaa agtcatactg gtaagtggag tgatataaat      1980
aaaagccaaa aggatataca aaaaactgat gagtattatg aagtaactca aaagcattct      2040
```

-continued

```
aatacagata gtaaatatgc atatgtgttg tatccaggct tatctaaaga tgtctttaaa    2100
tccaaagcaa gcaaagtaac tgtcgttaag caagaagatg acttccacgt tgtgaaagat    2160
aatgaatcgg tttgggctgg tatcaattat agtgatagcg ctaaaacttt tgaaattaat    2220
aacactaaag tcgaagttaa agccaaagga atgtttattc ttacaaagaa agatgataac    2280
acttatgaat gtagcttcta taatcccgaa tctacaaatt ccgtttcaga tattgaatct    2340
aaaatttcaa tgactggata ctctattata aacaaaaata cgtcgacttc taatgaatcc    2400
ggcgtacgct ttgaattaac taaataa                                        2427
```

<210> SEQ ID NO 33
<211> LENGTH: 423
<212> TYPE: RNA
<213> ORGANISM: Staphylococcus aureus

<400> SEQUENCE: 33

```
auggcaaaag guaauuuauu uaaagcgauu uuagguauag guggcgcugu agcagcugua     60
cuuguuacac guaaagauag ucgugacaag cugaaagcag aauauaauaa auacaaacaa    120
gauccucaaa gcuauaaaga uaaugcuaag gauaaagcga cgcaauuagg aacaauugca    180
aaugaaacaa uuaagaagu aaaaacaaau ccgaagaau augcuaauag auuaaaaaau     240
aauccaaaag cauuuuucga agaagaaaaa ucaaauuuua ccgaauauga caauaagacu    300
gacgaaagua uugaaaaagg uaaauuugau gaugaaggug gcgcagcacc aaauaauaau    360
uuacguaucg ucacugaaga agauuuaaaa aagaauaaaa augcauuguc ugauaaagaa    420
uaa                                                                  423
```

<210> SEQ ID NO 34
<211> LENGTH: 582
<212> TYPE: RNA
<213> ORGANISM: Staphylococcus aureus

<400> SEQUENCE: 34

```
augaaaaaau ugguuucaau uguuggcgca acauuauugu uagcuggaug uggaucacaa     60
aauuuagcac cauuagaaga aaaaacaaca gauuuaagag aagauaaauca ucaacucaaa    120 cuagauauuc aagaacuuaa ucaacaaauu agugauucua aaucuaaaau uaaagggcuu    180
gaaaaggaua agaaaauag uaaaaaaacu gcaucuaaua uacgaaaauu uaaauugaug    240
aauguuacau caacauacua cgacaaaguu gcuaaagcuu ugaaauccua uaacgauauu    300
gaaaaggaug uaaguaaaaa caaggcgau aagaauguuc aaucgaaauu aaaucaaauu    360
ucuaaugaua uucaaagugc ucacacuuca uacaagaug cuaucgaugg uuuaucacuu    420
agugaugaug auaaaaaaac gucuaaaaau ucgauaaau uaaacucuga uuugaaucau    480
gcauuugaug auauuaaaaa uggcuaucaa aauaagaua aaaaacaacu uacaaaagga    540
caacaagcgu ugucaaaauu aaacuuaaau gcaaaaucau ga                       582
```

<210> SEQ ID NO 35
<211> LENGTH: 630
<212> TYPE: RNA
<213> ORGANISM: Staphylococcus aureus

<400> SEQUENCE: 35

```
augaaaaaau uaguuacagg guuauuagca uuaucauuau uuuuagcugc auguggucaa     60
gauagugacc aacaaaaaga caguaauaaa gaaaagaug auaaagcgaa acugaacaa     120 caagauaaaa aaacaaauga uucaucuaaa gauaagaaag acaauaaaga ugauaguaaa    180
```

```
gacguaaaca aagauaauaa agauaauagu gcaaacgaua accagcaaca aucuaauuca        240
aaugcaacaa acaaugacca aaaucaaacg aauaauaacc agucaaacag uggacaaacg        300
acuaacaauc aaaaaucaag uuacguugca ccauauuaug acaaaacgc agcgccagug         360 gcucgucaaa uuuauccauu uaaugguaau aaaucacaag cauuacaaca auugccuaau        420
uuccaaacag cuuuaaaugc agcuaacaac gaagcaaaua aauuugguaa uggucauaaa        480
guuuauaaug auuauucaau ugaagaacau aaugguaacu auaaguaugu uuuuaguuuu        540
aaagacccaa acguaaaugg aaaauauuca auuguaacgg uugauuauac uggacaagca        600
augguuacug auccaaacua ccaacaauaa                                         630

<210> SEQ ID NO 36
<211> LENGTH: 729
<212> TYPE: RNA
<213> ORGANISM: Staphylococcus aureus

<400> SEQUENCE: 36
augaaaaaag uaaugggggau auuauuagca aguacacuua ucuuaggugc uuguggacau        60
caucaagaua gugcaaaaaa agagagcacu agucacaaaa agaaagaaaa ugacaaugaa       120
gaauuaaaug aagaacuuaa agaauuuaaa agcaaaaaaa auauggauau aaaaauuaaa       180
ggcgauacua uuguuaguga caaauuugaa gcuaaaauaa aagaaccguu uaucaucaau       240 gaaaagaug agaaaagaa auauaucgcu uuuaaaaugg aauuacgc uaaaaaagac          300 gauaaagauu uaaauccauc uucuauuucu caugacuaua uuaauaucac ucaagaugau       360
aaaaauacag uaaauaaauu aagagauggu uaucuuuuaa gugauaaaaa uuauaaagau       420
uggacagaac auaaccaaga ucaaauuaaa aaaggcaaaa cugcacaagc cauguuuauc       480
uaugaguuaa gaggugaugg aaacauuaau uuaaauguc cauaaauacuc agaagauaaa       540 acaguugauu cuaaaucauu caaauuuagu aaacuuaaaa ccgaagauuu uucucauaga       600
gcggaaacaa gggaagaagu agaaaagaaa gaaaaagaau uugaagaaga guacaaaaaa       660
gaacaagaac gagagaaaga aaaagaaaag caaaaagaug acgaccacag ugguuuagau       720
gaaguauaa                                                              729

<210> SEQ ID NO 37
<211> LENGTH: 984
<212> TYPE: RNA
<213> ORGANISM: Staphylococcus aureus

<400> SEQUENCE: 37
augaaaaaau ggcaauuugu ugguacuaca gcuuuaggug caacacuauu auuaggugcu        60 uguggguggcg guaauggugg cagugguaau agugauuuaa aaggggaagc uaaagggggau      120 ggcucaucaa caguagcacc aauuguggag aaauuaaaug aaaaaugggc ucaagaucac       180
ucggaugcua aaaucucagc aggacaagcu gguacaggug cugguuucca aaaauucauu       240
gcaggagaua ucgacuucgc ugaugcuucu agaccaauua aagaugaaga gaagcaaaaa       300
uuacaagaua agaauaucaa auacaaagaa uucaaaauug cgcaagaugg uguaacgguu       360
gcuguaaaua agaaaauga uuuuguagau gaauugacaa acagcaauu aaaagcaauu       420 uauucuggaa aagcuaaaac auggaaagau guuaauagua auggccaga uaaaaaaaua       480 aaugcuguau caccaaacuc aagucaauggu acuuaugacu cuuugaaaa ugaaguaaug       540 aauaagaag auauuaaagc agaaaaaaau gcugauacaa augcuaucgu uucuucgua         600 acgaaaaaca aagagggaau cggauacuuu ggauauaacu ucuacguaca aaauaaagau       660
```

| | |
|---|---:|
| aaauuaaaag aaguuaaaau caaagaugaa aaugguaaag caacagagcc uacgaaaaaa | 720 |
| acaauucaag auaacucuua ugcauuaagu agaccauuau ucauuuaugu aaaugaaaaa | 780 |
| gcauugaaag auaauaaagu aaugucagaa uuuaucaaau cgucuuaga agauaaaggu | 840 |
| aaagcagcug aagaaggugg auaguagca gcaccagaga aaacauacaa aucacaauua | 900 |
| gaugauuuaa aagcauuuau ugauaaaaau caaaaaucag acgacaagaa aucgaugau | 960 |
| aaaaagucug aagacaagaa auaa | 984 |

<210> SEQ ID NO 38
<211> LENGTH: 1074
<212> TYPE: RNA
<213> ORGANISM: Staphylococcus aureus

<400> SEQUENCE: 38

| | |
|---|---:|
| augaaaggua aauuuuuaaa aguuaguucu uuauucguug caacuuugac aacagcgaca | 60 |
| cuugugaguu uccagcagc aaaugcguua ucuucaaaag cuaggacaa ucauccacaa | 120 |
| caaacgcaga cagacaaaca gcaaacaccu aagauucaaa aaggcgguaa ccuuaaacca | 180 |
| uuagaacaac gugaacgcgc uaauguuaua uuaccaaaua acgaucguca ccaaaucaca | 240 |
| gaucaacga augucauua ugcaccuguu acuuauauuc aaguugaagc accuacuggu | 300 |
| acauuuauug cuucggugu aguuguaggu aaagauacac uuuuaacaaa uaaacacauc | 360 |
| guagaugcua cgcacgguga uccucaugcu uuaaaagcau cgcuucgc aauuaaccaa | 420 |
| gacaauuauc cuaauggugg uuucacugcu gaacaaauca cuaaauauuc aggcgaaggu | 480 |
| gauuuagcaa ucguuaaauu cuccccuaau gagcaaaaca aacauauugg cgaaguaguu | 540 |
| aaaccagcaa caaugaguaa uaaugcugaa acacaaguua accaaaauau uacuguaaca | 600 |
| ggauauccug ugauaaaacc ugucgcaaca augugggaaa guaaaggaaa auaacguac | 660 |
| uuaaaaggug aagcaaugca auaugauuua aguacaacug gugguaacuc agguucaccu | 720 |
| guauuuaaug aaaaaaauga agucauuggc auucauggg guggcguucc aaaucaauuu | 780 |
| aacggugcag uauuuauuaa ugaaaaugua cgcaacuucu aaaacaaaa auuugaagau | 840 |
| aucaauuucg caaaugauga ccacccuaac aacccuugaua auccagcaa uccaaauaau | 900 |
| ccggacaauc cuaacaaccc ugauaacccu aacaaccug auauccaga caauccuaau | 960 |
| aauccugaua accuuaacaa cccggacaau ccaaauaacc cugaccaacc uaacaacca | 1020 |
| aauaacccgg acaauggcga uaacaauau ucagacaacc cugacgcugc auaa | 1074 |

<210> SEQ ID NO 39
<211> LENGTH: 1200
<212> TYPE: RNA
<213> ORGANISM: Staphylococcus aureus

<400> SEQUENCE: 39

| | |
|---|---:|
| augaagcgua cauuaguauu auugauuaca gcuaucuuua uacucgcugc uugugguaac | 60 |
| cauaaggaug accaggcugg aaaagauaau caaaaacaua caauaguuc aaaucaagua | 120 |
| aagaaauug cuacggauaa aaaugacaa ggugauaacu aucguacauu guuaccauuu | 180 |
| aaagaaagcc aggcaagagg acuuuuacaa gauaacaugg caaauaguua uaauggcggc | 240 |
| gacuuugaag augguuuauu gaacuuaagu aaagaagugu uccaacaga caaauauuug | 300 |
| uaucaagaug gucaauuuuu ggacaagaaa acauuaaug ccuauuuaaa ucuuaaguau | 360 |
| acaaaacgug aaaucgauaa aaugucugaa aagauaaaa aagacaagaa agcgaaugaa | 420 |
| aauuuaggac uuaauccauc acacgaaggu gaaacagauc cugaaaagau ugcagaaaaa | 480 |

| | |
|---|---|
| ucaccagccu auuuaucuaa cauuuuagag caagauuuuu augguggugg agauacaaaa | 540 |
| gguaagaaua uuaaaggau gacgauuggu uuagcuauga auaguguuua uuacuauaaa | 600 |
| aaagaaaaag auggaccgac uuuuaguaaa aaacuagaug auagcgaagu uaaaaagcaa | 660 |
| gguaaacaaa uggcuaguga gauauuauca agguuacgug aaaaugauga uuaaaaagau | 720 |
| auaccaauuc auuuugcaau uuauaagcaa ucaagugaag auucaaucac accaggugaa | 780 |
| uuuaucacuc aagcgacugc agaaaagagu caaacaaagc uuaaugaaug gcauaauauc | 840 |
| aaugaaaaau cagcuuuauu accuucuuca acagcagcag auuaugauga aaauuuaaau | 900 |
| aauaauuuca agcaauuuaa ugauaauuug caaucauauu uuucuaauuu cacacaagca | 960 |
| guaggaaaag uuaaauuugu ugauaaaaag ccacaacgau uaguaguaga uuuaccaauc | 1020 |
| gauuacuaug gacaagcuga aacaauuggu auuacacagu acguuacuga acaagcgaau | 1080 |
| aaauauuucg auaaaaucga uaacuaugaa auucggauua aagaugguaa ccaaccacgu | 1140 |
| gcuuuaauua guaagacaaa agaugacaaa gaaccgcaag uucauauuua caguaauuaa | 1200 |

<210> SEQ ID NO 40
<211> LENGTH: 1488
<212> TYPE: RNA
<213> ORGANISM: Staphylococcus aureus

<400> SEQUENCE: 40

| | |
|---|---|
| augagggaaa auuuuaaguu acguaaaaug aaagucgggu uaguaucugu ugcaauuaca | 60 |
| auguuauaua ucaugacaaa cggacaagca gaagcaucag aggcuaauga gaagccaagu | 120 |
| acaaaucaag aaucaaaagu uguuucacag acugaacaaa auucaaaaga aacaaaaaca | 180 |
| guagaaucua auaagaacuu uguuaaauua gauacuauua aaccuggagc ucaaaagaua | 240 |
| acgggaacua cuuuaccaaa ucacuauguu uuauuaacag uugaugggaa aagugcggau | 300 |
| ucaguagaaa auggcgguuu gguuuuuguu gaagcaaaug acaaaggaga uuugaguac | 360 |
| ccuuuaaaua aucguaaaau uguucauaau caagaaauug agguuucguc gucaagcccu | 420 |
| gauuuaggug aagaugaaga agaugaagag guggaagaag cuucaacuga uaaagcuggc | 480 |
| guugaggaag aaaguacaga agcuaaaguu acuuacacaa caccgcgaua ugaaaaagcg | 540 |
| uaugaaauac cgaaagaaca acuaaaagaa aaagauggac aucaccaagu uuuuaucgaa | 600 |
| ccuauuacug aaggaucagg uauuauuaaa gggcauacgu cuguaaaagg uaaaguugcu | 660 |
| uuaucuauua uaauaaaauu uauuaauuuu gaagagagcg uuaagggcgg aguuaguaaa | 720 |
| gaagacacua aagcuaguuc agauggauauc uggaugccua uugaugacaa aggauacuuu | 780 |
| aacuuugacu ucaaaacgaa acguuucgau aauuuagagu uaaagaagg uaaugacauu | 840 |
| ucacuaacau uugcaccuga ugaugaagaa gaugcauuaa aaccuuuaau uuucaaaacu | 900 |
| aaaguaacga gcuuagaaga uaucgauaaa gcagaaacua auauagacca uacuaaacuc | 960 |
| aacaaaguga aaguuuuaga uaauguuaaa gaagauuuac auugaauga auauauugga | 1020 |
| agcuuauauc auacagacaa agguaaaggu auucuugaua agaagguac uaaaguaauu | 1080 |
| aaaggaaaga cuaaauucgc gaauugcagua gugaagguag acucugaacu agguguaagca | 1140 |
| caauuauucc cugauuuaca aguaaaugaa aaaggugaau uuagcuuuga cucacauggu | 1200 |
| gcugguuuua gauacaaaaa uggagaaaaa uuaaacuuca cagugguuga uccuauuaca | 1260 |
| ggugacuugu uaaguaauga guuguuucu aagagauug uauuugaaga aacaccgaa | 1320 |
| caaaagcgg aucgugaguu ugacgaaaaa cuugaaaaua cgccugcuua cuacaaguua | 1380 |

| | |
|---|---|
| uacggcgaua aaauaguugg auucgauacu aacgauuucc cgauuacuug guucuaucca | 1440 |
| uuggugaaa agaaaguuga acguacaaca ccuaaauuag aaaaauaa | 1488 |

<210> SEQ ID NO 41
<211> LENGTH: 1524
<212> TYPE: RNA
<213> ORGANISM: Staphylococcus aureus

<400> SEQUENCE: 41

| | |
|---|---|
| augucuaaaa aguuaaaaau auaauuccu auuauuauug ucuuauuauu aauaggugga | 60 |
| aucgcauggg gaguuuaugc auuuuuugca aacacaccga aaaauacaua cuuaaaaagu | 120 |
| gaacaacaaa cugcaaaaau guauaaagau auuuuaaug accguuuuga aaacgaagug | 180 |
| aaguuccaag aaaagaugaa agauaauuca uuuuuaucuu cauuagaauu aagcgcagau | 240 |
| gcaucugaug aaauuguuaa agggcuuggu auuccuaaau cuguuguuaa ugcuucgaaa | 300 |
| auuaaaaugu cauauggaca ugauccuaaa aaagagaaau caaugauuaa ucuugaacca | 360 |
| acaauagcag acucugcauu agggaaauuc caguuagcug cagauaaaga uaagcauuau | 420 |
| uucgaaucac cauuauuuaa agggaaauau aguguuaaua auucugauuu auuaucaacu | 480 |
| uauucaaaac uuacagguga agaugaagaa acagcaaaag aaaauggauu ucaaaccaa | 540 |
| caacuaaauu uaaauacucu uuucaguaau gcucaagcac aacaagugua cuacagcaaa | 600 |
| auugccgaaa aauauuccga acuuaugguc gacaaauuag augacgauaa uuugauaaa | 660 |
| gguaaaaaag aagaaauuaa gguuaaugu gaaaaguaca aguuagacc ugucacguua | 720 |
| acacuuagca gagcugacac uaaaaaaauu acauuagcug uauuagaaga agcuaaaaag | 780 |
| gauaaagacc uuaaaaaauu aauggaagaa caagguacua caaaagacuu ugaaaaagac | 840 |
| auuaaaaag caauugacga ugucaaagaa acuaaaaagg augaauuugc uaaauucaa | 900 |
| ucuaaaauuu auaccgaaaa acauacgauu guaaaacgag aaauuacuau uacagacaaa | 960 |
| gaaaauaaua aaacuaaaau caaagguacu aauacuuuag aagacgauaa guuaaaacua | 1020 |
| gauuacgcac uugauuucga ucaagauaaa uacacguaug cugaagcgaa auauacaauu | 1080 |
| aaaggcguau cuucuaagga aaaagacaau aaauacagug auaaaucga uuugguaaa | 1140 |
| aagacagaau augaugaauc aaaaucaaa uuagauaacc aagaaaaagu agauggcaca | 1200 |
| aaacgucaag auaagguaa aaucacuguc gcguuagaua aauauagcga cgaaaaugaa | 1260 |
| uucacuuuug aaaauaauau agauucgac guaaaaaaua cacucagaa aucacguua | 1320 |
| aauaucggca ucaaauaugc ugaagaacca auuaauuuca uuuaaaauc uagcacaaaa | 1380 |
| uugaaagcag auauugauuu ugaugauagu ggugcgaaag auuucaauag ucuaucuuca | 1440 |
| aaagaccgug aaaacuuga aaagaaauc gaaaaaaaug gcggcaaaau guuugaauca | 1500 |
| auuuuaaaaa aggcaucuaa auaa | 1524 |

<210> SEQ ID NO 42
<211> LENGTH: 1530
<212> TYPE: RNA
<213> ORGANISM: Staphylococcus aureus

<400> SEQUENCE: 42

| | |
|---|---|
| gugaggaaau uuucaagaua ugcauuuaca aguauggcaa caguaacguu gcugagcucu | 60 |
| uugacaccug cagcacuagc gagugauacg aaucacaaac cagcaacuuc agauauuaau | 120 |
| uuugaauca cgcaaaagag ugaugcaguu aaagcauuaa aagaguuacc uaaaucgaa | 180 |
| aaugugaaaa aucauuauca agauuacucu guuacagaug uaaaaacaga uaagaaagga | 240 |

```
uucacgcauu acacguuaca accgagugug gaugguguge augegecuga caaagaagug    300 aaagugcaug cggacaaauc ggguaaaguc guuuuaauca acggugauac ugaugcgaag    360
aaaguaaagc cgacaaauaa agugacauua agcaaggaug aagcggcuga caaagcauuu    420
aacgcaguua agauugauaa aaauaaagcu aaaaaccucc aagaugacgu uaucaaagaa    480
aauaaagucg aaaucgaugg ugacaguaau aaauacauuu acaauauuga auuauuaca     540 guaacaccag aaauuucaca uuggaaaguu aaaauugaug cagacacagg agcaguuguu    600
gaaaaaacga acuuaguuaa agaagcagca gcaacuggca cagguaaagg ugugcuugga    660
gaucaaaaag auaucaauau caauaguauu gaugguggau uuaguuuaga ggauuugacg    720
caucaaggua aauuaucagc auacaauuuu aacgaucaaa caggucaagc gacauuaauu    780
acuaaugaag augaaaacuu cgucaaagau gaucaacgug cugguguaga ugcgaauuau    840
uaugcuaaac aaacauauga uuacuacaaa aauacauuug gucgugaguc uuacgauaac    900
caugguaguc caauaugucuc auuaacacau guaaaucauu auggggacaa agauaacaga    960
aauaacgcug caugggauug gagacaaaaug auuuauggu auggcgaugg ccgcacguuu    1020
acaaauuuau caggugcaaa ugacuaguag ca cauga gag u uaacacaugg cgugacacaa    1080
gaaacggcga auuagaagua uaagaucaa ucuggugcgu uaaaugaaag cuuuucagau    1140
guuuuuggau acuuuguaga ugaugaggau uucuuugaugg gugaagaugu uuacacacca    1200
ggaaaagagg gagaugcuuu acgaagcaug ucaaacccag aacaauuugg ucaaccaucu    1260
cauaugaaag acuauguaua cacugaaaaa gauaacggug gugugcauac gaauucuggc    1320
auuccaaaua aagcagcuua uaacguaauu caagcaauag ggaaaucuaa aucagaacaa    1380
auuuacuacc gagcauuaac ggaauacuua acaaguaauu caaacuucaa agauuguaaa    1440
gaugcauuau accaagcggc uaagauuuua uaugacgagc aaacagcuga acaaguauau    1500
gaagcaugga acgaaguugg cgucgaguaa                                    1530
```

<210> SEQ ID NO 43
<211> LENGTH: 1548
<212> TYPE: RNA
<213> ORGANISM: Staphylococcus aureus

<400> SEQUENCE: 43

```
augaaaaaga aauuaggguau guuacuucuu guaccagccg uaacuuuauc auuagccgca    60
ugugggaaug augauggaaa agauaaagau ggcaagguaa caauuaaaac gacaguuuau    120
ccauugcaau cauuugcaga gcaaauuggu ggaaaacacg ugaagguauc aucaaucuau    180
ccagcaggga cagauuuaca uagcuaugaa ccaacacaaa aagauauauu aagugcaagc    240
aagucagacu uguuuaugua acaggggau aauuugauc cgguugcaa gaaaguugca     300 ucuacuauua agauaaaga uaaaaaacug ucuuuagaag auaaauuaga uaaagcaaag    360
cuuuuaacug aucaacacga acauggugaa gagcaugaac augagggaca ugaucauggg    420
aaagaagaac aucaucauca uggcggauau gauccacacg uaugguuaga uccuaaaauu    480
aaccaaacuu ucgcuaaaga aauuaaagau gaauuaguga agaaagaucc aaaacauaaa    540
gaugacuaug agaaaacua caaaaaauua acgacgauc uuaagaaaau ugauaacgau    600
augaagcaag uuacuaaaga uaagcaaggu aaugcaguau caauucaca ugaaucaauu    660 ggauacuuag cugaucguua ugguuuguu caaaaaggua uucaaaacau gaugcugaa    720 gauccaucac aaaaagaauu gacuaaaaau guuaaagaaa uuagagauag caaugcuaaa    780
uauauucuuu acgaagauaa uguugcgaau aaagugacug aaacaauucg uaaagaaaca    840
```

| | |
|---|---|
| gaugcgaagc cuuuaaaauu cuacaacaug gagucuuuaa auaaagaaca acagaaaaaa | 900 |
| gauaauauua ccuaucaauc auuaaugaaa ucgaauauug aaaauaucgg uaaagcuuua | 960 |
| gacaguggug uuaaagugaa agacgacaaa gcugaaagua aacacgacaa agcaauuucu | 1020 |
| gaugggauau uuaaagauga gcaaguuaaa gaccgugaau uaagcgauua ugcuggugaa | 1080 |
| uggcaaucug uuuacccuua cuuaaaagac gguacgcuug augaagugau ggaacauaaa | 1140 |
| gcugaaaaug auccgaagaa aucugcuaaa gauuuaaaag cuuauuauga caaaggauau | 1200 |
| aaaacugaua uuacuaacau ugauauaaaa ggaaaugaaa uuacauuuac uaaagauggu | 1260 |
| acgaaacaca cugguaaaua ugaauacaau gguaagaaaa cauugaaaua uccuaaaggu | 1320 |
| aaccguggcg ugagauuuau guuuaaauug gucgauggua augauaaaga cuuaccgaaa | 1380 |
| uucauccaau uuagcgauca caacauugca ccuaaaaagg cagaacacuu ccauaucuuu | 1440 |
| auggguaaug auaaugacgc guuauaaaaa gaaauggaua acuggccaac auauuauccu | 1500 |
| ucaaaauuaa auaaagacca aaucaaagaa gaaauguuag cgcauuaa | 1548 |

<210> SEQ ID NO 44
<211> LENGTH: 1695
<212> TYPE: RNA
<213> ORGANISM: Staphylococcus aureus

<400> SEQUENCE: 44

| | |
|---|---|
| augguguuau auaucauuuu ggcaauaauu gugauuauau ugauugcugu agguguauua | 60 |
| uucuauuuac guucaaauaa aagacaaaua auagaaaaag caaucgaacg uaaaaaugaa | 120 |
| auugaaacgu uaccuuuuga ucaaaaccuu gcacaauuau cuaaguugaa uuuaaaaggu | 180 |
| gaaacaaaaa cgaaauacga ugcaaugaaa aaggacaacg uagaaaguac aaauaaguau | 240 |
| cuagcuccug uggaagaaaa aauccauauu gcugaggcuu auugauaaa auuuaguuuc | 300 |
| aacgcaucuc aaugugaaau ugaugaugca aaugaguuga uggauaguua cgaacaaagc | 360 |
| uaucagcaac aauuagaaga uguaaaugaa auuauugcgu uauacaaaga uaaugaugaa | 420 |
| uuauaugaca aauguaaggu ugauuaucgu gaaaugaaac gugauguuuu agcaaaucgu | 480 |
| caucaauuug gugaggcagc aagucuucuu gaaacgaaaa uugaaaaauu cgagccaagg | 540 |
| uuagagcaau augaaguacu aaaagcugau ggauauuaug uacaagcgca caaccauaua | 600 |
| gcugccuuga augaacaaau gaaacagcua agaucuuaua uggaagaaau accagaauua | 660 |
| auuagagaaa cucaaaaaga auuaccuggu caauuccaag auuuaaaaua ugguugccgu | 720 |
| gaucuuaaag uugaagggua ugaucggau cacguaaaag uagacaguac auuacaaagc | 780 |
| uuaaaaacag agcuuaguuu cguugaacca uuaauuaguc gcuuagaauu agaagaagcu | 840 |
| aaugauaaac uagcuaauau caaugauaag uuagaugaca guaugauuuu aauugaacau | 900 |
| gaaguuaaag cuaaaaauga ugucgaagaa acaaaagaua ucauuacgga uaacuuauuc | 960 |
| aaagcaaaag acaugaauua uacauugcaa acagaaauug aauauguacg ugaaaacuac | 1020 |
| uauauaaaug aaucugaugc ucagaguguu cgucaauuug aaaaugaaau ucaaaguuua | 1080 |
| auuucuguau augaugauau uuuaaagaa augucuaaau cugcuuacg auauagcgag | 1140 |
| guucaggaua auuuacaaua uuuagaagau caugucacag uuauuaauga caaacaagaa | 1200 |
| aagcuacaaa aucaucugau ucaauugcgu gaagaugaag cagaagcaga agacaaucug | 1260 |
| uuacgaguac aaucgaagaa agaagaagug uaucgucgau uacuugcuuc uaacuuaaca | 1320 |
| agcguuccug aaagguuuau caucaugaaa aaugaaauug aucaugaagu cugaugauguu | 1380 |
| aacgaacaau uuagugaacg uccaauacac guuaaacagu uaaaagauaa agugucuaaa | 1440 |

| | |
|---|---:|
| auugugauuc aaaugaauac auuugaagau gaagcaaaug auguucuugu uaaugcuguu | 1500 |
| uaugcagaga aauuaauuca auauggaaau agauaucgua aggacuauag caauguugau | 1560 |
| aagagcuuaa augaagcuga acgauuauuu aaaaauaauc gcuauaagcg ugcgauugaa | 1620 |
| auugcagagc aagcucuuga aaguguugag ccagguguca cuaaacauau ugaagaagaa | 1680 |
| guuauuaagc aauag | 1695 |

```
<210> SEQ ID NO 45
<211> LENGTH: 1860
<212> TYPE: RNA
<213> ORGANISM: Staphylococcus aureus

<400> SEQUENCE: 45
```

| | |
|---|---:|
| augccuaaaa auaaaauuuu aauuuauuug cuaucaacua cgcucguauu accuacuuua | 60 |
| guuucaccua ccgcuuaugc ugacacaccu caaaaagaua cuacagcuaa gacaacaucu | 120 |
| caugauucca aaaaaucuac ugaugaugaa acuucuaagg auacuacaag uaaagauauu | 180 |
| gauaaagcag acaacaauaa uacuaguaac caagacaaua acgacaaaaa aguuaaaacu | 240 |
| auagacgaca gcacuucaga cucuaacaau aucaugugau uuauuuauaa gaauuuacca | 300 |
| caaaccaaua uaaccaauu gcuaaccaaa auaaauacg ugauaauua cucauuaaca | 360 |
| acuuuaauc aaaacuuauu caauuuaaau ucggauauuu cugauuacga acaaccucgu | 420 |
| aauggugaaa agucaacaaa ugauucgauu aaaaacagug auaauagcau caaaaaugau | 480 |
| acggauacgc aaucaucuaa acaagauaaa gcagacaauc aaaaagcacc uaaaucaaac | 540 |
| aauacaaac caaguacauc uaauaagcaa ccaaauucgc caaagccaac acaaccaaau | 600 |
| caaucaaaua gucaaccagc aagugacgau aaaguaaauc aaaaaucuuc aucgaaagau | 660 |
| aaucaaucaa ugucagauuc ggcuuuagau ucuauuuugg aucaauacag ugaagaugca | 720 |
| aagaaaacac aaaaagauua cgcaucucaa ucuaaaaaag acaaaaauga aaaaucuaau | 780 |
| acaaagaauc cacaguuacc aacacaagau gaauugaaac auaaaucuaa accgcucaa | 840 |
| ucauucaaua acgauguuaa ucaaaaggau acacgugcaa caucacuauu cgaaacagau | 900 |
| ccuaguauau cuaacaauga ugauaggga caauuuaacg uuguugacuc aaaagauaca | 960 |
| cgucaauuug ucaaaucaau ugcuaaagau gcacaccgca uuggucaaga uaacgauauu | 1020 |
| uaugcgucug ucaugauugc ccaagcaauc uuagaaucug acucaggucg uagugcuuua | 1080 |
| gcuaagucac caaaccauaa uuuauucggu aucaaaggug cuuugaagg gaauucuguu | 1140 |
| ccuuuaaca cauugaagc ugauggauau caauuguaua guuaaagc uggauuccga | 1200 |
| aaauauccaa gcacgaaaga aucacuaaaa gauuacucug accuuauuaa aaaugguauu | 1260 |
| gauggcaauc gaacaauuua uaaaccaaca uggaaaucgg agccgauuc uuauaaagau | 1320 |
| gcaacaucac acuuaucuaa aacauaugcu acagauccaa acaugcuaa gaaauuaaac | 1380 |
| aguauuauua aacacuauca auuaacucag uuugacgaug aacguaugcc agauuuagau | 1440 |
| aaaaugaac guucuaucaa ggauuaugau gauucaucag augaauucaa accuuuccgc | 1500 |
| gagguaucug auaauaugcc auaccacau ggccaaugua cuugguacgu auauaaccgu | 1560 |
| augaaacaau uuggacuauc uaucucaggu gauuaggug augcacauaa uuggaauaau | 1620 |
| cgagcucaau accgugauua ucaaguaagu cauacaccaa aacgucaugc ugcuguugua | 1680 |
| uuugaggcug acaauuuugg ugcagaucaa cauuacgguc auagcauu uguugaaaaa | 1740 |
| guuacagug augguucuau cguuauuuca gaauccaaug uuaaaggauu agguaucauu | 1800 |
| ucucauagaa cuaucaaugc agcugccgcu gaagaauuau cauauauuac agguaaauaa | 1860 |

<210> SEQ ID NO 46
<211> LENGTH: 2046
<212> TYPE: RNA
<213> ORGANISM: Staphylococcus aureus

<400> SEQUENCE: 46

| | | | | | | |
|---|---|---|---|---|---|---|
| augaugaaaa | gucaaaauaa | guauaguauu | cguaaauuua | guguaggugc | aucuuccauu | 60 |
| uuaauagcua | cauuacuauu | uuuaaguggu | ggacaagcac | aagcagcuga | gaagcaagug | 120 |
| aauaugggaa | auucacagga | ggauacaguu | acagcacaau | cuauggggga | ucaacaaacu | 180 |
| agggaaaaug | cuauuauca | acgugaaaac | ggguugacg | aacagcaaca | uacugaaaau | 240 |
| uuaacuaaga | acuugcauaa | ugauaaaaca | auaucagaag | aaaaucaucg | uaaaacagau | 300 |
| gauuugaaua | aagaucaacu | aaaggaugau | aaaaaaucau | cgcuuaauaa | uaaaaauauu | 360 |
| caacgugaua | caacaaaaaa | uaacaaugcu | aauccuaggg | auguaaauca | aggguuagaa | 420 |
| caggcuauua | augauggcaa | acaaaguaaa | guggcgucac | agcaacaguc | aaaagaggca | 480 |
| gauaauaguc | aagacuuaaa | cgcuaauaac | aaucuaccuu | cacaaagucg | aacaaaggua | 540 |
| ucaccaucau | uaaauaaguc | agaucaaaca | agucaacgag | aaauuguuaa | ugagacagaa | 600 |
| auagagaaag | uacaaccgca | acaaaagaau | caagcgaaug | auaaaauuac | ugaccacaau | 660 |
| uuuaacaaug | aacaagaagu | gaaaccucaa | aaagacgaaa | aaacacuauc | aguuucagau | 720 |
| uuaaaaaaca | aucaaaaauc | accaguugaa | ccaacaaagg | acaaugacaa | gaaaaaugga | 780 |
| uuaaauuuau | uaaaaaguag | ugcaguagca | acguuaccaa | acaaagggac | aaaggaacuu | 840 |
| acugcaaaag | cgaaagguga | ucaaacgaau | aaaguugcca | aacaagggca | guauaaaaau | 900 |
| caagauccua | uaguuuuagu | gcaugguuuc | aaugggguua | cagaugauau | uaauccuuca | 960 |
| guguuagcuc | auuauggggg | cgguaauaaa | augaacauuc | gccaagauuu | agaagaaaau | 1020 |
| gguuacaaag | cuuaugaagc | aaguauaagu | gcuuuuggaa | guaacuauga | ccgcgcaguu | 1080 |
| gaacuuuauu | auuauaucaa | aggcggucgu | guagauuaug | gugcagcaca | ugcagcaaaa | 1140 |
| uauggacaug | aacguuaugg | aaaaacauac | gaaggaauuu | acaaagacug | gaaaccagga | 1200 |
| cagaagguac | accuuguugg | acauaguaug | ggggucaaa | cgauacguca | acuagaagaa | 1260 |
| uuacugcgua | augguagucg | ugaagaaaua | gaguaucaaa | agaaacauag | uggcgaaauu | 1320 |
| ucuccacuau | ucaaagguaa | uaaugacaau | augauuucau | caauuacuac | uuuaggaacg | 1380 |
| ccacauaaug | gaacgcaugc | uucagauuua | gcugguaaug | aagcuuuagu | gagacaaauu | 1440 |
| guauuugaua | ucgguaaaau | guuuggUaau | aaaaauucaa | gaguagacuu | cggguuggcu | 1500 |
| caaugggguc | uaaaacagaa | gccaaaugaa | ucauauauug | auuaugucaa | acgcguuaaa | 1560 |
| caaucuaauu | uauggaaauc | aaaagauaau | ggauuuuacg | aucugacgcg | ugagggugca | 1620 |
| acagauuuaa | aucguaaaac | gucguugaac | ccuaacauug | uguauaaaac | auacacuggu | 1680 |
| gaagcaacgc | acaaagcauu | aaauagcgau | agacaaaaag | cagacuuaaa | uauguuuuuc | 1740 |
| ccauuuguga | uuacuggUaa | cuuaaucggu | aaagcuacug | aaaaagaaug | gcgagaaaac | 1800 |
| gauguuuuag | uauccguuau | uucuuccucaa | cauccauuua | aucaagcuua | uacaaaugcg | 1860 |
| acggauaaaa | uucaaaaagg | cauuuggcaa | guaacgccua | caaaacauga | uugggaucau | 1920 |
| guugauuuug | ucggacaaga | uaguucgauu | acagucgcgca | caagagaaga | auuacaagau | 1980 |
| uuuuggcauc | auuuagcaga | cgauuuagug | aaaacugaaa | aggugacuga | uacuaagcaa | 2040 |
| gcauaa | | | | | | 2046 |

```
<210> SEQ ID NO 47
<211> LENGTH: 2421
<212> TYPE: RNA
<213> ORGANISM: Staphylococcus aureus

<400> SEQUENCE: 47
augacaaaua aaaugaagaa auggcaaaaa uuauccacca uuacguuauu aaugaccgga      60
gugauugcuu uaaauaaugg ugaauuuaga aauguugaua aacaucaaau cgcuguggcu     120
gauacgaaug uucaaacgcc agauuaugaa aaauugaaga agacguggcu cgacguuaac     180
uacgguuaug aucaguauga ugagaauaau caagauauga agaagaaguu ugaugcuaaa     240
gaaaaagaag ccaagaaguu acuugaugac augaaaacug uacgaauaga acauauuug      300 uggucaggag cugaaaaccu ugaaacuaau ucuucucaca ugacaaaaac cuaucguaau     360
aucgagaaaa ucgcagaauc aaugcaacau aagaauacgg uauuaaaaac aguugaaaac     420
aaguugaaaa uaaagaagc ccuagauugg augcacaaaa auguuuaugg caagaauccu     480
ucucaaaaag ucgaggauuu aacuaaaaau cguaaggggc aaacuacacc caagaauaac     540
ucauugaauu gguggauua ugaaauuggu acgccaagag cauuaacaaa uacacuacuu     600
cuaauggaug auaugcucac uaagaugaa augaaaaauu auucaaaacc uauuaguaca     660
uaugcaccau ccagugacaa aauuuuaucu ucuguuggug aaucagaaga ugcuaaaggu     720
ggaaauuuag uggacauuuc uaaaguaaaa cuuuuagaaa guguuauuga agaagaugua     780
gauauguuga aaaagucuau agauucuuuu aauaaagugu ucacuuaugu ucaagauucu     840
gccacuggua aggucgcaa uggauucuau aaagauggcu cuuacauuga ucaucaagau     900
gucccuuaca cuggugcuua ugguguugua cuauuagagg guauuucuca aaugaugccg     960
augauaaaag aaucuccuuu uaaaacuaca caagauaaug cuacauuaag caauuggauu    1020
gacgaagggu uuaugccauu aaucuauaaa ggugaaauga uggauuuauc acgagguaga    1080
gcuaucaguc gugaaaauga aacgagucau acagcgucag cgacuguaau gaaaucauug    1140
uugagauuga augauaccau ggaugauuca acaaaaacua gauauaagca aaucguuaaa    1200
acuucuguua auucgauuc aaguuacaac caaaauaauu auuuaaauuc auauucagac    1260
auagcuaaaa ugaaaaaguu aaugaaugau aguacauuau cuaaaacga uuuaacacag    1320 caacuuaaaa uauauaauga cauggaucgu gucaccuauc acaauaaaga ccuggacuuu    1380
gcauuugguu uaaguaugac aucgaaaaac aucgcacgau acgaaaauau caacggagag    1440
aacuuaaaag guuggcacac cggugcaggc augucuuauu uauauaacag cgaugucaaa    1500
cacuaucgcg auaacuucug ggcaacagcc gauaugacuu gucuuccagg cacuacuacu    1560
uuaaaugaua ugccaucuac uaauacaaag aaugauaaau cuuuuguugg cgggacaaaa    1620
uuaaauaaua aauacgcaag caucgguaug gauuuugaaa ucaggacaa aacuuuaacu    1680 gccaaaaaau cauauuucau auuaaacgau aaaauugucu cuuaggaac uggcauuaaa    1740 aguacgauu caucaaagaa uccaguuaca aguuugaaa ucgcaaagc aaauggguau     1800 aaauuauuua agaugauau ugaaauuacc acuucagaug uuaaugcuca ggaaacccau    1860
ucagucuuuu uagagccaa cgauacuaaa aagaacauug guuaucauuu cuuagacaag    1920
ccaaaaauaa cuguaaaaaa agaaagucau acggguaagu ggagugaaau uaauaaagu    1980 caaaaaaaag augacaaaaa agaugagaau augaaguaa cucaaacaca uaauacaucu    2040
gacaguaaau augcauaugu uuuguauccu gguuaucaa aaagcgauuu uaaaucgaag    2100
aauaauaaug uaaguauugu uaaacaagau gaagauuuuc auguaauaa agauaaugau    2160
```

-continued

| | |
|---|---|
| ggcguauuug cugggguuaa uuauagugau aauacuaaau cuuuugauau aaacggaauu | 2220 |
| acuguugaau uaaagaaaa aggcauguuu guaauuaaaa agaaagauga uaaagcauau | 2280 |
| aaauguagcu ucuauaaucc ugaaacuaca aauaccgcuu caaauauaga aucaaaaauu | 2340 |
| uuuauuaaag guuacaccau aacuaauaaa agugcauaa acucuaauga ugcuggugua | 2400 |
| aacuuugaau uaacuaaaua a | 2421 |

```
<210> SEQ ID NO 48
<211> LENGTH: 2427
<212> TYPE: RNA
<213> ORGANISM: Staphylococcus aureus

<400> SEQUENCE: 48
```

| | |
|---|---|
| augacauaua gaaugaagaa auggcaaaaa uuguccacca uuacguuauu aauggcuggu | 60 |
| gugauuacuu ugaauggugg ugaauucaga aguauugaua aacaucaaau cgcuguggcu | 120 |
| gauacgaaug uucaaacgac agauuaugaa aaguugagga acauauggcu ggacguuaac | 180 |
| uaugguuaug auaaguauga ugagaauaau ccagauauga agaagaaguu ugaggcuacg | 240 |
| gagaaugagg cagagaaauu acucaaggaa augaaaacug aaagugauag gaaauacuug | 300 |
| ugggaaagcu caaaagauuu agauacgaag ucugcggaua ugacucguac cuaucguaau | 360 |
| auugagaaaa ucucagaagc gaugaaacau aaaaauacua auuaaaaac agaugaaaac | 420 |
| aagacaaaag uaaagaugc acuugagugg cugcauaaaa augcauaugg aaaagaacca | 480 |
| gauaaaaaag uugcugauuu gaccucaaac uuuaaaaaua aaacuucuag aaauaccaac | 540 |
| uuaaauuggu gggauuauga aauuggaaca ccuagagcau uaacaaauac gcuuauacuc | 600 |
| uuacaagaag auuucacuga ugaagaaaag aaaaaauaua cagcuccuau uaaaacuuuc | 660 |
| gccccagaua gugacaaaau auuaucuucu guaggaaaau cugaaccugc uaaaggcgga | 720 |
| aauuuaguag acauuucuaa aguaaaacuu uuagaaagua uuaucgaaga agacaaagau | 780 |
| augaugaaaa agucuauaga uucauuuaau acagucuuca cuuacgcgca aaauucugcc | 840 |
| acuggaaaag aacguaaugg auucuauaaa gauggcucuu acaugauca ucaagacguc | 900 |
| ccauacacug gugcuuaugg cguugacua uuagagggua uuucucaaau gaugccgaug | 960 |
| auaaaagaaa caccuuuuaa ugauaguaac caaaaugaua caaccuuaaa aucauggauu | 1020 |
| gacgacggau uuaugccacu cauuuauaaa ggugaaauga uggauuuauc aagaggauga | 1080 |
| gcuaucaguc gugaaaauga aacgagucac ucagcaucug caacaguaau gaaaucauug | 1140 |
| uugagauuga gugauaccau ggauaagucu acaaaagcua auauaaaaa gauugucaag | 1200 |
| acuucaguag agucagauuc aaguuauaaa caaccgauu auuuaagcuc uuauucggau | 1260 |
| auaagcaaaa ugaagucuuu aauggaagac agcacuauuu cuacuaacgg uuuaacacaa | 1320 |
| caacuuaaaa uauauaauga cauggaucgu gucaccuauc acaauaaagg cuuagacuuu | 1380 |
| gcauuugguu uaaguaugac gucgaaaaac gucgcacguu acgaaaguau caacggagag | 1440 |
| aacuuaaaag guuggcacac uggugcugga augucuuauu uauacaauag cgaugugaaa | 1500 |
| cacuaccgug auaacuucug ggcgacagcu gauaugaaac guuagcagg uacuacaacu | 1560 |
| uuagauaaug aagaaccuaa aagucgcgau guuaaaagu cuaguaaaac uuuuguagga | 1620 |
| ggaacaaaau ucgaugacca acaugcuagu aucggaaugg auuugaaaa ucaggacaaa | 1680 |
| acuuuaacug ccaaaaaauc auauuucaua uuaaacgaua aaauugucuu cuuaggaacu | 1740 |
| ggcauuaaaa guacgauuc aucaaagaau ccaguuacaa cgauugaaaa ucgcaaagcg | 1800 |
| aaugauuaua aauuauauaa agaugauacg caaacaacca auccgauaa ucaggaaacc | 1860 |

-continued

```
aauucccucu uuuuagaguc aacgaauagc acucaaaaca auauagguua ucauuuuuua      1920
aacgaaucga aaauaacugu aaaaaaagaa agucauacug guaaguggag ugauauaaau      1980
aaaagccaaa aggauauaca aaaaacugau gaguauuaug aaguaacuca aaagcauucu      2040
aaucagaaua guaaauaugc auaugucuug uauccaggcu uaucuaaaga ugucuuuaaa      2100
uccaaagcaa gcaaaguaac ugucguuaag caagaagaug acuccacgu ugugaaagau       2160 aaugaaucgg uuugggcugg uaucaauuau agugauagcg cuaaaacuuu ugaaauuaau      2220
aacacuaaag ucgaaguuaa agccaaagga auguuauuc uuacaaagaa agaugauaac       2280
acuuaugaau guagcuucua uaucccgaa ucuacaaauu ccguuucaga uauugaaucu        2340
aaaauuucaa ugacuggaua cucuauuaua aacaaaaaua cgucgacuuc uaaugaaucc      2400
ggcguacgcu uugaauuaac uaaauaa                                          2427
```

<210> SEQ ID NO 49
<211> LENGTH: 412
<212> TYPE: PRT
<213> ORGANISM: Staphylococcus aureus

<400> SEQUENCE: 49

```
Ile Asp Ser Lys Asn Lys Pro Ala Asn Ser Asp Ile Lys Phe Glu Val
1               5                   10                  15

Thr Gln Lys Ser Asp Ala Val Lys Ala Leu Lys Glu Leu Pro Lys Ser
            20                  25                  30

Glu Asn Val Lys Asn Ile Tyr Gln Asp Tyr Ala Val Thr Asp Val Lys
        35                  40                  45

Thr Asp Lys Lys Gly Phe Thr His Tyr Thr Leu Gln Pro Ser Val Asp
    50                  55                  60

Gly Val His Ala Pro Asp Lys Glu Val Lys Val His Ala Asp Lys Ser
65                  70                  75                  80

Gly Lys Val Val Leu Ile Asn Gly Asp Thr Asp Ala Lys Lys Val Lys
                85                  90                  95

Pro Thr Asn Lys Val Thr Leu Ser Lys Asp Asp Ala Ala Asp Lys Ala
            100                 105                 110

Phe Lys Ala Val Lys Ile Asp Lys Asn Lys Ala Lys Asn Leu Lys Asp
        115                 120                 125

Lys Val Ile Lys Glu Asn Lys Val Glu Ile Asp Gly Asp Ser Asn Lys
    130                 135                 140

Tyr Val Tyr Asn Val Glu Leu Ile Thr Val Thr Pro Glu Ile Ser His
145                 150                 155                 160

Trp Lys Val Lys Ile Asp Ala Gln Thr Gly Glu Ile Leu Glu Lys Met
                165                 170                 175

Asn Leu Val Lys Glu Ala Ala Glu Thr Gly Lys Gly Lys Gly Val Leu
            180                 185                 190

Gly Asp Thr Lys Asp Ile Asn Ile Asn Ser Ile Asp Gly Gly Phe Ser
        195                 200                 205

Leu Glu Asp Leu Thr His Gln Gly Lys Leu Ser Ala Phe Ser Phe Asn
    210                 215                 220

Asp Gln Thr Gly Gln Ala Thr Leu Ile Thr Asn Glu Asp Glu Asn Phe
225                 230                 235                 240

Val Lys Asp Glu Gln Arg Ala Gly Val Asp Ala Asn Tyr Tyr Ala Lys
                245                 250                 255

Gln Thr Tyr Asp Tyr Tyr Lys Asp Thr Phe Gly Arg Glu Ser Tyr Asp
            260                 265                 270
```

```
Asn Gln Gly Ser Pro Ile Val Ser Leu Thr His Val Asn Asn Tyr Gly
            275                 280                 285
Gly Gln Asp Asn Arg Asn Asn Ala Ala Trp Ile Gly Asp Lys Met Ile
290                 295                 300
Tyr Gly Asp Gly Asp Gly Arg Thr Phe Thr Ser Leu Ser Gly Ala Asn
305                 310                 315                 320
Asp Val Val Ala His Glu Leu Thr His Gly Val Thr Gln Glu Thr Ala
                325                 330                 335
Asn Leu Glu Tyr Lys Asp Gln Ser Gly Ala Leu Asn Glu Ser Phe Ser
            340                 345                 350
Asp Val Phe Gly Tyr Phe Val Asp Asp Glu Asp Phe Leu Met Gly Glu
        355                 360                 365
Asp Val Tyr Thr Pro Gly Lys Glu Gly Asp Ala Leu Arg Ser Met Ser
    370                 375                 380
Asn Pro Glu Gln Phe Gly Gln Pro Ala His Met Lys Asp Tyr Val Phe
385                 390                 395                 400
Thr Glu Lys Asp Asn Gly Gly Val His Thr Asn Ser
                405                 410

<210> SEQ ID NO 50
<211> LENGTH: 1239
<212> TYPE: DNA
<213> ORGANISM: Staphylococcus aureus

<400> SEQUENCE: 50
attgattcaa aaaataaacc agctaattct gatattaaat ttgaggtgac tcaaaagagt      60
gatgcggtca agcattaaa agaattgcct aaatccgaaa atgtaaaaaa tatttatcaa     120
gattacgctg ttactgatgt aaaaactgat aaaaaaggat ttacgcatta tacattgcaa     180
ccgagtgttg atggtgttca tgcacctgac aaagaagtga agtcacacgc agacaaatca     240
ggaaaagtcg ttttaatcaa tggggatact gatgcgaaga agtaaagcc aacgaataaa     300 gtgacattaa gtaaagatga cgcagccgac aaagcattta agcagttaa gattgataag     360 aataagcga aaaatcttaa agataaagtc attaaagaaa acaaagttga atcgatggt      420 gacagtaata aatacgttta taatgttgag ttaattacag tgacaccaga aatttcacat     480
tggaaagtta aaattgatgc tcaaactggc gaattttag aaaaaatgaa cttagttaaa     540
gaagctgcag aaactggtaa aggaaaaggt gtacttggcg atacaaaaga tatcaatatc     600
aatagtattg acggtggatt tagcctagaa gatttaacgc atcaaggtaa attatcagca     660
tttagcttta tgatcaaac aggtcaagca acattgatta ctaatgaaga tgaaaacttc     720
gtaaaagatg agcaacgtgc tggcgtagat gcaaattatt acgctaaaca aacatatgat     780
tattacaaag acacatttgg tcgtgaatca tatgacaacc aaggtagtcc aattgtttca     840
ttaacgcatg ttaataacta cggtggtcaa gataacagaa taatgccgc atggatcggt     900 gacaaaatga tctatggtga tggtgatggt cgcacattca caagtttatc gggtgcaaat     960
gacgtagtag cacacgaatt aacacacggt gtgacacaag agacagcgaa cttagaatat    1020
aaggaccagt caggcgctct aaatgaaagc ttttcagatg ttttttggata ctttgtagat    1080 gacgaggatt tcttaatggg tgaagatgtc tacacacctg gaaagagggg agacgcttta    1140
cgcagcatgt caaacccaga acaatttggt caaccagctc atatgaaaga ctatgtattc    1200
actgaaaaag ataatggtgg cgtacatacg aattcttaa                           1239
```

<210> SEQ ID NO 51
<211> LENGTH: 1239
<212> TYPE: RNA
<213> ORGANISM: Staphylococcus aureus

<400> SEQUENCE: 51

| | | | | | |
|---|---|---|---|---|---|
| auugauucaa | aaaauaaacc | agcuaauucu | gauauuaaau | uugaggugac | ucaaaagagu | 60 |
| gaugcgguca | aagcauuaaa | agaauugccu | aaauccgaaa | auguaaaaaa | uauuuaucaa | 120 |
| gauuacgcug | uuacugaugu | aaaaacgau | aaaaaggau | uuacgcauua | uacauugcaa | 180 |
| ccgaguguug | augguguuca | ugcaccugac | aaagaaguga | aaguacacgc | agacaaauca | 240 |
| ggaaaagucg | uuuuaaucaa | uggggauacu | gaugcgaaga | aaguaaagcc | aacgaauaaa | 300 |
| gugacauuaa | guaaagauga | cgcagccgac | aaagcauuua | aagcaguuaa | gauugauaag | 360 |
| aauaaagcga | aaaaucuuaa | agauaaaguc | auuaaagaaa | acaaaguuga | aaucgauggu | 420 |
| gacaguaaua | aauacguuua | uaauguugag | uuaauuacag | ugacaccaga | aauuucacau | 480 |
| uggaaaguua | aaauugaugc | ucaaacuggc | gaaauuuuag | aaaaaaugaa | cuuaguuaaa | 540 |
| gaagcugcag | aaacugguaa | aggaaaaggu | guacuuggcg | auacaaaaga | uaucaauauc | 600 |
| aauaguauug | acgguggauu | uagccuagaa | gauuuaacgc | aucaagguaa | auuaucagca | 660 |
| uuuagcuuua | augaucaaac | aggucaagca | acauugauua | cuaaugaaga | ugaaaacuuc | 720 |
| guaaaagaug | agcaacgugc | uggcguagau | gcaaauuauu | acgcuaaaca | aacauaugau | 780 |
| uauuacaaag | acacauuugg | ucgugaauca | uaugacaacc | aagguagucc | aauuguuuca | 840 |
| uuaacgcaug | uuaauaacua | cggugucaa | gauaacagaa | auaaugccgc | auggaucggu | 900 |
| gacaaaauga | ucuaugguga | uggugauggu | cgcacauuca | caaguuuauc | gggugcaaau | 960 |
| gacguaguag | cacacgaauu | aacacacggu | gugacacaag | agacagcgaa | cuuagaauau | 1020 |
| aaggaccagu | caggcgcucu | aaaugaaagc | uuuucagaug | uuuuuggaua | cuuuguagau | 1080 |
| gacgaggauu | ucuuaauggg | ugaagauguc | uacacaccug | gaaaagaggg | agacgcuuua | 1140 |
| cgcagcaugu | caaacccaga | acaauuuggu | caaccagcuc | auaugaaaga | cuauguauuc | 1200 |
| acugaaaaag | auaauggugg | cguacauacg | aauucuuaa | | | 1239 |